(12) United States Patent
Barth et al.

(10) Patent No.: US 11,999,758 B2
(45) Date of Patent: Jun. 4, 2024

(54) INHIBITORS OF THE YAP/TAZ-TEAD INTERACTION AND THEIR USE IN THE TREATMENT OF CANCER

(71) Applicant: INVENTIVA, Daix (FR)

(72) Inventors: Martine Barth, Asnieres les Dijon (FR); Sylvie Contal, Pouilley-les-Vignes (FR); Jean-Louis Junien, Paris (FR); Christine Massardier, Dijon (FR); Christian Montalbetti, Fontaine-lès-Dijon (FR); Anne Soude, Marsannay-la-Côte (FR)

(73) Assignee: INVENTIVA, Daix (FR)

( * ) Notice: Subject to any disclaimer, the term of this patent is extended or adjusted under 35 U.S.C. 154(b) by 566 days.

(21) Appl. No.: 17/278,429

(22) PCT Filed: Oct. 2, 2019

(86) PCT No.: PCT/EP2019/076681
§ 371 (c)(1),
(2) Date: Mar. 22, 2021

(87) PCT Pub. No.: WO2020/070181
PCT Pub. Date: Apr. 9, 2020

(65) Prior Publication Data
US 2021/0323982 A1    Oct. 21, 2021

(30) Foreign Application Priority Data
Oct. 2, 2018   (EP) ..................... 18306294

(51) Int. Cl.
*C07F 5/02*   (2006.01)
*A61P 35/00*  (2006.01)

(52) U.S. Cl.
CPC .............. *C07F 5/025* (2013.01); *A61P 35/00* (2018.01)

(58) Field of Classification Search
CPC ........ C07F 5/025; A61P 35/00; C07D 487/04; C07D 495/04; A61K 31/69
See application file for complete search history.

(56) References Cited

U.S. PATENT DOCUMENTS 8,314,098 B2 * 11/2012 Yamamoto ................ A61P 7/06
                                                 514/233.2

FOREIGN PATENT DOCUMENTS

| CN | 109 912 609     | 6/2019 |
| CN | 109912609 A *   | 6/2019 |

(Continued)

OTHER PUBLICATIONS

S. Sarkar et al., "Antimalarial Activity of Small-Molecule Benzothiazole Hydrazones", Antimicrobial Agents and Chemotherapy, vol. No. 60, No. 7, Jul. 1, 2016, pp. 4217-4228.

(Continued)

*Primary Examiner* — Matthew P Coughlin
*Assistant Examiner* — Ashli Ariana Chicks
(74) *Attorney, Agent, or Firm* — Clark & Brody LP

(57) ABSTRACT

The invention relates to compounds of formula (I):

(Continued)

wherein $R_1$, $R_2$, $R_3$, $R_4$, $R_5$ and

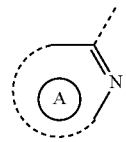

are as defined in the description.

19 Claims, 1 Drawing Sheet

(56) References Cited

FOREIGN PATENT DOCUMENTS

| WO | 2004/087153 | 10/2004 | | |
|---|---|---|---|---|
| WO | 2013/123071 | 8/2013 | | |
| WO | 2015/097237 | 7/2015 | | |
| WO | 2017/053706 | 3/2017 | | |
| WO | 2017/064277 | 4/2017 | | |
| WO | WO-2017064277 A1 * | 4/2017 | ........... | A61K 31/428 |

OTHER PUBLICATIONS

K. M. Khan et al., "Synthesis of phenyl...glycation of proteins", Med. Chem. Res. (2015) 24:3077-3085.

* cited by examiner

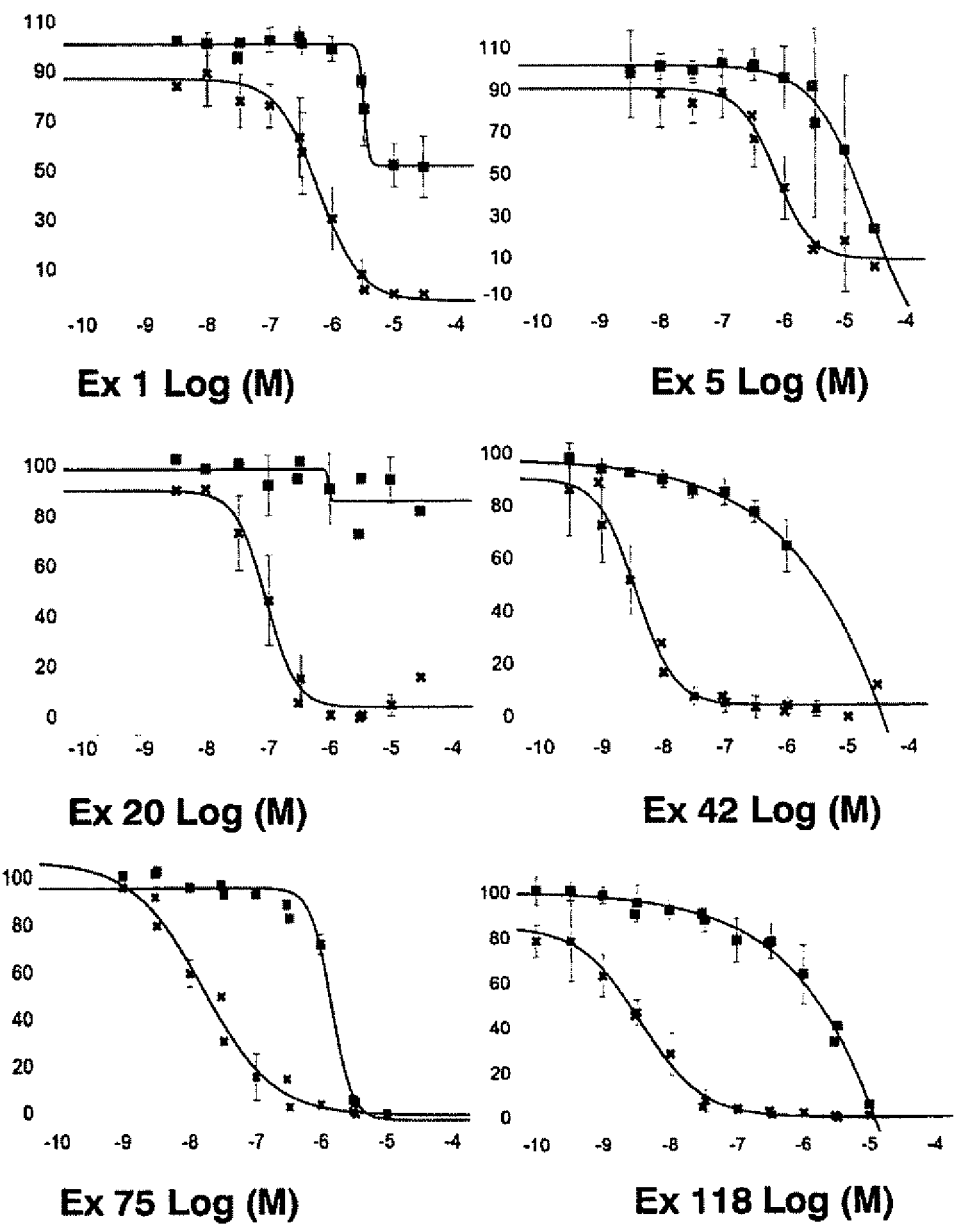

INHIBITORS OF THE YAP/TAZ-TEAD INTERACTION AND THEIR USE IN THE TREATMENT OF CANCER

FIELD OF THE INVENTION

The present invention concerns new compounds inhibitors of the YAP/TAZ-TEAD interaction, and their use in therapy, particularly in the treatment of cancer such as malignant mesothelioma, non-small cell lung cancer, uveal melanoma, renal cancer.

The hippo pathway regulates ceil proliferation, cell death and cell differentiation in multicellular organisms to ensure normal tissue development (Tumaneng K et al., Curr. Biol., 2013, 22, R368-379; Yu Fx. et al., Genes Dev. 2013, 27, 355-371, Moon S et al. Cell Mol Life Science, 2018, 13, 2303-2319). Over the past years, various genetic and biochemical studies in *Drosophila* and mammals have defined a highly conserved core hippo signaling module (Huang et al., Cell, 2005, 122, 421-434; Zeng et al., Cancer Cell, 208, 13, 188-192; Badouel et al., Curr. Opin. Cell. Biol., 2009, 21, 837-843).

Essentially, the core hippo signaling module is composed of members of Ste20-like kinase, (MST1/2) and a large tumor suppressor 1/2 (LATS1/2), together with MOB activator 1A (MOB1A) and MOB1B and the AGC (protein kinase A(PKA)/PKG/PKC-like) kinase families (Hong W et al., Cell. Dev. Biol., 2012, 23, 785-793).

Lats1 and 2, AGC kinases (homologous to *Drosophila* Warts), are activated by association with Mob1 (Mps one binder kinase activator-like 1A and 1B) (Mats in *Drosophila*) and also by phosphorylation by the STE20 family protein kinases MST1 and 2 (Hippo in *Drosophila*). The final output of hippo signaling is the inhibition of the transcriptional co-activators YAP (Yes-associated protein; Yorkie in *drosophila*)/TAZ (transcriptional co-activator with PDZ-binding motif) by phosphorylation by the complex Lats/Mob, in flies and mammals (Hong W et al., Cell. Dev. Biol., 2012, 23, 785-793; Zhao et al., Cancer Res., 2009, 69, 1089-98; Lei et al., Mol. Cell. Biol., 2008, 28, 2426-2436).

Functionally, when the hippo pathway is activated, YAP and TAZ are sequestered in the cytoplasm and degraded. Conversely, when the Hippo pathway is deactivated, YAP and TAZ translocate into the nucleus and promote transcription of downstream genes by forming complexes with transcription factors, such as transcriptional enhancer factors (TEF; also referred to as TEAD) and others. TEADs seem to be the key mediators of the growth and the tumorigenic potential of YAP/TAZ. (Zhao et al., Genes Dev., 2008, 22, 1962-1971; Harvey et al., Nat. Rev. Cancer, 2013, 13, 246-257; Lin K et al., Trends Biochem Science, 2017, 42, 862-872; Pobbati A, Cancer Biol therapy, 2013, 390-398) by inducing the expression of target genes, such as CTGF, Cyr61, FGF1 (Wang L et al., Tumor Biol., 2014, 14, 463-468).

Hyperactivation of YAP and TAZ subsequent to a deregulation of the hippo pathway is widespread in cancer, indeed, the levels and nuclear localization of YAP/TAZ are elevated in many tumors such as lung, thyroid, skin, ovarian, colorectal, prostate, pancreas, esophagus, liver and breast cancer (Harvey et al., Nat, Rev. Cancer, 2013, 13, 246-257; Avruch et al., Cell Cycle, 2012, 1090-1096; De Christofaro T, Eur. J. Cancer, 2011, 926-933; Zhou et al., Oncogene, 2011, 30, 2181-2186; Wang et al., Cancer Sci., 2010, 101, 1279-85; Chad et al., Cancer Res., 2010, 70, 8517-25; Steinhardt et al., Hum. Pathol., 2008, 39, 1582-9, Zhao et al. Genes Dev., 2007, 21: 2747-2761; Dong et al. Ceil, 2007, 130: 1120-1133; Holden J, Cancers, 2018, 10, ASAP).

Although hippo signaling is clearly altered in human cancer, only few germline and somatic mutation of hippo signaling components have been described so far, this is especially true of the core hippo pathway genes. Only neurofibromin 2 (NF2 or merlin in *Drosophila*) an upstream component of the hippo pathway core component has been linked to a heritable cancer syndrome and classified as a tumor suppressor gene. Hundreds of somatically acquired mutation have been reported in NF2, predominantly in meningiomas, mesotheliomas and peripheral nerve sheath tumors, but also in other cancer types. (Harvey et al., Nat. Rev. Cancer, 2013, 13, 246-257; Bianchi et al., Nat. Genet., 1994, 6, 185-192; Ruttledge et al., Nat. Genet., 1994, 6, 180-184).

Malignant pleural mesothelioma (MPM) is an aggressive human malignancy, mostly associated with asbestos exposure (Carbone et al., Clin. Cancer Res., 2012, 18, 598-604). About 3 out of 4 mesotheliomas are pleural mesotheliomas. MPM is a rare disease with a 15-year cumulative frequency during 1994-2008 in the 56 countries reporting MPM to be 174300 cases (Park et al., Environ. Health Perspect., 2011, 119, 514-518). However, the real incidence of MPM is unknown, since there are countries for which MPM mortality is not reported, including asbestos producers. Despite treatment with chemotherapy, radiation therapy or surgery, the prognosis is poor; the median survival time of patients after diagnosis is only 7-12 months. (Bianchi et al. Natl. Acad. Sci., USA, 1995, 92, 10854-10858; Sekido et al., Cancer Res., 1995, 55, 1227; Deguen et al., Int. J. Cancer, 1998, 77, 554-560).

Malignant pleural mesothelioma shows frequent inactivation of the NF2-tumor suppressor gene, indeed data mining of the catalogue of somatic mutations in cancers shows that the genes that are mostly mutated in MPM are cyclin-dependent kinase activator (CDKN2A), neurofibromatosis type 2 and BRCA-associated protein 1 (BAP1) (Forbe et al., Nucleic Acids Res., 2011, 39, D945-950).

Recently, besides the NF2 mutation, genetic alterations in the components of the hippo-signaling pathway have also been identified, including inactivating mutations of Lats1/2 and amplification of YAP. Together with NF2 mutation, MPM shows frequent Merlin-Hippo pathway inactivation, which leads to YAP activation over 70% of MPM cases (Bott et al., Nat. Genet., 2011, 43, 668-672; Murakami et al., Cancer Res., 2011, 71, 873-883; Yokoyama et al., Carcinogenesis, 2008, 29, 2139-2146; Sekido et al., Pathol. Int., 2011, 61, 331-344; Woodward et al., Transl. Lung Res., 2017, 6, 335-342; Sekido et al., Cancers, 2018, ASAP).

Inhibition of the activity of Hippo pathway effectors YAP and TAZ is likely to represent a valuable approach for the treatment of several cancers since the Hippo pathway deregulation is largely observed in many cancers, leading to YAP/TAZ nuclear translocation.

Therefore, disruption of hippo pathway downstream YAP/TAZ-TEAD interaction is believed to abrogate the oncogenic property of YAP/TAZ. The compounds of invention are designed to block this interaction upon binding to TEAD and can be further developed into drugs for cancers especially for the treatment of malignant mesothelioma.

WO 2004/087153 and WO 2013/123071 disclose hundreds of small molecules susceptible to be used generally in relation with cancer treatments. Two hydrozobenzothiazole derivatives, different from the one disclosed in the present application, are disclosed but no YAP/TAZ-TEAD interaction inhibiting activity is reported, not to mention specific anticancer activity.

The invention provides new compounds identified as inhibitors of the YAP/TAZ-TEAD interaction, and particularly new hydrazoboroaryl derivatives inhibiting YAP/TAZ-TEAD interaction.

BRIEF DISCLOSURE OF THE INVENTION

The present invention concerns a compound of formula (I):

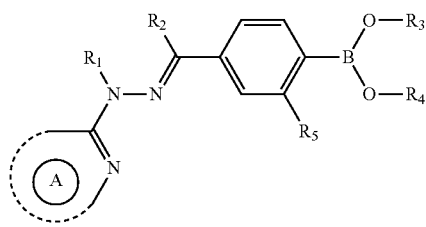

wherein:

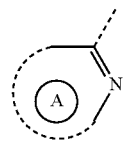

is a substituted or unsubstituted N-containing monocyclic, bicyclic or tricyclic heteroaryl;

$R_1$ is H, an alkyl optionally substituted with one or two groups $R_6$ or an aryl optionally substituted with one or more groups $R_6$;

$R_2$ is H or alkyl; or $R_1$ and $R_2$ are bound together to form a 5- or 6-membered heterocycle;

$R_3$ and $R_4$ independently are H, an alkyl optionally substituted with one or two groups $R_6$; or $R_3$ and $R_4$ are bound together to form a 5- to 8-membered heterocycle;

$R_5$ is H, a halogen, an alkyl optionally substituted with 1 or 2 groups $R_6$, an alkoxy optionally substituted with 1 or 2 groups $R_6$; or $R_4$ and $R_5$ are bound together to form a 5- to 7-membered heterocycle;

$R_6$ is hydroxy, alkoxy, —$NR_{15}R_{16}$, —CO—Y—$R_{17}$, —CN, —$CF_3$, aryl;

$R_{15}$ and $R_{16}$ are independently H, alkyl, —CO-alkyl or form together with the nitrogen atom a 3- to 6-membered cyclic group;

Y is —O— or —$NR_{18}$—;

$R_{17}$ is H or alkyl;

$R_{10}$ is H, alkyl or hydroxyalkyl;

or pharmaceutically acceptable salts thereof.

The invention also concerns a compound of formula (Ib):

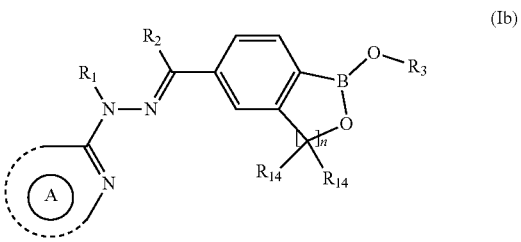

wherein:

$R_3$ is H or an alkyl optionally substituted with one or two groups $R_6$;

Each $R_{14}$ is independently H, an alkyl optionally substituted with one or two groups $R_6$, an aryl, —$NR_{15}R_{16}$, or —CO—Y—$R_{17}$; and n is 1, 2 or 3;

or pharmaceutically acceptable salts thereof;

with

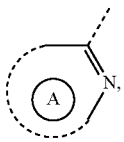

$R_1$, $R_2$, $R_{15}$, $R_{16}$ and $R_{17}$ being as defined above and below.

The invention also concerns a compound of formula (I) or (Ib), for use as a medicament, particularly for use in the treatment of a cancer indication where YAP is localized in the nucleus of the tumor cells, such as lung, thyroid, ovarian, colorectal, prostate, pancreas, esophagus, liver, breast and skin cancer, more particularly in the treatment of malignant mesothelioma The invention also concerns a pharmaceutical composition comprising a compound of formula (I) or (Ib) and a pharmaceutically acceptable vehicle or excipient.

BRIEF DISCLOSURE OF THE FIGURE

FIG. 1 represents the anti-proliferative activity of representative compounds of the invention as inhibitors of the YAP/TAZ-TEAD interaction in mesothelioma cells NCI-H2052 (x) and MetSA (■)

DETAILED DISCLOSURE OF THE INVENTION

The compounds of formula (I) described herein and their pharmaceutically acceptable salts are representatives of this new class of compounds, inhibitors of the YAP/TAZ-TEAD interaction.

According to the present invention, the term "alkyl" of the prefix "alk" means a linear or branched $C_1$-$C_6$ alkyl or alkylene moiety, particularly a $C_1$-$C_4$ alkyl or alkylene moiety, more particularly $C_1$, $C_2$, $C_3$ or $C_4$ alkyl or alkylene moieties, including the groups methyl or methylene, ethyl or ethylene, propyl or propylene, isopropyl or isopropylene, butyl or butylene, isobutyl or isobutylene and tertiobutyl or tertiobutylene. In particular embodiments, the alkyl moieties are selected among methyl or methylene, ethyl or ethylene, propyl or propylene.

According to the invention, the term "cycloalkyl" means a 3- to 6-membered hydrocarbon cycle, which can be bridged particularly cyclopropyl, cyclobutyl, cyclopentyl and cyclohexyl. According to the present invention, the "halo" group is selected among F, Cl, Br or I, particularly F or Cl.

According to the present invention, "aryl" means an aromatic (hetero)cycle comprising 1 or 2 rings, including phenyl, naphthyl, pyrazolyl, pyridyl, indolyl, isoindolyl, thienyl, thiazolyl, benzimidazolyl, benzotriazolyl, and derivatives thereof. The aryl groups are optionally substituted by one or more substituents selected from alkyl, alkoxy and halo groups.

In one embodiment, when $R_3$ is H and $R_4$ and $R_5$ are bound together to form a 5-membered heterocycle, then $R_1$ is not H.

In one embodiment, $R_1$ is an alkyl optionally substituted with one or two groups $R_6$ or an aryl optionally substituted with one or more groups $R_6$. $R_1$ is preferably an alkyl, particularly selected among methyl, ethyl, n-propyl, i-propyl, sec-butyl, optionally substituted with an alkoxy ($R_6$ is alkoxy), particularly methoxy.

$R_2$ is preferably H.

When $R_1$ and $R_2$ are bound together to form a 5- or 6-membered heterocycle, they particularly represent a moiety selected from —$C(R_{19})_2$—$C(R_{20})_2$—, —$C(R_{19})_2$—$C(R_{20})_2$—$C(R_{21})_2$— and —$C(R_{19})_2$—$C(R_{20})_2$—O— wherein $R_{19}$, $R_{20}$ and $R_{21}$ are each independently H or alkyl. Independently means that both $R_{19}$, both $R_{20}$ and both $R_{21}$ respectively can be the same or different. In one embodiment, all $R_{19}$, $R_{20}$ and $R_{21}$ are the same. In another embodiment, at least one of $R_{19}$, $R_{20}$ and $R_{21}$ is different from the other $R_{19}$, $R_{20}$ or $R_{21}$. In a particular embodiment, at least one $R_{19}$ is H and at least one $R_{20}$ is alkyl. In another embodiment, at least one $R_{19}$ is H and at least one $R_{20}$ is H and one of the other $R_{19}$ or $R_{20}$ is alkyl, particularly one $R_{19}$ is alkyl and both $R_{20}$ are H. In another embodiment, at least one $R_{19}$ is H and at least one $R_{20}$ is alkyl and one of the other $R_{19}$ or $R_{20}$ is alkyl, particularly both $R_{19}$ are H and both $R_{20}$ are alkyl. In preferred embodiments, both $R_{21}$ are H.

In one embodiment, $R_3$ and $R_4$ are independently H or alkyl. In another embodiment, both $R_3$ and $R_4$ are H or an alkyl, particularly the same alkyl. The alkyl group for $R_3$ and $R_4$ is preferably methyl or ethyl, more preferably methyl.

In another embodiment, $R_3$ and $R_4$ are bound together form a 5- to 8-membered heterocycle. Such heterocycle is particularly 4,4,5,5-tetramethyl-1,3,2-dioxaborolan-2-yl, 5,5-dimethyl-1,3,2-dioxaborinan-2-yl or 1,3,6,2-dioxazaborocane-4,8-dione.

In one embodiment, $R_5$ is selected among H, alkoxy, particularly methoxy or ethoxy, optionally substituted with one methoxy or ethoxy, such as methoxyethoxy, and —F or Cl, preferably Cl.

In one embodiment $R_4$ and $R_5$ are bound together to form a 5- to 7-membered heterocycle which is optionally substituted with one or more groups selected from alkyl and alkoxy.

In one embodiment, $R_3$ is H, $R_4$ and $R_5$ are bound together to form a 5-membered heterocycle, and $R_1$ is an alkyl optionally substituted with one or two groups $R_6$ or an aryl optionally substituted with one or more groups $R_6$.

In one embodiment, $R_6$ is hydroxy, alkoxy, —$NR_{15}R_{16}$, —CO—Y—$R_{17}$, —CN, —$CF_3$, or aryl.

$R_{15}$ and $R_{16}$ are independently H, alkyl, —CO-alkyl or form together with the nitrogen atom a 3- to 6-membered cyclic group.

In one embodiment, Y is —O— or —$NR_{18}$—.

In one embodiment, $R_{17}$ is H or alkyl.

In one embodiment, $R_{16}$ is H, alkyl or hydroxyalkyl or $R_{17}$ and $R_{18}$ are bound together to form a 4- to 7-membered cyclic group.

When $R_{15}$ and $R_{16}$ together with the nitrogen atom form a 3- to 6-membered cyclic group, including 3-, 4-, 5- or 6-membered cycles, said group is preferably selected from aziridinyl, azetidinyl, diazetidinyl, pyrrolidinyl, pyrrolinyl, pyrrolyl, imidazolidinyl, imidazolyl, pyrazolidinyl, pyrazolyl, piperidinyl, piperazinyl, pyrazinyl, triazinyl, morphonlinyl, oxazinyl, thiomorpholinyl, thiazinyl. A preferred cyclic group is morpholinyl. The 3- to 6-membered cyclic group may be substituted by one or more groups selected from alkyl and halo.

The same definition applies when $R_{17}$ and $R_{18}$ are bound together to form a 4- to 7-membered cyclic group, in case X is —$NR_{18}$—. Preferably, the cyclic group is selected among azetidine, pyrrolidine, piperidine, morpholine, azepane and oxazepane.

In preferred embodiments, $R_6$ is an alkoxy, particularly methoxy or ethoxy.

In particular embodiments, $R_3$ is H or an alkyl optionally substituted with one or two groups $R_6$, and $R_4$ and $R_5$ are bound together to form a 5- to 7-membered heterocycle. Said compounds of the invention are more particularly compounds of formula (Ib):

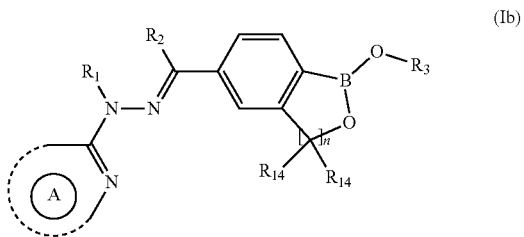

(Ib)

wherein:
each $R_{14}$ is independently H, an alkyl optionally substituted with one or two groups $R_6$, an aryl, —$NR_{15}R_{16}$, or —CO—Y—$R_{17}$;
n is 1, 2 or 3; and

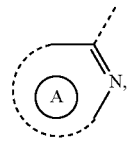

$R_1$, $R_2$, $R_3$, $R_{15}$, $R_{16}$ and $R_{17}$ are as defined above and below;
and pharmaceutically acceptable salts thereof.

In some embodiments, $R_3$ and all $R_{14}$ are H. In another embodiment $R_3$ is H, one $R_{14}$ is an alkyl, particularly methyl, and the other $R_{14}$ are H.

In a particular embodiment, n is 1 and both $R_{14}$ are H or one $R_{14}$ is H and the other is methyl.

In one embodiment

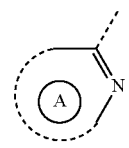

is a N-containing monocyclic or bicyclic heteroaryl. Said heteroaryls are known, such as derivatives of saccharine, including tetrahydrosaccharine, derivatives of pyridazine, derivatives of quinazoline, derivatives of thieno-pyrimidine, derivatives of pyrrolo-pyrimidine, derivatives of pyrrolo-pyrimidinone, derivatives of dihydro pyrrolo-pyrimidine, derivatives of pyrazolo-pyrimidine, derivatives of furano-pyrimidine, derivatives of dihydro furano-pyrimidine, derivatives of thiazolo-pyrimidine, derivatives of purinone, derivatives of dihydro pyrido-pyrimidinone, derivatives of tetrahydrobenzothieno-pyrimidine, in one aspect of this embodiment the N-containing monocyclic or bicyclic heteroraryl is selected from derivatives of saccharine, including tetrahydrosaccharine, derivatives of pyridazine, derivatives of quinazoline, derivatives of thieno-pyrimidine, derivatives of pyrrolo-pyrimidine, derivatives of pyrazolo-pyrimidine, and derivatives of furano-pyrimidine.

More particularly, the N-containing monocyclic or bicyclic heteroaryl is selected among the groups of formulae (II), (ill), (IV), (V), (VI), (VII), (VIII), (IX) (X), (XI), (XII), (XIII), (XIV), (XV), (XVI), (XVII) and (XVIII).

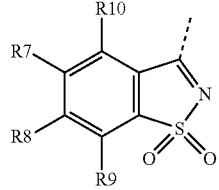
(II)

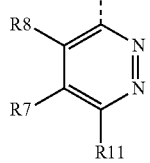
(III)

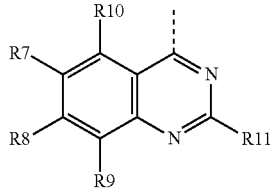
(IV)

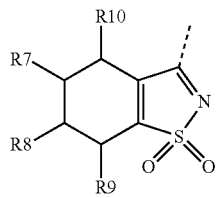
(V)

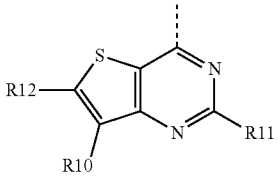
(VI)

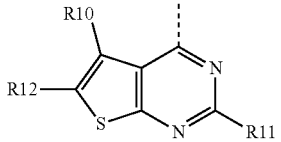
(VII)

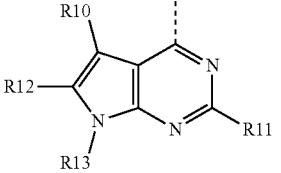
(VIII)

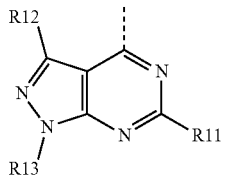
(IX)

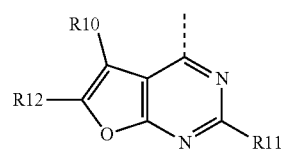
(X)

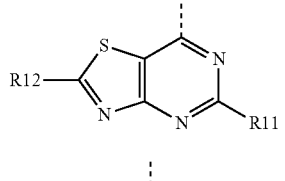
(XI)

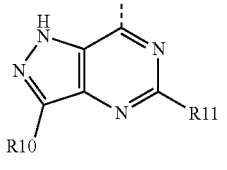
(XII)

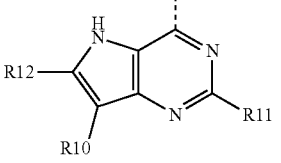
(XIII)

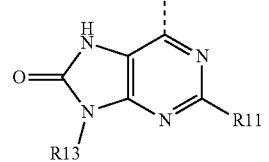
(XIV)

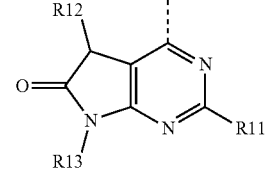
(XV)

-continued

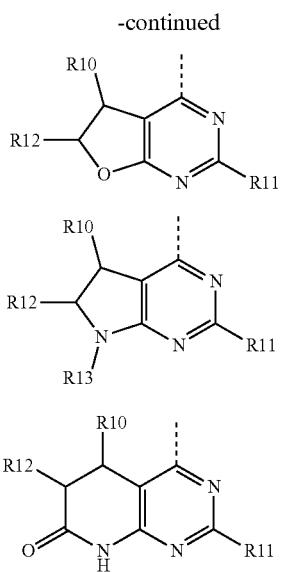

(XVI)

(XVII)

(XVIII)

wherein:

$R_7$, $R_8$, $R_9$ and $R_{10}$ are each independently H, a halogen, an alkyl optionally substituted with 1 or 2 groups $R_6$, a perfluoroalkyl, an alkoxy optionally substituted with 1 or 2 groups $R_6$, or a cyano group.

$R_{10}$ can also represent a cycloalkyl, an aryl, —$NR_{15}R_{16}$ where $R_{15}$ and $R_{16}$ are as defined above, or —CO—Y—$R_{22}$ where Y is as defined above and $R_{22}$ is H, alkyl optionally substituted with hydroxy or alkoxy, or —$NR_{15}R_{16}$ where $R_{15}$ and $R_{16}$ are as defined above.

$R_{10}$ can also be bound together with $R_{12}$ to form a 6-membered carbocycle.

$R_{11}$, $R_{12}$, and $R_{13}$ are each independently H, an alkyl optionally substituted with 1 or 2 groups $R_6$, a perfluoroalkyl.

$R_{12}$ can also represent an alkylthio or a group —$NR_{15}R_{16}$ where $R_{15}$ and $R_{16}$ are as defined above.

$R_{13}$ can also represent a cycloalkyl optionally substituted with hydroxy or alkoxyalkyl.

$R_7$ is particularly H, an alkyl, such as methyl, ethyl, n-propyl or i-propyl, optionally substituted with one $R_6$, with $R_6$ being particularly selected among hydroxyl, alkoxy (e.g. methoxy, ethoxy) and a halide, particularly F.

$R_8$ is particularly H, an alkyl, such as methyl or ethyl, a halogen, particularly F, or a cyano group.

$R_9$ and $R_{10}$ are particularly each independently H, an alkyl, such as methyl or ethyl, or an alkoxy, such as methoxy or ethoxy.

In one embodiment, $R_{10}$ is —CO—Y—$R_{22}$ or —$NR_{15}R_{16}$ wherein Y, $R_{15}$, $R_{16}$, $R_{22}$ are as defined above. Particularly Y is —$NR_{18}$— wherein $R_{18}$ is as defined above.

$R_{11}$ and $R_{12}$ are particularly each independently H, an alkyl, such as methyl or ethyl, or a perfluoroalkyl such as trifluoromethyl. In particular $R_{11}$ and $R_{12}$ are both H.

$R_{13}$ is particularly H or an alkyl, such as methyl or ethyl.

In one embodiment, in the groups of formula (II) and (V), $R_8$ is H when one of $R_7$ or $R_9$ is not H.

In one embodiment, $R_8$, $R_9$ and $R_{10}$ are H and $R_7$ is particularly H, an alkyl, such as methyl, ethyl, n-propyl or i-propyl, optionally substituted with one $R_6$, $R_6$ being particularly selected among hydroxyl, alkoxy (e.g. methoxy, ethoxy) and a halogen, particularly F. In another embodiment, $R_8$ and $R_{10}$ are H and $R_7$ and $R_9$ are not H as defined above.

In one embodiment, the N-containing monocyclic or bicyclic heteroaryl is a group of formula (II) or a group of formula (VI).

In one embodiment,

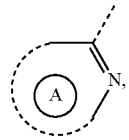

$R_1$, $R_2$, $R_3$, $R_4$ and $R_5$ are as defined in priority application EP18306294.2.

In a particular embodiment, compounds of formula (I) where $R_4$ and $R_5$ are not bound together are selected from:
[4-[(E)-[(1,1-dioxo-1,2-benzothiazol-3-yl)-isobutyl-hydrazono]methyl]-2-methoxy-phenyl]boronic acid
[4-[(E)-[isobutyl-(5-methoxy-1,1-dioxo-1,2-benzothiazol-3-yl)hydrazono]methyl]-2-methoxy-phenyl]boronic acid
[4-[(E)-[(5,7-dimethoxy-1,1-dioxo-1,2-benzothiazol-3-yl)-isobutyl-hydrazono]methyl]-2-methoxy-phenyl]boronic acid
[4-[(E)-[(1,1-dioxo-1,2-benzothiazol-3-yl)-ethyl-hydrazono]methyl]-2-methoxy-phenyl]boronic acid
[4-[(E)-[(1,1-dioxo-1,2-benzothiazol-3-yl)-(2-methoxyethyl)hydrazono]methyl]-2-methoxy-phenyl]boronic acid
[2-chloro-4-[(E)-[(1,1-dioxo-1,2-benzothiazol-3-yl)-isobutyl-hydrazono]methyl]phenyl]boronic acid
[4-[(E)-[isobutyl-(5-methyl-1,1-dioxo-1,2-benzothiazol-3-yl)hydrazono]methyl]-2-methoxy-phenyl]boronic acid
[4-[(E)-[(1,1-dioxo-1,2-benzothiazol-3-yl)-isobutyl-hydrazono]methyl]phenyl]boronic acid
[4-[(E)-[isobutyl-[5-(2-methoxyethoxy)-1,1-dioxo-1,2-benzothiazol-3-yl]hydrazono]methyl]-2-methoxy-phenyl]boronic acid
[4-[(E)-[(6-cyano-1,1-dioxo-1,2-benzothiazol-3-yl)-isobutyl-hydrazono]methyl]-2-methoxy-phenyl]boronic acid
[4-[(E)-[(1,1-dioxo-1,2-benzothiazol-3-yl)-isobutyl-hydrazono]methyl]-2-(2-methoxyethoxy)phenyl]boronic acid
[4-[(E)-[[5-(3-hydroxypropoxy)-1,1-dioxo-1,2-benzothiazol-3-yl]-isobutyl-hydrazono]methyl]-2-methoxy-phenyl]boronic acid
[4-[(E)-[isobutyl-(8-methoxyquinazolin-4-yl)hydrazono]methyl]-2-methoxy-phenyl]boronic acid
[4-[(E)-[(1,1-dioxo-1,2-benzothiazol-3-yl)-isobutyl-hydrazono]methyl]-2-ethoxy-phenyl]boronic acid
[2-chloro-4-[(E)-[(5,7-dimethoxy-1,1-dioxo-1,2-benzothiazol-3-yl)-isobutyl-hydrazono]methyl]phenyl]boronic acid
[4-[(E)-[(1,1-dioxo-1,2-benzothiazol-3-yl)-sec-butyl-hydrazono]methyl]-2-methoxy-phenyl]boronic acid
[4-[(E)-[(6,8-dimethoxyquinazolin-4-yl)-isobutyl-hydrazono]methyl]-2-methoxy-phenyl]boronic acid
[4-[(E)-[(7-fluoroquinazolin-4-yl)-isobutyl-hydrazono]methyl]-2-methoxy-phenyl]boronic acid
[4-[(E)-[isobutyl-(6-methoxyquinazolin-4-yl)hydrazono]methyl]-2-methoxy-phenyl]boronic acid
[4-[(E)-[isobutyl(thieno[3,2-d]pyrimidin-4-yl)hydrazono]methyl]-2-methoxy-phenyl]boronic acid
[4-[(E)-[ethyl-(8-methoxyquinazolin-4-yl)hydrazono]methyl]-2-methoxy-phenyl]boronic acid
[2-methoxy-4-[(E)-[(8-methoxyquinazolin-4-yl)-methyl-hydrazono]methyl]phenyl]boronic acid

[4-[2-(1,1-dioxo-1,2-benzothiazol-3-yl)-3-methyl-4,5-dihydro-3H-pyridazin-6-yl]-2-methoxy-phenyl]boronic acid
[4-[2-(5,7-dimethoxy-1,1-dioxo-1,2-benzothiazol-3-yl)-3-methyl-4,5-dihydro-3H-pyridazin-6-yl]-2-methoxy-phenyl]boronic acid
[2-methoxy-4-[2-(8-methoxyquinazolin-4-yl)-3-methyl-4,5-dihydro-3H-pyridazin-6-yl]phenyl]boronic acid
[4-[2-(1,1-dioxo-1,2-benzothiazol-3-yl)-4,4-dimethyl-3,5-dihydropyridazin-6-yl]-2-methoxy-phenyl]boronic acid
[4-[4-(1,1-dioxo-1,2-benzothiazol-3-yl)-6-methyl-5,6-dihydro-1,3,4-oxadiazin-2-yl]-2-methoxy-phenyl]boronic acid
[2-methoxy-4-[(E)-[methyl-(5-methylpyridazin-3-yl)hydrazono]methyl]phenyl]boronic acid
2-[4-[(E)-[(1,1-dioxo-1,2-benzothiazol-3-yl)-isobutyl-hydrazono]methyl]-2-methoxy-phenyl]-6-methyl-1,3,6,2-dioxazaborocane-4,8-dione
[4-[(E)-[ethyl-(7-methylthieno[3,2-d]pyrimidin-4-yl)hydrazono]methyl]-2-methoxy-phenyl]boronic acid
[4-[(E)-[ethyl(thieno[3,2-d]pyrimidin-4-yl)hydrazono]methyl]-2-methoxy-phenyl]boronic acid
[4-[(E)-[ethyl(thiazolo[4,5-d]pyrimidin-7-yl)hydrazono]methyl]-2-methoxy-phenyl]boronic acid
[4-[(E)-[ethyl(furo[2,3-d]pyrimidin-4-yl)hydrazono]methyl]-2-methoxy-phenyl]boronic acid
[4-[(E)-[ethyl-(7-methylpyrrolo[2,3-d]pyrimidin-4-yl)hydrazono]methyl]-2-methoxy-phenyl]boronic acid
[4-[(E)-[isobutyl-(7-methylthieno[3,2-d]pyrimidin-4-yl)hydrazono]methyl]-2-methoxy-phenyl]boronic acid
[4-[(E)-[isobutyl-(2-methylthieno[3,2-d]pyrimidin-4-yl)hydrazono]methyl]-2-methoxy-phenyl]boronic acid
[4-[(E)-[isobutyl-(6-methylthieno[3,2-d]pyrimidin-4-yl)hydrazono]methyl]-2-methoxy-phenyl]boronic acid
[2-methoxy-4-[(E)-[2-methoxyethyl(thieno[3,2-d]pyrimidin-4-yl)hydrazono]methyl]-phenyl]boronic acid
[2-methoxy-4-[(E)-[methyl-(7-methylthieno[3,2-d]pyrimidin-4-yl)hydrazono]methyl]-phenyl]boronic acid
[2-methoxy-4-(3-methyl-2-thieno[3,2-d]pyrimidin-4-yl-4,5-dihydro-3H-pyridazin-6-yl)phenyl]boronic acid
[2-methoxy-4-[3-methyl-2-(7-methylpyrrolo[2,3-d]pyrimidin-4-yl)-4,5-dihydro-3H-pyridazin-6-yl]phenyl]boronic acid
[4-[4-(7-fluoroquinazolin-4-yl)-6-methyl-5,6-dihydro-1,3,4-oxadiazin-2-yl]-2-methoxy-phenyl]boronic acid
and pharmaceutically acceptable salts thereof.

In another particular embodiment, compounds of formula (Ib) are selected from:
N-[(E)-(1-hydroxy-3H-2,1-benzoxaborol-5-yl)methyleneamino]-N-isobutyl-1,1-dioxo-1,2-benzothiazol-3-amine
N-[(E)-(1-hydroxy-3H-2,1-benzoxaborol-5-yl)methyleneamino]-N-(2-methoxyethyl)-1,1-dioxo-1,2-benzothiazol-3-amine
N-[(E)-(1-hydroxy-3H-2,1-benzoxaborol-5-yl)methyleneamino]-N-(3-methoxypropyl)-1,1-dioxo-1,2-benzothiazol-3-amine
N-[(E)-(1-hydroxy-3H-2,1-benzoxaborol-5-yl)methyleneamino]-N-methyl-1,1-dioxo-1,2-benzothiazol-3-amine
N-ethyl-N-[(E)-(1-hydroxy-3H-2,1-benzoxaborol-5-yl)methyleneamino]-1,1-dioxo-1,2-benzothiazol-3-amine
5-fluoro-N-[(E)-(1-hydroxy-3H-2,1-benzoxaborol-5-yl)methyleneamino]-N-isobutyl-1,1-dioxo-1,2-benzothiazol-3-amine
N-[(E)-(1-hydroxy-3H-2,1-benzoxaborol-5-yl)methyleneamino]-N-isobutyl-5-methyl-1,1-dioxo-1,2-benzothiazol-3-amine
N-[(E)-(1-hydroxy-3H-2,1-benzoxaborol-5-yl)methyleneamino]-N-isobutyl-6-methoxy-1,1-dioxo-1,2-benzothiazol-3-amine
N-[(E)-(1-hydroxy-3H-2,1-benzoxaborol-5-yl)methyleneamino]-N-isobutyl-6-methyl-1,1-dioxo-1,2-benzothiazol-3-amine
N-[(E)-(1-hydroxy-3H-2,1-benzoxaborol-5-yl)methyleneamino]-N-isobutyl-8-methoxy-quinazolin-4-amine
N-[(E)-(1-hydroxy-3H-2,1-benzoxaborol-5-yl)methyleneamino]-8-methoxy-N-methyl-quinazolin-4-amine
N-ethyl-N-[(E)-(1-hydroxy-3H-2,1-benzoxaborol-5-yl)methyleneamino]-8-methoxy-quinazolin-4-amine
N-[(E)-(1-hydroxy-3H-2,1-benzoxaborol-5-yl)methyleneamino]-N-isobutyl-thieno[3,2-d]pyrimidin-4-amine
N-[(E)-(1-hydroxy-3H-2,1-benzoxaborol-5-yl)methyleneamino]-N,5-dimethyl-1,1-dioxo-1,2-benzothiazol-3-amine
N-[(E)-(1-hydroxy-3H-2,1-benzoxaborol-5-yl)methyleneamino]-5-methoxy-N-methyl-1,1-dioxo-1,2-benzothiazol-3-amine
N-ethyl-N-[(E)-(1-hydroxy-3H-2,1-benzoxaborol-5-yl)methyleneamino]thieno[3,2-d]pyrimidin-4-amine
N-ethyl-N-[(E)-(1-hydroxy-3H-2,1-benzoxaborol-5-yl)methyleneamino]-7H-pyrrolo[2,3-d]pyrimidin-4-amine
N-ethyl-N-[(E)-(1-hydroxy-3H-2,1-benzoxaborol-5-yl)methyleneamino]thieno[2,3-d]pyrimidin-4-amine
N-ethyl-N-[(E)-(1-hydroxy-3H-2,1-benzoxaborol-5-yl)methyleneamino]-1-methyl-pyrazolo[3,4-d]pyrimidin-4-amine
N-ethyl-N-[(E)-(1-hydroxy-3H-2,1-benzoxaborol-5-yl)methyleneamino]-7-methyl-thieno[3,2-d]pyrimidin-4-amine
N-ethyl-N-[(E)-(1-hydroxy-3H-2,1-benzoxaborol-5-yl)methyleneamino]furo[2,3-d]pyrimidin-4-amine
N-ethyl-N-[(E)-(1-hydroxy-3H-2,1-benzoxaborol-5-yl)methyleneamino]-7-methyl-pyrrolo[2,3-d]pyrimidin-4-amine
N-ethyl-N-[(E)-(1-hydroxy-3H-2,1-benzoxaborol-5-yl)methyleneamino]-2-methyl-thieno[3,2-d]pyrimidin-4-amine
N-[(E)-(1-hydroxy-3,4-dihydro-2,1-benzoxaborinin-6-yl)methyleneamino]-N-isobutyl-1,1-dioxo-1,2-benzothiazol-3-amine;
N-[(E)-(1-hydroxy-4,5-dihydro-3H-2,1-benzoxaborepin-7-yl)methyleneamino]-N-isobutyl-1,1-dioxo-1,2-benzothiazol-3-amine
N-[(E)-(1-hydroxy-7-methoxy-3H-2,1-benzoxaborol-5-yl)methyleneamino]-N-isobutyl-1,1-dioxo-1,2-benzothiazol-3-amine
N-[(E)-(1-hydroxy-3-methyl-3H-2,1-benzoxaborol-5-yl)methyleneamino]-N-isobutyl-1,1-dioxo-1,2-benzothiazol-3-amine
N-[(E)-(1-hydroxy-3-methyl-3H-2,1-benzoxaborol-5-yl)methyleneamino]-N-methyl-1,1-dioxo-1,2-benzothiazol-3-amine
N-[(E)-(1-hydroxy-3H-2,1-benzoxaborol-5-yl)methyleneamino]-N-methyl-1,1-dioxo-4,5,6,7-tetrahydro-1,2-benzothiazol-3-amine
3-[6-(1-hydroxy-3H-2,1-benzoxaborol-5-yl)-3-methyl-4,5-dihydro-3H-pyridazin-2-yl]-1,2-benzothiazole 1,1-dioxide
4-[6-(1-hydroxy-3H-2,1-benzoxaborol-5-yl)-3-methyl-4,5-dihydro-3H-pyridazin-2-yl]-8-methoxy-quinazoline N-[(E)-(1-hydroxy-3H-2,1-benzoxaborol-5-yl)methyl-eneamino]-5-methoxy-N-methyl-pyridazin-3-amine
N-[(E)-(1-hydroxy-3H-2,1-benzoxaborol-5-yl)methyl-eneamino]-N-methyl-2-methylsulfanyl-thiazolo[4,5-d]pyrimidin-7-amine
N-[(E)-(1-hydroxy-3H-2,1-benzoxaborol-5-yl)methyl-eneamino]-N,1-dimethyl-pyrazolo[3,4-d]pyrimidin-4-amine
N-[(E)-(1-hydroxy-3H-2,1-benzoxaborol-5-yl)methyl-eneamino]-N,7-dimethyl-thieno[3,2-d]pyrimidin-4-amine
N-ethyl-N-[(E)-(1-hydroxy-3H-2,1-benzoxaborol-5-yl)methyleneamino]-1H-pyrazolo[4,3-d]pyrimidin-7-amine
N7-ethyl-N7-[(E)-(1-hydroxy-3H-2,1-benzoxaborol-5-yl)methyleneamino]-N2,N2-dimethyl-thiazolo[4,5-d]pyrimidine-2,7-diamine
N-ethyl-N-[(E)-(1-hydroxy-3H-2,1-benzoxaborol-5-yl)methyleneamino]-3-methyl-1H-pyrazolo[4,3-d]pyrimidin-7-amine
N-ethyl-N-[(E)-(1-hydroxy-3H-2,1-benzoxaborol-5-yl)methyleneamino]-5H-pyrrolo[3,2-d]pyrimidin-4-amine
N-ethyl-N-[(E)-(1-hydroxy-3H-2,1-benzoxaborol-5-yl)methyleneamino]-2-morpholino-thiazolo[4,5-d]pyrimidin-7-amine
N-ethyl-N-[(E)-(1-hydroxy-3H-2,1-benzoxaborol-5-yl)methyleneamino]-2-methylsulfanyl-thiazolo[4,5-d]pyrimidin-7-amine hydrochloride
N-ethyl-N-[(E)-(1-hydroxy-3H-2,1-benzoxaborol-5-yl)methyleneamino]-7-propyl-pyrrolo[2,3-d]pyrimidin-4-amine
N,7-diethyl-N-[(E)-(1-hydroxy-3H-2,1-benzoxaborol-5-yl)methylene amino]pyrrolo[2,3-d]pyrimidin-4-amine
N-ethyl-N-[(E)-(1-hydroxy-3H-2,1-benzoxaborol-5-yl)methyleneamino]-1H-pyrazolo[3,4-d]pyrimidin-4-amine
N-ethyl-N-[(E)-(1-hydroxy-3H-2,1-benzoxaborol-5-yl)methyleneamino]thiazolo[4,5-d]pyrimidin-7-amine
N-ethyl-N-[(E)-(1-hydroxy-3H-2,1-benzoxaborol-5-yl)methyleneamino]-2,7-dimethyl-thieno[3,2-d]pyrimidin-4-amine
N-ethyl-7-fluoro-N-[(E)-(1-hydroxy-3H-2,1-benzoxaborol-5-yl)methyleneamino]-quinazolin-4-amine
N-ethyl-N-[(E)-(1-hydroxy-3H-2,1-benzoxaborol-5-yl)methyleneamino]-6-methyl-thieno[3,2-d]pyrimidin-4-amine
N-ethyl-N-[(E)-(1-hydroxy-3H-2,1-benzoxaborol-5-yl)methyleneamino]-6,7,8,9-tetrahydrobenzothiopheno[3,2-d]pyrimidin-4-amine
N-[(E)-(1-hydroxy-3H-2,1-benzoxaborol-5-yl)methyl-eneamino]-N-isobutyl-2-methylsulfanyl-thiazolo[4,5-d]pyrimidin-7-amine
N-[(E)-(1-hydroxy-3H-2,1-benzoxaborol-5-yl)methyl-eneamino]-N-isobutyl-7-methyl-thieno[3,2-d]pyrimidin-4-amine
N-[(E)-(1-hydroxy-3H-2,1-benzoxaborol-5-yl)methyl-eneamino]-N-(2-methoxyethyl)-7-methyl-thieno[3,2-d]pyrimidin-4-amine
N-[(E)-(1-hydroxy-3H-2,1-benzoxaborol-5-yl)methyl-eneamino]-N-(2-methoxyethyl)-2-methylsulfanyl-thiazolo[4,5-d]pyrimidin-7-amine, hydrochloride
N-[(E)-(1-hydroxy-3H-2,1-benzoxaborol-5-yl)methyl-eneamino]-N-(3-methoxypropyl)-2-methylsulfanyl-thiazolo[4,5-d]pyrimidin-7-amine
2-[[(E)-(1-hydroxy-3H-2,1-benzoxaborol-5-yl) methyl-eneamino]-(7-methylthieno[3,2-d]pyrimidin-4-yl) amino]ethanol
6-[[(E)-(1-hydroxy-3H-2,1-benzoxaborol-5-yl)methyl-eneamino]-methyl-amino]-9-methyl-7H-purin-8-one
4-[[(E)-(1-hydroxy-3H-2,1-benzoxaborol-5-yl)methyl-eneamino]-methyl-amino]-7-methyl-5H-pyrrolo[2,3-d]pyrimidin-6-one
Example 100: 4-[[(E)-(1-hydroxy-3H-2,1-benzoxaborol-5-yl)methyleneamino]-methyl-amino]-6,8-dihydro-5H-pyrido[2,3-d]pyrimidin-7-one
N-[(E)-(1-hydroxy-3H-2,1-benzoxaborol-5-yl)methyl-eneamino]-N-methyl-5,6-dihydrofuro[2,3-d]pyrimidin-4-amine
N-[(E)-(1-hydroxy-3H-2,1-benzoxaborol-5-yl)methyl-eneamino]-N-methyl-7-phenyl-thieno[3,2-d]pyrimidin-4-amine
7-cyclopropyl-N-[(E)-(1-hydroxy-3H-2,1-benzoxaborol-5-yl)methyleneamino]-N-methyl-thieno[3,2-d]pyrimidin-4-amine
N-[(E)-(1-hydroxy-3H-2,1-benzoxaborol-5-yl)methyl-eneamino]-N-methyl-7-morpholino-thieno[3,2-d]pyrimidin-4-amine
7-ethyl-N-[(E)-(1-hydroxy-3H-2,1-benzoxaborol-5-yl)methyleneamino]-N-methyl-thieno[3,2-d]pyrimidin-4-amine
N-[(E)-(1-hydroxy-3H-2,1-benzoxaborol-5-yl)methyl-eneamino]-N,7-dimethyl-5,6-dihydropyrrolo[2,3-d]pyrimidin-4-amine
9-cyclobutyl-6-[[(E)-(1-hydroxy-3H-2,1-benzoxaborol-5-yl)methyleneamino]-methyl-amino]-7H-purin-8-one
6-[[(E)-(1-hydroxy-3H-2,1-benzoxaborol-5-yl)methyl-eneamino]-methyl-amino]-9-[3-(methoxymethyl)cy-clobutyl]-7H-purin-8-one
6-[[(E)-(1-hydroxy-3H-2,1-benzoxaborol-5-yl)methyl-eneamino]-methyl-amino]-9-(3-hydroxycyclobutyl)-7H-purin-8-one hydrochloride
9-(3-bicyclo[1.1.1]pentanyl)-6-[[(E)-(1-hydroxy-3H-2,1-benzoxaborol-5-yl)methyleneamino]-methyl-amino]-7H-purin-8-one
7-cyclobutyl-4-[[(E)-(1-hydroxy-3H-2,1-benzoxaborol-5-yl)methyleneamino]-methyl-amino]-5H-pyrrolo[2,3-d]pyrimidin-6-one
4-[ethyl-[(E)-(1-hydroxy-3H-2,1-benzoxaborol-5-yl)meth-yleneamino]amino]-N-propyl-thieno[3,2-d]pyrimidine-7-carboxamide
4-[ethyl-[(E)-(1-hydroxy-3H-2,1-benzoxaborol-5-yl)meth-yleneamino]amino]-N,N-dimethyl-thieno[3,2-d]pyrimidine-7-carboxamide
N,N-dibutyl-4-[ethyl-[(E)-(1-hydroxy-3H-2,1-benzoxa-borol-5-yl)methyleneamino]-amino]thieno[3,2-d]pyrimidine-7-carboxamide
4-[ethyl-[(E)-(1-hydroxy-3H-2,1-benzoxaborol-5-yl)meth-yleneamino]amino]-N-(oxetan-3-yl)thieno[3,2-d]pyrimidine-7-carboxamide
4-[ethyl-[(E)-(1-hydroxy-3H-2,1-benzoxaborol-5-yl)meth-yleneamino]amino]-N-(4-methoxybutyl)thieno[3,2-d]pyrimidine-7-carboxamide
4-[6-(1-hydroxy-3H-2,1-benzoxaborol-5-yl)-3-methyl-4,5-dihydro-3H-pyridazin-2-yl]furo[2,3-d]pyrimidine
4-[6-(1-hydroxy-3H-2,1-benzoxaborol-5-yl)-3-methyl-4,5-dihydro-3H-pyridazin-2-yl]-7-methyl-thieno[3,2-d]pyrimidine
(+) 4-[6-(1-hydroxy-3H-2,1-benzoxaborol-5-yl)-3-methyl-4,5-dihydro-3H-pyridazin-2-yl]-7-methyl-thieno[3,2-d]pyrimidine
(−) 4-[6-(1-hydroxy-3H-2,1-benzoxaborol-5-yl)-3-methyl-4,5-dihydro-3H-pyridazin-2-yl]-7-methyl-thieno[3,2-d]pyrimidine
4-[6-(1-hydroxy-3H-2,1-benzoxaborol-5-yl)-3-methyl-4,5-dihydro-3H-pyridazin-2-yl]thieno[3,2-d]pyrimidine 4-[6-(1-hydroxy-3H-2,1-benzoxaborol-5-yl)-3-methyl-4,5-dihydro-3H-pyridazin-2-yl]-6,7,8,9-tetrahydrobenzothiopheno[3,2-d]pyrimidine 7-[6-(1-hydroxy-3H-2,1-benzoxaborol-5-yl)-3-methyl-4,5-dihydro-3H-pyridazin-2-yl]-2-methylsulfanyl-thiazolo[4,5-d]pyrimidine N-[(E)-(1-hydroxy-3H-2,1-benzoxaborol-5-yl)methyleneamino]-7-(methoxymethyl)-N-methyl-thieno[3,2-d]pyrimidin-4-amine and pharmaceutically acceptable salts thereof.

According to the invention, pharmaceutically acceptable salts are salts of acids or bases, known for their use in the preparation of active principles for use in therapy. Examples of pharmaceutically acceptable acids suitable as source of anions are those disclosed in the *Handbook of Pharmaceutical Salts: Properties, Selection and Use* (P. H. Stahl and C. G. Wermuth, Weinheim/Zürich:Wiley-VCHA/HCA, 2002).

The present invention also concerns a pharmaceutical composition comprising at least one compound of formula (I) as described herein or one of its pharmaceutically acceptable salts as the active principle. Pharmaceutical compositions and method for their preparation are well known in the art. Particularly, the composition comprises at least the compound of general formula (I) or one of its pharmaceutically acceptable salts as the active principle and at least one pharmaceutically acceptable excipient.

The pharmaceutical composition of the invention is formulated for administration by usual routes particularly the oral, sublingual, subcutaneous, intramuscular, intravenous, transdermal, local or rectal routes. The form of the pharmaceutical composition is particularly chosen among the group consisting of tablets, capsules, powders, granules and oral solutions or suspensions, sublingual forms of administration, subcutaneous, topical, intramuscular, intravenous, intranasal or intraocular forms of administration and rectal forms of administration.

Such forms, excipients and methods for their preparation are well known in the art, such as described in the art (Handbook of pharmaceutical Excipients, Rowe et al., seventh edition, June 2012; Rules and Guidance For Pharma Manufacturers and distributors 205, Medicines and Healthcare products Regulatory Agency, London UK).

Pharmaceutical compositions are designed for their intended use in therapy. The choice of components, their form and composition are governed by rules of the pharmacopeia. As such, they differ structurally from other compositions such as reactants used in laboratory experiments or compositions for applications on plants or non-living material.

Therefore, the present invention also concerns the compounds of formula (I) as described herein, for use in therapy, particularly in the treatment of any cancer indication where YAP is localized in the nucleus of the tumor cells, such as lung, thyroid, ovarian, colorectal, prostate, pancreas, esophagus, liver, breast and skin cancer, more particularly in the treatment of malignant mesothelioma.

The invention also concerns a method for treating cancer in a patient in need thereof, comprising administering a therapeutically effective amount of a compound of formula (I) as described herein, wherein the cancer is any cancer indication where YAP is localized in the nucleus of the tumor cells, such as lung, thyroid, ovarian, colorectal, prostate, pancreas, esophagus, liver, breast and skin cancer, particularly malignant mesothelioma.

The skilled practitioner, depending on the activity of the compound of formula (I) and the body weight of the patient, shall determine the appropriate dose of compound and the administration regimen. Such a dose is generally between 5 mg and 1000 mg per day orally for an adult. In general the doctor will determine the appropriate dosage depending on the age, weight and any other factors specific to the subject to be treated.

In a particular embodiment, the inhibitor of the YAP/TAZ-TEAD interaction, and particularly the compounds of formula (I) are used together or separately in combination with another treatment of cancer, particularly malignant mesothelioma, such as surgery, chemotherapy (with among other cisplatin, carboplatin, alimta (pemetrexed), gemcitabine and doxorubicin) and radiation.

General Synthetic Schemes

Compounds of the invention may be prepared using the synthetic transformations illustrated in schemes I, II, VII, XVIII, XIX, XX. Starting materials are commercially available or may be prepared by procedures described herein (schemes III-VI, Viii-XVII), by literature procedures, or by procedures well known to one skilled in the art of organic chemistry.

In scheme I, step a, an aldehyde (commercially available or prepared following schemes XIII-XVII) in solution in alcohol or THF is reacted with a commercially available hydrazine in the presence or not of an organic or inorganic base (such as sodium acetate, triethylamine, sodium hydrogencarbonate, potassium carbonate) (see for example, Kurian et al., Bioorg. Med. Chem. Lett., 2014, 24(17), 41764180; Loghmani-Khouzani et al., J. Chem. Res. Syn., 2001, (2), 80-81). In step b, the hydrazono derivative (obtained in step a) and a halogeno heterocycle (commercially available or obtained following schemes XI-XII) react together in the presence or not of an organic or inorganic base (see for example, Haffner et al., Bioorg. Med. Chem. Lett., 2010, 20(23), 6989-92; Haffner et al., Bioorg. Med. Chem. Lett., 2010, 20(23), 6983-88).

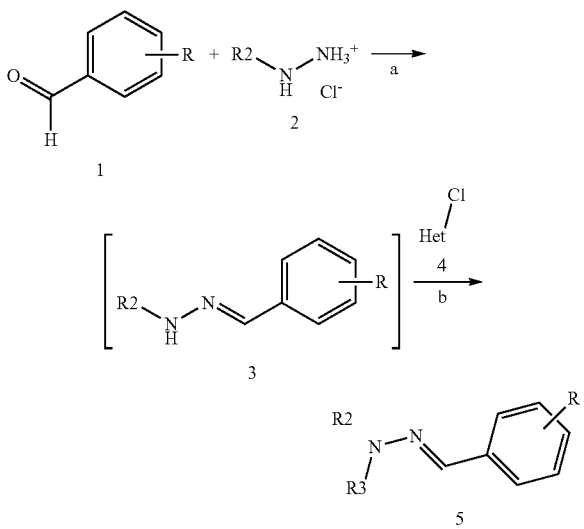

Scheme I

In scheme II, step a, aromatic substitution of the halogeno heterocycle (commercially available or prepared using transformations described in schemes XI-XII) with the hydrazine can be done under similar conditions as described in scheme I step b. In step b, the heterocycle-hydrazine derivative obtained in step a is reacted with an aldehyde (commercially available or prepared following schemes XIII-XVII) under similar conditions as described in scheme I, step a.

Scheme II

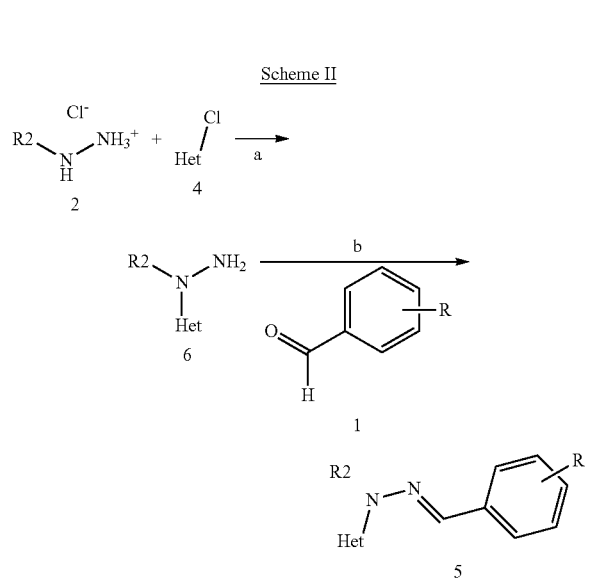

In scheme III, step a, condensation of the tert-butoxycarbonyl hydrazide with an aldehyde (commercially available or prepared following schemes XIII-XVII) is done using similar conditions as described in scheme I, step a. In step b, alkylation is done using a halogeno alkylating agent with an inorganic or organic base (such as triethylamine, pyridine, potassium carbonate, cesium carbonate . . . ) in dimethylformamide. In step c, cleavage of the tert-butylcarboxyl protecting group is carried out using hydrochloric acid in dioxane. Step d can be done under similar conditions used in Scheme I step b.

Scheme III

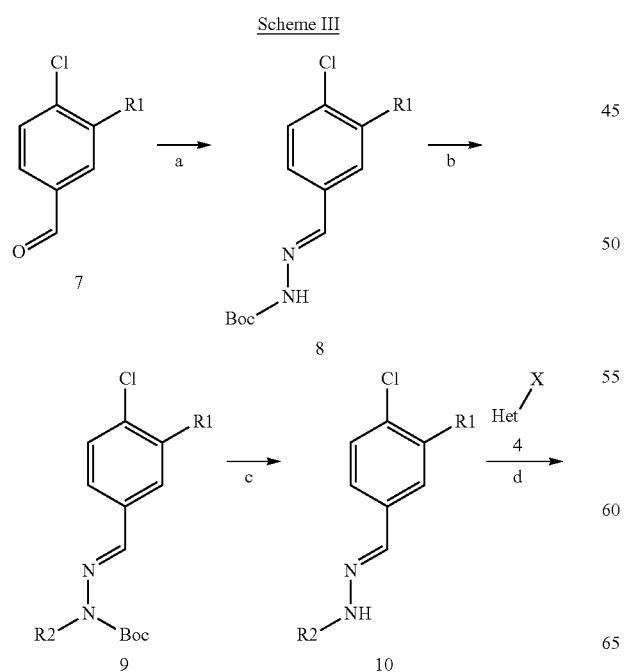

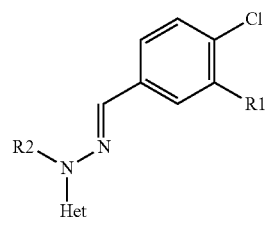

In scheme IV, step a, the formation of the Weinreb amide is done using classical conditions with methoxymethanamine in the presence of pyridine in dichloromethane. In step b, the ketone is obtained from the corresponding bromo derivative with the Weinreb amide using butyl lithium as base in THF (see for example WO 00/04013). In step c, cyclisation to the tetrahydropyridazine is done with hydrazine hydrate in ethanol (see for example, Gouauit et al., Journal of Pharmacy and Pharmacology, 2001, 53(7), 981-985). In step d, aromatic substitution is done using a halogeno hetero-aryl either in THF or with copper iodide in isopropanol depending of the nature of heterocycle.

Scheme IV

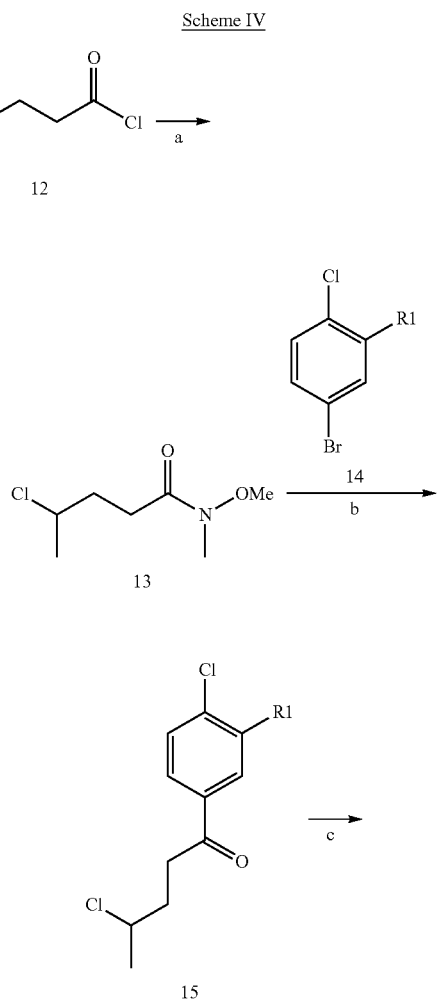

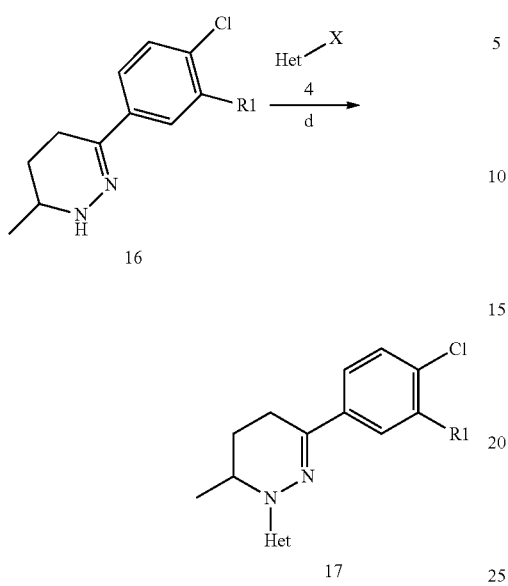

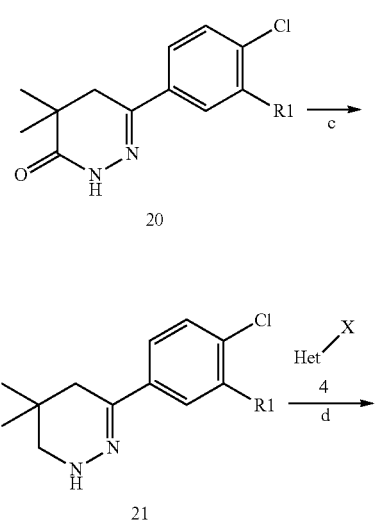

In scheme V, step a, succinic ring opening is done using a phenylmagnesiumbromide (prepared from the corresponding phenylbromide with magnesium turnings) in THF (see for example, Sakai et al. Chemistry Letters, 2015, 44(11), 1503-1505). In step b, cyclisation to the tetrahydropyridazine is done with hydrazine hydrate in ethanol as described in scheme IV step c. In step c, the reduction is done using lithium aluminium hydride in THF (see for example, Winton. et al., Journal of Heterocyclic Chemistry, 1984, 21(3), 889-91). Step d is done using similar conditions as described for Scheme IV step d.

Scheme V

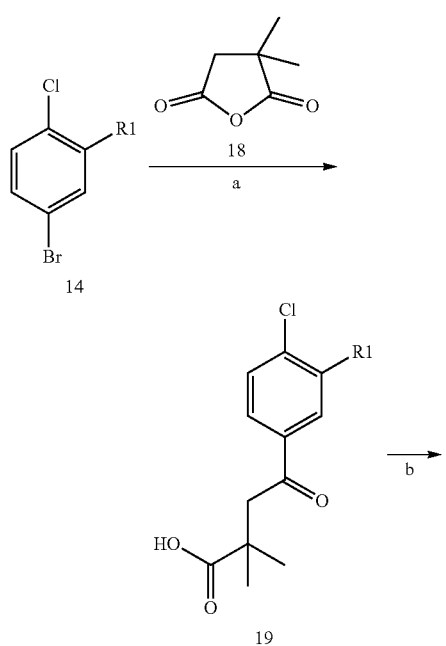

In scheme VI, step a, oxidation of benzaldehyde to benzoic acid is done with iodine, potassium hydroxide in methanol (Yamada S et al., Tetrahedron Letters, 1992, 33, 4329-4332). In step b, acylhydrazine formation is performed with hydrazine hydrate in ethanol. In step c, acylation of hydrazine is done with 2-chloro-propionyl chloride in dioxane (U.S. Pat. No. 6,197,766). In step d, cyclisation is done with triethylamanine in DMF under microwave irradiation at 150° C. In step e, reduction is done using borane in THF (see for example, Hudlicky Reductions in Organic Chemistry ACS monograph 188 second edition). Step f is performed using the same conditions as described in scheme IV step d.

Scheme VI

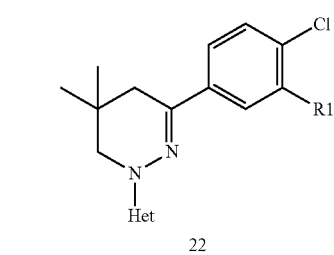

In scheme VIII, step a, aromatic substitution of the bromo derivative (prepared following scheme I) with bis pinacolborane is done in the presence of palladium catalyst (see for example, Dzhevakov et al., Adv. Synth. Catal., 2016, 358(6), 977-983; WO 2009/029998). In step b, the pinacol borane analog is hydrolyzed with hydrogen peroxide to give the corresponding phenol derivative (see for example WO 2007/038367).

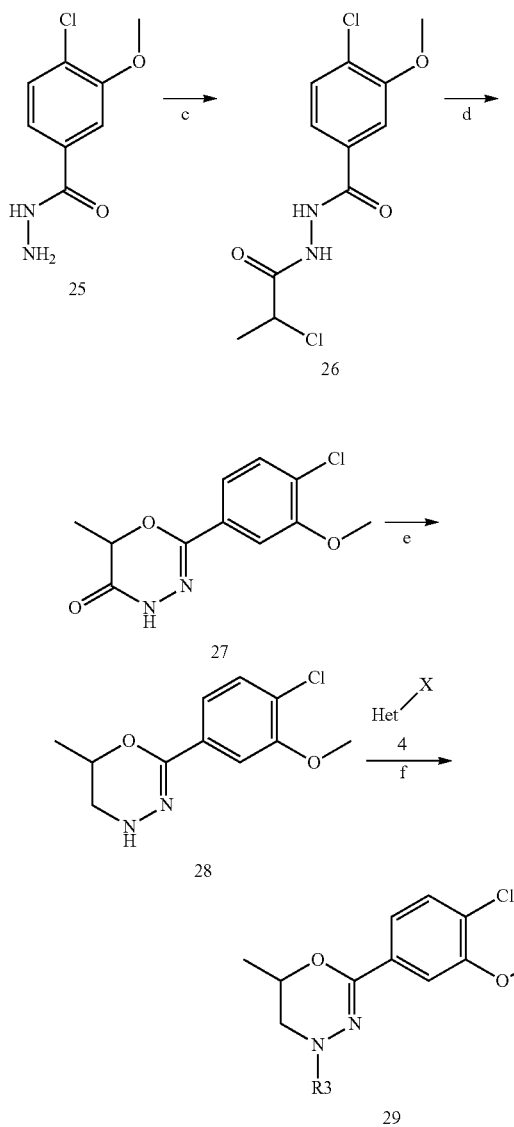

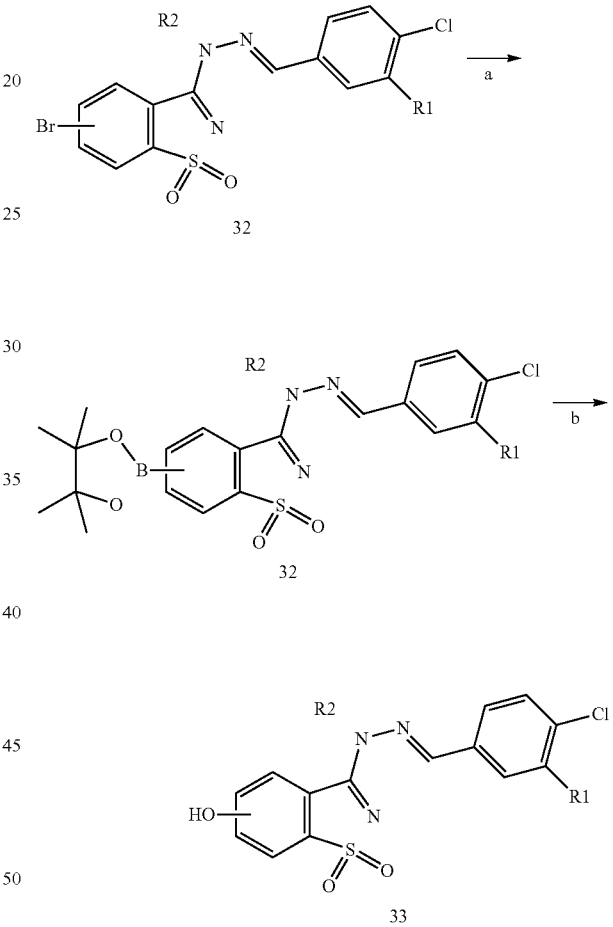

Scheme VIII

In scheme VII, step a, formation of the phenyl boronic derivative is done from the corresponding chloro analog (prepared following schemes I-VI, VIII-X) with tetrahydroxy diboron in the presence of XPHOS palladacycle and 2-dicyclohexylphosphino-2',4',6'-triisopropylbiphenyl in ethanol (see for example, Molander G et al., J Am Chem Soc, 2012, 134, 11667-11673).

Scheme VII

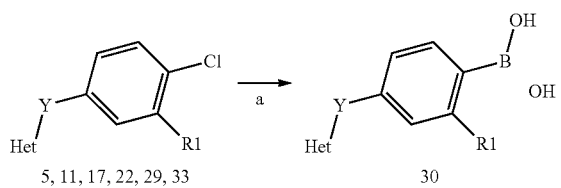

In scheme IX, step a and b, alkylation of the hydroxyl group (prepared following scheme VIII) can be done either using halogeno alkylating agent with an inorganic or organic base (such as triethylamine, pyridine, potassium carbonate, cesium carbonate) or by a Mitsunobu reaction in the presence of triphenyl phosphine and azodicarboxylate reagents (such as diethyl azodicarboxylate, diisopropyl azodicarboxylate). In step c, cleavage of the protective group of R5, if needed, is done using classical methods (for example tributyl ammonium fluoride in THF for silyl group) (see for example, Green et al., Protective Group in Organic Synthesis, Wiley, third edition).

Scheme IX

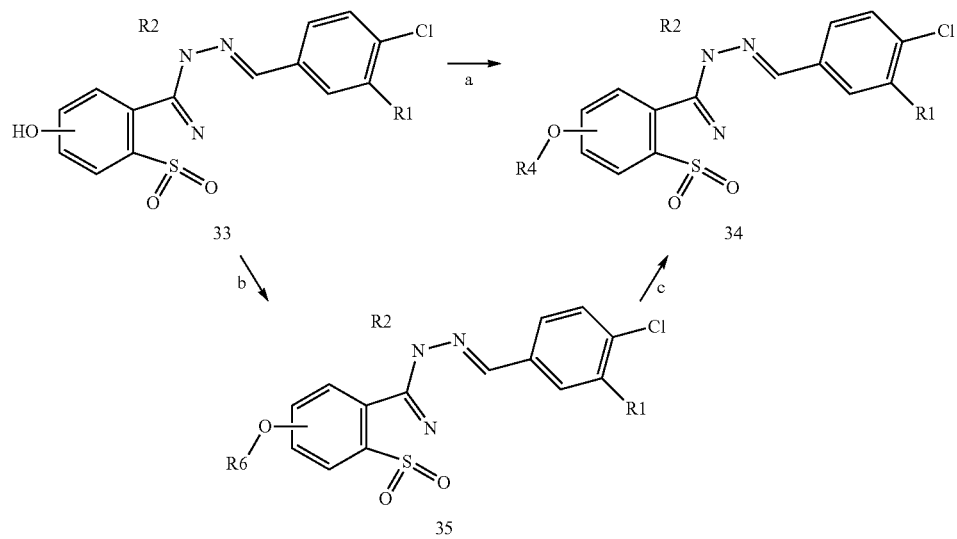

In scheme X, step a, formation of the trifluoromethanesulfonate is done starting from the corresponding phenol (prepared following scheme VIII) with trifluoromethanesulfonic anhydride in the presence of di-isopropylethylamine in dichloromethane. In step b, cyanation is done using zinc cyanide and tetrakis(triphenylphosphine)palladium in DMF under microwave irradiation (see for example, Sandgren V et al Bioorganic & Medicinal Chemistry, 2012, 20(14), 4377-4389).

Scheme X

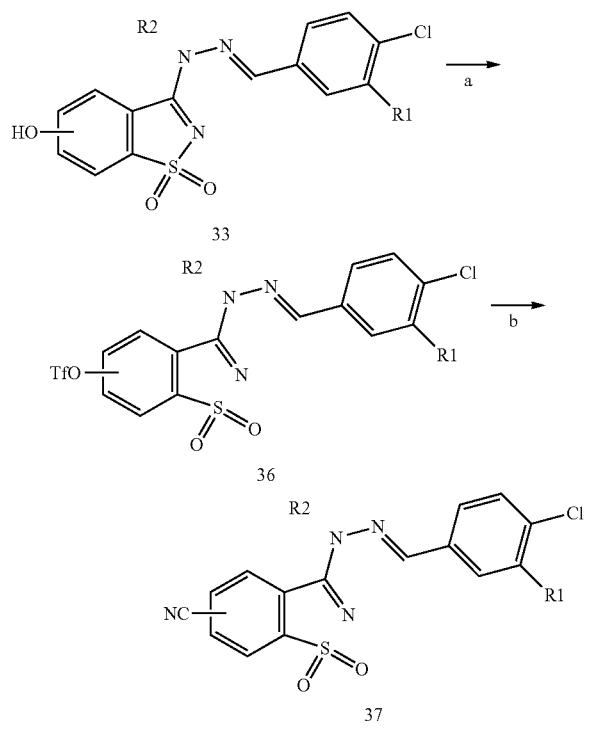

Chloro-saccharin preparations are described in schemes XI and XII. In scheme XI, step a, sulfonylation is done starting from commercially available phenylsulfonyl chloride with ammonia in methanol or dichloromethane (see for example, Blanchet et al., JOC, 2007, 72(9), 3199-3206; Schneider et al., 2011, Org. Lett., 13(14) 3588-3591). In step b, oxidation of the methyl group is performed with potassium permanganate in acetone (see for example, Sam et al., JACS, 1972, 94, 4024-4025). In step c, cyclisation into saccharin is obtained using sulfuric acid (see for example WO 2010/100139). In step d, the saccharin derivative can also be prepared in one step by cyclisation of commercially available 2-methoxycabonyl-phenyl sulfonyl chloride with ammonia in tetrahydrofuran (see for example U.S. Pat. No. 5,306,818; Kim et al., Bioorg. Med. Chem. Lett., 2008, 18(14), 4181-4185). In step e, the saccharin analog (commercially available or prepared following schemes XI and XII) is reacted with thionyl-chloride in the presence of dimethylformamide or other chlorinating agent such as phosphorous pentachloride, phosphorous oxychloride, oxalyl chloride (see for example, Differding et al., Hel. Chim. Acta, 1989; 72(6), 1248-52; Raw et al., Tet. Lett., 2011, 52(50), 6775-78).

Scheme XI

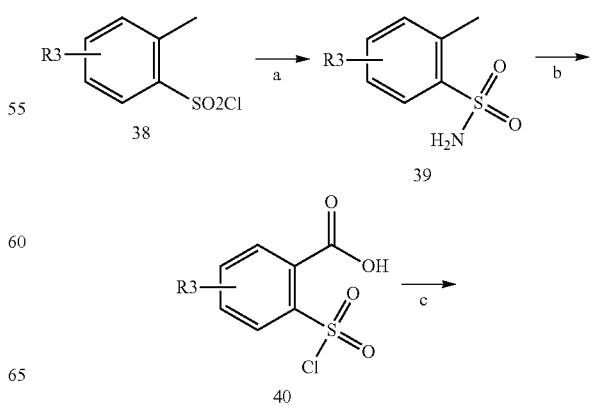

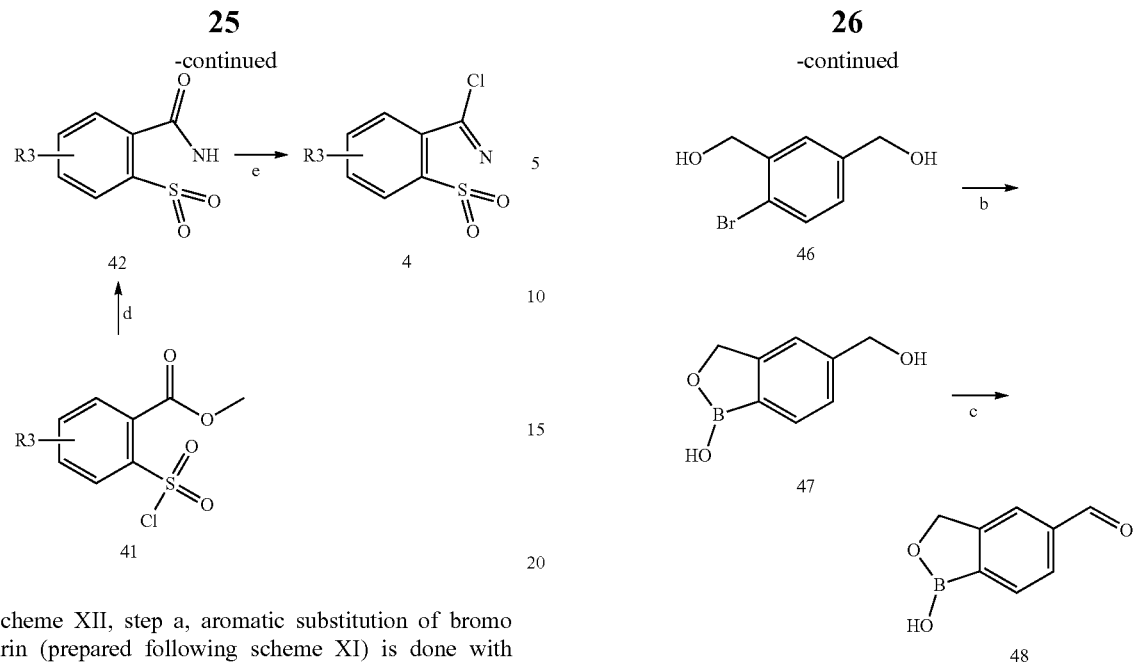

In scheme XII, step a, aromatic substitution of bromo saccharin (prepared following scheme XI) is done with trimethylboroxine in the presence of potassium carbonate and 1,1'-bis(diphenylphosphino)ferrocene-palladium(ii)dichloride dichloromethane complex in ethylene glycol dimethyl ether (see for example WO 2014/077401).

Scheme XII

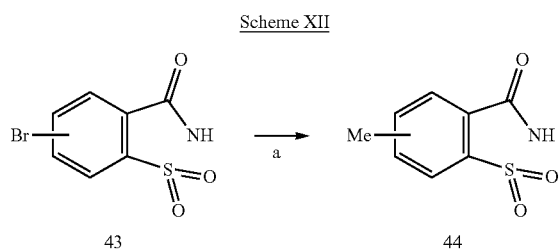

Benzoxaboroles and analogs preparations are described in schemes XIII-XVII. In scheme XIII, step a, reduction of the diacid is done with borane in THF. In step b, formation of oxaborole is done with tetrahydroxy diboron in the presence of XPHOS palladacycle and 2-dicyclohexylphosphino-2',4',6'-triisopropylbiphenyl in ethanol (see for example, Lafitte G et al Tetrahedron Letters 2017, 58, 3757-3759). In step c, oxidation of the alcohol into the aldehyde is performed using either manganese dioxide, Dess-Martin reagent, pyridinium dichromate, pyridinium chlorochromate or Swern reaction (see for example, Timmer et al., Chem. Commun. (Cambridge, United Kingdom), 2016, 52(83), 12326-12329; Fuchida et al., Bul. Chem. Soc. Jp., 2015, 88(6) 784-791; Garcia et al., Chem. Commun. (Cambridge, United Kingdom), 2016, 52(58), 9059-9062).

Scheme XIII

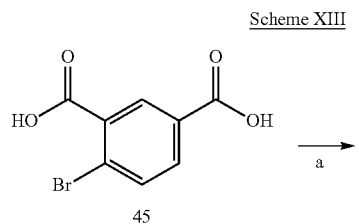

In scheme XIV, step a, protection of the phenol group with a tert-butoxycarbonyl is done using classical conditions, e.g. tert-Butyl dicarbonate in the presence of DMAP in dichloromethane (see for example, Green et al., Protective Group in Organic Synthesis, Wiley, third edition). In step b, bromation is obtained with 2,2,6,6-tetramethylpiperidinylmagnesium chloride lithium chloride complex and 1,2-dibromotetrachloroethane in THF (Noncovich, A et al Tetrahedron Letters, 2015, 56(33), 4836-4839). In step c, BOC cleavage is done with trifluoroacetic acid in dichloromethane. In step d, the phenol is methylated with iodomethane in the presence of potassium carbonate in DMF. In step e, the di-acid is saponified with lithium hydroxide in a mixture THF/water. In step f, the di-alcohol is obtained using borane as reducing agent in THF. Steps g and h are performed using the same conditions described in scheme XIII step b and c.

Scheme XIV

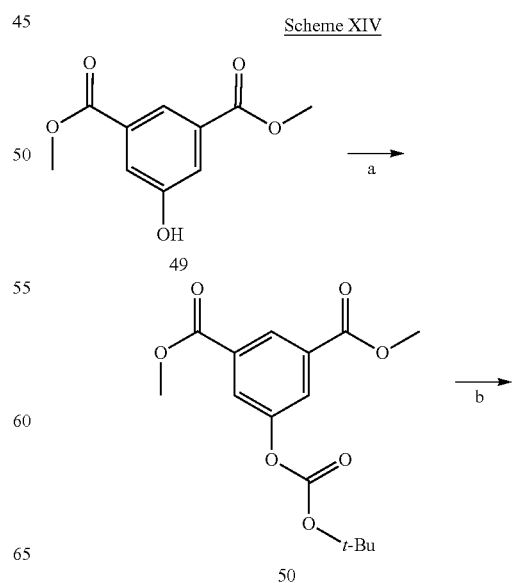

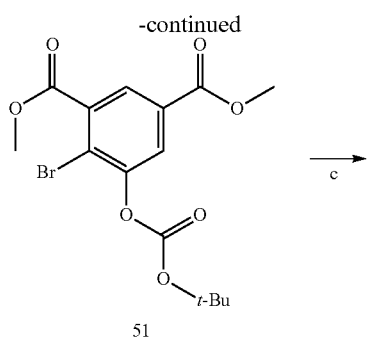
51

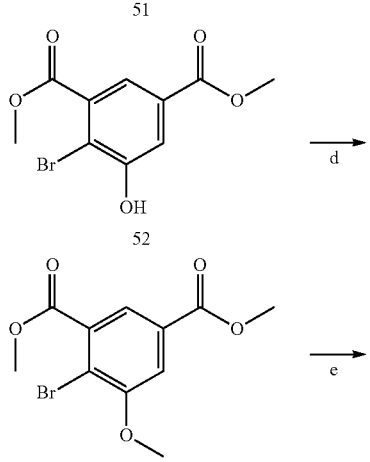
52

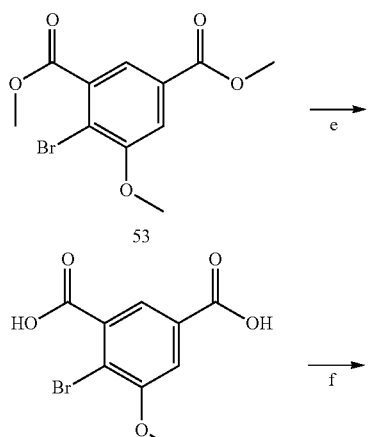
53

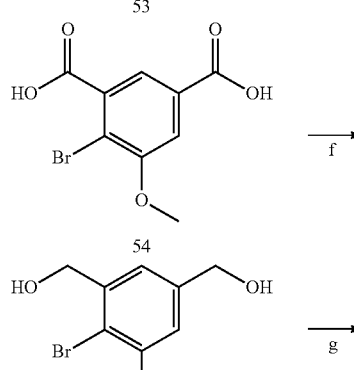
54

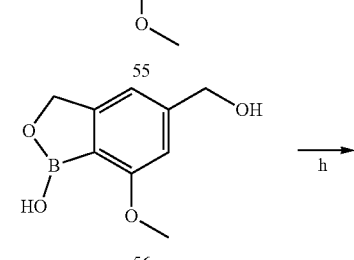
55

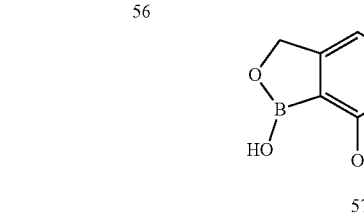
56

57

Hishikawa K et al., Journal of the American Chemical Society, 2009, 131(22), 7488-7489). In step c, monomethylation of the aldehyde is done with methylmagnesium bromide in THF (see for example WO 2017/133517). In step d, tert butyl is cleaved by acidic hydrolysis with trifluoroacetic acid. In step e, reduction to alcohol is performed using borane in THF. In step f, cyclisation to the oxaborole is obtained using the conditions described in scheme XIII step b. In step g, oxidation to the aldehyde is done using similar conditions described in scheme XIII.

Scheme XV

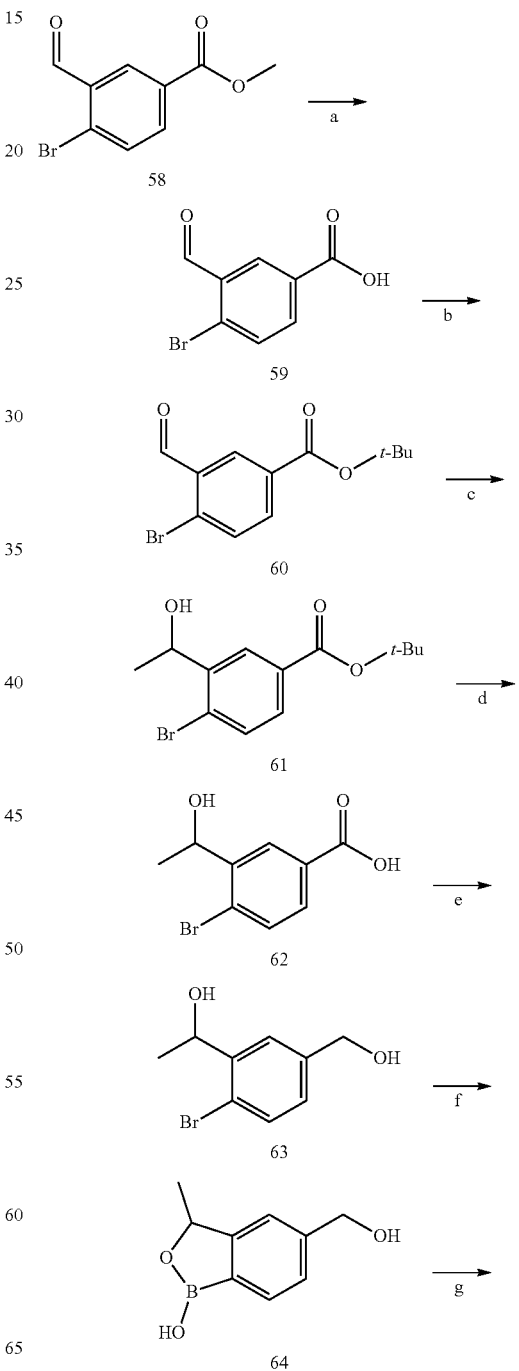

In scheme XV, step a, saponification is done with lithium hydroxide in THF/water. In step b, the tert-butyl ester is obtained using tert-butanol in the presence of tert-Butyl dicarbonate and DMAP as base in THF (see for example, -continued

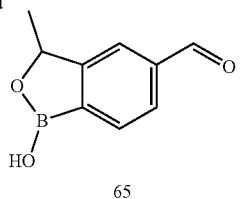

65

-continued

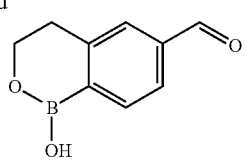

74

In scheme XVI, step a, bromation in done using n-bromosuccinimide and azoisobutyronitrile in chloroform, the side gem-dibromo derivative formed during the reaction is cleaved by treating the crude mixture with diethyl phosphite and DIPEA in THF (see for example, Wulff, J, Diss. Abstr. Int., B 2005, 2004, 65(12), 6399). In step b, cyanation is done using classical conditions, potassium cyanide in methanol. In step c, nitrile is hydrolyzed with potassium hydroxide in methanol/water at 100° C. In step d, the di-acid is reduced using borane in THF. In steps e and f, cyclisation and oxidation are done using conditions described in scheme XIII steps b and c respectively.

In scheme XVII, step a, the Wittig alkene formation is done using classical conditions, triethyl phosphonoacetate, potassium carbonate and 1,8-diazabicyclo(5.4.0)undec-7-ene. In step b, reduction of the double bond is performed using benzene sulfonyl hydrazide in toluene. In step c, saponification is done with lithium hydroxide in THF/water. In step d, the alcohol is obtained using borane as reducing agent in THF. In steps e and f cyclisation and oxidation are done using conditions described in scheme XIII steps b and c respectively.

Scheme XVI

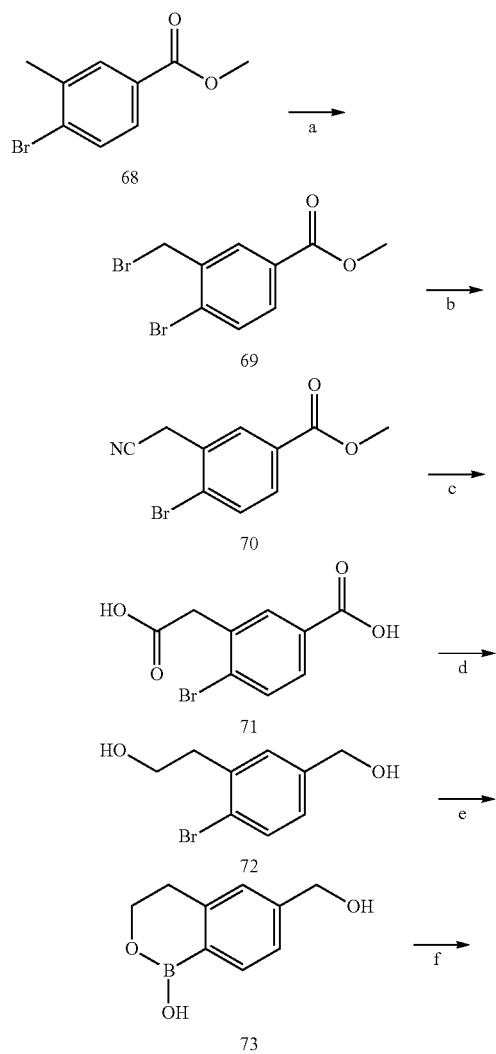

Scheme XVII

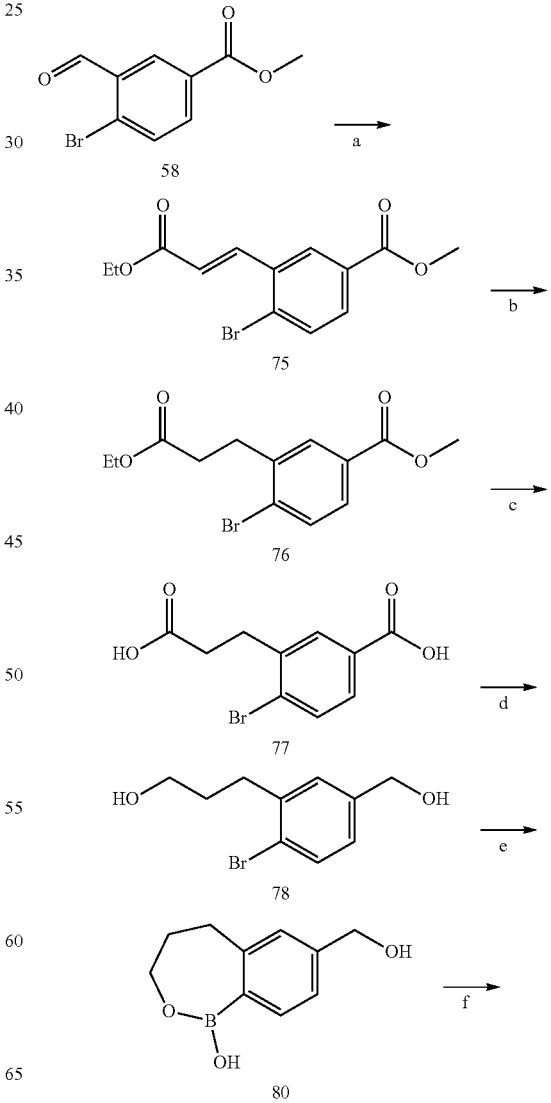

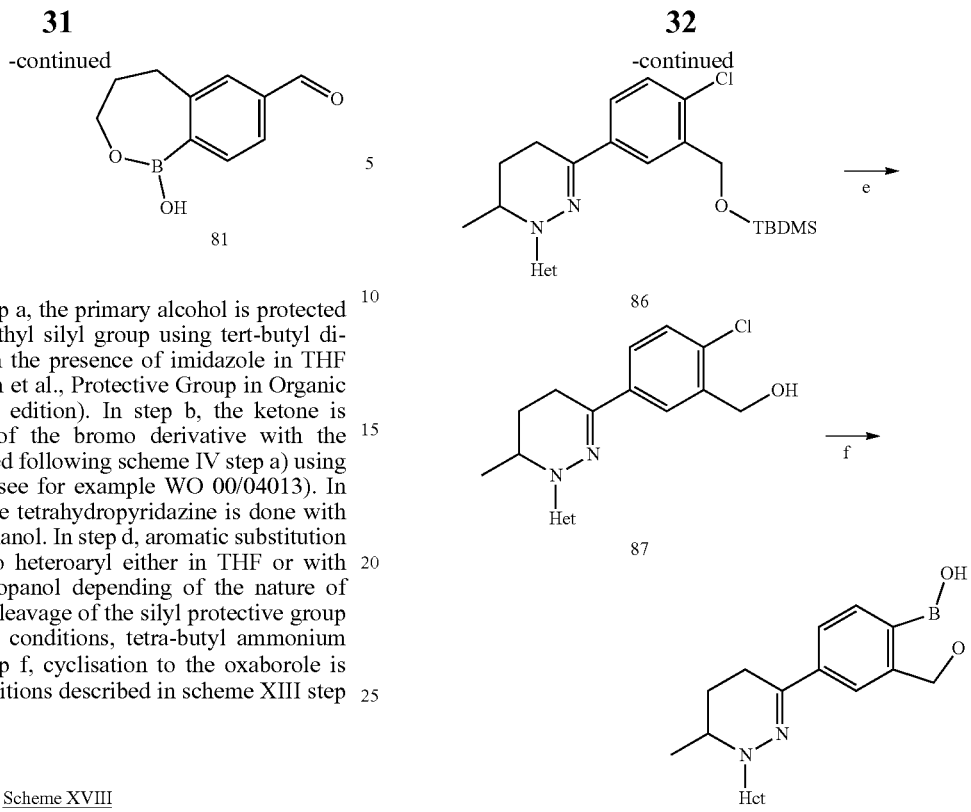

In scheme XVIII, step a, the primary alcohol is protected with a tert-butyl di-methyl silyl group using tert-butyl di-methyl silyl chloride in the presence of imidazole in THF (see for example, Green et al., Protective Group in Organic Synthesis, Wiley, third edition). In step b, the ketone is obtained by reaction of the bromo derivative with the Weinreb amide (prepared following scheme IV step a) using butyl lithium in THE (see for example WO 00/04013). In step c, cyclisation to the tetrahydropyridazine is done with hydrazine hydrate in ethanol. In step d, aromatic substitution is done using halogeno heteroaryl either in THF or with copper iodide in isopropanol depending of the nature of heterocycle. In step e, cleavage of the silyl protective group is done using classical conditions, tetra-butyl ammonium fluoride in THF. In step f, cyclisation to the oxaborole is obtained using the conditions described in scheme XIII step b.

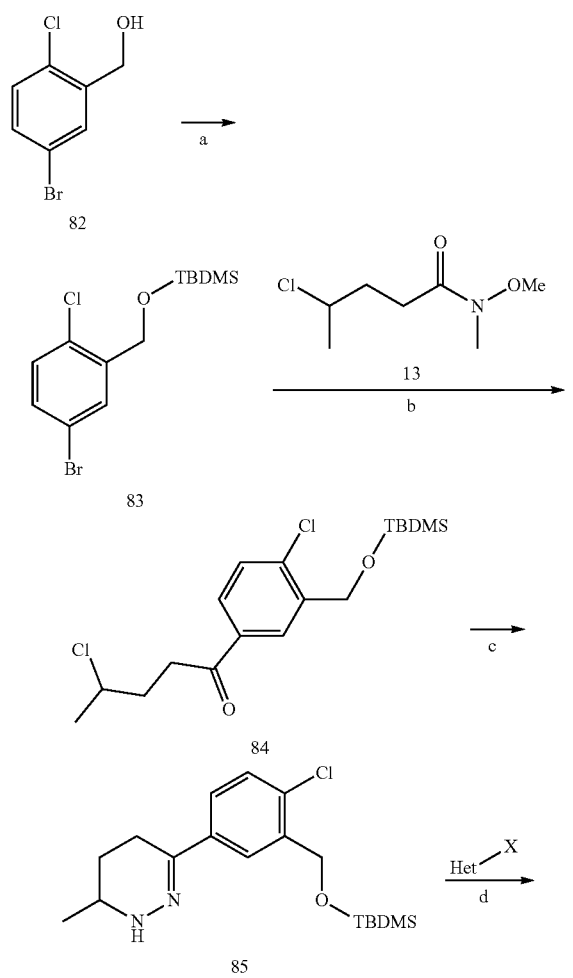

In scheme XIX, step a, boronic acid is di-alkylated with diol reagents in toluene (see for example, Li et al., Org. Proc. Res. Dev., 2016, 20(8), 1489-1499; Dastbaravardeh et al., Org. Lett., 2012, 14(7), 1930-1933) or di-acylated with di-acid reagents in toluene and/or dimethylsulfoxide in the presence or not of a dehydrating agent such as magnesium sulfate (see for example WO 2014/028384).

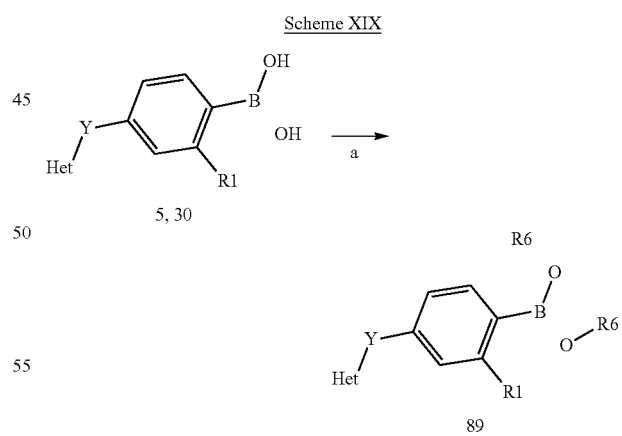

In scheme XX, step a, alkylation of the phenol is done with a halogeno alkyl in the presence of cesium carbonate as base in DMF. In step b, reduction to the alcohol is obtained with Dibal-H in dichloromethane. In step c, oxidation to the aldehyde is done with TEMPO and iodobenzene diacetate in dichloromethane. Steps d, e, f are performed following the conditions described in the scheme III steps a, b and c respectively. Step g is done using conditions described in scheme I step b. In step h, aromatic substitution of the bromo derivative with bis pinacolborane is done following conditions described in scheme VIII step a. In step i, the pinacol borane analog is hydrolyzed in acidic medium with hydrogen chloride in acetonitrile.

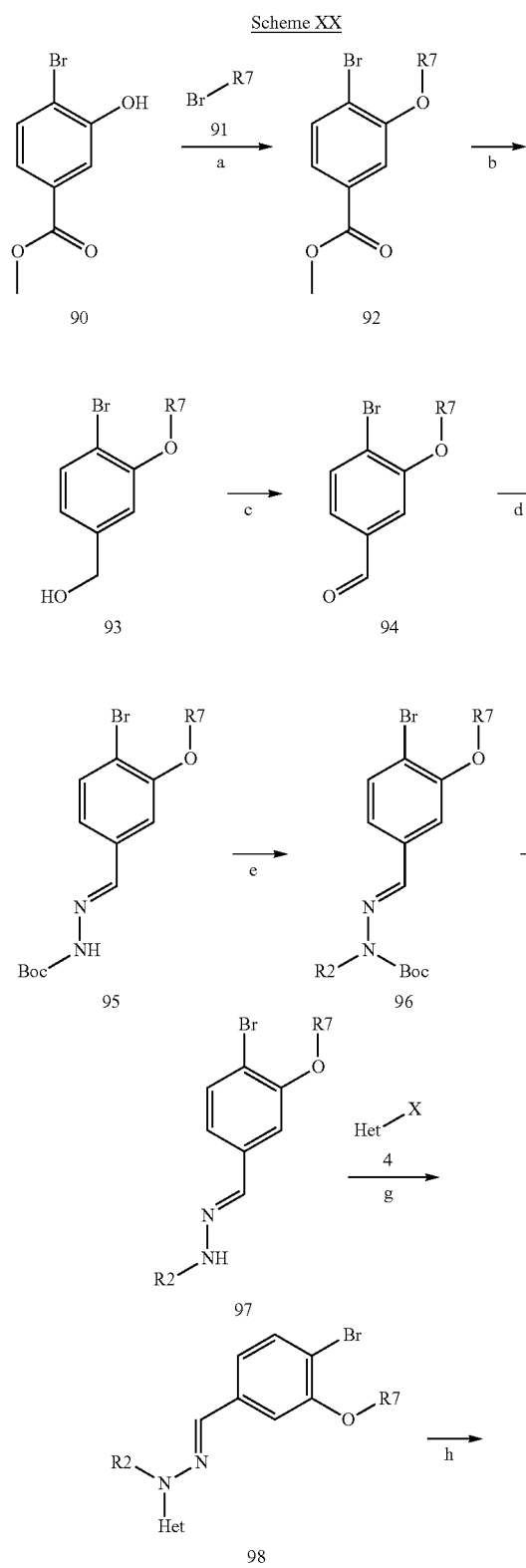

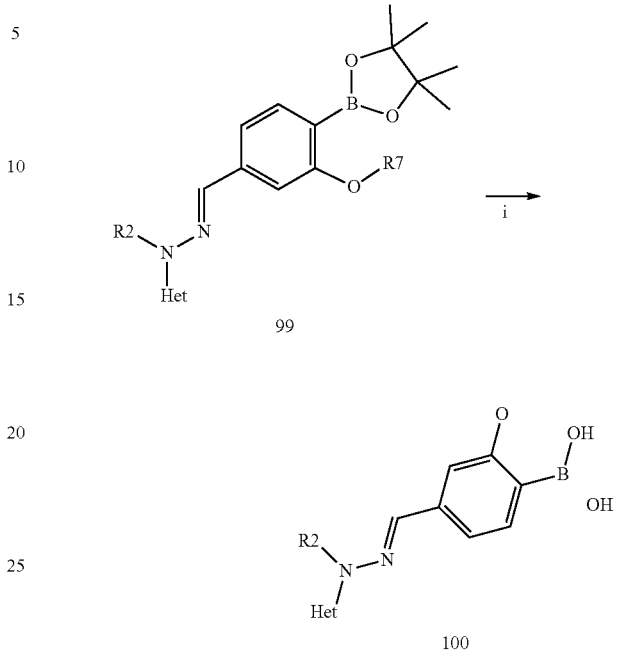

In scheme XXI, step a, formation of the boronic acid is done using the conditions described in scheme XIII step b. In step b, cleavage of the silyl protective group is done with hydrochloric acid in dioxane (see for example Green et al., Protective Group in Organic Synthesis, Wiley, third edition) giving directly the benzoxaborole. In step c, the aromatic substitution is obtained using the conditions described in scheme XVII step d.

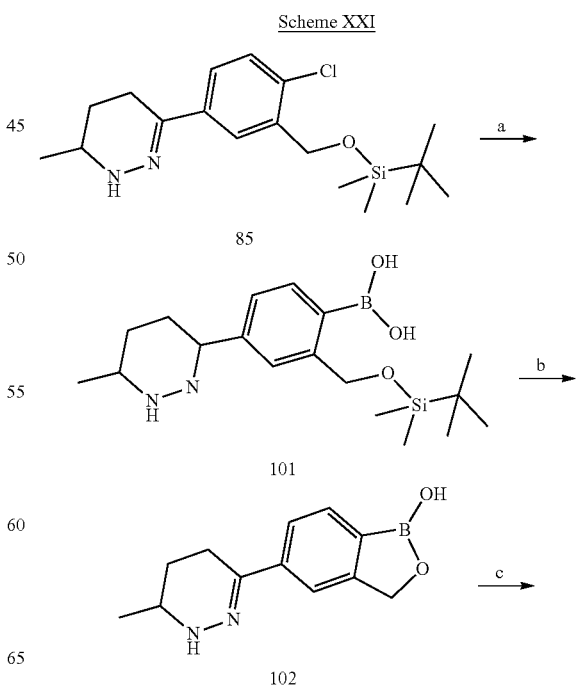

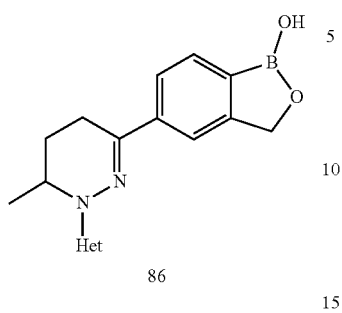

86

In Scheme XXII, step a, the commercially available thienopyrimidine derivative is saponified with lithium hydroxide in THF. The hydrazono derivative is obtained using the conditions described in scheme I or II. In Step b, the amide formation is done using classical coupling agents (such as o-(7-azabenzotriazol-1-yl)-N,N,N',N'-tetramethyl-uronium hexafluoro-phosphate, 1-hydroxy-7-azabenzotriazole, dicyclohexyl carbodiimide, 1-ethyl-3-(3-dimethylaminopropyl)carbodiimide, or 1-hydroxy benzotriazole).

Scheme XXII

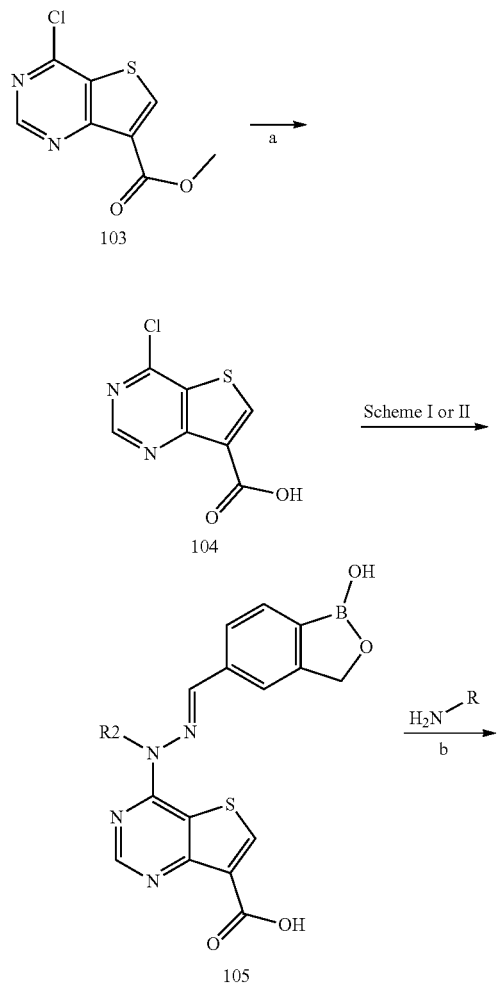

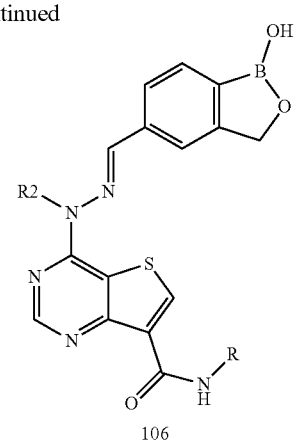

106

In scheme XXIII, step a, the methylthio derivative is obtained by reaction with sodium methanethiolate in THF (see for example WO 2004/013141). In step b, the R group (in case of C—C bond formation) is introduced via a Suzuki reaction (see for example WO 2009/062258) or by photochemistry with a trifluoroborate derivative in the presence of nickel and iridium (see for example, Karakaya et al., Org. Lett. 2015, 17, 3294). In case of C—N bond formation, the amino group is introduce using classical coupling conditions with either palladium or copper catalysts (see for example WO 2016/109559, WO 2013/078126), In step c, chlorination is done using sulfurylchloride in dichloromethane.

Scheme XXIII

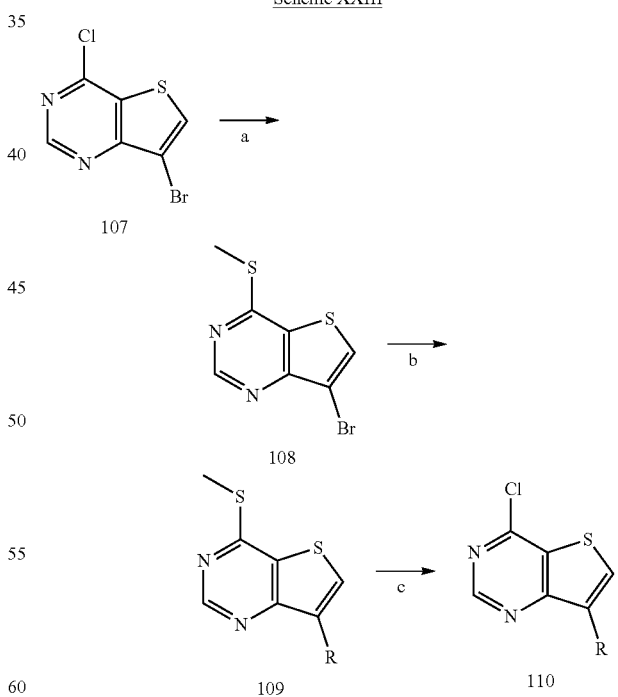

In scheme XXIV, step a, the formation of the heterocycle is done with formamidine acetate in ethanol (see for example Berg et al., Chem Med Chem, 2009, 4(2), 249-260). In step b, chlorination is done using the conditions describe in Scheme XI step e.

Scheme XXIV

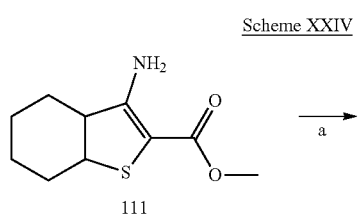

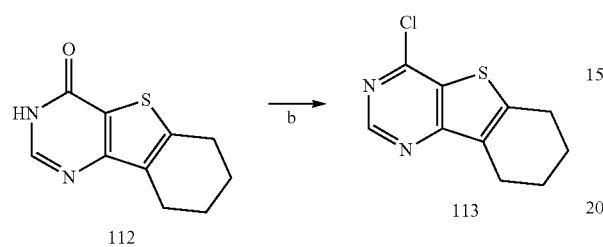

In scheme XXV, step a, pyrrolo-pyrimidine derivatives and/or tetrahydro forms are alkylated using alkylating reagents (such as halogeno or sulfate derivatives) in the presence of a base (such as cesium carbonate, sodium carbonate, sodium hydroxide) in DMF.

Scheme XXV

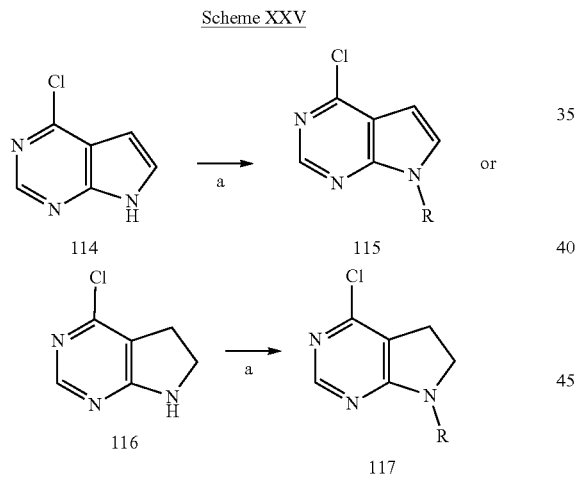

In scheme XXVI, step a, aromatic substitution is done with a primary amine in the presence of a base (such as triethylamine, sodium hydrogeno carbonate) in ethanol. In step b, cyclisation is done using carbonyl di-imidazole in THF (see for example WO 2011/157397).

Scheme XXVI

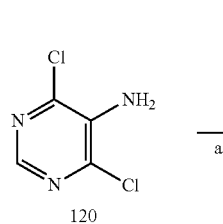

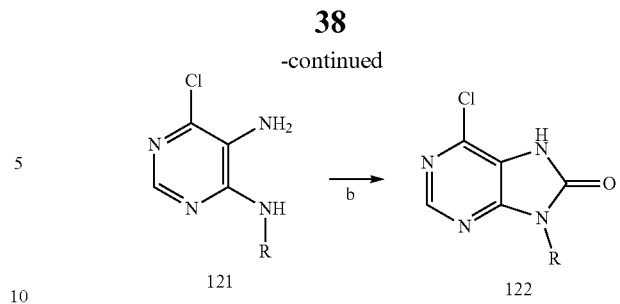

In scheme XXVII, step a, aromatic substitution and cyclic aminolysis are done in one step by reacting a primary amine in the presence of a base (such as di-isopropyl ethyl amine) in DMF or acetonitrile (see for example, Vaid et al., Synthesis, 2012, 44(15), 2396-2400)

Scheme XXVII

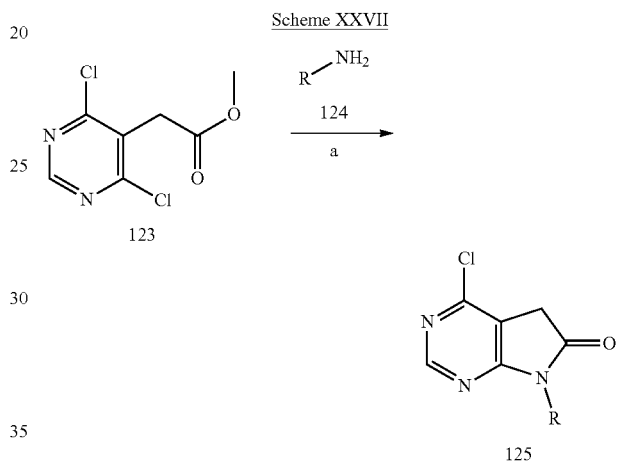

Abbreviations

Ac=Acetyl; AcOH=Acetic acid; ACN=Acetonitrile; Bn=Benzyl; Boc=t-Butoxycarbonyl; Boc$_2$O=Di-tert-butyl-dicarbonate; BSA=Bovine serum albumin; Bt=Benzotriazolyl; n-BuLi=n-Butyllithium; s-BuLi=sec-Butyllithium; t-BuLi=tert-Butyllithium; Bu$_4$NBr=tetrabutyl ammonium bromide; CaCl$_2$=Calcium chloride; CDCl$_3$=Chloroform deutered; CDI=Carbonyl diimidazole; Cs$_2$CO$_3$=Cesium carbonate; d=Doublet; dba=Dibenzylidene acetone; DCC=Dicyclohexylcarbodiimide; DCE=Dichlororethane; DCM=Dichloro-methane; D$_2$O=water deutered; dd=Doublet of doublets; DEAD=Diethyl azodicarboxylate; DIAD=Diisopropyl azodicarboxylate; DIBAL=Diisobutylaluminum hydride; DIPEA=Diisopropylethylamine; DMF=N,N-Dimethylformamide; DMSO=Dimethylsulfoxide; dppf=1,1'-bis(diphenyl-phosphino)ferrocene; EDCl=1-ethyl-3-(3-dimethyl aminopropyle) carbodiimide hydrochloride; eq=Equivalent(s); EtOAc=Ethyl acetate; Et$_2$O=Ether; EtOH=Ethanol; g=Gram(s); h=Hour(s); HATU=O-(7-azabenzotriazol-1-yl)-N,N,N',N'-tetramathyluroniom hexafluorophosphate; HCl=Hydrochloric acid; Hz=Hertz; HOAt=1-hydroxy-7-azabenzotriazole; HCOOH=formic acid; HOBt=Hydroxybenzo triazole; HMDS=1,1,1,3,3,3-hexamethyldisilazane; KF=Potassium fluoride; K$_2$CO$_3$=Potassium carbonate; KOH=potassium hydroxide; LC/MS=Liquid chromatography/mass spectrometry; LDA=Lithium diisopropylamide; LiAlH$_4$=Lithium aluminium hydride; LiHMDS=Lithium bis(trimethylsilyl)amide; m=Multiplet; min=Minute; MeOH=Methanol; mg=Milligram; MgSO$_4$=Magnesium sulfate; min=Minute(s); mmol=Millimole; mp=Melting point; MW=Microwave; N=Normal; NaCl=Sodium chloride; NaH=Sodium hydride; NaHCO$_3$=Sodium bicarbonate; NaBH$_3$CN=Sodium cyanoborohydride; Na$_2$CO$_3$=Sodium carbonate; NaOH=Sodium hydroxide; Na$_2$SO$_4$=Sodium sulfate; NBS=N-bromosuccinimide; NH$_3$=Ammonia; NH$_4$Cl=Ammonium chloride; NMM=N-methyl morpholine; NMP=M-methylpyrrolidone; NMR=Nuclear magnetic resonance; PBS=Phosphate buffered saline; PCC=Pyridinium chlorochromate; PDC=Pyridinium dichromate; Pd/C=Palladium on carbon; PdCl$_2$(dppf)=Dichloro [1,1'-bis(diphenyl phosphino) ferrocene] palladium (II); Pd$_2$(dba)$_3$=Bis(dibenzylideneacetone) palladium(0); Pd(OAc)$_2$=Palladium (II) acetate; Pd(PPh$_3$)$_4$=Tetrakis(triphenylphosphine)palladium (0); Ph=Phenyl; ppm=Parts per million; PPTS=Pyridinium p-toluenesulfonate; PrOH=Propanol; PSI=Pounds per square inch; q=Quadruplet; quant=Quantitative; quint=Quintuplet; Rt=Retention time; rt=Room temperature; s=singlet; sept=septuplet; sext sextuplet; SiO$_2$=Silica; SnCl2 tin chloride; t=triplet; TBAF=Tetrabutyl ammonium fluoride; TBDMS=t-butyldimethylsilyl; TEA=Triethylamine; TEMPO=2,2,6,6-tetramethyl-1-piperidinyloxy free radical; TFA=Trifluoroacetic acid; THF=Tetrahydrofuran; TMEDA=N, N, N', N'-tetramethyl ethylene diamine.

General

Reagents and solvents obtained from commercial suppliers are used without further purification unless otherwise stated. Analytical data is included within the procedures below. $^1$H NMR spectra were recorded on a Bruker Advance spectrometer. Chemical shifts are reported in ppm (t) and were calibrated using the undeuterated solvent resonance as internal standard. Melting points were determined on a hotstage apparatus and are uncorrected.

Analytical Methods

| Method | Description |
|---|---|
| A | Column: KINETEX XB-C18 core-shell (Dimensions: 30 × 3 mm, 2.6 μm)<br>Column temperature: 45° C.<br>Mobile Phase: A1: Water (0.1% v/v AcOH) B1: MeCN (0.1% v/v AcOH)<br>Gradient: from 10% to 100% B1 within 3.15 min<br>Flow rate: 1.4 ml/min, UV detection: DAD 210-260 nm, MS detection: ESI positive |
| B | Column: KINETEX EVO C18 (Dimensions: 50 × 4.6 mm, 5 μm)<br>Column temperature: 25° C.<br>Mobile Phase: A2: MeCN:H$_2$O = 5:95 with 20 mM NH$_4$HCO$_2$ buffer, pH = 7.4,<br>B2: MeCN:H$_2$O = 80:20 with 20 mM NH$_4$HCO$_2$ buffer, pH =7.4<br>Gradient from 5% to 100% B2 within 4.50 min<br>Flow rate: 1.3 ml/min, UV detection: DAD 220-254 nm, MS detection: APCI positive |
| C | Column: KINETEX EVO C18 (Dimensions: 50 × 4.6 mm, 5 μm)<br>Column temperature: 25° C.<br>Mobile Phase: A1: Water (0.05% v/v TFA), B1: MeCN (0.05% v/v TFA)<br>Gradient: from 5% to 100% B1 within 4.50 min<br>Flow rate: 1.3 ml/min, UV detection: DAD 220-254 nm, MS detection: APCI positive |
| D | Column: KINETEX EVO C18 (Dimensions: 50 × 4.6 mm, 5 μm)<br>Column temperature: 25° C.<br>Mobile Phase: A2: MeCN:H$_2$O = 5:95 with 20 mM NH$_4$HCO$_2$ buffer, pH = 7,<br>B2: MeCN:H$_2$O = 80:20 with 20 mM NH$_4$HCO$_2$ buffer, pH =7.4<br>Gradient: from 30% to 100% B2 within 4.50 min<br>Flow rate: 1.3 ml/min, UV detection: DAD 220-254 nm, MS detection: APCI positive |
| E | Column: KINETEX EVO C18 (Dimensions: 50 × 4.6 mm, 5 μm)<br>Column temperature: 35° C.<br>Mobile Phase: A2: MeCN:H$_2$O =5:95 with 20 mM NH$_4$HCO$_2$ buffer, pH =7.4,<br>B2: MeCN:H$_2$O = 80:20 with 20 mM NH$_4$HCO$_2$ buffer, pH = 7.4<br>Gradient: from 5% to 100% B2 within 4.00 min<br>Flow rate: 1.3 ml/min, UV detection: DAD 220 nm, MS detection: APCI positive |
| F | Column: ACQUITY UPLC BEH C18 (Dimensions: 50 × 2.1 mm x 1.7 μm)<br>Column temperature: 45° C.<br>Mobile phase: A1: Water (0.1% v/v AcOH), B1: ACN (0.1 v/v AcOH)<br>Gradient: from 5 to 95% B1 within 2.49 min<br>Flow rate: 0.8 mL/min, UV detection: DAD210-260 nm, MS detection: ESI positive |
| G | Column: X bridge C18 (Dimensions: 50 × 2.1 mm x 2.6 μm)<br>Column temperature: 45° C.<br>Mobile phase: A1: Water (0.1% v/v AcOH, B1: ACN (0.1 v/v AcOH)<br>Gradient: from 10 to 100% B1 within 2.80 min<br>Flow rate: 0.8 mL/min, UV detection: DAD210-260 nm, MS detection: ESI positive |
| H | Column: X bridge C18 (Dimensions: 50 × 2.1 mm x 3.5 μm)<br>Column temperature: 45° C.<br>Mobile phase: A1: Water (0.1% v/v AcOH, B1: ACN (0.1 v/v AcOH)<br>Gradient: from 40 to 100% B1 within 3.00 min<br>Flow rate: 1.4 mL/min UV detection: DAD210-260 nm MS detection: ESI positive |

Example 1: [4-[(E)-[(1,1-dioxo-1,2-benzothiazol-3-yl)-isobutyl-hydrazono]methyl]-2-methoxy-phenyl] boronic acid Step A: 3-chloro-1,2-benzothiazole 1,1-dioxide A mixture of saccharin (70.00 g; 382.13 mmol; 1.00 eq.), thionyl chloride (41.58 mL; 573.19 mmol; 1.50 eq.) and a catalytic amount of DMF (2.10 mL) in 1,4-dioxane (350 mL) was heated for 24 h under reflux. The reaction mixture was concentrated, co-evaporated 4 times with toluene (200 mL) and dried to give 3-chloro-1,2-benzothiazole 1,1-dioxide (77.00 g; 99%), used without purification. $^1$H NMR (DMSO-d6, 300 MHz): δ 8.19 (dd, J=1.0 Hz, J=7.0 Hz, 1H); 7.99 (m, 3H).

Step B: [4-[(E)-(isobutylhydrazono)methyl]-2-methoxy-phenyl]boronic acid

To a solution of 4-formyl-2-methoxyphenylboronic acid (5.00 g; 27.80 mmol; 1.00 eq.) in EtOH (85 mL) was added 2-methylpropylhydrazine hydrochloride (4.15 g; 33.30 mmol; 1.20 eq.). The solution was stirred at rt until completion. The mixture was poured onto water and the resulting precipitate was filtered, washed with water then diisopropyl ether and dried to give [4-[(E)-(isobutylhydrazono)methyl]-2-methoxy-phenyl]boronic acid (5.40 g; 78%) as a white solid. $^1$H NMR (DMSO-d6, 300 MHz): δ 7.58 (s, 2H); 7.50 (m, 3H); 7.08 (s, 1H); 7.00 (d, J=7.5 Hz, 1H); 3.81 (s, 3H); 2.94 (t, J=5.9 Hz, 2H); 1.85 (m, 1H); 0.93 (d, J=6.5 Hz, 6H).

Step C: [4-[(E)-[(1,1-dioxo-1,2-benzothiazol-3-yl)-isobutyl-hydrazono]methyl]-2-methoxy-phenyl]boronic acid 3-chloro-1,2-benzothiazole 1,1-dioxide (6.10 g; 30.30 mmol; 1.4 eq.; purity ~85%) was added to a solution of [4-[(E)-(isobutylhydrazono)methyl]-2-methoxy-phenyl]boronic acid (5.40 g; 21.70 mmol; 1.0 equiv) in THF (50 mL) and the mixture was stirred under reflux until completion. Then, it was poured onto water and the resulting precipitate was triturated in MeOH, filtered, washed with MeCN and dried to give [4-[(E)-[(1,1-dioxo-1,2-benzothiazol-3-yl)-isobutyl-hydrazono]methyl]-2-methoxy-phenyl]boronic acid (5.70 g; 63%) as a white solid. $^1$H NMR (DMSO-d6, 300 MHz): δ 8.86 (dd, J=7.7 Hz, J=1.6 Hz, 1H); 8.55 (s, 1H); 8.10 (d, J=6.7 Hz, J=1.6 Hz, 1H); 7.89 (m, 4H); 7.70 (d, J=7.7 Hz, 1H); 7.47 (m, 2H); 4.29 (d, J=7.7H, 2H); 3.93 (s, 3H); 2.28 (m, 1H); 0.99 (d, J=6.7 Hz, 6H).

Example 2: [4-[(E)-[isobutyl-(5-methoxy-1,1-dioxo-1,2-benzothiazol-3-yl)hydrazono]methyl]-2-methoxy-phenyl]boronic acid

Step A: 3-chloro-5-methoxy-1,2-benzothiazole 1,1-dioxide

The compound was prepared using the same procedure detailed in example 1 step A starting from 5 methoxy-1,1-dioxo-1,2-benzothiazol-3-one (1.00 g; 4.69 mmol; 1.00 eq.) giving 3-chloro-5-methoxy-1,2-benzothiazole 1,1-dioxide (1.08 g; 99%) as a pale yellow solid. $^1$H NMR (DMSO-d6, 300 MHz): δ 8.09 (dd, J=0.5 Hz, J=8.4 Hz, 1H); 7.49 (dd, J=2.5 Hz, J=8.4 Hz, 1H); 7.46 (m, 3H); 3.94 (s, 3H).

Step B: [4-[(E)-[isobutyl-(5-methoxy-1,1-dioxo-1,2-benzothiazol-3-yl)hydrazono]methyl]-2-methoxy-phenyl]boronic acid The compound was prepared using the same procedure detailed in example 1 step C starting from 3-chloro-5-methoxy-1,2-benzothiazole 1,1-dioxide (108.0 mg; 0.47 mmol; 1.17 eq.) and [4-[(E)-(isobutylhydrazono)methyl]-2-methoxy-phenyl]boronic acid (example 1, step B), (100.0 mg; 0.40 mmol; 1.00 eq.) giving [4-[(E)-[isobutyl-(5-methoxy-1,1-dioxo-1,2-benzothiazol-3-yl)hydrazono]methyl]-2-methoxy-phenyl]boronic acid (59.0 mg; 33%) as a white solid. $^1$H NMR (DMSO-d6, 400 MHz): δ 8.54 (s, 1H); 8.40 (d, J=2.2 Hz, 1H); 8.02 (d, J=8.6 Hz, 1H); 7.87 (s, 2H); 7.66 (d, J=7.9 Hz, 1H); 7.46 (m, 2H); 7.42 (dd, J=2.4 Hz, J=8.6 Hz, 1H); 4.26 (d, J=7.9 Hz, 2H); 3.92 (s, 3H); 3.91 (s, 3H); 2.28 (m, 1H); 0.99 (d, J=6.8 Hz, 6H). mp: 235° C.

Example 3: [4-[(E)-[(5,7-dimethoxy-1,1-dioxo-1,2-benzothiazol-3-yl)-isobutyl-hydrazono] methyl]-2-methoxy-phenyl]boronic acid

Step A: 3-chloro-5,7-dimethoxy-1,2-benzothiazole 1,1-dioxide

The compound was prepared using the same procedure detailed in example 1 step A starting from 5,7-dimethoxy-1,1-dioxo-1,2-benzothiazol-3-one (9.00 g; 37.00 mmol; 1.00 eq.) giving crude 3-chloro-5,7-methoxy-1,2-benzothiazole 1,1-dioxide (9.68 g; 99%) as a beige solid, used in the next step without purification.

Step B: [4-[(E)-[(5,7-dimethoxy-1,1-dioxo-1,2-benzothiazol-3-yl)-isobutyl-hydrazono]methyl]-2-methoxy-phenyl]boronic acid 4-formyl-2-methoxyphenylboronic acid (7.66 g; 42.55 mmol; 1.15 eq.) was dissolved into THF (150 mL) and 2-methylpropylhydrazine hydrochloride (5.30 g; 42.55 mmol; 1.15 eq.) was added. The reaction mixture was stirred at rt until complete formation of the hydrazone intermediate. Then, a solution of 3-chloro-5,7-dimethoxy-1,2-benzothiazole 1,1-dioxide (9.68 g; 37.00 mmol; 1.00 eq.) in THF (200 mL) was added and the mixture was stirred under reflux until completion. After being cooled to rt, insolubles were filtered and washed twice with THF. The filtrate was concentrated to dryness and the obtained residue triturated in EtOH until cleaned precipitation occurred. The precipitate was filtered and washed successively by EtOH (3×) and water (3×). The obtained solid was suspended into DMF, sonicated during 20 minutes, filtered and washed by DMF. This process was performed until purity was good enough, after which the solid was dried under vacuum to give [4-[(E)-[(5,7-dimethoxy-1,1-dioxo-1,2-benzothiazol-3-yl)-isobutyl-hydrazono]methyl]-2-methoxy-phenyl]boronic acid (2.85 g; 16%) as a white solid. $^1$H NMR (DMSO-d6, 400 MHz): δ 8.49 (s, 1H); 7.97 (d, J=2.0 Hz, 1H); 7.86 (s, 2H); 7.65 (d, J=7.7 Hz, 1H); 7.44 (m, 2H); 7.02 (d, J=2.0 Hz, 1H); 4.23 (d, J=7.7 Hz, 2H); 4.00 (s, 3H); 3.93 (s, 3H); 3.91 (s, 3H); 2.25 (m, 1H); 0.97 (d, J=6.6 Hz, 6H). mp: 262° C.

Example 4: [4-[(E)-[(1,1-dioxo-1,2-benzothiazol-3-yl)-ethyl-hydrazono]methyl]-2-methoxy-phenyl] boronic acid

Step A: [4-[(E)-(ethylhydrazono)methyl]-2-methoxy-phenyl]boronic acid

Sodium acetate (83.9 mg; 1.02 mmol; 1.15 eq.) and ethylhydrazine hydrochloride (94.4 mg; 0.98 mmol; 1.10 eq.) were added to a solution of 4-formyl-2-methoxyphenylboronic acid (160.0 mg; 0.89 mmol; 1.00 eq.) in ethanol (4 mL). The mixture was heated 15 min at 80° C. under microwave irradiation. Additional ethylhydrazine hydrochloride (18.0 mg; 0.19 mmol; 0.20 eq.) was added and the reaction was heated again at 80° C. 15 min under microwave irradiation. Then, the mixture was filtered and the solid washed once with EtOH. The filtrate was concentrated to dryness to give crude [4-[(E)-(ethylhydrazono)methyl]-2-methoxy-phenyl]boronic acid (197.0 mg; 99%) as an orange syrup, used in the next step without purification. LC-MS (Method A): Rt=1.29 min; MS: m/z=223 [M+H]$^+$

Step B: [4-[(E)-[(1,1-dioxo-1,2-benzothiazol-3-yl)-ethyl-hydrazono]methyl]-2-methoxy-phenyl] boronic acid The compound was prepared using the same procedure detailed in example 1 step C starting from 3-chloro-1,2-benzothiazole 1,1-dioxide (example 1, step A), (127.0 mg; 0.63 mmol; 1.00 eq.) and [4-[(E)-(ethylhydrazono)methyl]-2-methoxy-phenyl]boronic acid (139.9 mg; 0.63 mmol; 1.00 eq.) giving [4-[(E)-[(1,1-dioxo-1,2-benzothiazol-3-yl)-ethyl-hydrazono]methyl]-2-methoxy-phenyl] boronic acid (160.0 mg; 65%) as a beige solid. $^1$H NMR (DMSO-d6, 400 MHz): δ 8.85 (d, J=7.7 Hz, 1H); 8.55 (s, 1H); 8.10 (d, J=7.3 Hz, 1H); 7.92 (m, 2H); 7.86 (s, 2H); 7.70 (d, J=7.7 Hz, 1H); 7.47 (m, 2H); 4.42 (q, J=7.0 Hz, 2H); 3.92 (s, 3H); 1.31 (t, J=6.9 Hz, 3H). mp: 197-199° C.

Example 5: [4-[(E)-[(1,1-dioxo-1,2-benzothiazol-3-yl)-(2-methoxyethyl)-hydrazono]methyl]-2-methoxy-phenyl]boronic acid

Step A: [2-methoxy-4-[(E)-(2-methoxyethylhydrazono)methyl]phenyl]boronic acid The compound was prepared using the same procedure detailed in example 4 step A starting from 4-formyl-2-methoxyphenylboronic acid (5.00 g; 27.78 mmol; 1.00 eq.) and (2-methoxyethyl) hydrazine hydrochloride (3.52 g; 27.78 mmol; 1.00 eq.) giving crude [2-methoxy-4-[(E)-(2-methoxyethylhydrazono)methyl]phenyl]boronic acid (7.00 g; 99%), used in the next step without purification. LC-MS (Method A): Rt=1.22 min; MS: m/z=253 [M+H]$^+$

Step B: [4-[(E)-[(1,1-dioxo-1,2-benzothiazol-3-yl)-(2-methoxyethyl)hydrazono]methyl]-2-methoxy-phenyl]boronic acid The compound was prepared using the same procedure detailed in example 1 step C starting from 3-chloro-1,2-benzothiazole 1,1-dioxide (example 1, step A), (5.60 g; 27.78 mmol; 1.00 eq.) and [2-methoxy-4-[(E)-(2-methoxy-ethylhydrazono)methyl]phenyl]boronic acid (7.00 g; 27.78 mmol; 1.00 eq.) giving [4-[(E)-[(1,1-dioxo-1,2-benzothiazol-3-yl)-(2-methoxyethyl)hydrazono] methyl]-2-methoxy-phenyl]boronic acid (5.66 g; 49%) as a beige solid. $^1$H NMR (DMSO-d6, 400 MHz): δ 8.84 (m, 1H); 8.60 (s, 1H); 8.10 (m, 1H); 7.86 (m, 4H); 7.70 (d, J=7.7 Hz, 1H); 7.43 (m, 2H); 4.59 (t, J=5.5 Hz, 2H); 3.93 (s, 3H); 3.74 (t, J=5.6 Hz, 2H); 3.31 (s, 3H). mp: 240° C.

Example 6: [2-chloro-4-[(E)-[(1,1-dioxo-1,2-benzothiazol-3-yl)-isobutyl-hydrazono]methyl] phenyl] boronic acid

Step A: [2-chloro-4-[(E)-(isobutylhydrazono) methyl]phenyl]boronic acid

The compound was prepared using the same procedure detailed in example 4 step A starting from (2-chloro-4-formylphenyl)boronic acid (200.0 mg; 1.08 mmol; 1.00 eq.) and 2-methylpropyl hydrazine hydrochloride (135.2 mg; 1.08 mmol; 1.00 eq.) giving crude [2-chloro-4-[(E)-(isobutylhydrazono)methyl]phenyl]boronic acid (300.0 mg; quantitative) as a yellow oil, used in the next step without purification. LC-MS (Method A): Rt=1.79 min; MS: m/z=255 [M+H]$^+$

Step B: [2-chloro-4-[(E)-[(1,1-dioxo-1,2-benzothiazol-3-yl)-isobutyl-hydrazono]methyl]phenyl] boronic acid The compound was prepared using the same procedure detailed in example 1 step C starting from 3-chloro-1,2-benzothiazole 1,1-dioxide (example 1, step A), (173.4 mg; 0.86 mmol; 1.00 eq.) and [2-chloro-4-[(E)-(isobutylhydrazono)methyl]phenyl]boronic acid (218.9 mg; 0.86 mmol; 1.00 eq.) giving [2-chloro-4-[(E)-[(1,1-dioxo-1,2-benzothiazol-3-yl)-isobutyl-hydrazono]methyl]phenyl] boronic acid (296.0 mg; 82%) as a pale yellow solid. $^1$H NMR (DMSO-d6, 400 MHz): δ 8.77 (m, 1H); 8.55 (s, 1H); 8.44 (m, 2H); 8.10 (m, 1H); 7.92 (m, 2H); 7.83 (m, 2H); 7.61 (d, J=7.5 Hz, 1H); 4.27 (d, J=7.7 Hz, 2H); 2.27 (m, 1H); 0.98 (d, J=6.6 Hz, 6H). mp: 178-189° C.

Example 7: [4-[(E)-[isobutyl-(5-methyl-1,1-dioxo-1,2-benzothiazol-3-yl)hydrazono]-methyl]-2-methoxy-phenyl]boronic acid

Step A: 3-chloro-5-methyl-1,2-benzothiazole 1,1-dioxide

The compound was prepared using the same procedure detailed in example 1 step A starting from 5-methyl-1,1-dioxo-1,2-benzothiazol-3-one (115.0 mg; 0.58 mmol; 1.00 eq.) giving crude 3-chloro-5-methyl-1,2-benzothiazole 1,1-dioxide (125.0 mg; 99%), used in the next step without purification.

Step B: [4-[(E)-[isobutyl-(5-methyl-1,1-dioxo-1,2-benzothiazol-3-yl)hydrazono]methyl]-2-methoxy-phenyl]boronic acid The compound was prepared using the same procedure detailed in example 1 step C starting from 3-chloro-5-methyl-1,2-benzothiazole 1,1-dioxide (125.1 mg; 0.58 mmol; 1.00 eq.) and [4-[(E)-(isobutylhydrazono)methyl]-2-methoxy-phenyl]boronic acid (example 1, step B), (145.1 mg; 0.58 mmol; 1.00 eq.) giving [4-[(E)-[isobutyl-(5-methyl-1,1-dioxo-1,2-benzothiazol-3-yl)hydrazono] methyl]-2-methoxy-phenyl]boronic acid (18.0 mg; 7%) as a white solid. $^1$H NMR (DMSO-d6, 400 MHz): δ 8.70 (s, 1H); 8.54 (s, 1H); 7.97 (d, J=7.9 Hz, 1H); 7.87 (s, 2H); 7.71 (s, 1H); 7.70 (s, 1H); 7.46 (m, 2H); 4.29 (d, J=7.7 Hz, 2H); 3.94 (s, 3H); 2.52 (s, 3H); 2.27 (m, 1H); 0.98 (d, J=6.8 Hz, 6H).

Example 8: [4-[(E)-[(1,1-dioxo-1,2-benzothiazol-3-yl)-isobutyl-hydrazono]methyl-phenyl] boronic acid The compound was prepared using the same procedure detailed in example 3 step B starting from 3-chloro-1,2-benzothiazole 1,1-dioxide (example 1, step A), (224.0 mg; 1.11 mmol; 1.00 eq.), 2-methylpropylhydrazine hydrochloride (166.0 mg; 1.33 mmol; 1.20 eq.) and 4-formylphenyl-boronic acid (200.0 mg; 1.33 mmol; 1.20 eq.) giving [4-[(E)-[(1,1-dioxo-1,2-benzothiazol-3-yl)-isobutyl-hydrazono]methyl]phenyl]boronic acid (31.0 mg; 7%) as a white solid. $^1$H NMR (DMSO-d$_6$+10% v/v D$_2$O, 400 MHz): δ 8.88 (dd, J=1.1 Hz, J=6.8 Hz, 1H); 8.52 (s, 1H); 8.07 (m, 1H); 7.93 (m, 6H); 4.31 (d, J=7.7 Hz, 2H); 2.27 (m, 1H); 0.99 (d, J=6.6 Hz, 6H). mp: 313-343° C.

Example 9: [4-[(E)-[isobutyl-[5-(2-methoxyethoxy)-1,1-dioxo-1,2-benzothiazol-3-yl]hydrazono]methyl]-2-methoxy-phenyl]boronic acid Step A: 4-bromo-2-methyl-benzenesulfonamide Ammonia in MeOH (50.00 mL; 7.00 mol/L; 350.00 mmol; 5.00 V) was added dropwise to a solution of 4-bromo-2-methylbenzenesulfonyl chloride (10.00 g; 37.10 mmol; 1.00 eq.) in THF (80 mL) and the reaction was stirred 1 h at rt. The solid was filtered and washed twice with THF. The filtrate was concentrated to dryness and dried under vacuum to give 4-bromo-2-methyl-benzenesulfonamide (9.10 g; 98%) as a beige solid. $^1$H NMR (DMSO-$d_6$, 300 MHz): δ 7.76 (d, J=8.4 Hz, 1H); 7.64 (dd, J=0.7 Hz, J=1.8 Hz, 1H); 7.59 (ddd, J=0.5 Hz, J=2.1 Hz, J=8.4 Hz, 1H); 7.44 (m, 2H); 2.57 (s, 3H).

Step B: 5-bromo-2-sulfamoyl-benzoic acid

Potassium permanganate (14.37 g; 90.90 mmol; 2.50 eq.) was added to a suspension of 4-bromo-2-methyl-benzenesulfonamide (9.10 g; 36.38 mmol; 1.00 eq.) in 1.0 M aqueous NaOH (109 mL). The reaction was then stirred 2 h at 100° C. and cooled to rt. After filtration, the filtrate was acidified to pH 1 with conc. HCl and the solid formed was filtered, washed with water and dried under vacuum to give 5-bromo-2-sulfamoyl-benzoic acid (4.84 g; 63%) as a white solid. H NMR (DMSO-$d_6$, 300 MHz): δ 13.92 (br s, 1H); 7.93 (dd, J=2.0 Hz, J=8.3 Hz, 1H); 7.88 (m, 2H); 7.28 (s, 2H).

Step C: 5-bromo-1,1-dioxo-1,2-benzothiazol-3-one 5-bromo-2-sulfamoyl-benzoic acid (6.30 g; 22.49 mmol; 1.00 eq.) was dissolved in sulfuric acid (16 mL) and the reaction was stirred 1 h at rt. The reaction was then poured onto ice (250 mL) and the solid was filtered. It was washed with water (3×) and dried under vacuum to give 5-bromo-1,1-dioxo-1,2-benzothiazol-3-one (5.25 g; 89%) as a white solid. $^1$H NMR (DMSO-ds, 300 MHz): δ 8.13 (dd, J=1.8 Hz, J=8.1 Hz, 1H); 8.10 (dd, J=0.7 Hz, J=1.8 Hz, 1H); 8.07 (dd, J=0.7 Hz, J=8.1 Hz, 1H).

Step D: 5-bromo-3-chloro-1,2-benzothiazole 1,1-dioxide 5-bromo-1,1-dioxo-1,2-benzothiazol-3-one (2.50 g; 9.54 mmol; 1.00 eq.) was suspended into phosphorus(V) oxychloride (9.00 mL; 0.10 mol; 10.00 eq.) and the mixture was stirred 2 h under reflux. The reaction was then concentrated to dryness and co-evaporated 3 times with toluene to give 5-bromo-3-chloro-1,2-benzothiazole 1,1-dioxide (theor.=2.68 g), used in the next step without purification.

Step E: N-[(E)-(4-chloro-3-methoxy-phenyl)methyleneamino]-2-methyl-propan-1-amine The compound was prepared using the same procedure detailed in example 4 step A starting from 4-chloro-3-methoxybenzaldehyde (1.63 g; 9.56 mmol; 1.00 eq.) and 2-methylpropylhydrazine hydrochloride (1.19 g; 9.56 mmol; 1.00 eq.) giving crude N-[(E)-(4-chloro-3-methoxy-phenyl)methyleneamino]-2-methyl-propan-1-amine (theor.=2.30 g), used in the next step without purification. LC-MS (Method A): Rt=2.33 min; MS: m/z=241 [M+H]$^+$.

Step F: 5-bromo-N-[(E)-(4-chloro-3-methoxy-phenyl)methyleneamino]-N-isobutyl-1,1-dioxo-1,2-benzothiazol-3-amine The compound was prepared using the same procedure detailed in example 1 step C starting from 5-bromo-3-chloro-1,2-benzothiazole 1,1-dioxide (2.68 g; 9.54 mmol; 1.00 eq.) and N-[(E)-(4-chloro-3-methoxy-phenyl)methyleneamino]-2-methyl-propan-1-amine (2.30 g; 9.54 mmol; 1.00 eq.) giving 5-bromo-N-[(E)-(4-chloro-3-methoxy-phenyl)methyleneamino]-N-isobutyl-1,1-dioxo-1,2-benzothiazol-3-amine (1.90 g; 41%) as a pale yellow solid. $^1$H NMR (DMSO-d6, 300 MHz): δ 8.99 (d, J=1.5 Hz, 1H); 8.57 (s, 1H); 8.11 (dd, J=1.7 Hz, J=8.1 Hz, 1H); 8.08 (d, J=7.9 Hz, 1H); 7.64 (d, J=8.1 Hz, 1H); 7.60 (d, J=1.8 Hz, 1H); 7.44 (dd, J=1.7 Hz, J=8.2 Hz, 1H); 4.27 (d, J=7.8 Hz, 2H); 4.03 (s, 3H); 2.25 (m, 1H); 0.99 (d, J=6.8 Hz, 6H).

Step G: N-[(E)-(4-chloro-3-methoxy-phenyl)methyleneamino]-N-isobutyl-1,1-dioxo-5-(4,4,5,5-tetramethyl-1,3,2-dioxaborolan-2-yl)-1,2-benzothiazol-3-amine Bis(pinacolato)diboron (785.7 mg; 3.09 mmol; 1.00 eq.), potassium acetate (911.0 mg; 9.28 mmol; 3.00 eq.) and 1,1'-Bis(diphenylphosphino)ferrocene-palladium(II)dichloride dichloromethane complex (252.7 mg; 0431 mmol; 0.10 eq.) were added to a solution of 5-bromo-N-[(E)-(4-chloro-3-methoxy-phenyl)methyleneamino]-N-isobutyl-1,1-dioxo-1,2-benzothiazol-3-amine (1.50 g; 3.09 mmol; 1.00 eq.) in 1,4-dioxane (30 mL) under nitrogen atmosphere. The reaction was then stirred 1 h under reflux. The reaction was then cooled to rt and dioxane was removed. The residue was diluted with DCM and the organic phase was washed twice with water, dried over MgSO$_4$ and concentrated. The dark residue was purified by chromatography (30 to 50% EtOAc in cyclohexane) to give N-[(E)-(4-chloro-3-methoxy-phenyl)methyleneamino]-N-isobutyl-1,1-dioxo-5-(4,4,5,5-tetramethyl-1,3,2-dioxaborolan-2-yl)-1,2-benzothiazol-3-amine (1.40 g; 85%) as a beige solid. $^1$H NMR (DMSO-$d_6$, 300 MHz): δ 9.17 (s, 1H); 8.57 (s, 1H); 8.09 (m, 2H); 7.63 (m, 2H); 7.53 (d, J=8.1 Hz, 1H); 4.27 (d, J=7.8 Hz, 2H); 3.97 (s, 3H); 2.30 (m, 1H); 1.33 (s, 12H); 0.99 (d, J=6.6 Hz, 6H).

Step H: 3-[[(E)-(4-chloro-3-methoxy-phenyl)methyleneamino]-isobutyl-amino]-1,1-dioxo-1,2-benzothiazol-5-ol N-[(E)-(4-chloro-3-methoxy-phenyl)methyleneamino]-N-isobutyl-1,1-dioxo-5-(4,4,5,5-tetramethyl-1,3,2-dioxaborolan-2-yl)-1,2-benzothiazol-3-amine (700.0 mg; 1.32 mmol; 1.00 eq.) was suspended in THF (25 mL). Hydrogen peroxide (187 μL; 3.29 mmol; 2.50 eq.) and sodium hydroxide (1.97 mL; 1M in water; 1.97 mmol; 1.50 eq.) were added and the mixture was stirred 30 min at rt. The reaction was then acidified to pH 1 with 1N HCl and was concentrated to dryness. The residue was taken up into water and the resulting solid was filtered, washed with water and dried to give 3-[[(E)-(4-chloro-3-methoxy-phenyl)methyleneamino]-isobutyl-amino]-1,1-dioxo-1,2-benzothiazol-5-ol (500.0 mg; 90%) as a brown solid, used in next step without purification. $^1$H NMR (DMSO-$d_6$, 300 MHz): δ 10.89 (br s, 1H); 8.51 (s, 1H); 8.18 (d, J=2.1 Hz, 1H); 7.86 (d, J=8.4 Hz, 1H); 7.62 (m, 2H); 7.46 (dd, J=1.7 Hz, J=8.2

Hz, 1H); 7.19 (dd, J=2.2 Hz, J=8.3 Hz, 1H); 4.24 (d, J=7.6 Hz, 2H); 3.99 (s, 3H); 2.26 (m, 1H); 0.98 (d, J=6.8 Hz, 6H).

Step I: N-[(E)-(4-chloro-3-methoxy-phenyl)methyleneamino]-N-isobutyl-5-(2-methoxy ethoxy)-1,1-dioxo-1,2-benzothiazol-3-amine Cesium carbonate (231.7 mg; 0.71 mmol; 1.50 eq.) was added to a suspension of 3-[[(E)-(4-chloro-3-methoxy-phenyl)methyleneamino]-isobutyl-amino]-1,1-dioxo-1,2-benzothiazol-5-ol (200.0 mg; 0.47 mmol; 1.00 eq.) in DMF (1.00 mL) and the mixture was stirred 10 min at rt. Then, 2-bromoethylmethyl ether (90 μL; 0.95 mmol; 2.00 eq.) was added and the reaction was stirred 1 h at 50° C. The reaction was cooled to rt and water was added followed by EtOAc. The organic phase was recovered and the aqueous phase extracted with EtOAc once. The combined organic phases were washed with water and brine and then concentrated to dryness to give N-[(E)-(4-chloro-3-methoxy-phenyl)methyleneamino]-N-isobutyl-5-(2-methoxyethoxy)-1,1-dioxo-1,2-benzothiazol-3-amine (170.0 mg; 75%) as a beige solid. $^1$H NMR (300 MHz, DMSO-d6) δ 8.54 (s, 1H); 8.37 (d, J=2.3 Hz, 1H); 8.01 (d, J=8.6 Hz, 1H); 7.61 (m, 2H); 7.44 (m, 2H); 4.26 (m, 4H); 4.00 (s, 3H); 3.67 (m, 2H); 3.32 (s, 3H); 2.27 (m, 1H); 0.98 (d, J=6.8 Hz, 6H).

Step J: [4-[(E)-[isobutyl-[5-(2-methoxyethoxy)-1,1-dioxo-1,2-benzothiazol-3-yl]hydrazono]methyl]-2-methoxy-phenyl]boronic acid In a Q-tube, tetrahydroxydiboron (95.3 mg; 1.06 mmol; 3.00 eq.), N-[(E)-(4-chloro-3-methoxy-phenyl)methyleneamino]-N-isobutyl-5-(2-methoxyethoxy)-1,1-dioxo-1,2-benzothiazol-3-amine (170.0 mg; 0.35 mmol; 1.00 eq.) and potassium acetate (104.3 mg; 1.06 mmol; 3.00 eq.) were dissolved in EtOH (4 mL). The mixture was degassed then chloro(2-dicyclohexylphosphino-2%4',6'-triisopropyl-1,1'-biphenyl)[2-(2'-amino-1,1'-biphenyl)]palladium(II) (55.7 mg; 0.07 mmol; 0.20 eq.) and 2-dicyclohexylphosphino-2',4',6'-triisopropylbiphenyl (16.9 mg; 0.04 mmol; 0.10 eq.) were added. The reaction was stirred at 80° C. for 1 h and cooled to rt. 1N HCl was added until pH=2 and the mixture was extracted with EtOAc. The organic phase was washed with water (3×) and brine, dried over MgSO₄, filtered and concentrated to dryness. The residue obtained was first purified by chromatography (0 to 5% MeOH in DCM) and then by LCMS-Preparative (Column: Kinetex C18, 30×150 mm 5 μm (phenomenex); Flow rate: 42 ml/min; Elution: H2O, 0.1% HCOOH/ACN, 0.1% HCOOH; Gradient: 10 to 100% ACN over 12 minutes) to give [4-[(E)-[isobutyl-[5-(2-methoxyethoxy)-1,1-dioxo-1,2-benzothiazol-3-yl]hydrazono]methyl]-2-methoxy-phenyl]boronic acid (50.0 mg; 59%) as a beige solid. $^1$H NMR (400 MHz, DMSO-d6) δ 8.53 (s, 1H); 8.42 (d, J=2.2 Hz, 1H); 8.01 (d, J=8.4 Hz, 1H); 7.87 (s, 2H); 7.67 (d, J=7.3 Hz, 1H); 7.44 (m, 3H); 4.27 (m, 4H); 3.93 (s, 3H); 3.68 (m, 2H); 3.32 (s, 3H); 2.27 (m, 1H); 0.98 (d, J=6.6 Hz, 6H). mp: 194° C.

Example 10: [4-[(E)-[(6-cyano-1,1-dioxo-1,2-benzothiazol-3-yl)-isobutyl-hydrazono]-methyl]-2-methoxy-phenyl]boronic acid Step A: 5-bromo-2-methyl-benzenesulfonamide The compound was prepared using the same procedure detailed in example 9 step A starting from 5-bromo-2-methylbenzenesulfonyl chloride (100.00 g; 0.37 mol; 1.00 eq.) giving 5-bromo-2-methyl-benzenesulfonamide (92.00 g; 99%) as a beige solid. $^1$H NMR (DMSO-d₆, 300 MHz): δ 7.95 (d, J=2.1 Hz, 1H); 7.69 (dd, J=2.1 Hz, J=8.1 Hz, 1H); 7.47 (br s, 2H); 7.35 (d, J=8.1 Hz, 1H); 2.54 (s, 3H).

Step B: 4-bromo-2-sulfamoyl-benzoic acid

The compound was prepared using the same procedure as in example 9 step B starting from 5-bromo-2-methyl-benzenesulfonamide (50.00 g; 0.20 mol; 1.00 eq.) giving 4-bromo-2-sulfamoyl-benzoic acid (43 g; 77%) as a white solid. $^1$H NMR (DMSO-d₆, 300 MHz): δ 13.82 (br s, 1H); 8.09 (d, J=2.0 Hz, 1H); 7.91 (dd, J=2.0 Hz, J=8.3 Hz, 1H); 7.67 (d, J=8.3 Hz, 1H); 7.35 (s, 2H).

Step C: 6-bromo-1,1-dioxo-1,2-benzothiazol-3-one

The compound was prepared using the same procedure detailed in example 9 step C starting from 4-bromo-2-sulfamoyl-benzoic acid (81.00 g; 0.289 mol; 1.00 eq.) giving 6-bromo-1,1-dioxo-1,2-benzothiazol-3-one (69.30 g; 91%) as a white solid. $^1$H NMR (DMSO-d₆, 300 MHz): δ 8.48 (d, J=1.7 Hz, 1H); 8.08 (dd, J=1.7 Hz, J=8.1 Hz, 1H); 7.85 (d, J=8.1 Hz, 1H).

Step D: 6-bromo-3-chloro-1,2-benzothiazole 1,1-dioxide

The compound was prepared using the same procedure detailed in example 9 step D starting from 6-bromo-1,1-dioxo-1,2-benzothiazol-3-one (2.50 g; 9.54 mmol; 1.00 eq.) giving 6-bromo-3-chloro-1,2-benzothiazole 1,1-dioxide (theor.=2.68 g), used in the next step without purification.

Step E: 6-bromo-N-[(E)-(4-chloro-3-methoxy-phenyl)methyleneamino]-N-isobutyl-1,1-dioxo-1,2-benzothiazol-3-amine The compound was prepared using the same procedure detailed in example 1 step C starting from 6-bromo-3-chloro-1,2-benzothiazole 1,1-dioxide (2.68 g; 9.54 mmol; 1.00 eq.) and N-[(E)-(4-chloro-3-methoxy-phenyl)methyleneamino]-2-methyl-propan-1-amine (example 9, step E), (2.30 g; 9.54 mmol; 1.00 eq.) giving 6-bromo-N-[(E)-(4-chloro-3-methoxy-phenyl)methyleneamino]-N-isobutyl-1,1-dioxo-1,2-benzothiazol-3-amine (2.20 g; 47%) as a pale yellow solid. $^1$H NMR (DMSO-d6, 300 MHz): δ 8.68 (d, J=8.6 Hz, 1H); 8.55 (s, 1H); 8.46 (d, J=1.8 Hz, 1H); 8.15 (dd, J=1.8 Hz, J=8.6 Hz, 1H); 7.60 (m, 2H); 7.48 (dd, J=1.8 Hz, J=8.3 Hz, 1H); 4.26 (d, J=7.8 Hz, 2H); 3.99 (s, 3H); 2.26 (m, 1H); 0.98 (d, J=6.6 Hz, 6H).

Step F: N-[(E)-(4-chloro-3-methoxy-phenyl)methyleneamino]-N-isobutyl-1,1-dioxo-6-(4,4,5,5-tetramethyl-1,3,2-dioxaborolan-2-yl)-1,2-benzothiazol-3-amine The compound was prepared using the same procedure detailed in example 9 step G starting from 6-bromo-N-[(E)-(4-chloro-3-methoxy-phenyl)methyleneamino]-N-isobutyl-1,1-dioxo-1,2-benzothiazol-3-amine (2.20 g; 4.54 mmol; 1.00 eq.) giving N-[(E)-(4-chloro-3-methoxy-phenyl)methyleneamino]-N-isobutyl-1,1-dioxo-6-(4,4,5,5-tetramethyl-1,3,2-dioxaborolan-2-yl)-1,2-benzothiazol-3-amine (2.10 g; 87%) as an orange solid. $^1$H NMR (DMSO-d6, 300 MHz): δ 8.85 (d, J=8.4 Hz, 1H); 8.56 (s, 1H); 8.17 (dd, J=1.1 Hz, J=8.0 Hz, 1H); 8.10 (s, 1H); 7.62 (m, 2H); 7.52 (dd, J=1.7

Hz, J=8.1 Hz, 1H); 4.28 (d, J=7.8 Hz, 2H); 4.00 (s, 3H); 2.28 (m, 1H); 1.07 (s, 12H); 0.99 (d, J=6.6 Hz, 6H).

Step G: 3-[[(E)-(4-chloro-3-methoxy-phenyl)methyleneamino]-isobutyl-amino]-1,1-dioxo-1,2-benzothiazol-6-ol The compound was prepared using the same procedure detailed in example 9 step H starting from N-[(E)-(4-chloro-3-methoxy-phenyl)methyleneamino]-N-isobutyl-1,1-dioxo-6-(4,4,5,5-tetramethyl-1,3,2-dioxaborolan-2-yl)-1,2-benzothiazol-3-amine (2.10 g; 3.95 mmol; 1.00 eq.) giving 3-[[(E)-(4-chloro-3-methoxy-phenyl)methyleneamino]-isobutyl-amino]-1,1-dioxo-1,2-benzothiazol-6-ol (1.30 g; 78%) as a pale yellow solid. $^1$H NMR (DMSO-d6, 300 MHz): δ 11.27 (s, 1H); 8.60 (d, J=8.8 Hz, 1H); 8.49 (s, 1H); 7.60 (m, 2H); 7.46 (dd, J=1.8 Hz, J=8.3 Hz, 1H); 7.30 (d, J=2.3 Hz, 1H); 7.20 (dd, J=2.4 Hz, J=8.8 Hz, 1H); 4.22 (d, J=7.8 Hz, 2H); 3.98 (s, 3H); 2.25 (m, 1H); 0.97 (d, J=6.8 Hz, 6H).

Step H: [3-[[(E)-(4-chloro-3-methoxy-phenyl)methyleneamino]-isobutyl-amino]-1,1-dioxo-1,2-benzothiazol-6-yl] trifluoromethanesulfonate 3-[[(E)-(4-chloro-3-methoxy-phenyl)methyleneamino]-isobutyl-amino]-1,1-dioxo-1,2-benzothiazol-6-ol (500.0 mg; 1.19 mmol; 1.00 eq.) was dissolved in DCM (15 mL) and cooled to 0° C. Then N,N-diisopropylethylamine (240 μL; 1.48 mmol; 1.25 eq) followed by trifluoromethane sulfonic anhydride (250 μL; 1.48 mmol; 1.25 eq.) were added. After 3 h at rt, additional N,N-diisopropylethylamine (240 μL; 1.48 mmol; 1.25 eq) and trifluoromethane sulfonic anhydride (250 μL; 1.48 mmol; 1.25 eq.) were added. After 18 h at rt, additional N,N-diisopropylethylamine (490 μL; 2.96 mmol; 2.50 eq) and trifluoromethane sulfonic anhydride (490 μL; 2.96 mmol; 2.50 eq.) were added again. After a further 5 h at rt, the reaction mixture was diluted with water and extracted with DCM (×3). Combined organic phases were washed with brine, dried with MgSO$_4$ and concentrated under vacuum. The residue was taken up into DCM and 1N HCl was added. The organic phase was then washed with water, dried with MgSO$_4$ and concentrated to dryness to give [3-[[(E)-(4-chloro-3-methoxy-phenyl) methyleneamino]-isobutyl-amino]-1,1-dioxo-1,2-benzothiazol-6-yl]trifluoromethanesulfonate (749.0 mg; 87%) as a brown solid. $^1$H NMR (DMSO-d6, 300 MHz): δ 8.94 (d, J=8.9 Hz, 1H); 8.59 (s, 1H); 8.56 (d, J=2.3 Hz, 1H); 8.11 (dd, J=2.4 Hz, J=8.8 Hz, 1H); 7.61 (m, 2H); 7.51 (dd, J=1.8 Hz, J=8.4 Hz, 1H); 4.28 (d, J=7.8 Hz, 2H); 3.98 (s, 3H); 2.27 (m, 1H); 0.99 (d, J=6.6 Hz, 6H).

Step I: 3-[[(E)-(4-chloro-3-methoxy-phenyl)methyleneamino]-isobutyl-amino]-1,1-dioxo-1,2-benzothiazole-6-carbonitrile

[3-[[(E)-(4-chloro-3-methoxy-phenyl)methyleneamino]-isobutyl-amino]-1,1-dioxo-1,2-benzothiazol-6-yl] trifluoromethanesulfonate (400.0 mg; 0.55 mmol; 1.00 eq.) was dissolved in DMF (3 mL). Zinc cyanide (64.4 mg; 0.55 mmol; 1.00 eq.) and tetrakis(triphenylphosphine)palladium (0) (63.4 mg; 0.05 mmol; 0.10 eq.) were added. The reaction mixture was heated under microwave irradiation at 150° C. for 35 min. Then, it was diluted and extracted with EtOAc. The organic layer was washed with brine and concentrated under vacuum. The residue was purified by chromatography (0 to 30% EtOAc in cyclohexane) to give 3-[[(E)-(4-chloro-3-methoxy-phenyl)methyleneamino]-isobutyl-amino]-1,1-dioxo-1,2-benzothiazole-6-carbonitrile (75.0 mg; 32%) as a pale yellow solid. $^1$H NMR (DMSO-d6, 300 MHz): δ 8.94 (d, J=8.4 Hz, 1H); 8.80 (s, 1H); 8.60 (s, 1H); 8.43 (dd, J=1.4 Hz, J=8.2 Hz, 1H); 7.61 (m, 2H); 7.48 (dd, J=1.5 Hz, J=7.9 Hz, 1H); 4.28 (d, J=7.8 Hz, 2H); 3.99 (s, 3H); 2.28 (m, 1H); 0.99 (d, J=6.6 Hz, 6H).

Step J: [4-[(E)-[(6-cyano-1,1-dioxo-1,2-benzothiazol-3-yl)-isobutyl-hydrazono]methyl]-2-methoxy-phenyl]boronic acid The compound was prepared using the same procedure detailed in example 9 step J starting from 3-[[(E)-(4-chloro-3-methoxy-phenyl)methyleneamino]-isobutyl-amino]-1,1-dioxo-1,2-benzo-thiazole-6-carbonitrile (60.0 mg; 0.13 mmol; 1.00 eq.) giving [4-[(E)-[(6-cyano-1,1-dioxo-1,2-benzothiazol-3-yl)-isobutyl-hydrazono]methyl]-2-methoxy-phenyl]boronic acid (10.0 mg; 18%) as a pale yellow solid. $^1$H NMR (DMSO-d6, 400 MHz): δ 8.98 (d, J=8.4 Hz, 1H); 8.81 (d, J=1.1 Hz, 1H); 8.60 (s, 1H); 8.46 (dd, J=1.4 Hz, J=8.3 Hz, 1H); 7.90 (s, 2H); 7.70 (d, J=7.5 Hz, 1H); 7.45 (m, 2H); 4.29 (d, J=7.7 Hz, 2H); 3.92 (s, 3H); 2.27 (m, 1H); 0.99 (d, J=6.6 Hz, 6H).

Example 11: [4-[(E)-[(1,1-dioxo-1,2-benzothiazol-3-yl)-isobutyl-hydrazono]methyl]-2-(2-methoxy ethoxy)phenyl]boronic acid

Step A: methyl 4-bromo-3-(2-methoxyethoxy)benzoate

The compound was prepared using the same procedure detailed in example 9 step I starting from methyl 4-bromo-3-hydroxybenzoate (2.00 g; 8.66 mmol; 1.00 eq.) and 1-bromo-2-methoxyethane (1.22 mL; 12.98 mmol; 1.50 eq.) giving methyl 4-bromo-3-(2-methoxyethoxy)benzoate (1.47 g; 59%). LC-MS (Method B): Rt=2.73 min; MS: m/z=257-259 [M+H−OMe]$^+$.

Step B: [4-bromo-3-(2-methoxyethoxy)phenyl] methanol

Methyl 4-bromo-3-(2-methoxyethoxy)benzoate (1.47 g; 5.07 mmol; 1.00 eq.) was dissolved in DCM (50 mL) and cooled to 0° C., then DIBAL-H (15.2 mL; 15.2 mmol; 3.00 eq.; 1 M solution in cyclohexane) was added over 15 min. The mixture was stirred 5 h at rt. After addition of saturated aqueous ammonium chloride, the resultant biphasic mixture was stirred vigorously for 2 h, and then extracted with DCM. The organic layer was dried over Na$_2$SO$_4$, filtered and concentrated to dryness to give [4-bromo-3-(2-methoxyethoxy)phenyl]methanol (1.08 g; 82%). LC-MS (Method B): Rt=2.16 min; MS: m/z=243-245 [M+H−OH]$^+$

Step C: 4-bromo-3-(2-methoxyethoxy)benzaldehyde

A vessel was sequentially charged with DCM (9 mL), [4-bromo-3-(2-methoxyethoxy)phenyl]methanol (1.10 g; 4.14 mmol; 1.00 eq.) and iodobenzene diacetate (1.47 g; 4.55 mmol; 1.10 eq.). Upon dissolution of the iodobenzene diacetate (endotherm), TEMPO (65.0 mg; 0.41 mmol; 0.10 eq.) was added and the resultant mixture was stirred 2 h at rt. DCM was evaporated and the residue was purified by column chromatography (0 to 40% EtOAc in n-heptane) to give 4-bromo-3-(2-methoxyethoxy)benzaldehyde (830.0 mg; 77%). LC-MS (Method B): Rt=1.36 min; MS: m/z=258-260 [M+H]$^+$.

Step D: tert-butyl N-[(E)-[4-bromo-3-(2-methoxy-ethoxy)phenyl]methyleneamino] carbamate Tert-Butyl carbazate (296.0 mg; 2.24 mmol; 0.70 eq.) was added to a suspension of 4-bromo-3-(2-methoxyethoxy)benzaldehyde (830.0 mg; 3.20 mmol; 1.00 eq.) in EtOH (18 mL) and the reaction was stirred at rt overnight. After concentration under vacuum, the residue was triturated with n-heptane and filtered to give tert-butyl N-[(E)-[4-bromo-3-(2-methoxyethoxy)phenyl]methyleneamino] carbamate (895.0 mg; 75%). LC-MS (Method D): Rt=2.05 min; MS: m/z=317-319 [M+H−tBu]$^+$.

Step E: tert-butyl N-[(E)-[4-bromo-3-(2-methoxy-ethoxy)phenyl]methyleneamino]-N-isobutyl-carbamate The compound was prepared using the same procedure detailed in example 9 step I starting from tert-butyl N-[(E)-[4-bromo-3-(2-methoxyethoxy)phenyl]methyleneamino] carbamate (300.0 mg; 0.80 mmol; 1.00 eq.) and 1-bromo-2-methylpropane (165.0 mg; 1.21 mmol; 1.50 eq.) giving tert-butyl N-[(E)-[4-bromo-3-(2-methoxyethoxy)phenyl]methyleneamino]-N-isobutyl-carbamate (293.0 mg; 85%). LC-MS (Method D): Rt=2.73 min; MS: m/z=373-375 [M+H−tBu]$^+$.

Step F: N-[(E)-[4-bromo-3-(2-methoxyethoxy)phenyl]methyleneamino]-2-methyl-propan-1-amine A solution of tert-butyl N-[(E)-[4-bromo-3-(2-methoxyethoxy)phenyl]methyleneamino]-N-isobutyl-carbamate (293.0 mg; 0.68 mmol; 1.00 eq.) in HCl 4.0M solution in 1,4-dioxane (3.5 mL) was stirred 15 min at rt. The reaction was concentrated under vacuum to give N-[(E)-[4-bromo-3-(2-methoxyethoxy)phenyl]methyleneamino]-2-methyl-propan-1-amine (261.0 mg; quant.), used directly in the next step without purification. LC-MS (Method B): Rt=3.11 min; MS: m/z=329-331 [M+H]$^+$.

Step G: N-[(E)-[4-bromo-3-(2-methoxyethoxy)phenyl]methyleneamino]-N-isobutyl-1,1-dioxo-1,2-benzothiazol-3-amine The compound was prepared using the same procedure detailed in example 1 step C starting from 3-chloro-1,2-benzothiazole 1,1-dioxide (example 1, step A), (160.0 mg; 0.79 mmol; 1.00 eq.) and N-[(E)-[4-bromo-3-(2-methoxyethoxy)phenyl]methyleneamino]-2-methyl-propan-1-amine (261.0 mg; 0.79 mmol; 1.00 eq.) giving N-[(E)-[4-bromo-3-(2-methoxyethoxy)phenyl] methyleneamino]-N-isobutyl-1,1-dioxo-1,2-benzothiazol-3-amine (343.0 mg; 87%). $^1$H NMR (DMSO-d6, 300 MHz): δ 8.82 (m, 1H); 8.53 (s, 1H); 8.10 (m, 1H); 7.90 (m, 1H); 7.78 (d, J=8.3 Hz, 1H); 7.60 (s, 1H); 7.42 (d, J=8.3 Hz, 1H); 4.31 (m, 4H); 3.77 (t, J=4.5 Hz, 2H); 3.36 (s, 3H); 2.26 (m, 1H); 0.99 (d, J=6.7 Hz, 6H).

Step H: N-isobutyl-N-[(E)-[3-(2-methoxyethoxy)-4-(4,4,5,5-tetramethyl-1,3,2-dioxaborolan-2-yl)phenyl]methyleneamino]-1,1-dioxo-1,2-benzothiazol-3-amine The compound was prepared using the same procedure detailed in example 9 step G starting from N-[(E)-[4-bromo-3-(2-methoxyethoxy)phenyl]methyleneamino]-N-isobutyl-1,1-dioxo-1,2-benzothiazol-3-amine (260.0 mg; 0.53 mmol; 1.00 eq.) giving N-isobutyl-N-[(E)-[3-(2-methoxyethoxy)-4-(4,4,5,5-tetramethyl-1,3,2-dioxaborolan-2-yl)phenyl] methyleneamino]-1,1-dioxo-1,2-benzothiazol-3-amine (100.0 mg; 56%). LC-MS (Method F): Rt=2.56 min; MS: m/z=542 [M+H]$^+$.

Step I: [4-[(E)-[(1,1-dioxo-1,2-benzothiazol-3-yl)-isobutyl-hydrazono]methyl]-2-(2-methoxyethoxy)phenyl]boronic acid N-isobutyl-N-[(E)-[3-(2-methoxyethoxy)-4-(4,4,5,5-tetramethyl-1,3,2-dioxaborolan-2-yl)phenyl]methyleneamino]-1,1-dioxo-1,2-benzothiazol-3-amine (100.0 mg; 0.18 mmol; 1.00 eq.) was suspended in a mixture of acetonitrile (2.3 mL) and HCl (1M in water, 1.00 mL; 1.00 mmol; 5.56 eq.). Then, the mixture was heated at 50° C. until completion, cooled to rt and concentrated under vacuum. The residue was purified by column chromatography (50 to 100% EtOAc in n-heptane) to give [4-[(E)-[(1,1-dioxo-1,2-benzothiazol-3-yl)-isobutyl-hydrazono]methyl]-2-(2-methoxyethoxy)phenyl]boronic acid (10.0 mg; 12%) as a white solid. $^1$H NMR (CDCl$_3$, 300 MHz): δ 8.78 (d, J=7.6 Hz, 1H); 8.07 (s, 1H); 7.97 (m, 2H); 7.69 (m, 2H); 7.38 (d, J=7.6 Hz, 1H); 7.28 (s, 1H); 5.89 (s, 2H); 4.28 (m, 4H); 3.82 (t, J=4.5 Hz, 2H); 3.49 (s, 3H); 2.34 (m, 1H); 1.08 (d, J=6.7 Hz, 6H). mp: 150-152° C.

Example 12: [4-[(E)-[[5-(3-hydroxypropoxy)-1,1-dioxo-1,2-benzothiazol-3-yl]-isobutyl-hydrazono]methyl]-2-methoxy-phenyl]boronic acid

Step A: 5-[3-[tert-butyl(dimethyl)silyl]oxypropoxy]-N-[(E)-(4-chloro-3-methoxy-phenyl) methyleneamino]-N-isobutyl-1,1-dioxo-1,2-benzothiazol-3-amine The compound was prepared using the same procedure detailed in example 9 step I starting from 3-[[(E)-(4-chloro-3-methoxy-phenyl)methyleneamino]-isobutyl-amino]-1,1-dioxo-1,2-benzothiazol-5-ol (example 9, step H), (250.0 mg; 0.59 mmol; 1.00 eq.) and (3-bromopropoxy)-tert-butyldimethylsilane (210 μL; 0.89 mmol; 1.50 eq.) giving 5-[3-[tert-butyl(dimethyl)silyl]oxypropoxy]-N-[(E)-(4-chloro-3-methoxy-phenyl)methyleneamino]-N-isobutyl-1,1-dioxo-1,2-benzothiazol-3-amine (352.0 mg; 99%) as a beige solid. $^1$H NMR (DMSO-d6, 300 MHz): δ 8.56 (s, 1H); 8.37 (d, J=2.1 Hz, 1H); 8.02 (d, J=8.4 Hz, 1H); 7.64 (d, J=1.8 Hz, 1H); 7.61 (d, J=8.3 Hz, 1H); 7.49 (dd, J=1.8 Hz, J=8.3 Hz, 1H); 7.43 (dd, J=2.3 Hz, J=8.4 Hz, 1H); 4.28 (d, J=7.6 Hz, 2H); 4.21 (t, J=6.1 Hz, 2H); 4.00 (s, 3H); 3.75 (t, J=6.1 Hz, 2H); 2.28 (m, 1H); 1.93 (m, 2H); 1.00 (d, J=6.8 Hz, 6H); 0.82 (s, 9H); 0.00 (s, 6H).

Step B: 3-[[3-[[(E)-(4-chloro-3-methoxy-phenyl)methyleneamino]-isobutyl-amino]-1,1-dioxo-1,2-benzothiazol-5-yl]oxy]propan-1-ol 5-[3-[tert-butyl(dimethyl)silyl]oxypropoxy]-N-[(E)-(4-chloro-3-methoxy-phenyl)methyleneamino]-N-isobutyl-1,1-dioxo-1,2-benzothiazol-3-amine (352.0 mg; 0.59 mmol; 1.00 eq.) was dissolved into THF (2 mL). Tetrabutylammonium fluoride 1M in THF (1.78 mL; 1.00 mol/L; 1.78 mmol; 3.00 eq.) was added and the mixture was stirred 1 h at rt. After concentration, the residue was taken up into EtOAc and washed twice by a saturated solution of NaHCO$_3$. The organic phase was then dried over MgSO₄, filtered and concentrated to dryness. The residue was purified by column chromatography (50 to 100% EtOAc in cyclohexane) to give 3-[[3-[[(E)-(4-chloro-3-methoxy-phenyl)methyleneamino]-isobutyl-amino]-1,1-dioxo-1,2-benzothiazol-5-yl]oxy] propan-1-ol (290.0 mg; 100%) as a beige solid. $^1$H NMR (DMSO-d6, 300 MHz): δ 8.54 (s, 1H); 8.36 (m, 1H); 8.00 (d, J=8.4 Hz, 1H); 7.63 (m, 2H); 7.47 (m, 1H); 7.41 (m, 1H); 4.61 (t, J=5.0 Hz, 1H); 4.26 (d, J=7.8 Hz, 2H); 4.20 (t, J=6.5 Hz, 2H); 3.99 (s, 3H); 3.56 (q, J=5.9 Hz, 2H); 2.25 (m, 1H); 1.89 (quint., J=6.2 Hz, 2H); 0.98 (d, J=6.6 Hz, 6H).

Step C: [4-[(E)-[[5-(3-hydroxypropoxy)-1,1-dioxo-1,2-benzothiazol-3-yl]-isobutyl-hydrazono] methyl]-2-methoxy-phenyl]boronic acid The compound was prepared using the same procedure detailed in example 9 step J starting from 3-[[3-[[(E)-(4-chloro-3-methoxy-phenyl)methyleneamino]-isobutyl-amino]-1,1-dioxo-1,2-benzothiazol-5-yl]oxy]propan-1-ol (284.0 mg; 0.59 mmol; 1.00 eq.) giving [4-[(E)-[[5-(3-hydroxypropoxy)-1,1-dioxo-1,2-benzothiazol-3-yl]-isobutyl-hydrazono]methyl]-2-methoxy-phenyl] boronic acid (11.0 mg; 4%) as a beige solid. $^1$H NMR (DMSO-d6, 400 MHz): δ 8.53 (s, 1H); 8.41 (d, J=2.4 Hz, 1H); 8.00 (d, J=8.4 Hz, 1H); 7.88 (s, 2H); 7.67 (d, J=7.5 Hz, 1H); 7.43 (m, 3H); 4.61 (t, J=5.2 Hz, 1H); 4.27 (d, J=7.7 Hz, 2H); 4.20 (t, J=6.4 Hz, 2H); 3.92 (s, 3H); 3.55 (m, 2H); 2.27 (m, 1H); 1.89 (quint., J=6.3 Hz, 2H); 0.98 (d, J=6.8 Hz, 6H).

Example 13: [4-[(E)-[isobutyl-(8-methoxyquinazolin-4-yl)hydrazono]methyl]-2-methoxy-phenyl]boronic acid The compound was prepared using the same procedure detailed in example 3 step B starting from 4-chloro-8-methoxyquinazoline (200.0 mg; 1.03 mmol; 1.00 eq.), 2-methylpropylhydrazine hydrochloride (128.1 my; 1.03 mmol; 1.00 eq.) and 4-formyl-2-methoxyphenylboronic acid (184.9 mg; 1.03 mmol; 1.00 eq.) giving [4-[(E)-[isobutyl-(8-methoxyquinazolin-4-yl)hydrazono]methyl]-2-methoxy-phenyl]boronic acid (276.8 mg; 66%) as a yellow solid. $^1$H NMR (DMSO-d₆, 400 MHz): δ 8.73 (s, 1H); 8.57 (dd, J=0.8 Hz, J=8.7 Hz, 1H); 8.25 (s, 1H); 7.77 (s, 2H); 7.64 (d, J=7.5 Hz, 1H); 7.52 (t, J=8.3 Hz, 1H); 7.42 (s, 1H); 7.35 (dd, J=0.9 Hz, J=3.7 Hz, 1H); 7.33 (d, J=3.3 Hz, 1H); 4.45 (d, J=7.5 Hz, 2H); 3.95 (s, 3H); 3.86 (s, 3H); 2.31 (m, 1H); 0.96 (d, J=6.6 Hz, 6H).

Example 14: [4-[(E)-[(1,1-dioxo-1,2-benzothiazol-3-yl)-isobutyl-hydrazono]methyl]-2-ethoxyphenyl]boronic acid The compound was prepared using the same procedure detailed in example 3 step B starting from 3-chloro-1,2-benzothiazole 1,1-dioxide (example 1, step A), (52.0 mg; 0.26 mmol; 1.00 eq.), 2-methylpropylhydrazine hydrochloride (32.1 mg; 0.26 mmol; 1.00 eq.) and (2-ethoxy-4-formylphenyl)boronic acid (50.0 mg; 0.26 mmol; 1.00 eq.) giving [4-[(E)-[(1,1-dioxo-1,2-benzothiazol-3-yl)-isobutyl-hydrazono]methyl]-2-ethoxyphenyl]boronic acid (12.0 mg; 11%) as a white solid. $^1$H NMR (DMSO-d₆, 400 MHz): δ 8.85 (m, 1H); 8.54 (s, 1H); 8.10 (m, 1H); 7.90 (m, 2H); 7.83 (s, 2H); 7.71 (d, J=7.9 Hz, 1H); 7.46 (m, 2H); 4.28 (d, J=7.9 Hz, 2H); 4.22 (q, J=7.0 Hz, 2H); 2.28 (m, 1H); 1.43 (t, J=6.9 Hz, 3H); 0.99 (d, J=6.8 Hz, 6H).

Example 15: [2-chloro-4-[(E)-[(5,7-dimethoxy-1,1-dioxo-1,2-benzothiazol-3-yl)-isobutyl-hydrazono]methyl]phenyl]boronic acid The compound was prepared using the same procedure detailed in example 3 step B starting from 3-chloro-5,7-methoxy-1,2-benzothiazole 1,1-dioxide (example 3, step A), (107.3 mg; 0.41 mmol; 1.00 eq.), 2-methylpropylhydrazine hydrochloride (51.2 mg; 0.41 mmol; 1.00 eq.) and (2-chloro-4-formylphenyl)boronic acid (75.6 mg; 0.41 mmol; 1.00 eq.) giving [2-chloro-4-[(E)-[(5,7-dimethoxy-1,1-dioxo-1,2-benzothiazol-3-yl)-isobutyl-hydrazono]methyl]phenyl]boronic acid (24.0 mg; 12%) as a white solid. $^1$H NMR (DMSO-d₆, 400 MHz): δ 8.50 (s, 1H); 8.45 (s, 2H); 7.92 (d, J=2.0 Hz, 1H); 7.87 (d, J=1.1 Hz, 1H); 7.75 (dd, J=1.3 Hz, J=7.7 Hz, 1H); 7.57 (d, J=7.5 Hz, 1H); 7.01 (d, J=1.8 Hz, 1H); 4.23 (d, J=7.5 Hz, 2H); 3.97 (s, 6H); 2.25 (m, 1H); 0.97 (d, J=6.6 Hz, 6H). mp: 211° C.

Example 16: [4-[(E)-[(1,1-dioxo-1,2-benzothiazol-3-yl)-sec-butyl-hydrazono]methyl]-2-methoxyphenyl]boronic acid

Step A: tert-butyl N-[(E)-(4-chloro-3-methoxy-phenyl)methyleneamino]carbamate The compound was prepared using the same procedure detailed in example 11 step D starting from 4-chloro-3-methoxybenzaldehyde (300.0 mg; 1.76 mmol; 1.00 eq.) giving tert-butyl N-[(E)-(4-chloro-3-methoxy-phenyl)methyleneamino]carbamate (483.0 mg; 96%) as a white solid. $^1$H NMR (DMSO-d₆, 300 MHz): δ 11.00 (br s, 1H); 7.97 (s, 1H); 7.45 (d, J=8.1 Hz, 1H); 7.34 (d, J=1.8 Hz, 1H); 7.17 (dd, J=1.7 Hz, J=8.2 Hz, 1H); 3.89 (s, 3H); 1.47 (s, 9H).

Step B: tert-butyl N-[(E)-(4-chloro-3-methoxy-phenyl)methyleneamino]-N-sec-butyl-carbamate The compound was prepared using the same procedure detailed in example 9 step I starting from tert-butyl N-[(E)-(4-chloro-3-methoxy-phenyl)methyleneamino]carbamate (253.0 mg; 0.89 mmol; 1.00 eq.) and 2-bromobutane (6×105 μL; 0.98 mmol; 6×1.10 eq.) giving tert-butyl N-[(E)-(4-chloro-3-methoxy-phenyl)methyleneamino]-N-sec-butyl-carbamate (200.0 mg; 66%). $^1$H NMR (DMSO-d₆, 300 MHz): δ 8.88 (s, 1H); 7.47 (d, J=8.3 Hz, 1H); 7.45 (d, J=1.7 Hz, 1H); 7.30 (dd, J=1.7 Hz, J=8.2 Hz, 1H); 4.24 (m, 1H); 3.89 (s, 3H); 1.71 (m, 1H); 1.55 (m, 1H); 1.47 (s, 9H); 1.22 (d, J=6.6 Hz, 3H); 0.82 (t, J=7.3 Hz, 3H).

Step C: N-[(E)-(4-chloro-3-methoxy-phenyl)methyleneamino]butan-2-amine

The compound was prepared using the same procedure detailed in example 11 step F starting from tert-butyl N-[(E)-(4-chloro-3-methoxy-phenyl)methyleneamino]-N-sec-butyl-carbamate (200.0 mg; 0.59 mmol; 1.00 eq.) giving N-[(E)-(4-chloro-3-methoxy-phenyl)methylene amino]butan-2-amine (theor.=141.3 mg) as a yellow oil, used in the next step without purification. LC-MS (Method A): Rt=2.32 min; MS: m/z=241 [M+H]⁺.

Step D: N-[(E)-(4-chloro-3-methoxy-phenyl)methyleneamino]-1,1-dioxo-N-sec-butyl-1,2-benzothiazol-3-amine The compound was prepared using the same procedure as in example 1 step C starting from 3-chloro-1,2-benzothiazole 1,1-dioxide (example 1, step A), (106.3 mg; 0.53 mmol; 1.00 eq.) and N-[(E)-(4-chloro-3-methoxy-phenyl)methyleneamino]butan-2-amine (141.0 mg; 0.53 mmol; 1.00 eq.) giving N-[(E)-(4-chloro-3-methoxy-phenyl)methyleneamino]-1,1-dioxo-N-sec-butyl-1,2-benzothiazol-3-amine (80.0 mg; 37%) as a beige solid. LC-MS (Method A): Rt=2.41 min; MS: m/z=406 [M+H]⁺.

Step E: [4-[(E)-[(1,1-dioxo-1,2-benzothiazol-3-yl)-sec-butyl-hydrazono]methyl]-2-methoxy-phenyl]boronic acid The compound was prepared using the same procedure detailed in example 9 step J starting from N-[(E)-(4-chloro-3-methoxy-phenyl)methyleneamino]-1,1-dioxo-N-sec-butyl-1,2-benzothiazol-3-amine (80.0 mg; 0.20 mmol; 1.00 eq.) giving [4-[(E)-[(1,1-dioxo-1,2-benzothiazol-3-yl)-sec-butyl-hydrazono]methyl]-2-methoxy-phenyl]boronic acid (13.0 mg; 16%) as a white solid. ¹H NMR (DMSO-d6, 400 MHz): δ 8.71 (s, 1H); 8.58 (m, 1H); 8.08 (m, 1H); 7.87 (s, 2H); 7.85 (m, 2H); 7.69 (d, J=7.7 Hz, 1H); 7.48 (m, 2H); 5.00 (m, 1H); 3.90 (s, 3H); 2.19 (m, 1H); 1.93 (m, 1H); 1.57 (d, J=6.8 Hz, 3H); 0.91 (t, J=7.4 Hz, 3H).

Example 17: [4-[(E)-[(6,8-dimethoxyquinazolin-4-yl)-isobutyl-hydrazono]methyl]-2-methoxyphenyl]boronic acid The compound was prepared using the same procedure as in example 3 step B starting from 4-chloro-6,8-dimethoxyquinazoline (200.0 mg; 0.89 mmol; 1.00 eq.), 2-methylpropylhydrazine hydrochloride (110.9 mg; 0.89 mmol; 1.00 eq.) and 4-formyl-2-methoxyphenylboronic acid (160.2 mg; 0.89 mmol; 1.00 eq.) giving [4-[(E)-[(6,8-dimethoxyquinazolin-4-yl)-isobutyl-hydrazono]methyl]-2-methoxy-phenyl]boronic acid (55.0 mg; 14%) as a yellow solid. ¹H NMR (DMSO-d₆, 400 MHz): δ 8.61 (s, 1H); 8.19 (s, 1H); 8.01 (d, J=2.6 Hz, 1H); 7.76 (s, 2H); 7.60 (d, J=7.5 Hz, 1H); 7.43 (dd, J=1.1 Hz, J=7.7 Hz, 1H); 7.40 (d, J=1.1 Hz, 1H); 7.01 (d, J=2.6 Hz, 1H); 4.42 (d, J=7.7 Hz, 2H); 3.94 (s, 3H); 3.84 (s, 3H); 3.80 (s, 3H); 2.31 (m, 1H); 0.96 (d, J=6.8 Hz, 6H). mp: 204° C.

Example 18: [4-[(E)-[(7-fluoroquinazolin-4-yl)-isobutyl-hydrazono]methyl]-2-methoxyphenyl]boronic acid The compound was prepared using the same procedure detailed in example 3 step B starting from 4-chloro-7-fluoroquinazoline (100.0 mg; 0.55 mmol; 1.00 eq.), 2-methylpropylhydrazine hydrochloride (68.3 mg; 0.55 mmol; 1.00 eq.) and 4-formyl-2-methoxyphenylboronic acid (98.6 mg; 0.55 mmol; 1.00 eq.) giving [4-[(E)-[(7-fluoroquinazolin-4-yl)-isobutyl-hydrazono]methyl]-2-methoxy-phenyl]boronic acid (120.0 mg; 55%) as a yellow solid. ¹H NMR (DMSO-d₆, 500 MHz): δ 9.16 (dd, J=6.5 Hz, J=9.5 Hz, 1H); 8.74 (s, 1H); 8.33 (s, 1H); 7.78 (s, 2H); 7.66 (d, J=7.6 Hz, 1H); 7.57 (m, 2H); 7.41 (s, 1H); 7.36 (dd, J=1.0 Hz, J=7.6 Hz, 1H); 4.47 (d, J=7.6 Hz, 2H); 3.88 (s, 3H); 2.33 (m, 1H); 0.97 (d, J=6.7 Hz, 6H). mp: 175° C.

Example 19: [4-[(E)-[isobutyl-(6-methoxyquinazolin-4-yl)hydrazono]methyl]-2-methoxyphenyl]boronic acid The compound was prepared using the same procedure detailed in example 3 step B starting from 4-chloro-6-methoxyquinazoline (200.0 mg; 1.03 mmol; 1.00 eq.), 2-methylpropylhydrazine hydrochloride (128.1 mg; 1.03 mmol; 1.00 eq.) and 4-formyl-2-methoxyphenylboronic acid (184.9 mg; 1.03 mol; 1.00 eq.) giving [4-[(E)-[isobutyl-(6-methoxyquinazolin-4-yl)hydrazono]methyl]-2-methoxyphenyl]boronic acid (164.0 mg; 39%) as a yellow solid. ¹H NMR (DMSO-d₆, 500 MHz): δ 8.65 (s, 1H); 8.54 (d, J=2.9 Hz, 1H); 8.25 (s, 1H); 7.82 (d, J=9.2 Hz, 1H); 7.77 (s, 2H); 7.62 (d, J=7.6 Hz, 1H); 7.59 (dd, J=2.9 Hz, J=9.1 Hz, 1H); 7.44 (d, J=7.6 Hz, 1H); 7.41 (m, 1H); 4.45 (d, J=7.7 Hz, 2H); 3.86 (s, 3H); 3.82 (s, 3H); 2.33 (m, 1H); 0.97 (d, J=6.7 Hz, 6H). mp: 164° C.

Example 20: [4-[(E)-[isobutyl(thieno[3,2-d]pyrimidin-4-yl)hydrazono]methyl]-2-methoxy-phenyl]boronic acid The compound was prepared using the same procedure detailed in example 3 step B starting from 4-chlorothieno[3,2-D]pyrimidine (100.0 mg; 0.59 mmol; 1.00 eq.), 2-methylpropylhydrazine hydrochloride (73.0 mg; 0.59 mmol; 1.00 eq.) and 4-formyl-2-methoxyphenylboronic acid (105.5 mg; 0.59 mmol; 1.00 eq.) giving [4-[(E)-[isobutyl(thieno[3,2-d]pyrimidin-4-yl)hydrazono]methyl]-2-methoxy-phenyl]boronic acid (101.0 mg; 45%) as a white solid. ¹H NMR (DMSO-d₆, 400 MHz): δ 8.67 (s, 1H); 8.35 (d, J=5.7 Hz, 1H); 8.25 (s, 1H); 7.80 (s, 2H); 7.68 (m, 2H); 7.52 (dd, J=1.1 Hz, J=7.5 Hz, 1H); 7.49 (d, J=5.5 Hz, 1H); 4.40 (d, J=7.7 Hz, 2H); 3.96 (s, 3H); 2.28 (m, 1H); 0.95 (d, J=6.8 Hz, 6H). mp: 170° C.

Example 21: [4-[(E)-[ethyl-(8-methoxyquinazolin-4-yl)hydrazono]methyl]-2-methoxy-phenyl]boronic acid The compound was prepared using the same procedure detailed in example 3 step B starting from 4-chloro-8-methoxyquinazoline (200.0 mg; 1.03 mmol; 1.00 eq.), ethylhydrazine dihydrochloride (136.7 mg; 1.03 mmol; 1.00 eq.) and 4-formyl-2-methoxyphenylboronic acid (184.9 mg; 1.03 mmol; 1.00 eq.) giving [4-[(E)-[ethyl-(8-methoxyquinazolin-4-yl)hydrazono]methyl]-2-methoxy-phenyl]boronic acid (64.9 mg; 17%) as a yellow solid. ¹H NMR (DMSO-d₆, 400 MHz): δ 8.96 (s, 1H); 8.75 (m, 2H); 7.79 (m, 1H); 7.70 (m, 2H); 7.49 (d, J=1.1 Hz, 1H); 7.46 (dd, J=1.3 Hz, J=7.5 Hz, 1H); 4.71 (q, J=6.9 Hz, 2H); 4.09 (s, 3H); 3.89 (s, 3H); 1.34 (t, J=7.0 Hz, 3H).

Example 22: [2-methoxy-4-[(E)-[(8-methoxyquinazolin-4-yl)-methyl-hydrazono]-methyl]phenyl]boronic acid The compound was prepared using the same procedure detailed in example 3 step B starting from 4-chloro-8-methoxyquinazoline (200.0 mg; 1.03 mmol; 1.00 eq.), methyl hydrazine (55 μL; 1.03 mmol; 1.00 eq.) and 4-formyl-2-methoxyphenylboronic acid (184.9 mg; 1.03 mmol; 1.00 eq.) giving [2-methoxy-4-[(E)-[(8-methoxyquinazolin-4-yl)-methyl-hydrazono]-methyl]phenyl]boronic acid (218.6 mg; 58%) as a yellow solid. ¹H NMR (DMSO-d₆, 400 MHz): δ 8.93 (s, 1H); 8.81 (dd, J=0.9 Hz, J=8.8 Hz, 1H); 8.63 (s, 1H); 7.79 (m, 1H); 7.69 (d, J=7.5 Hz, 1H); 7.67

(d, J=7.9 Hz, 1H); 7.45 (d, J=0.9 Hz, 1H); 7.43 (dd, J=1.1 Hz, J=7.5 Hz, 1H); 4.08 (s, 3H); 4.01 (s, 3H); 3.89 (s, 3H).

Example 23: N-[(E)-(1-hydroxy-3H-2,1-benzoxaborol-5-yl)methyleneamino]-N-isobutyl-1,1-dioxo-1,2-benzothiazol-3-amine

Step A: [4-bromo-3-(hydroxymethyl)phenyl]methanol

2-Bromobenzene-1,5-dicarboxylic acid (2.00 g; 8.16 mmol; 1.00 eq.) was dissolved in THF (20 mL). Then, a solution of borane-tetrahydrofuran complex (28.57 mL; 1.00 mol/L; 28.57 mmol; 3.50 eq.) was slowly added and the reaction mixture was stirred at rt overnight. After being quenched with MeOH, THF was evaporated and EtOAc was added. The organic phase was recovered and the aqueous phase extracted once with EtOAc. Combined organic phases were washed with water and brine, dried over MgSO$_4$, filtered and concentrated to dryness to give [4-bromo-3-(hydroxymethyl)phenyl]methanol (1.00 g; 56%) as a white solid. $^1$H NMR (DMSO-d$_6$, 300 MHz): δ 7.51 (m, 1H); 7.49 (d, J=8.1 Hz, 1H); 7.13 (m, 1H); 5.41 (t, J=5.5 Hz, 1H); 5.27 (t, J=5.7 Hz, 1H); 4.49 (m, 4H).

Step B: (1-hydroxy-3H-2,1-benzoxaborol-5-yl)methanol

The compound was prepared using the same procedure detailed in example 9 step J starting from [4-bromo-3-(hydroxymethyl)phenyl]methanol (130.0 mg; 0.60 mmol; 1.00 eq.) giving (1-hydroxy-3H-2,1-benzoxaborol-5-yl)methanol (93.0 mg; 95%) as a yellow solid. $^1$H NMR (DMSO-d6, 300 MHz): δ 9.09 (s, 1H); 7.66 (d, J=7.4 Hz, 1H); 7.34 (m, 1H); 7.28 (m, 1H); 5.24 (t, J=5.8 Hz, 1H); 4.97 (s, 2H); 4.55 (d, J=5.6 Hz, 2H).

Step C: 1-hydroxy-3H-2,1-benzoxaborole-5-carbaldehyde

Celite (450.0 mg) and PCC (212.9 mg; 0.99 mmol; 1.80 eq.) were added to a solution of (1-hydroxy-3H-2,1-benzoxaborol-5-yl)methanol (90.0 mg; 0.55 mmol; 1.00 eq.) in DCM (10 mL). The reaction mixture was stirred at rt overnight, filtered and the solid washed with DCM. The filtrate was concentrated to dryness and the residue purified by column chromatography (gradient DCM/(DCM/EtOH 90/10) from 5 to 80%) to give 1-hydroxy-3H-2,1-benzoxaborole-5-carbaldehyde (54.0 mg; 61%) as a beige solid. $^1$H NMR (DMSO-d6, 300 MHz): δ 10.09 (s, 1H); 9.47 (s, 1H); 7.93 (m, 2H); 7.88 (m, 1H); 5.09 (s, 2H).

Step D: N-[(E)-(1-hydroxy-3H-2,1-benzoxaborol-5-yl)methyleneamino]-2-methyl-propan-1-amine The compound was prepared using the same procedure detailed in example 4 step A starting from 1-hydroxy-3H-2,1-benzoxaborole-5-carbaldehyde (28.0 mg; 0.17 mmol; 1.00 eq.) and 2-methylpropylhydrazine hydrochloride (21.5 g; 0.17 mmol; 1.00 eq.) giving crude N-[(E)-(1-hydroxy-3H-2,1-benzoxaborol-5-yl)methyleneamino]-2-methyl-propan-1-amine (34.0 mg; 85%) used in the next step without purification. LC-MS (Method A): Rt=1.77 min; MS: m/z=233 [M+H]$^+$.

Step E: N-[(E)-(1-hydroxy-3H-2,1-benzoxaborol-5-yl)methyleneamino]-N-isobutyl-1,1-dioxo-1,2-benzothiazol-3-amine The compound was prepared using the same procedure detailed in example 1 step C starting from 3-chloro-1,2-benzothiazole 1,1-dioxide (example 1, step A), (29.5 mg; 0.15 mmol; 1.00 eq.) and N-[(E)-(1-hydroxy-3H-2,1-benzoxaborol-5-yl)methyleneamino]-2-methyl-propan-1-amine (34.0 mg; 0.15 mmol; 1.00 eq.) giving N-[(E)-(1-hydroxy-3H-2,1-benzoxaborol-5-yl)methyleneamino]-N-isobutyl-1,1-dioxo-1,2-benzothiazol-3-amine (25.0 mg; 43%) as a beige solid. $^1$H NMR (DMSO-d6, 400 MHz): δ 9.37 (s, 1H); 8.84 (d, J=7.9 Hz, 1H); 8.63 (s, 1H); 8.10 (dd, J=0.7 Hz, J=7.5 Hz, 1H); 7.96 (m, 1H); 7.90 (m, 4H); 5.11 (s, 2H); 4.32 (d, J=7.9 Hz, 2H); 2.28 (m, 1H); 0.99 (d, J=6.6 Hz, 6H). mp: 112-196° C.

Example 24: N-[(E)-(1-hydroxy-3H-2,1-benzoxaborol-5-yl)methyleneamino]-N-(2-methoxyethyl)-1,1-dioxo-1,2-benzothiazol-3-amine The compound was prepared using the same procedure detailed in example 3 step B starting from 3-chloro-1,2-benzothiazole 1,1-dioxide (example 1, step A), (62.3 mg; 0.31 mmol; 1.00 eq.), (2-methoxyethyl)hydrazine hydrochloride (39.1 mg; 0.31 mmol; 1.00 eq.) and 1-hydroxy-3H-2,1-benzoxaborole-5-carbaldehyde (example 23, step C), (50.0 mg; 0.31 mmol; 1.00 eq.) giving N-[(E)-(1-hydroxy-3H-2,1-benzoxaborol-5-yl)methyleneamino]-N-(2-methoxyethyl)-1,1-dioxo-1,2-benzothiazol-3-amine (100.0 mg; 81%) as a beige solid. $^1$H NMR (DMSO-d$_6$, 400 MHz): δ 9.37 (br s, 1H); 8.82 (d, J=7.7 Hz, 1H); 8.68 (s, 1H); 8.10 (m, 1H); 7.91 (m, 5H); 5.11 (s, 2H); 4.61 (t, J=5.6 Hz, 2H); 3.75 (t, J=5.5 Hz, 2H); 3.30 (s, 3H). mp: 227° C.

Example 25: N-[(E)-(1-hydroxy-3H-2,1-benzoxaborol-5-yl)methyleneamino]-N-(3-methoxypropyl)-1,1-dioxo-1,2-benzothiazol-3-amine The compound was prepared using the same procedure detailed in example 3 step B starting from 3-chloro-1,2-benzothiazole 1,1-dioxide (example 1, step A), (49.8 mg; 0.25 mmol; 1.00 eq.), (3-methoxypropyl)hydrazine hydrochloride (34.7 mg; 0.25 mmol; 1.00 eq.) and 1-hydroxy-3H-2,1-benzoxaborole-5-carbaldehyde (example 23, step C), (40.0 mg; 0.25 mmol; 1.00 eq.) giving N-[(E)-(1-hydroxy-3H-2,1-benzoxaborol-5-yl)methyleneamino]-N-(3-methoxypropyl)-1,1-dioxo-1,2-benzothiazol-3-amine (20.0 mg; 20%) as a beige solid. $^1$H NMR (DMSO-d$_6$, 400 MHz): δ 9.36 (s, 1H); 8.83 (d, J=7.7 Hz, 1H); 8.58 (s, 1H); 8.10 (dd, J=0.8 Hz, J=7.4 Hz, 1H); 7.96 (m, 1H); 7.88 (m, 4H); 5.11 (s, 2H); 4.45 (t, J=7.3 Hz, 2H); 3.47 (t, J=5.9 Hz, 2H); 3.26 (s, 3H); 1.99 (m, 2H).

Example 26: N-[(E)-(1-hydroxy-3H-2,1-benzoxaborol-5-yl)methyleneamino]-N-methyl-1,1-dioxo-1,2-benzothiazol-3-amine The compound was prepared using the same procedure detailed in example 3 step B starting from 3-chloro-1,2-benzothiazole 1,1-dioxide (example 1, step A), (62.3 mg; 0.31 mmol; 1.00 eq.), methyl hydrazine (16 μL; 0.31 mmol; 1.00 eq.) and 1-hydroxy-3H-2,1-benzoxaborole-5-carbaldehyde (example 23, step C), (50.0 mg; 0.31 mmol; 1.00 eq.) giving N-[(E)-(1-hydroxy-3H-2,1-benzoxaborol-5-yl)methyleneamino]-N-methyl-1,1-dioxo-1,2-benzothiazol-3-amine (7.0 my; 6%) as a grey solid. $^1$H NMR (DMSO-d$_6$, 400 MHz): δ 9.36 (s, 1H); 8.89 (d, J=7.9 Hz, 1H); 8.54 (s, 1H); 8.10 (dd, J=0.7 Hz, J=7.5 Hz, 1H); 7.97 (m, 1H); 7.88 (m, 4H); 5.12 (s, 2H); 3.83 (s, 3H).

Example 27: N-ethyl-N-[(E)-(1-hydroxy-3H-2,1-benzoxaborol-5-yl)methyleneamino]-1,1-dioxo-1,2-benzothiazol-3-amine The compound was prepared using the same procedure detailed in example 3 step B starting from 3-chloro-1,2-benzothiazole 1,1-dioxide (example 1, step A), (62.3 mg; 0.31 mmol; 1.00 eq.), 1-ethylhydrazine hydrochloride (29.8 mg; 0.31 mmol; 1.00 eq.) and 1-hydroxy-3H-2,1-benzoxaborole-5-carbaldehyde (example 23, step C), (50.0 mg; 0.31 mmol; 1.00 eq.) giving N-ethyl-N-[(E)-(1-hydroxy-3H-2,1-benzoxaborol-5-yl)methyleneamino]-1,1-dioxo-1,2-benzothiazol-3-amine (30.0 mg; 26%) as a beige solid. $^1$H NMR (DMSO-d$_6$, 400 MHz): δ 9.36 (s, 1H); 8.83 (d, J=7.9 Hz, 1H); 8.62 (s, 1H); 8.10 (m, 1H); 7.96 (m, 1H); 7.89 (m, 4H); 5.11 (s, 2H); 4.44 (q, J=6.9 Hz, 2H); 1.31 (t, J=7.0 Hz, 3H). mp: 218° C.

Example 28: 5-fluoro-N-[(E)-(1-hydroxy-3H-2,1-benzoxaborol-5-yl)methyleneamino]-N-isobutyl-1,1-dioxo-1,2-benzothiazol-3-amine Step A: 3-chloro-5-fluoro-1,2-benzothiazole 1,1-dioxide The compound was prepared using the same procedure detailed in example 1 step A starting from 5-fluoro-1,1-dioxo-1,2-benzothiazol-3-one (100.0 mg; 0.50 mmol; 1.00 eq.) giving crude 3-chloro-5-fluoro-1,2-benzothiazole 1,1-dioxide (theo=109.2 mg), used in the next step without purification.

Step B: 5-fluoro-N-[(E)-(1-hydroxy-3H-2,1-benzoxaborol-5-yl)methyleneamino]-N-isobutyl-1,1-dioxo-1,2-benzothiazol-3-amine The compound was prepared using the same procedure detailed in example 3 step B starting from 3-chloro-5-fluoro-1,2-benzothiazole 1,1-dioxide (109.2 mg; 0.50 mmol; 1.00 eq.), 2-methylpropylhydrazine hydrochloride (62.3 mg; 0.50 mmol; 1.00 eq.) and 1-hydroxy-3H-2,1-benzoxaborole-5-carbaldehyde (example 23, step C), (81.0 mg; 0.50; 1.00 eq.) giving 5-fluoro-N-[(E)-(1-hydroxy-3H-2,1-benzoxaborol-5-yl)methyleneamino]-N-isobutyl-1,1-dioxo-1,2-benzothiazol-3-amine (85.0 mg; 41%) as a beige solid. $^1$H NMR (DMSO-ds, 400 MHz): δ 9.37 (s, 1H); 8.65 (s, 1H); 8.50 (dd, J=2.3 Hz, J=10.0 Hz, 1H); 8.20 (dd, J=5.1 Hz, J=8.4 Hz, 1H); 7.87 (m, 3H); 7.78 (m, 1H); 5.10 (s, 2H); 4.29 (d, J=7.7 Hz, 2H); 2.27 (m, 1H); 0.99 (d, J=6.6 Hz, 6H). mp: 230° C.

Example 29: N-[(E)-(1-hydroxy-3H-2,1-benzoxaborol-5-yl)methyleneamino]-N-isobutyl-5-methyl-1,1-dioxo-1,2-benzothiazol-3-amine The compound was prepared using the same procedure detailed in example 3 step B starting from 3-chloro-5-methyl-1,2-benzothiazole 1,1-dioxide (example 7, step A), (110.0 mg; 0.51 mmol; 1.00 eq.), 2-methylpropylhydrazine hydrochloride (63.6 mg; 0.51 mmol; 1.00 eq.) and 1-hydroxy-3H-2,1-benzoxaborole-5-carbaldehyde (example 23, step C), (82.6 mg; 0.51 mmol; 1.00 eq.) giving N-[(E)-(1-hydroxy-3H-2,1-benzoxaborol-5-yl)methyleneamino]-N-isobutyl-5-methyl-1,1-dioxo-1,2-benzothiazol-3-amine (53.0 mg; 25%) as a beige solid. $^1$H NMR (DMSO-d$_6$, 400 MHz): δ 9.35 (s, 1H); 8.69 (s, 1H); 8.63 (s, 1H); 7.97 (d, J=7.7 Hz, 1H); 7.91 (m, 2H); 7.86 (d, J=8.4 Hz, 1H); 7.70 (m, 1H); 5.11 (s, 2H); 4.29 (d, J=7.7 Hz, 2H); 2.53 (s, 3H); 2.27 (m, 1H); 0.98 (d, J=6.6 Hz, 6H). mp: 180° C.

Example 30: N-[(E)-(1-hydroxy-3H-2,1-benzoxaborol-5-yl)methyleneamino]-N-isobutyl-6-methoxy-1,1-dioxo-1,2-benzothiazol-3-amine Step A: 3-chloro-6-methoxy-1,2-benzothiazole 1,1-dioxide The compound was prepared using the same procedure detailed in example 1 step A starting from 6-methoxy-1,1-dioxo-1,2-benzothiazol-3-one (90.0 mg; 0.42 mmol; 1.00 eq.) giving crude 3-chloro-6-methoxy-1,2-benzothiazole 1,1-dioxide (theor.=97.8 mg), used in the next step without purification.

Step B: N-[(E)-(1-hydroxy-3H-2,1-benzoxaborol-5-yl)methyleneamino]-N-isobutyl-6-methoxy-1,1-dioxo-1,2-benzothiazol-3-amine The compound was prepared using the same procedure detailed in example 3 step B starting from 3-chloro-6-methoxy-1,2-benzothiazole 1,1-dioxide (97.8 mg; 0.42 mmol; 1.00 eq.), 2-methylpropylhydrazine hydrochloride (52.3 mg; 0.42 mmol; 1.00 eq.) and 1-hydroxy-3H-2,1-benzoxaborole-5-carbaldehyde (example 23, step C), (68.0 mg; 0.42 mmol; 1.00 eq.) giving N-[(E)-(1-hydroxy-3H-2,1-benzoxaborol-5-yl)methyleneamino]-N-isobutyl-6-methoxy-1,1-dioxo-1,2-benzothiazol-3-amine (36.0 mg; 20%) as a beige solid. $^1$H NMR (DMSO-ds, 400 MHz): δ 9.36 (br s, 1H); 8.72 (d, J=8.8 Hz, 1H); 8.59 (s, 1H); 7.88 (m, 3H); 7.66 (d, J=2.4 Hz, 1H); 7.46 (dd, J=2.4 Hz, J=9.0 Hz, 1H); 5.11 (s, 2H); 4.28 (d, J=7.9 Hz, 2H); 3.97 (s, 3H); 2.27 (m, 1H); 0.98 (d, J=6.6 Hz, 6H). mp: 168° C.

Example 31: N-[(E)-(1-hydroxy-3H-2,1-benzoxaborol-5-yl)methyleneamino]-N-isobutyl-6-methyl-1,1-dioxo-1,2-benzothiazol-3-amine Step A: 6-methyl-1,1-dioxo-1,2-benzothiazol-3-one 1,1'-bis(diphenylphosphino)ferrocene-palladium(II)dichloride dichloromethane complex (46.7 mg; 0.06 mmol; 0.05 eq.) and trimethylboroxine (240 μL; 1.72 mmol; 1.50 eq.) were added to a solution of 6-bromo-1,1-dioxo-1,2-benzothiazol-3-one (example 10, step C), (300.0 mg; 1.14 mmol; 1.00 eq.) in ethylene glycol dimethyl ether (3 mL), previously degassed with argon. A solution of K$_2$CO$_3$ (237.3 mg; 1.72 mmol; 1.50 eq.) in water (1 mL) was added and the reaction mixture was stirred 15 min at 120° C. under microwave irradiation. Then, it was filtered and the filtrate was concentrated. The residue was taken up into water and extracted twice with EtOAc. The aqueous phase was acidified with 1N HCl and extracted twice with EtOAc. Combined organic phases were dried over MgSO$_4$, filtered and concentrated under vacuum to give 6-methyl-1,1-dioxo-1,2-benzothiazol-3-one (theor.=225.7 mg) as a brown powder, used in the next step without purification. $^1$H NMR (DMSO-d$_6$, 300 MHz): δ 7.99 (m, 1H); 7.88 (d, J=7.9 Hz, 1H); 7.73 (m, 1H); 2.52 (s, 3H).

Step B: 3-chloro-6-methyl-1,2-benzothiazole 1,1-dioxide

The compound was prepared using the same procedure detailed in example 1 step A starting from 6-methyl-1,1-dioxo-1,2-benzothiazol-3-one (224.8 mg; 1.14 mmol; 1.00 eq.) giving crude 3-chloro-6-methyl-1,2-benzothiazole 1,1-dioxide (theo=245.8 mg), used in the next step without purification.

Step C: N-[(E)-(1-hydroxy-3H-2,1-benzoxaborol-5-yl)methyleneamino]-N-isobutyl-6-methyl-1,1-dioxo-1,2-benzothiazol-3-amine The compound was prepared using the same procedure detailed in example 3 step B starting from 3-chloro-6-methyl-1,2-benzothiazole 1,1-dioxide (245.8 mg; 1.14 mmol; 1.00 eq.), 2-methylpropylhydrazine hydrochloride (113.7 mg; 0.91 mmol; 0.80 eq.) and 1-hydroxy-3H-2,1-benzoxaborole-5-carbaldehyde (example 23, step C), (147.7 mg; 0.91 mmol; 0.80 eq.) giving N-[(E)-(1-hydroxy-3H-2,1-benzoxaborol-5-yl)methyleneamino]-N-isobutyl-6-methyl-1,1-dioxo-1,2-benzothiazol-3-amine (24.0 mg; 5%) as a beige solid. $^1$H NMR (DMSO-d$_6$, 400 MHz): δ 9.36 (s, 1H); 8.69 (d, J=8.1 Hz, 1H); 8.60 (s, 1H); 7.92 (m, 1H); 7.88 (m, 3H); 7.76 (m, 1H); 5.11 (s, 2H); 4.29 (d, J=7.7 Hz, 2H); 2.52 (s, 3H); 2.27 (m, 1H); 0.98 (d, J=6.8 Hz, 6H). mp: 182° C.

Example 32: N-[(E)-(1-hydroxy-3H-2,1-benzoxaborol-5-yl)methyleneamino]-N-isobutyl-8-methoxy-quinazolin-4-amine The compound was prepared using the same procedure detailed in example 3 step B starting from 4-chloro-8-methoxyquinazoline (200.0 mg; 1.03 mmol; 1.00 eq.), 2-methylpropylhydrazine hydrochloride (128.1 mg; 1.03 mmol; 1.00 eq.) and 1-hydroxy-3H-2,1-benzoxaborole-5-carbaldehyde (example 23, step C), (166.4 mg; 1.03 mmol; 1.00 eq.) giving N-[(E)-(1-hydroxy-3H-2,1-benzoxaborol-5-yl)methyleneamino]-N-isobutyl-8-methoxy-quinazolin-4-amine (33.0 mg; 8%) as a yellow solid. $^1$H NMR (DMSO-d$_6$, 400 MHz): δ 9.26 (s, 1H); 8.73 (s, 1H); 8.50 (dd, J=0.9 Hz, J=8.8 Hz, 1H); 8.31 (s, 1H); 7.78 (m, 3H); 7.53 (m, 1H); 7.34 (m, 1H); 5.05 (s, 2H); 4.46 (d, J=7.7 Hz, 2H); 3.95 (s, 3H); 2.31 (m, 1H); 0.96 (d, J=6.6 Hz, 6H).

Example 33: N-[(E)-(1-hydroxy-3H-2,1-benzoxaborol-5-yl)methyleneamino]-8-methoxy-N-methyl-quinazolin-4-amine The compound was prepared using the same procedure detailed in example 3 step B starting from 4-chloro-8-methoxyquinazoline (200.0 mg; 1.03 mmol; 1.00 eq.), methyl hydrazine (55 μL; 1.03 mmol; 1.00 eq.) and 1-hydroxy-3H-2,1-benzoxaborole-5-carbaldehyde (example 23, step C), (166.4 mg; 1.03 mmol; 1.00 eq.) giving N-[(E)-(1-hydroxy-3H-2,1-benzoxaborol-5-yl)methyleneamino]-8-methoxy-N-methyl-quinazolin-4-amine (171.4 mg; 48%) as a yellow solid. $^1$H NMR (DMSO-d$_6$, 400 MHz): δ 8.91 (s, 1H); 8.81 (d, J=8.8 Hz, 1H); 8.69 (m, 1H); 7.86 (m, 4H); 7.68 (d, J=7.9 Hz, 1H); 5.11 (s, 2H); 4.09 (s, 3H); 4.03 (m, 3H).

Example 34: N-ethyl-N-[(E)-(1-hydroxy-3H-2,1-benzoxaborol-5-yl)methyleneamino]-8-methoxy-quinazolin-4-amine The compound was prepared using the same procedure detailed in example 3 step B starting from 4-chloro-8-methoxyquinazoline (200.0 mg; 1.03 mmol; 1.00 eq.), ethylhydrazine dihydrochloride (136.7 mg; 1.03 mmol; 1.00 eq.) and 1-hydroxy-3H-2,1-benzoxaborole-5-carbaldehyde (example 23, step C), (166.4 mg; 1.03 mmol; 1.00 eq.) giving N-ethyl-N-[(E)-(1-hydroxy-3H-2,1-benzoxaborol-5-yl)methyleneamino]-8-methoxy-quinazolin-4-amine (158.8 mg; 43%) as a yellow solid. $^1$H NMR (DMSO-d$_6$, 400 MHz): δ 9.42 (br s, 1H); 8.95 (s, 1H); 8.78 (s, 1H); 8.73 (d, J=9.5 Hz, 1H); 7.90 (m, 3H); 7.80 (m, 1H); 7.68 (d, J=8.1 Hz, 1H); 5.10 (s, 2H); 4.72 (q, J=6.8 Hz, 2H); 4.09 (s, 3H); 1.34 (t, J=7.0 Hz, 3H).

Example 35: N-[(E)-(1-hydroxy-3H-2,1-benzoxaborol-5-yl)methyleneamino]-N-isobutyl-thieno[3,2-d]pyrimidin-4-amine The compound was prepared using the same procedure detailed in example 3 step B starting from 4-chlorothieno[3,2-d]pyrimidine (100.0 mg; 0.59 mmol; 1.00 eq.), 2-methylpropylhydrazine hydrochloride (73.0 mg; 0.59 mmol; 1.00 eq.) and 1-hydroxy-3H-2,1-benzoxaborole-5-carbaldehyde (example 23, step C), (94.9 mg; 0.59 mmol; 1.00 eq.) giving N-[(E)-(1-hydroxy-3H-2,1-benzoxaborol-5-yl)methyleneamino]-N-isobutyl-thieno[3,2-d]pyrimidin-4-amine (10.2 mg; 5%) as a white solid. $^1$H NMR (DMSO-d$_6$, 400 MHz): δ 9.31 (s, 1H); 8.67 (s, 1H); 8.34 (m, 2H); 8.01 (d, J=7.7 Hz, 1H); 7.97 (s, 1H); 7.86 (d, J=7.7 Hz, 1H); 7.50 (d, J=5.7 Hz, 1H); 5.10 (s, 2H); 4.42 (br d, J=7.3 Hz, 2H); 2.28 (m, 1H); 0.95 (d, J=6.6 Hz, 6H).

Example 36: N-[(E)-(1-hydroxy-3H-2,1-benzoxaborol-5-yl)methyleneamino]-N,5-dimethyl-1,1-dioxo-1,2-benzothiazol-3-amine The compound was prepared using the same procedure detailed in example 3 step B starting from 3-chloro-5-methyl-1,2-benzothiazole 1,1-dioxide (example 7, step A), (109.0 mg; 0.51 mmol; 1.00 eq.), methyl hydrazine (27 μL; 0.51 mmol; 1.00 eq.) and 1-hydroxy-3H-2,1-benzoxaborole-5-carbaldehyde (example 23, step C), (81.9 mg; 0.51 mmol; 1.00 eq.) giving N-[(E)-(1-hydroxy-3H-2,1-benzoxaborol-5-yl)methyleneamino]-N,5-dimethyl-1,1-dioxo-1,2-benzothiazol-3-amine (46.0 mg; 25%) as a beige solid. $^1$H NMR (DMSO-d$_6$, 400 MHz): δ 9.39 (s, 1H); 8.71 (s, 1H); 8.52 (s, 1H); 7.97 (d, J=7.7 Hz, 1H); 7.90 (d, J=7.7 Hz, 1H); 7.88 (s, 1H); 7.84 (d, J=7.7 Hz, 1H); 7.71 (dd, J=0.7 Hz, J=7.7 Hz, 1H); 5.11 (s, 2H); 3.80 (s, 3H); 2.54 (s, 3H). mp: 260° C.

Example 37: N-[(E)-(1-hydroxy-3H-2,1-benzoxaborol-5-yl)methyleneamino]-5-methoxy-N-methyl-1,1-dioxo-1,2-benzothiazol-3-amine The compound was prepared using the same procedure detailed in example 3 step B starting from 3-chloro-5-methoxy-1,2-benzothiazole 1,1-dioxide (example 2, step A), (217.0 mg; 0.94 mmol; 1.00 eq.), methyl hydrazine (50 μL; 0.94 mmol; 1.00 eq.) and 1-hydroxy-3H-2,1-benzoxaborole-5-carbaldehyde (example 23, step C), (151.2 mg; 0.94 mmol; 1.00 eq.) giving N-[(E)-(1-hydroxy-3H-2,1-benzoxaborol-5-yl)methyleneamino]-5-methoxy-N-methyl-1,1-dioxo-1,2-benzothiazol-3-amine (17.0 mg; 5%) as a beige solid. $^1$H NMR (DMSO-d$_6$, 400 MHz): δ 9.35 (s, 1H); 8.54 (s, 1H); 8.41 (d, J=2.4 Hz, 1H); 7.99 (d, J=8.6 Hz, 1H); 7.87 (m, 3H); 7.39 (dd, J=2.3 Hz, J=8.5 Hz, 1H); 5.07 (s, 2H); 3.97 (s, 3H); 3.81 (s, 3H).

Example 38: N-ethyl-N-[(E)-(1-hydroxy-3H-2,1-benzoxaborol-5-yl)methyleneamino]-thieno[3,2-d]pyrimidin-4-amine The compound was prepared using the same procedure detailed in example 3 step B starting from 4-chlorothieno[3,2-d]pyrimidine (100.0 mg; 0.59 mmol; 1.00 eq.), ethylhydrazine dihydrochloride (78.0 mg; 0.59 mmol; 1.00 eq.) and 1-hydroxy-3H-2,1-benzoxaborole-5-carbaldehyde (example 23, step C), (94.9 mg; 0.59 mmol; 1.00 eq.) giving N-ethyl-N-[(E)-(1-hydroxy-3H-2,1-benzoxaborol-5-yl)methyleneamino]thieno[3,2-d]pyrimidin-4-amine (100.9 mg; 51%) as a white solid. $^1$H NMR (DMSO-$d_6$, 400 MHz): δ 9.36 (s, 1H); 8.69 (s, 1H); 8.32 (m, 2H); 7.99 (d, J=7.7 Hz, 1H); 7.95 (s, 1H); 7.86 (d, J=7.5 Hz, 1H); 7.49 (d, J=5.7 Hz, 1H); 5.10 (s, 2H); 4.54 (q, J=7.1 Hz, 2H); 1.24 (t, J=6.9 Hz, 3H).

Example 39: N-ethyl-N-[(E)-(1-hydroxy-3H-2,1-benzoxaborol-5-yl)methyleneamino]-7H-pyrrolo[2,3-d]pyrimidin-4-amine The compound was prepared using the same procedure detailed in example 3 step B starting from 4-chloro-4,7-diazaindole (100.0 mg; 0.65 mmol; 1.00 eq.), ethylhydrazine dihydrochloride (86.6 mg; 0.65 mmol; 1.00 eq.) and 1-hydroxy-3H-2,1-benzoxaborole-5-carbaldehyde (example 23, step C), (105.5 mg; 0.65 mmol; 1.00 eq.) giving N-ethyl-N-[(E)-(1-hydroxy-3H-2,1-benzoxaborol-5-yl)methyleneamino]-7H-pyrrolo[2,3-d]pyrimidin-4-amine (95.0 mg; 45%) as a beige solid. $^1$H NMR (DMSO-$d_s$, 400 MHz): δ 11.87 (br s, 1H); 9.27 (s, 1H); 8.36 (s, 1H); 8.22 (s, 1H); 7.82 (m, 3H); 7.34 (m, 1H); 7.08 (dd, J=2.0 Hz, J=3.3 Hz, 1H); 5.09 (s, 2H); 4.53 (d, J=7.0 Hz, 2H); 1.23 (t, J=6.9 Hz, 3H). mp: 245° C.

Example 40: N-ethyl-N-[(E)-(1-hydroxy-3H-2,1-benzoxaborol-5-yl)methyleneamino]-thieno[2,3-d]pyrimidin-4-amine The compound was prepared using the same procedure detailed in example 3 step B starting from 4-chlorothieno[2,3-d]pyrimidine (100.0 mg; 0.59 mmol; 1.00 eq.), ethylhydrazine dihydrochloride (78.0 mg; 0.59 mmol; 1.00 eq.) and 1-hydroxy-3H-2,1-benzoxaborole-5-carbaldehyde (example 23, step C), (94.9 mg; 0.59 mmol; 1.00 eq.) giving N-ethyl-N-[(E)-(1-hydroxy-3H-2,1-benzoxaborol-5-yl)methyleneamino]thieno[2,3-d]pyrimidin-4-amine (100.0 mg; 50%) as a grey solid. $^1$H NMR (DMSO-$d_6$, 400 MHz): δ 9.30 (s, 1H); 8.63 (s, 1H); 8.35 (s, 1H); 8.21 (d, J=6.2 Hz, 1H); 7.85 (d, J=8.1 Hz, 1H); 7.80 (m, 2H); 7.77 (d, J=5.9 Hz, 1H); 5.09 (s, 2H); 4.56 (q, J=6.9 Hz, 2H); 1.25 (t, J=7.0 Hz, 3H). mp: 251° C.

Example 41: N-ethyl-N-[(E)-(1-hydroxy-3H-2,1-benzoxaborol-5-yl)methyleneamino]-1-methyl-pyrazolo[3,4-d]pyrimidin-4-amine The compound was prepared using the same procedure detailed in example 3 step B starting from 4-chloro-1-methyl-1H-pyrazolo[3,4-d]pyrimidine (100.0 mg; 0.59 mmol; 1.00 eq.), ethylhydrazine dihydrochloride (79.0 mg; 0.59 mmol; 1.00 eq.) and 1-hydroxy-3H-2,1-benzoxaborole-5-carbaldehyde (example 23, step C), (96.1 mg; 0.59 mmol; 1.00 eq.) giving N-ethyl-N-[(E)-(1-hydroxy-3H-2,1-benzoxaborol-5-yl)methyleneamino]-1-methyl-pyrazolo[3,4-d]pyrimidin-4-amine (48.8 mg; 24%) as a pale yellow solid. $^1$H NMR (DMSO-$d_6$, 500 MHz): δ 9.30 (s, 1H); 8.53 (s, 1H); 8.43 (s, 1H); 8.41 (m, 1H); 7.86 (m, 3H); 5.10 (s, 2H); 4.54 (q, J=6.8 Hz, 2H); 3.99 (s, 3H); 1.23 (t, J=6.9 Hz, 3H).

Example 42: N-ethyl-N-[(E)-(1-hydroxy-3H-2,1-benzoxaborol-5-yl)methyleneamino]-7-methyl-thieno[3,2-d]pyrimidin-4-amine The compound was prepared using the same procedure detailed in example 3 step B starting from 4-chloro-7-methylthieno[3,2-d]pyrimidine (100.0 mg; 0.54 mmol; 1.00 eq.), ethylhydrazine dihydrochloride (72.0 mg: 0.54 mmol: 1.00 eq.) and 1-hydroxy-3H-2,1-benzoxaborole-5-carbaldehyde (example 23, step C), (87.7 mg; 0.54 mmol; 1.00 eq.) giving N-ethyl-N-[(E)-(1-hydroxy-3H-2,1-benzoxaborol-5-yl)methyleneamino]-7-methyl-thieno[3,2-d]pyrimidin-4-amine (31.7 mg; 17%) as a white solid. $^1$H NMR (DMSO-$d_6$, 500 MHz): δ 9.29 (s, 1H); 8.72 (s, 1H); 8.31 (s, 1H); 8.00 (br d, J=7.7 Hz, 1H); 7.97 (s, 1H); 7.95 (s, 1H); 7.86 (d, J=7.7 Hz, 1H); 5.10 (s, 2H); 4.55 (q, J=6.6 Hz, 2H); 2.39 (s, 3H); 1.24 (t, J=6.9 Hz, 3H).

Example 43: N-ethyl-N-[(E)-(1-hydroxy-3H-2,1-benzoxaborol-5-yl)methyleneamino]furo[2,3-d]pyrimidin-4-amine The compound was prepared using the same procedure detailed in example 3 step B starting from 4-chlorofuro[2,3-d]pyrimidine (100.0 mg; 0.65 mmol; 1.00 eq.), ethylhydrazine dihydrochloride (86.1 mg; 0.65 mmol; 1.00 eq.) and 1-hydroxy-3H-2,1-benzoxaborole-5-carbaldehyde (example 23, step C), (104.8 mg; 0.65 mmol; 1.00 eq.) giving N-ethyl-N-[(E)-(1-hydroxy-3H-2,1-benzoxaborol-5-yl)methyleneamino]furo[2,3-d] pyrimidin-4-amine (30.0 mg; 14%) as a white solid. $^1$H NMR (DMSO-$d_6$, 400 MHz): 9.29 (s, 1H); 8.52 (s, 1H); 8.33 (s, 1H); 8.01 (d, J=2.4 Hz, 1H); 7.83 (m, 3H); 7.40 (d, J=2.2 Hz, 1H); 5.09 (s, 2H); 4.53 (q, J=7.1 Hz, 2H); 1.23 (t, J=7.0 Hz, 3H). mp: 225° C.

Example 44: N-ethyl-N-[(E)-(1-hydroxy-3H-2,1-benzoxaborol-5-yl)methyleneamino]-7-methyl-pyrrolo[2,3-d]pyrimidin-4-amine The compound was prepared using the same procedure detailed in example 3 step B starting from 4-chloro-7-methyl-7H-pyrrolo[2,3-d]pyrimidine (103.5 mg; 0.62 mmol; 1.00 eq.), ethylhydrazine dihydrochloride (82.1 mg; 0.62 mmol; 1.00 eq.) and 1-hydroxy-3H-2,1-benzoxaborole-5-carbaldehyde (example 23, step C), (100.0 mg; 0.62 mmol; 1.00 eq.) giving N-ethyl-N-[(E)-(1-hydroxy-3H-2,1-benzoxaborol-5-yl)methyleneamino]-7-methyl-pyrrolo[2,3-d]pyrimidin-4-amine (56.1 mg; 27%) as a white solid. $^1$H NMR (DMSO-$d_6$, 400 MHz): δ 9.26 (s, 1H); 8.40 (s, 1H); 8.23 (s, 1H); 7.83 (m, 2H); 7.80 (s, 1H); 7.38 (d, J=3.5 Hz, 1H); 7.07 (d, J=3.3 Hz, 1H); 5.08 (s, 2H); 4.53 (q, J=7.0 Hz, 2H); 3.79 (s, 3H); 1.22 (t, J=6.9 Hz, 3H).

Example 45: N-ethyl-N-[(E)-(1-hydroxy-3H-2,1-benzoxaborol-5-yl)methyleneamino]-2-methyl-thieno[3,2-d]pyrimidin-4-amine The compound was prepared using the same procedure detailed in example 3 step B, starting from 4-chloro-2-methylthieno[3,2-d]pyrimidine (114.0 mg; 0.62 mmol; 1.00 eq.), ethylhydrazine dihydrochloride (82.1 mg; 0.62 mmol; 1.00 eq.) and 1-hydroxy-3H-2,1-benzoxaborole-5-carbaldehyde (example 23, step C), (100.0 mg; 0.62 mmol; 1.00 eq.), (with hydrazone formation 10 min under microwave irradiation at 80° C. then coupling 1 h under microwave irradiation at 120° C.) giving N-ethyl-N-[(E)-(1-hydroxy-3H-2,1-benzoxaborol-5-yl)methyleneamino]-2-methyl-thieno[3,2-d]pyrimidin-4-amine (66.3 mg; 30%) as a beige solid. $^1$H NMR (DMSO-dc, 400 MHz): δ 9.29 (s, 1H); 8.30 (s, 1H); 8.27 (d, J=5.5 Hz, 1H); 7.99 (d, J=7.7 Hz, 1H); 7.95 (s, 1H); 7.85 (d, J=7.7 Hz, 1H); 7.40 (d, J=5.7 Hz, 1H); 5.10 (s, 2H); 4.55 (q, J=6.8 Hz, 2H); 2.59 (s, 3H); 1.23 (t, J=7.0 Hz, 3H).

Example 46: N-[(E)-(1-hydroxy-3,4-dihydro-2,1-benzoxaborinin-6-yl)methyleneamino]-N-isobutyl-1,1-dioxo-1,2-benzothiazol-3-amine Step A: methyl 4-bromo-3-(bromomethyl)benzoate Methyl 4-bromo-3-methylbenzoate (3.00 g; 13.10 mmol; 1.00 eq.) was dissolved in chloroform (12 mL). NBS (2.45 g; 13.77 mmol; 1.05 eq.) and azoisobutyronitrile (0.21 g; 1.31 mmol; 0.10 eq.) were added, and the mixture was refluxed for 24 h. Then, additional NBS (1.23 g; 6.91 mmol; 0.53 eq.) and azoisobutyronitrile (0.11 g; 0.66 mmol; 0.05 eq.) were added and the reaction was further heated under reflux for 16 h. After being cooled to rt, the reaction was filtered and the solid was washed with chloroform. The filtrate was concentrated and the residue purified by column chromatography (gradient 0 to 10% of EtOAc in cyclohexane) giving a white solid containing 60% of product and 40% of dibrominated by-product. The solid was then dissolved in THF (50 mL) and treated with DIPEA (1.73 mL; 10.48 mmol; 2.00 eq.) and diethyl phosphite (1.35 mL; 10.48 mmol; 2.00 eq.) in order to reduce the dibromo by-product. The reaction mixture was stirred 1 h at 0° C. and then 15 h at rt. It was filtered and the solid washed with THF. The filtrate was concentrated and the residue taken up into EtOAc. The resulting organic phase was washed with water and the aqueous phase was extracted twice with EtOAc. Combined organic phases were washed with brine, dried over MgSO$_4$, filtered and concentrated. The residue was purified by column chromatography (gradient 0 to 10% of EtOAc in cyclohexane) to give methyl 4-bromo-3-(bromomethyl)benzoate (3.43 g; 85%) as a white solid. $^1$H NMR (CDCl$_3$, 300 MHz): δ 8.12 (d, J=2.1 Hz, 1H); 7.82 (dd, J=2.1 Hz, J=8.4 Hz, 1H); 7.67 (d, J=8.4 Hz, 1H); 4.62 (s, 2H); 3.92 (s, 3H).

Step B: methyl 4-bromo-3-(cyanomethyl)benzoate

Methyl 4-bromo-3-(bromomethyl)benzoate (3.40 g; 11.04 mmol; 1.00 eq.) was dissolved in MeOH (18 mL) then potassium cyanide (0.72 g; 11.04 mmol; 1.00 eq.) and water (0.60 mL) were added. The reaction mixture was heated under reflux overnight. After being cooled to rt, saturated aqueous NaHCO$_3$ solution and MeOH were added. MeOH was then removed and the resulting aqueous solution was extracted with EtOAc. The organic phase was washed with water twice and brine, dried over MgSO$_4$, filtered and concentrated. The residue was taken up into MeOH (50 mL) and the obtained precipitate was filtered and dried to give methyl 4-bromo-3-(cyanomethyl)benzoate (1.66 g; 54%) as a white solid. $^1$H NMR (CDCl$_3$, 300 MHz): δ 8.18 (d, J=2.1 Hz, 1H); 7.89 (dd, J=2.1 Hz, J=8.3 Hz, 1H); 7.71 (d, J=8.3 Hz, 1H); 3.94 (s, 3H); 3.89 (s, 2H).

Step C: 4-bromo-3-(carboxymethyl)benzoic acid

Methyl 4-bromo-3-(cyanomethyl)benzoate (1.66 g; 6.01 mmol; 1.00 eq.) was suspended in MeOH (12 mL) and a solution of KOH (1.20 g; 21.39 mmol; 3.56 eq.) in water (12 mL) was added. The reaction mixture was then stirred 15 h under reflux, cooled to rt and poured onto a mixture of ice (15 mL) and aqueous 5% NaOH solution (15 mL). The resulting aqueous solution was acidified with conc. HCl until pH=1-2 and the obtained precipitate was filtered and dried under vacuum at 50° C. to give 4-bromo-3-(carboxymethyl)benzoic acid (1.71 g; quantitative) as a white solid. $^1$H NMR (DMSO-d$_6$, 300 MHz): δ 7.96 (s, 1H); 7.72 (m, 2H); 3.82 (s, 2H).

Step D: 2-[2-bromo-5-(hydroxymethyl)phenyl]ethanol

The compound was prepared using the same procedure detailed in example 23 step A starting from 4-bromo-3-(carboxymethyl)benzoic acid (1.56 g; 6.01 mmol; 1.00 eq.) giving 2-[2-bromo-5-(hydroxymethyl)phenyl]ethanol (1.05 g; 76%) as a white solid. $^1$H NMR (DMSO-d6, 300 MHz): δ 7.50 (d, J=8.1 Hz, 1H); 7.28 (d, J=2.0 Hz, 1H); 7.09 (dd, J=2.1 Hz, J=8.1 Hz, 1H); 5.23 (t, J=5.7 Hz, 1H); 4.74 (t, J=5.4 Hz, 1H); 4.44 (d, J=5.6 Hz, 2H); 3.59 (dt, J=5.4 Hz, J=7.1 Hz, 2H); 2.84 (t, J=7.2 Hz, 2H).

Step E: (1-hydroxy-3,4-dihydro-2,1-benzoxaborinin-6-yl)methanol

The compound was prepared using the same procedure detailed in example 9 step J starting from 2-[2-bromo-5-(hydroxymethyl)phenyl]ethanol (150.0 mg; 0.65 mmol; 1.00 eq.) giving (1-hydroxy-3,4-dihydro-2,1-benzoxaborinin-6-yl)methanol (115.5 mg) as a yellow oil, used in the next step without purification. $^1$H NMR (DMSO-d6, 300 MHz): δ 8.35 (s, 1H); 7.63 (d, J=7.4 Hz, 1H); 7.17 (m, 2H); 5.18 (t, J=5.8 Hz, 1H); 4.49 (d, J=5.6 Hz, 2H); 4.05 (t, J=5.9 Hz, 2H); 2.84 (t, J=5.9 Hz, 2H).

Step F: 1-hydroxy-3,4-dihydro-2,1-benzoxaborinine-6-carbaldehyde

The compound was prepared using the same procedure detailed in example 23 step C starting from (1-hydroxy-3,4-dihydro-2,1-benzoxaborinin-6-yl)methanol (115.5 mg; 0.65 mmol; 1.00 eq.) giving 1-hydroxy-3,4-dihydro-2,1-benzoxaborinine-6-carbaldehyde (72.0 mg; 63%) as a beige solid. $^1$H NMR (DMSO-d6, 300 MHz): δ 10.02 (s, 1H); 8.73 (s, 1H); 7.88 (d, J=7.3 Hz, 1H); 7.76 (m, 2H); 4.11 (t, J=5.9 Hz, 2H); 2.98 (t, J=5.7 Hz, 2H).

Step G: N-[(E)-(1-hydroxy-3,4-dihydro-2,1-benzoxaborinin-6-yl)methyleneamino]-N-isobutyl-1,1-dioxo-1,2-benzothiazol-3-amine The compound was prepared using the same procedure detailed in example 3 step B, starting from 3-chloro-1,2-benzothiazole 1,1-dioxide (example 1, step A), (70.0 mg; 0.35 mmol; 0.90 eq.), 2-methylpropylhydrazine hydrochloride (48.1 mg; 0.39 mmol; 1.00 eq.) and 1-hydroxy-3,4-dihydro-2,1-benzoxaborinine-6-carbaldehyde (70.0 mg; 0.39 mmol; 1.00 eq.), (with hydrazone formation 10 min under microwave irradiation at 80° C. then coupling 1 h under reflux) giving N-[(E)-(1-hydroxy-3,4-dihydro-2,1-benzoxaborinin-6-yl)methyleneamino]-N-isobutyl-1,1-dioxo-1,2-benzothiazol-3-amine (60.0 mg; 38%) as a white solid. $^1$H NMR (DMSO-d$_6$, 400 MHz): & 8.85 (d, J=7.9 Hz, 1H); 8.62 (s, 1H); 8.56 (s, 1H); 8.10 (m, 1H); 7.95 (m, 1H); 7.90 (m, 1H); 7.85 (d, J=7.7 Hz, 1H); 7.78 (dd, J=1.3 Hz, J=7.7 Hz, 1H); 7.71 (s, 1H); 4.30 (d, J=7.7 Hz, 2H); 4.13 (t, J=5.9 Hz, 2H); 2.99 (t, J=5.8 Hz, 2H); 2.27 (m, 1H); 0.98 (d, J=6.8 Hz, 6H). mp: 194° C.

Example 47: N-[(E)-(1-hydroxy-4,5-dihydro-3H-2, 1-benzoxaborepin-7-yl)methyleneamino]-N-isobutyl-1,1-dioxo-1,2-benzothiazol-3-amine Step A: methyl 4-bromo-3-[(E)-3-ethoxy-3-oxo-prop-1-enyl]benzoate Triethyl phosphonoacetate (898 μL; 4.53 mmol; 1.10 eq.) was introduced into a round-bottomed flask. Then, $K_2CO_3$ (1.25 g; 9.05 mmol; 2.20 eq.) finely grounded was added followed by 1,8-diazabicyclo(5.4.0)undec-7-ene (135 μL; 0.91 mmol; 0.22 eq.) and methyl 4-bromo-3-formylbenzoate (1.00 g; 4.11 mmol; 1.00 eq.). After 30 min, the reaction mixture solidified and it was left at rt overnight. The mixture was then diluted with EtOAc and water. The organic phase was recovered and the aqueous one extracted twice with EtOAc. Combined organic phases were dried over $MgSO_4$, filtered and concentrated. The residue was purified by column chromatography (gradient 0 to 20% of EtOAc in cyclohexane) to give methyl 4-bromo-3-[(E)-3-ethoxy-3-oxo-prop-1-enyl]benzoate (1.11 g; 86%) as a pink solid. $^1$H NMR ($CDCl_3$, 300 MHz): δ 8.32 (d, J=1.7 Hz, 1H); 7.57 (m, 3H); 6.74 (d, J=16.0 Hz, 1H); 4.23 (q, J=7.1 Hz, 2H); 3.88 (s, 3H); 1.28 (t, J=7.1 Hz, 3H).

Step B: methyl 4-bromo-3-(3-ethoxy-3-oxo-propyl)benzoate

Benzenesulfonyl hydrazide (1.56 g; 9.04 mmol; 3.00 eq.) was added to a solution of 4-bromo-3-[(E)-3-ethoxy-3-oxo-prop-1-enyl]benzoate (944.0 mg; 3.01 mmol; 1.00 eq.) in toluene (30 mL). The reaction was stirred under reflux overnight, then cooled to rt and diluted with EtOAc. The resulting organic solution was washed with 1 N NaOH, water and brine, dried over $MgSO_4$, filtered and concentrated. The residue was first purified by column chromatography (gradient 0 to 10% of EtOAc in cyclohexane) and then by LCMS-Preparative (Column: Kinetex C18, 30×150 mm 5 μm (phenomenex); Flow rate: 42 ml/min; Elution: $H_2O$, 0.1% HCOOH/ACN, 0.1% HCOOH; Gradient: 10 to 100% ACN over 20 minutes) to give methyl 4-bromo-3-(3-ethoxy-3-oxo-propyl)benzoate (499.7 mg; 53%) as a pale yellow oil. H NMR (300 MHz, DMSO-d6) δ 7.91 (d, J=2.0 Hz, 1H); 7.76 (d, J=8.3 Hz, 1H); 7.72 (dd, J=2.0 Hz, J=8.3 Hz, 1H); 4.05 (q, J=7.1 Hz, 2H); 3.85 (s, 3H); 3.02 (t, J=7.4 Hz, 2H); 2.65 (t, J=7.4 Hz, 2H); 1.16 (t, J=7.1 Hz, 3H).

Step C: 4-bromo-3-(2-carboxyethyl)benzoic acid

Lithium hydroxide (111.7 mg; 4.66 mmol; 3.00 eq.) was added to a solution of methyl 4-bromo-3-(3-ethoxy-3-oxo-propyl)benzoate (490.0 mg; 1.55 mmol; 1.00 eq.) in THF (12 mL) and water (4 mL). The reaction was then stirred 2 h at rt then THF was evaporated and the residue was diluted with water. The pH was adjusted to 1 with 1N HCl and the precipitate obtained was filtered, washed with water and dried under vacuum to give 4-bromo-3-(2-carboxyethyl)benzoic acid (374.7 mg; 71%) as a white solid. $^1$H NMR (300 MHz, DMSO-d6) δ 7.89 (m, 1H); 7.72 (m, 2H); 2.98 (t, J=7.6 Hz, 2H); 2.58 (t, J=7.6 Hz, 2H).

Step D: 3-[2-bromo-5-(hydroxymethyl)phenyl]propan-1-ol

The compound was prepared using the same procedure detailed in example 23 step A starting from 4-bromo-3-(2-carboxyethyl)benzoic acid (374.7 mg; 1.10 mmol; 1.00 eq.) giving 3-[2-bromo-5-(hydroxymethyl)phenyl]propan-1-ol (222.2 mg; 83%) as a colorless oil. $^1$H NMR (DMSO-d6, 300 MHz): δ 7.50 (d, J=8.1 Hz, 1H); 7.26 (d, J=2.0 Hz, 1H); 7.07 (dd, J=2.2 Hz, J=8.2 Hz, 1H); 5.23 (t, J=5.8 Hz, 1H); 4.52 (t, J=5.1 Hz, 1H); 4.44 (d, J=5.6 Hz, 2H); 3.44 (dt, J=5.1 Hz, J=6.4 Hz, 2H); 2.70 (m, 2H); 1.70 (m, 2H).

Step E: (1-hydroxy-4,5-dihydro-3H-2,1-benzoxaborepin-7-yl)methanol

The compound was prepared using the same procedure detailed in example 9 step J starting from 3-[2-bromo-5-(hydroxymethyl)phenyl]propan-1-ol (220.0 mg; 0.90 mmol; 1.00 eq.) giving (1-hydroxy-4,5-dihydro-3H-2,1-benzoxaborepin-7-yl)methanol (199.1 mg; quantitative) as a beige solid. $^1$H NMR (DMSO-d6, 300 MHz): δ 8.34 (s, 1H); 7.48 (d, J=7.4 Hz, 1H); 7.13 (m, 2H); 5.15 (t, J=5.7 Hz, 1H); 4.48 (d, J=5.8 Hz, 2H); 3.74 (t, J=6.0 Hz, 2H); 2.77 (t, J=6.9 Hz, 2H); 1.93 (quint, J=6.5 Hz, 2H).

Step F: 1-hydroxy-4,5-dihydro-3H-2,1-benzoxaborepine-7-carbaldehyde

The compound was prepared using the same procedure detailed in example 23 step C starting from (1-hydroxy-4,5-dihydro-3H-2,1-benzoxaborepin-7-yl)methanol (170.0 mg; 0.89 mmol; 1.00 eq.) giving 1-hydroxy-4,5-dihydro-3H-2,1-benzoxaborepine-7-carbaldehyde (123.4 mg; 73%) as a brown oil. $^1$H NMR (DMSO-d6, 300 MHz): δ 10.01 (s, 1H); 8.74 (s, 1H); 7.75 (dd, J=1.3 Hz, J=7.4 Hz, 1H); 7.72 (m, 1H); 7.69 (m, 1H); 3.74 (t, J=6.1 Hz, 2H); 2.88 (t, J=7.1 Hz, 2H); 1.97 (quint., J=6.8 Hz, 2H).

Step G: N-[(E)-(1-hydroxy-4,5-dihydro-3H-2,1-benzoxaborepin-7-yl)methyleneamino]-N-isobutyl-1,1-dioxo-1,2-benzothiazol-3-amine The compound was prepared using the same procedure detailed in example 3 step B, starting from 3-chloro-1,2-benzothiazole 1,1-dioxide (example 1, step A), (114.6 mg; 0.57 mmol; 0.90 eq.), 2-methylpropylhydrazine hydrochloride (86.6 mg; 0.69 mmol; 1.10 eq.) and 1-hydroxy-4,5-dihydro-3H-2,1-benzoxaborepine-7-carbaldehyde (120.0 mg; 0.63 mmol; 1.00 eq.) giving N-[(E)-(1-hydroxy-4,5-dihydro-3H-2,1-benzoxaborepin-7-yl)methyleneamino]-N-isobutyl-1,1-dioxo-1,2-benzothiazol-3-amine (17.2 mg; 6%) as a white solid. $^1$H NMR (DMSO-$d_6$, 300 MHz): δ 8.86 (d, J=7.3 Hz, 1H); 8.61 (s, 1H); 8.55 (s, 1H); 8.09 (dd, J=1.0 Hz, J=7.3 Hz, 1H); 7.94 (dd, J=1.4 Hz, J=7.7 Hz, 1H); 7.90 (dd, J=1.0 Hz, J=7.4 Hz, 1H); 7.76 (dd, J=1.5 Hz, J=7.6 Hz, 1H); 7.69 (m, 2H); 4.30 (d, J=7.6 Hz, 2H); 3.80 (t, J=5.9 Hz, 2H); 2.90 (t, J=6.9 Hz, 2H); 2.27 (m, 1H); 2.01 (quint., J=6.4 Hz, 2H); 0.98 (d, J=6.6 Hz, 6H).

Example 48: N-[(E)-(1-hydroxy-7-methoxy-3H-2,1-benzoxaborol-5-yl)methyleneamino]-N-isobutyl-1,1-dioxo-1,2-benzothiazol-3-amine Step A: dimethyl 5-tert-butoxycarbonyloxybenzene-1,3-dicarboxylate Di-tert-butyl dicarbonate (3.92 mL; 18.32 mmol; 1.10 eq.) was added to a suspension of dimethyl 5-hydroxyisophthalate (3.50 g; 16.65 mmol; 1.00 eq.) and 4-dimethylaminopyridine (406.9 mg; 3.33 mmol; 0.20 eq.) in DCM (70 mL). The reaction mixture was stirred at rt until completion then water was added and the organic phase was recovered. The aqueous phase was extracted twice with DCM and combined organic phases were dried over MgSO$_4$, filtered and concentrated. The residue was purified by column chromatography (gradient 0 to 20% of EtOAc in cyclohexane) to give dimethyl 5-tert-butoxycarbonyloxybenzene-1,3-dicarboxylate (4.19 g; 81%) as a colorless oil. $^1$H NMR (DMSO-d$_6$, 300 MHz): δ 8.36 (m, 1H); 8.01 (m, 2H); 3.91 (m, 6H); 1.52 (s, 9H).

Step B: dimethyl 4-bromo-5-tert-butoxycarbonyloxy-benzene-1,3-dicarboxylate 2,2,6,6-tetramethylpiperidinylmagnesium chloride lithium chloride complex (13.5 mL; 1.00 mol/L; 13.50 mmol; 1.98 eq.) was added dropwise to a solution of dimethyl 5-tert-butoxycarbonyloxybenzene-1,3-dicarboxylate (2.11 g; 6.81 mmol; 1.00 eq.) in THF (32 mL) at 0° C. and the reaction was stirred at 0° C. for 1 h. After being cooled to −40° C., 1,2-dibromotetrachloroethane (3.32 g; 10.21 mmol; 1.50 eq.) was added. The reaction was stirred 30 min at −40° C., then warmed to rt and stirred until completion. Aqueous saturated NH$_4$Cl solution was added and the mixture was extracted with DCM (3×). Combined organic phases were dried over MgSO$_4$, filtered and concentrated. The residue was purified by column chromatography (gradient 0 to 20% of EtOAc in cyclohexane) to give dimethyl 4-bromo-5-tert-butoxycarbonyloxy-benzene-1,3-dicarboxylate (2.55 g; 96%) as a white solid. $^1$H NMR (DMSO-d$_6$, 300 MHz): δ 8.17 (d, J=2.0 Hz, 1H); 8.06 (d, J=2.0 Hz, 1H); 3.91 (s, 3H); 3.89 (s, 3H); 1.51 (s, 9H).

Step C: dimethyl 4-bromo-5-hydroxy-benzene-1,3-dicarboxylate

Trifluoroacetic acid (7.0 mL; 94.24 mmol; 2.75 V) was added to a solution of dimethyl 4-bromo-5-tert-butoxycarbonyloxy-benzene-1,3-dicarboxylate (2.55 g; 6.55 mmol; 1.00 eq.) in DCM (38 mL) and the reaction was stirred at rt until completion. The reaction was then diluted with DCM and water. The organic phase was recovered and the aqueous phase extracted twice with EtOAc. Combined organic phases were washed with water (5×), dried over MgSO$_4$, filtered, concentrated, co-evaporated with ACN (3×) and dried under vacuum to give dimethyl 4-bromo-5-hydroxy-benzene-1,3-dicarboxylate (1.57 g; 83%) as a beige solid. $^1$H NMR (DMSO-d$_6$, 300 MHz): δ 11.14 (s, 1H); 7.64 (s, 2H); 3.87 (s, 3H); 3.86 (s, 3H).

Step D: dimethyl 4-bromo-5-methoxy-benzene-1,3-dicarboxylate

Dimethyl 4-bromo-5-hydroxy-benzene-1,3-dicarboxylate (1.57 g; 5.43 mmol; 1.00 eq.) was dissolved in DMF (30 mL). K$_2$CO$_3$ (1.13 g; 8.15 mmol; 1.50 eq.) was added and the mixture was stirred 15 min at rt before methyl iodide (507 μL; 8.15 mmol; 1.50 eq.) was added. The reaction mixture was then stirred at rt until completion and diluted with water (200 mL). The resulting precipitate was filtered and dried under vacuum to give dimethyl 4-bromo-5-methoxy-benzene-1,3-dicarboxylate (1.55 g; 94%) as a beige solid. $^1$H NMR (DMSO-d$_6$, 300 MHz): δ 7.80 (d, J=1.8 Hz, 1H); 7.66 (d, J=2.0 Hz, 1H); 3.97 (s, 3H); 3.89 (s, 3H); 3.88 (s, 3H).

Step E: 4-bromo-5-methoxy-benzene-1,3-dicarboxylic acid

The compound was prepared using the same procedure detailed in example 47 step C starting from dimethyl 4-bromo-5-methoxy-benzene-1,3-dicarboxylate (1.55 g; 5.11 mmol; 1.00 eq.) giving 4-bromo-5-methoxy-benzene-1,3-dicarboxylic acid (1.30 g; 93%) as a white solid. $^1$H NMR (DMSO-d6, 300 MHz): δ 13.54 (br s, 2H); 7.73 (d, J=1.8 Hz, 1H); 7.62 (d, J=1.8 Hz, 1H); 3.96 (s, 3H).

Step F: [4-bromo-3-(hydroxymethyl)-5-methoxy-phenyl]methanol

The compound was prepared using the same procedure detailed in example 23 step A starting from 4-bromo-5-methoxy-benzene-1,3-dicarboxylic acid (1.30 g; 4.73 mmol; 1.00 eq.) giving [4-bromo-3-(hydroxymethyl)-5-methoxy-phenyl]methanol (691.4 mg; 59%) as a white solid. $^1$H NMR (DMSO-d6, 300 MHz): δ 7.12 (m, 1H); 6.94 (d, J=1.7 Hz, 1H); 5.38 (t, J=5.6 Hz, 1H); 5.29 (t, J=5.8 Hz, 1H); 4.49 (d, J=5.6 Hz, 4H); 3.83 (s, 3H).

Step G: (1-hydroxy-7-methoxy-3H-2,1-benzoxaborol-5-yl)methanol

The compound was prepared using the same procedure detailed in example 9 step J starting from [4-bromo-3-(hydroxymethyl)-5-methoxy-phenyl]methanol (690.0 mg; 2.79 mmol; 1.00 eq.) giving (1-hydroxy-7-methoxy-3H-2,1-benzoxaborol-5-yl)methanol (340.8 mg; 63%) as a white solid. $^1$H NMR (DMSO-d6, 300 MHz): δ 6.93 (d, J=0.8 Hz, 1H); 6.81 (s, 1H); 4.99 (s, 2H); 4.54 (s, 2H); 3.79 (s, 3H).

Step H: 1-hydroxy-7-methoxy-3H-2,1-benzoxaborole-5-carbaldehyde

Dess-Martin periodinane (5.30 mL; 15% w/w; 2.55 mmol; 1.50 eq.) was added dropwise to a solution of (1-hydroxy-7-methoxy-3H-2,1-benzoxaborol-5-yl)methanol (330.0 mg; 1.70 mmol; 1.00 eq.) in DCM (10 mL) at rt. The reaction was then stirred 24 h and filtered. The solid was washed with DCM (3×) and the filtrate was concentrated to dryness. The residue was purified twice by column chromatography (gradient 0 to 10% of EtOH in DCM) to give 1-hydroxy-7-methoxy-3H-2,1-benzoxaborole-5-carbaldehyde (101.0 mg; 31%) as a yellow oil. $^1$H NMR (DMSO-d$_6$, 300 MHz): δ 10.05 (s, 1H); 9.05 (s, 1H); 7.52 (d, J=0.8 Hz, 1H); 7.32 (m, 1H); 5.02 (s, 2H); 3.88 (s, 3H).

Step I: N-[(E)-(1-hydroxy-7-methoxy-3H-2,1-benzoxaborol-5-yl)methyleneamino]-N-isobutyl-1,1-dioxo-1,2-benzothiazol-3-amine The compound was prepared using the same procedure detailed in example 3 step B, starting from 3-chloro-1,2-benzothiazole 1,1-dioxide (example 1, step A), (106.1 mg; 0.53 mmol; 1.00 eq.), 2-methylpropylhydrazine hydrochloride (72.1 mg; 0.58 mmol; 1.10 eq.) and 1-hydroxy-7-methoxy-3H-2,1-benzoxaborole-5-carbaldehyde (101.0 mg; 0.53 mmol; 1.00 eq.), giving N-[(E)-(1-hydroxy-7-methoxy-3H-2,1-benzoxaborol-5-yl)methyleneamino]-N-isobutyl-1,1-dioxo-1,2-benzothiazol-3-amine (33.0 mg; 15%) as a yellow solid. $^1$H NMR (DMSO-d$_6$, 300 MHz): δ 8.94 (s, 1H); 8.86 (dd, J=1.6 Hz, J=6.9 Hz, 1H); 8.60 (s, 1H); 8.10 (m, 1H); 7.91 (m, 2H); 7.46 (s, 1H); 7.35 (s, 1H); 5.04 (s, 2H); 4.30 (d, J=7.6 Hz, 2H); 3.92 (s, 3H); 2.28 (m, 1H); 0.99 (d, J=6.6 Hz, 6H).

Example 49: N-[(E)-(1-hydroxy-3-methyl-3H-2,1-benzoxaborol-5-yl)methyleneamino]-N-isobutyl-1,1-dioxo-1,2-benzothiazol-3-amine Step A: 4-bromo-3-formyl-benzoic acid The compound was prepared using the same procedure detailed in example 47 step C starting from methyl 4-bromo- 3-formyl-benzoate (10.00 g; 41.14 mmol; 1.00 eq.) giving 4-bromo-3-formyl-benzoic acid (9.58 g; quantitative) as a white solid. ¹H NMR (DMSO-d6, 300 MHz): δ 13.48 (br s, 1H); 10.24 (s, 1H); 8.32 (d, J=2.1 Hz, 1H); 8.08 (dd, J=2.3 Hz, J=8.3 Hz, 1H); 7.94 (d, J=8.3 Hz, 1H).

Step B: tert-butyl 4-bromo-3-formyl-benzoate

The compound was prepared using the same procedure detailed in example 48 step A starting from 4-bromo-3-formyl-benzoic acid (9.58 g; 41.83 mmol; 1.00 eq.) giving tert-butyl 4-bromo-3-formyl-benzoate (4.23 g; 35%) as an orange oil. ¹H NMR (DMSO-d6, 300 MHz): δ 10.23 (s, 1H); 8.25 (d, J=2.3 Hz, 1H); 8.04 (dd, J=2.1 Hz, J=8.3 Hz, 1H); 7.94 (d, J=8.3 Hz, 1H); 1.57 (s, 9H).

Step C: tert-butyl 4-bromo-3-(1-hydroxyethyl)benzoate

Methylmagnesium bromide (2.92 mL; 3.00 mol/L; 8.77 mmol; 1.25 eq.) was added dropwise to a solution of tert-butyl 4-bromo-3-formyl-benzoate (2.00 g; 7.01 mmol; 1.00 eq.) in THF (40 mL) at −78° C. under argon atmosphere. The reaction was then stirred at −78° C. until completion. Saturated aqueous NH₄Cl solution was added and the reaction was allowed to warm to rt. The mixture was extracted with EtOAc (3×) and combined organic phases were dried over MgSO₄, filtered and concentrated. The residue was purified by column chromatography (gradient 0 to 20% of EtOAc in cyclohexane) to give tert-butyl 4-bromo-3-(1-hydroxyethyl)benzoate (1.44 g; 68%) as a pale yellow oil. ¹H NMR (DMSO-d₆, 300 MHz): δ 8.13 (td, J=0.7 Hz, J=1.6 Hz, 1H); 7.67 (m, 2H); 5.56 (d, J=4.3 Hz, 1H); 4.97 (dq, J=4.3 Hz, J=6.3 Hz, 1H); 1.55 (s, 9H); 1.31 (d, J=6.3 Hz, 3H).

Step D: 4-bromo-3-(1-hydroxyethyl)benzoic acid

The compound was prepared using the same procedure detailed in example 48 step C starting from tert-butyl 4-bromo-3-(1-hydroxyethyl)benzoate (1.44 g; 4.78 mmol; 1.00 eq.) giving 4-bromo-3-(1-hydroxyethyl)benzoic acid (1.06 g; 90%) as a beige solid. ¹H NMR (DMSO-d6, 300 MHz): δ 13.17 (br s, 1H); 8.18 (d, J=2.0 Hz, 1H); 7.70 (m, 2H); 5.47 (s, 1H); 4.97 (q, J=6.4 Hz, 1H); 1.31 (d, J=6.4 Hz, 3H).

Step E: 1-[2-bromo-5-(hydroxymethyl)phenyl]ethanol

The compound was prepared using the same procedure detailed in example 23 step A starting from 4-bromo-3-(1-hydroxyethyl)benzoic acid (1.06 g; 4.33 mmol; 1.00 eq.) giving 1-[2-bromo-5-(hydroxymethyl)phenyl]ethanol (679.8 mg; 68%) as a white solid. ¹H NMR (DMSO-d6, 300 MHz): δ 7.58 (d, J=2.1 Hz, 1H); 7.46 (d, J=8.1 Hz, 1H); 7.11 (dd, J=2.3 Hz, J=8.1 Hz, 1H); 5.37 (d, J=4.0 Hz, 1H); 5.27 (t, J=5.7 Hz, 1H); 4.94 (dq, J=4.3 Hz, J=6.3 Hz, 1H); 4.47 (d, J=5.6 Hz, 2H); 1.28 (d, J=6.3 Hz, 3H).

Step F: (1-hydroxy-3-methyl-3H-2,1-benzoxaborol-5-yl)methanol

The compound was prepared using the same procedure detailed in example 9 step J starting from 1-[2-bromo-5-(hydroxymethyl)phenyl]ethanol (679.0 mg; 2.94 mmol; 1.00 eq.) giving (1-hydroxy-3-methyl-3H-2,1-benzoxaborol-5-yl)methanol (253.3 mg; 48%) as a beige solid. ¹H NMR (DMSO-d6, 300 MHz): δ 7.66 (dd, J=7.6 Hz, J=18.3 Hz, 1H); 7.40 (m, 2H); 5.28 (m, 3H); 4.56 (m, 1H); 1.43 (m, 3H).

Step G: 1-hydroxy-3-methyl-3H-2,1-benzoxaborole-5-carbaldehyde

The compound was prepared using the same procedure detailed in example 48 step H starting from (1-hydroxy-3-methyl-3H-2,1-benzoxaborol-5-yl)methanol (253.3 mg; 1.42 mmol; 1.00 eq.) giving 1-hydroxy-3-methyl-3H-2,1-benzoxaborole-5-carbaldehyde (68.5 mg; 27%) as a brown oil. ¹H NMR (DMSO-d6, 300 MHz): δ 10.09 (s, 1H); 9.39 (s, 1H); 7.93 (d, J=0.8 Hz, 1H); 7.89 (dd, J=1.0 Hz, J=1.7 Hz, 2H); 5.32 (q, J=6.7 Hz, 1H); 1.45 (d, J=6.6 Hz, 3H).

Step H: N-[(E)-(1-hydroxy-3-methyl-3H-2,1-benzoxaborol-5-yl)methyleneamino]-N-isobutyl-1,1-dioxo-1,2-benzothiazol-3-amine The compound was prepared using the same procedure detailed in example 3 step B, starting from 3-chloro-1,2-benzothiazole 1,1-dioxide (example 1, step A), (77.9 mg; 0.39 mmol; 1.00 eq.), 2-methylpropylhydrazine hydrochloride (53.0 mg; 0.43 mmol; 1.10 eq.) and 1-hydroxy-3-methyl-3H-2,1-benzoxaborole-5-carbaldehyde (68.0 mg; 0.39 mmol; 1.00 eq.), giving N-[(E)-(1-hydroxy-3-methyl-3H-2,1-benzoxaborol-5-yl)methyleneamino]-N-isobutyl-1,1-dioxo-1,2-benzothiazol-3-amine (34.5 mg; 22%) as a white solid. ¹H NMR (DMSO-d_G, 300 MHz): δ 9.30 (s, 1H); 8.84 (dd, J=1.1 Hz, J=6.7 Hz, 1H); 8.63 (s, 1H); 8.10 (m, 1H); 7.92 (m, 5H); 5.34 (d, J=6.4 Hz, 1H); 4.31 (d, J=7.8 Hz, 2H); 2.29 (td, J=7.1 Hz, J=14.0 Hz, 1H); 1.48 (d, J=6.6 Hz, 3H); 0.99 (d, J=6.6 Hz, 6H). mp: 124-164° C.

Example 50: N-[(E)-(1-hydroxy-3-methyl-3H-2,1-benzoxaborol-5-yl)methyleneamino]-N-methyl-1,1-dioxo-1,2-benzothiazol-3-amine Step A: 1-(1,1-dioxo-1,2-benzothiazol-3-yl)-1-methyl-hydrazine 3-chloro-1,2-benzothiazole 1,1-dioxide (example 1, step A), (7.00 g; 34.72 mmol; 1.00 eq.) was dissolved into dry THF (56 mL) and then added dropwise to a solution of methyl hydrazine (2.22 mL; 41.66 mmol; 1.20 eq.) in THF (56 mL). The reaction mixture was stirred 1 h under reflux and the precipitate was filtered, washed by water and dried under vacuum at 50° C. to give 1-(1,1-dioxo-1,2-benzothiazol-3-yl)-1-methyl-hydrazine (5.32 g; 73%) as a white solid. ¹H NMR (DMSO-d&, 300 MHz): δ 8.98 (m, 1H); 7.93 (m, 1H); 7.77 (m, 2H); 5.61 (br s, 2H); 3.43 (s, 3H).

Step B: N-[(E)-(1-hydroxy-3-methyl-3H-2,1-benzoxaborol-5-yl)methyleneamino]-N-methyl-1,1-dioxo-1,2-benzothiazol-3-amine 1-(1,1-dioxo-1,2-benzothiazol-3-yl)-1-methyl-hydrazine (50.0 mg; 0.24 mmol; 1.00 eq.) was added to a suspension of 1-hydroxy-3-methyl-3H-2,1-benzoxaborole-5-carbaldehyde (example 49, step G), (50.0 mg; 0.28 mmol; 1.20 eq.) in THF (1.5 mL). The reaction was then stirred under reflux until completion, cooled to rt and concentrated. The residue was taken up into EtOH and the precipitate obtained was filtered, washed once with EtOH and dried under vacuum. The solid was then purified by LCMS-Preparative (Column:

Kinetex C18, 30×150 mm 5 μm (phenomenex); Flow rate: 42 ml/min; Elution: H₂O, 0.1% HCOOH/ACN, 0.1% HCOOH; Gradient: 10 to 100% ACN over 12 minutes) to give N-[(E)-(1-hydroxy-3-methyl-3H-2,1-benzoxaborol-5-yl)methyleneamino]-N-methyl-1,1-dioxo-1,2-benzothiazol-3-amine (37.0 mg; 42%) as a yellow solid. $_1$H NMR (400 MHz, DMSO-d6) δ 9.30 (s, 1H); 8.88 (d, J=7.5 Hz, 1H); 8.54 (s, 1H); 8.10 (m, 1H); 7.95 (m, 1H); 7.91 (dd, J=1.1 Hz, J=7.5 Hz, 1H); 7.88 (m, 2H); 7.83 (m, 1H); 5.34 (q, J=6.6 Hz, 1H); 3.82 (s, 3H); 1.47 (d, J=6.6 Hz, 3H).

Example 51: N-[(E)-(1-hydroxy-3H-2,1-benzoxaborol-5-yl)methyleneamino]-N-methyl-1,1-dioxo-4,5,6,7-tetrahydro-1,2-benzothiazol-3-amine Step A: 1,1-dioxo-4,5,6,7-tetrahydro-1,2-benzothiazol-3-one Aqueous ammonia solution 32% w/w (4.25 mL) was added dropwise at 0° C. to a solution of methyl 2-chlorosulfonylcyclohexene-1-carboxylate (850.0 mg; 3.56 mmol; 1.00 eq.) in THF (8.5 mL). Then, the reaction mixture was allowed to warm to rt, stirred 1 h and concentrated. The residue was dissolved into saturated aqueous NaHCO₃ solution and extracted once with diethyl ether. The aqueous phase was acidified to pH=1 with conc. HCl and extracted twice with EtOAc. The resulting organic phases were combined and washed with brine, dried over MgSO₄, filtered and concentrated to dryness to give 1,1-dioxo-4,5,6,7-tetrahydro-1,2-benzothiazol-3-one (528.7 mg; 79%) as a white solid. ¹H NMR (DMSO-d6, 300 MHz): δ 2.44 (m, 2H); 2.30 (m, 2H); 1.71 (m, 4H).

Step B: 3-chloro-4,5,6,7-tetrahydro-1,2-benzothiazole 1,1-dioxide

The compound was prepared using the same procedure detailed in example 9 step D starting from 1,1-dioxo-4,5,6,7-tetrahydro-1,2-benzothiazol-3-one (80.5 mg; 0.43 mmol; 1.00 eq.) giving 3-chloro-4,5,6,7-tetrahydro-1,2-benzothiazole 1,1-dioxide (88.0 mg; 99%), used in the next step without purification.

Step C: N-[(E)-(1-hydroxy-3H-2,1-benzoxaborol-5-yl)methyleneamino]methanamine

The compound was prepared using the same procedure detailed in example 4 step A starting from 1-hydroxy-3H-2,1-benzoxaborole-5-carbaldehyde (example 23, step C), (70.0 mg; 0.43 mmol; 1.00 eq.) and methyl hydrazine (23 μL; 0.43 mmol; 1.00 eq.) giving crude N-[(E)-(1-hydroxy-3H-2,1-benzoxaborol-5-yl)methyleneamino]methanamine (82.0 mg; 99%) as a black oil, used in the next step without purification.

Step D: N-[(E)-(1-hydroxy-3H-2,1-benzoxaborol-5-yl)methyleneamino]-N-methyl-1,1-dioxo-4,5,6,7-tetrahydro-1,2-benzothiazol-3-amine The compound was prepared using the same procedure detailed in example 1 step C starting from 3-chloro-4,5,6,7-tetrahydro-1,2-benzothiazole 1,1-dioxide (88.0 mg; 0.43 mmol; 1.00 eq.) and N-[(E)-(1-hydroxy-3H-2,1-benzoxaborol-5-yl)methyleneamino]methanamine (81.3 mg; 0.43 mmol; 1.00 eq.) giving N-[(E)-(1-hydroxy-3H-2,1-benzoxaborol-5-yl)methyleneamino]-N-methyl-1,1-dioxo-4,5,6,7-tetrahydro-1,2-benzothiazol-3-amine (21.0 mg; 14%) as a white solid. ¹H NMR (DMSO-d6, 400 MHz): δ 9.32 (br s, 1H); 8.35 (s, 1H); 7.83 (d, J=8.1 Hz, 1H); 7.75 (m, 2H); 5.06 (s, 2H); 3.68 (s, 3H); 2.94 (m, 2H); 2.52 (m, 2H); 1.72 (m, 4H).

Example 52: [4-[2-(1,1-dioxo-1,2-benzothiazol-3-yl)-3-methyl-4,5-dihydro-3H-pyridazin-6-yl]-2-methoxy-phenyl]boronic acid Step A: 4-chloro-N-methoxy-N-methyl-pentanamide To a suspension of 4-chloropentanoyl chloride (1.50 g; 9.68 mmol; 1.00 eq.) and O,N-dimethyl hydroxylamine hydrochloride (944.0 mg; 9.68 mmol; 1.00 eq.) in DCM (20 mL) at 0° C., was added a solution of pyridine (1.75 mL; 21.64 mmol; 2.24 eq.) in DCM (7.5 mL). The reaction mixture was kept stirring at 0° C. for 1 h, and warmed to rt overnight. Then, it was diluted with DCM (20 mL), and successively washed with aqueous 1N HCl solution (50 mL), aqueous saturated NaHCO₃ solution (50 mL) and brine (50 mL). The organic phase was dried over MgSO₄, filtered and concentrated to give 4-chloro-N-methoxy-N-methyl-pentanamide (1.23 g; 71%) as a colorless liquid. ¹H NMR (CDCl₃, 300 MHz): δ 4.13 (m, 1H); 3.71 (s, 3H); 3.19 (s, 3H); 2.65 (t, J=7.3 Hz, 2H); 2.15 (m, 1H); 1.92 (m, 1H); 1.55 (d, J=6.6 Hz, 3H).

Step B: 4-chloro-1-(4-chloro-3-methoxy-phenyl)pentan-1-one 4-bromo-1-chloro-2-methoxybenzene (957.0 mg; 4.32 mmol; 1.20 eq.) was diluted in THF (16 mL) and cooled to −78° C. Then, n-butyllithium 1.6M in hexane (3.20 mL; 1.60 mol/L; 5.12 mmol; 1.42 eq.) was added over 10 min, and the reaction was kept at −78° C. during 15 min. A solution of 4-chloro-N-methoxy-N-methyl-pentanamide (647.0 mg; 3.60 mmol; 1.00 eq.) in THF (3 mL) was then added over 5 min and the reaction was stirred 1 h at −78° C. The reaction mixture was finally quenched by addition of aqueous 1 N HCl (100 mL) and allowed to warm to rt. The mixture was extracted with EtOAc (3×) and combined organic phases were dried over MgSO₄, filtered, and concentrated. The residue was purified by column chromatography (gradient 0 to 5% of EtOAc in cyclohexane) to give 4-chloro-1-(4-chloro-3-methoxy-phenyl)pentan-1-one (310.0 mg; 33%) as a colorless solid. ¹H NMR (CDCl₃, 300 MHz): δ 7.54 (m, 1H); 7.51 (d, J=1.8 Hz, 1H); 7.46 (dd, J=0.5 Hz, J=8.1 Hz, 1H); 4.16 (m, 1H); 3.97 (s, 3H); 3.18 (m, 2H); 2.28 (m, 1H); 2.02 (m, 1H); 1.59 (d, J=6.4 Hz, 3H).

Step C: 3-(4-chloro-3-methoxy-phenyl)-6-methyl-1,4,5,6-tetrahydropyridazine 4-chloro-1-(4-chloro-3-methoxy-phenyl)pentan-1-one (303.0 mg; 1.16 mmol; 1.00 eq.) was dissolved in EtOH (6 mL) and hydrazine hydrate (360 μL; 3.97 mmol; 3.42 eq.) was added. Then, the mixture was stirred 1 h under reflux and concentrated under vacuum to give crude 3-(4-chloro-3-methoxy-phenyl)-6-methyl-1,4,5,6-tetrahydropyridazine (277.0 mg; quantitative) as a colorless gum, used in the next step without purification. ¹H NMR (DMSO-d6, 300 MHz): δ 7.36 (d, J=2.0 Hz, 1H); 7.33 (d, J=8.4 Hz, 1H); 7.19 (br s, 1H); 7.12 (dd, J=2.0 J=8.3 Hz, 1H); 3.85 (s, 3H); 3.02 (m, 1H); 2.53 (m, 2H); 1.95 (m, 1H); 1.51 (m, 1H); 1.09 (d, J=6.3 Hz, 3H).

Step D: 3-[6-(4-chloro-3-methoxy-phenyl)-3-methyl-4,5-dihydro-3H-pyridazin-2-yl]-1,2-benzothiazole 1,1-dioxide The compound was prepared using the same procedure detailed in example 1 step C starting from 3-chloro-1,2-benzothiazole 1,1-dioxide (example 1, step A), (113.0 mg; 0.56 mmol; 1.00 eq.) and 3-(4-chloro-3-methoxy-phenyl)-6-methyl-1,4,5,6-tetrahydropyridazine (134.3 mg; 0.56 mmol; 1.00 eq.) giving 3-[6-(4-chloro-3-methoxy-phenyl)-3-methyl-4,5-dihydro-3H-pyridazin-2-yl]-1,2-benzothiazole 1,1-dioxide (127.0 mg; 56%) as a white solid. $^1$H NMR (DMSO-d6, 300 MHz): δ 8.74 (m, 1H); 8.08 (m, 1H); 7.87 (m, 2H); 7.60 (m, 2H); 7.45 (dd, J=2.0 Hz, J=8.3 Hz, 1H); 4.92 (m, 1H); 3.97 (s, 3H); 3.06 (m, 1H); 2.80 (m, 1H); 2.11 (m, 2H); 1.33 (d, J=6.6 Hz, 3H).

Step E: [4-[2-(1,1-dioxo-1,2-benzothiazol-3-yl)-3-methyl-4,5-dihydro-3H-pyridazin-6-yl]-2-methoxy-phenyl]boronic acid The compound was prepared using the same procedure detailed in example 9 step J starting from 3-[6-(4-chloro-3-methoxy-phenyl)-3-methyl-4,5-dihydro-3H-pyridazin-2-yl]-1,2-benzothiazole 1,1-dioxide (122.0 mg; 0.30 mmol; 1.00 eq.) giving [4-[2-(1,1-dioxo-1,2-benzothiazol-3-yl)-3-methyl-4,5-dihydro-3H-pyridazin-6-yl]-2-methoxy-phenyl]boronic acid (32.0 mg; 26%) as a white solid. $^1$H NMR (DMSO-d6, 400 MHz): δ 8.80 (m, 1H); 8.09 (m, 1H); 7.88 (m, 4H); 7.69 (d, J=7.9 Hz, 1H); 7.43 (m, 2H); 4.93 (m, 1H); 3.91 (s, 3H); 3.04 (m, 1H); 2.82 (ddd, J=7.3 Hz, J=12.3 Hz, J=19.2 Hz, 1H); 2.16 (m, 2H); 1.34 (d, J=6.8 Hz, 3H). mp: 216-235° C.

Example 53: 3-[6-(1-hydroxy-3H-2,1-benzoxaborol-5-yl)-3-methyl-4,5-dihydro-3H-pyridazin-2-yl]-1,2-benzothiazole 1,1-dioxide

Step A: (5-bromo-2-chloro-phenyl)methoxy-tert-butyl-dimethyl-silane (5-bromo-2-chlorophenyl)methan-1-ol (2.00 g; 9.03 mmol; 1.00 eq.) was dissolved in DMF (30 mL), then the mixture was cooled down to 0° C. Imidazole (1.54 g; 22.58 mmol; 2.50 eq.) and tert-butyldimethylsilyl chloride (1.88 mL; 10.84 mmol; 1.20 eq.) were added and the mixture was stirred 2 h at 0° C., then 2 h at rt. The reaction mixture was concentrated and diluted with EtOAc. The resulting organic phase was washed with saturated aqueous NH$_4$Cl solution, dried over MgSO$_4$, filtered and concentrated to dryness to give crude (5-bromo-2-chloro-phenyl)methoxy-tert-butyl-dimethyl-silane (3.47 g; quantitative), used in the next step without purification. $^1$H NMR (DMSO-d6, 300 MHz): δ 7.52 (m, 1H); 7.40 (m, 1H); 7.29 (d, J=8.4 Hz, 1H); 4.61 (s, 2H); 0.80 (s, 9H); 0.00 (s, 6H).

Step B: 1-[3-[[tert-butyl(dimethyl)silyl]oxymethyl]-4-chloro-phenyl]-4-chloro-pentan-1-one The compound was prepared using the same procedure detailed in example 52 step B starting from (5-bromo-2-chloro-phenyl)methoxy-tert-butyl-dimethyl-silane (1.00 g; 2.98 mmol; 1.20 eq.) and 4-chloro-N-methoxy-N-methyl-pentanamide (example 52, step A), (495.4 mg; 2.48 mmol; 1.00 eq.) giving 1-[3-[[tert-butyl(dimethyl)silyl]oxymethyl]-4-chloro-phenyl]-4-chloro-pentan-1-one (560.0 mg; 60%) as a colorless oil. $^1$H NMR (DMSO-d6, 300 MHz): δ 8.00 (d, J=1.2 Hz, 1H); 7.78 (dd, J=1.9 Hz, J=8.2 Hz, 1H); 7.47 (d, J=8.4 Hz, 1H); 4.68 (s, 2H); 4.13 (m, 1H); 3.06 (t, J=7.2 Hz, 2H); 2.00 (m, 1H); 1.84 (m, 1H); 1.39 (d, J=6.4 Hz, 3H); 0.81 (s, 9H); 0.00 (s, 6H).

Step C: tert-butyl-[[2-chloro-5-(6-methyl-1,4,5,6-tetrahydropyridazin-3-yl)phenyl]methoxy]-dimethyl-silane The compound was prepared using the same procedure detailed in example 52 step C starting from 1-[3-[[tert-butyl(dimethyl)silyl]oxymethyl]-4-chloro-phenyl]-4-chloro-pentan-1-one (560.0 mg; 1.49 mmol; 1.00 eq.) giving crude tert-butyl-[[2-chloro-5-(6-methyl-1,4,5,6-tetrahydropyridazin-3-yl)phenyl]methoxy]-dimethyl-silane (526.0 mg) as a pale yellow oil, used in the next step without purification. LC-MS (Method A): Rt=2.71 min; MS: m/z=353 [M+H]$^+$.

Step D: tert-butyl-[[2-chloro-5-[2-(1,1-dioxo-1,2-benzothiazol-3-yl)-3-methyl-4,5-dihydro-3H-pyridazin-6-yl]phenyl]methoxy]-dimethyl-silane The compound was prepared using the same procedure detailed in example 1 step C starting from 3-chloro-1,2-benzothiazole 1,1-dioxide (example 1, step A), (300.5 mg; 1.49 mmol; 1.00 eq.) and tert-butyl-[[2-chloro-5-(6-methyl-1,4,5,6-tetrahydropyridazin-3-yl)phenyl]methoxy]-dimethyl-silane (526.0 mg; 1.49 mmol; 1.00 eq.) giving tert-butyl-[[2-chloro-5-[2-(1,1-dioxo-1,2-benzothiazol-3-yl)-3-methyl-4,5-dihydro-3H-pyridazin-6-yl]phenyl]methoxy]-dimethyl-silane (460.0 mg; 60%) as a beige solid. $^1$H NMR (DMSO-d6, 300 MHz): δ 8.55 (d, J=7.6 Hz, 1H); 7.97 (d, J=7.6 Hz, 1H); 7.88 (s, 1H); 7.72 (m, 3H); 7.50 (d, J=8.3 Hz, 1H); 4.80 (m, 1H); 4.72 (s, 2H); 2.88 (m, 1H); 2.69 (m, 1H); 2.04 (m, 2H); 1.22 (d, J=6.4 Hz, 3H); 0.76 (s, 9H); 0.00 (s, 6H).

Step E: [2-chloro-5-[2-(1,1-dioxo-1,2-benzothiazol-3-yl)-3-methyl-4,5-dihydro-3H-pyridazin-6-yl]phenyl]methanol The compound was prepared using the same procedure detailed in example 12 step B starting from tert-butyl-[[2-chloro-5-[2-(1,1-dioxo-1,2-benzothiazol-3-yl)-3-methyl-4,5-dihydro-3H-pyridazin-6-yl]phenyl]methoxy]-dimethyl-silane (400.0 mg; 0.77 mmol; 1.00 eq.) giving [2-chloro-5-[2-(1,1-dioxo-1,2-benzothiazol-3-yl)-3-methyl-4,5-dihydro-3H-pyridazin-6-yl]phenyl]methanol (312.0 mg; quantitative) as a yellow solid. $^1$H NMR (DMSO-d6, 300 MHz): δ 8.81 (m, 1H); 8.18 (d, J=2.1 Hz, 1H); 8.12 (m, 1H); 7.90 (m, 2H); 7.80 (dd, J=2.3 Hz, J=8.4 Hz, 1H); 7.62 (d, J=8.3 Hz, 1H); 5.63 (t, J=5.6 Hz, 1H); 4.98 (m, 1H); 4.69 (d, J=5.4 Hz, 2H); 3.04 (m, 1H); 2.87 (m, 1H); 2.17 (m, 2H); 1.37 (d, J=6.8 Hz, 3H).

Step F: 3-[6-(1-hydroxy-3H-2,1-benzoxaborol-5-yl)-3-methyl-4,5-dihydro-3H-pyridazin-2-yl]-1,2-benzothiazole 1,1-dioxide The compound was prepared using the same procedure detailed in example 9 step J starting from [2-chloro-5-[2-(1,1-dioxo-1,2-benzothiazol-3-yl)-3-methyl-4,5-dihydro-3H-pyridazin-6-yl]phenyl]methanol (312.0 mg; 0.77 mmol; 1.00 eq.) giving 3-[6-(1-hydroxy-3H-2,1-benzoxaborol-5-yl)-3-methyl-4,5-dihydro-3H-pyridazin-2-yl]-1,2-benzothiazole 1,1-dioxide (110.0 mg; 36%) as a white solid. $^1$H NMR (DMSO-d6, 400 MHz): δ 9.34 (s, 1H); 8.73 (m, 1H); 8.08 (m, 1H); 7.88 (m, 5H); 5.10 (s, 2H); 4.94 (m, 1H); 3.04 (m, 1H); 2.85 (m, 1H); 2.14 (m, 2H); 1.34 (d, J=6.6 Hz, 3H). mp: 230-250° C.

Example 54: [4-[2-(5,7-dimethoxy-1,1-dioxo-1,2-benzothiazol-3-yl)-3-methyl-4,5-dihydro-3H-pyridazin-6-yl]-2-methoxy-phenyl]boronic acid Step A: 3-[6-(4-chloro-3-methoxy-phenyl)-3-methyl-4,5-dihydro-3H-pyridazin-2-yl]-5,7-dimethoxy-1,2-benzothiazole 1,1-dioxide 3-(4-chloro-3-methoxy-phenyl)-6-methyl-1,4,5,6-tetrahydropyridazine (example 52, step C), (139.0 mg; 0.58 mmol; 1.00 eq.) was dissolved in phosphorus(V) oxychloride (2.00 mL; 21.20 mmol; 36.40 eq.). 5,7-dimethoxy-1,1-dioxo-1,2-benzothiazol-3-one (142.0 mg; 0.58 mmol; 1.00 eq.) was added and the reaction mixture was stirred under reflux overnight. Then, the reaction was poured onto ice (50 mL) and stirred 15 min at rt. The precipitate obtained was filtered, washed with water (3×), diethyl ether (3×) and dried at 50° C. under vacuum to give 3-[6-(4-chloro-3-methoxy-phenyl)-3-methyl-4,5-dihydro-3H-pyridazin-2-yl]-5,7-dimethoxy-1,2-benzothiazole 1,1-dioxide (219.0 mg; 76%) as a beige solid. $^1$H NMR (DMSO-d6, 300 MHz): δ 7.86 (d, J=1.8 Hz, 1H); 7.58 (m, 1H); 7.55 (d, J=1.8 Hz, 1H); 7.45 (dd, J=2.0 Hz, J=8.3 Hz, 1H); 6.99 (d, J=1.8 Hz, 1H); 4.86 (m, 1H); 3.99 (s, 3H); 3.96 (s, 3H); 3.86 (s, 3H); 3.01 (m, 1H); 2.78 (m, 1H); 2.09 (m, 2H); 1.30 (d, J=6.6 Hz, 3H).

Step B: [4-[2-(5,7-dimethoxy-1,1-dioxo-1,2-benzothiazol-3-yl)-3-methyl-4,5-dihydro-3H-pyridazin-6-yl]-2-methoxy-phenyl]boronic acid The compound was prepared using the same procedure detailed in example 9 step J starting from 3-[6-(4-chloro-3-methoxy-phenyl)-3-methyl-4,5-dihydro-3H-pyridazin-2-yl]-5,7-dimethoxy-1,2-benzothiazole 1,1-dioxide (214.0 mg; 0.46 mmol; 1.00 eq.) giving [4-[2-(5,7-dimethoxy-1,1-dioxo-1,2-benzothiazol-3-yl)-3-methyl-4,5-dihydro-3H-pyridazin-6-yl]-2-methoxy-phenyl]boronic acid (15.0 mg; 7%) as a white solid. $^1$H NMR (DMSO-d6, 400 MHz): δ 7.93 (d, J=2.0 Hz, 1H); 7.84 (s, 2H); 7.64 (d, J=7.5 Hz, 1H); 7.43 (dd, J=1.3 Hz, J=7.7 Hz, 1H); 7.40 (d, J=1.1 Hz, 1H); 7.00 (d, J=2.0 Hz, 1H); 4.85 (m, 1H); 3.99 (s, 3H); 3.90 (s, 3H); 3.87 (m, 3H); 3.04 (m, 1H); 2.80 (m, 1H); 2.10 (m, 2H); 1.31 (d, J=6.6 Hz, 3H).

Example 55: [2-methoxy-4-[2-(8-methoxyquinazolin-4-yl)-3-methyl-4,5-dihydro-3H-pyridazin-6-yl]phenyl]boronic acid Step A: 4-[6-(4-chloro-3-methoxy-phenyl)-3-methyl-4,5-dihydro-3H-pyridazin-2-yl]-8-methoxy-quinazoline 3-(4-chloro-3-methoxy-phenyl)-6-methyl-1,4,5,6-tetrahydropyridazine (example 52, step C), (320.0 mg; 1.24 mmol; 1.00 eq.), 4-chloro-8-methoxyquinazoline (260.9 mg; 1.34 mmol, 1.00 eq.) and copper(I) iodide (102.1 mg; 0.54 mmol; 0.40 eq.) were put into propan-2-ol (5 mL). The reaction mixture was then stirred 2 h at 100° C. under microwave irradiation and concentrated. The residue was taken up into EtOAc and washed with water. The aqueous phase was basified and extracted again with DCM. Combined organic phases were dried over MgSO$_4$, filtered and concentrated. The residue was purified by column chromatography (gradient 0 to 10% of EtOH in DCM) to give 4-[6-(4-chloro-3-methoxy-phenyl)-3-methyl-4,5-dihydro-3H-pyridazin-2-yl]-8-methoxy-quinazoline (276.0 mg; 52%) as a yellow oil. $^1$H NMR (CDCl$_3$, 300 MHz): δ 8.85 (s, 1H); 8.63 (dd, J=1.0 Hz, J=8.9 Hz, 1H); 7.62 (d, J=2.0 Hz, 1H); 7.41 (d, J=8.3 Hz, 1H); 7.33 (dd, J=7.8 Hz, J=8.8 Hz, 1H); 7.24 (dd, J=2.0 Hz, J=8.3 Hz, 1H); 7.13 (dd, J=0.9 Hz, J=7.8 Hz, 1H); 5.38 (m, 1H); 4.07 (s, 3H); 3.93 (s, 3H); 2.85 (m, 1H); 2.72 (m, 1H); 2.20 (m, 2H); 1.38 (d, J=6.6 Hz, 3H).

Step B: [2-methoxy-4-[2-(8-methoxyquinazolin-4-yl)-3-methyl-4,5-dihydro-3H-pyridazin-6-yl]phenyl] boronic acid The compound was prepared using the same procedure detailed in example 9 step J starting from 4-[6-(4-chloro-3-methoxy-phenyl)-3-methyl-4,5-dihydro-3H-pyridazin-2-yl]-8-methoxy-quinazoline (270.0 mg; 0.68 mmol; 1.00 eq.) giving [2-methoxy-4-[2-(8-methoxyquinazolin-4-yl)-3-methyl-4,5-dihydro-3H-pyridazin-6-yl]phenyl]boronic acid (36.0 mg; 13%) as a yellow solid. $^1$H NMR (DMSO-d6, 400 MHz): δ 8.70 (s, 1H); 8.63 (d, J=8.8 Hz, 1H); 7.76 (s, 2H); 7.65 (d, J=7.7 Hz, 1H); 7.47 (m, 2H); 7.38 (dd, J=1.1 Hz, J=7.7 Hz, 1H); 7.32 (s, 1H); 5.27 (m, 1H); 3.94 (s, 3H); 3.85 (s, 3H); 2.93 (m, 1H); 2.78 (m, 1H); 2.12 (m, 2H); 1.30 (d, J=6.6 Hz, 3H). mp: 112-117° C.

Example 56: 4-[6-(1-hydroxy-3H-2,1-benzoxaborol-5-yl)-3-methyl-4,5-dihydro-3H-pyridazin-2-yl]-8-methoxy-quinazoline Step A: [2-chloro-5-[2-(8-methoxyquinazolin-4-yl)-3-methyl-4,5-dihydro-3H-pyridazin-6-yl]phenyl] methanol The compound was prepared using the same procedure detailed in example 55 step A starting from tert-butyl-[[2-chloro-5-(6-methyl-1,4,5,6-tetrahydropyridazin-3-yl)phenyl]methoxy]-dimethyl-silane (example 53, step C), (362.7 mg; 1.03 mmol; 1.00 eq.) and 4-chloro-8-methoxyquinazoline (200.0 mg; 1.03 mmol, 1.00 eq.) giving [2-chloro-5-[2-(8-methoxyquinazolin-4-yl)-3-methyl-4,5-dihydro-3H-pyridazin-6-yl]phenyl])methanol (80.0 mg; 20%) as an orange oil. $^1$H NMR (DMSO-d6, 300 MHz): δ 8.74 (br s, 1H); 8.62 (d, J=8.4 Hz, 1H); 7.72 (dd, J=2.3 Hz, J=8.4 Hz, 1H); 7.50 (m, 2H); 7.39 (m, 1H); 5.49 (br s, 1H); 5.30 (m, 1H); 4.61 (br s, 2H); 3.97 (s, 3H); 2.86 (m, 2H); 2.13 (m, 2H); 1.30 (d, J=6.6 Hz, 3H).

Step B: 4-[6-(1-hydroxy-3H-2,1-benzoxaborol-5-yl)-3-methyl-4,5-dihydro-3H-pyridazin-2-yl]-8-methoxy-quinazoline The compound was prepared using the same procedure detailed in example 9 step J starting from [2-chloro-5-[2-(8-methoxyquinazolin-4-yl)-3-methyl-4,5-dihydro-3H-pyridazin-6-yl]phenyl]methanol (80.0 mg; 0.20 mmol; 1.00 eq.) giving 4-[6-(1-hydroxy-3H-2,1-benzoxaborol-5-yl)-3-methyl-4,5-dihydro-3H-pyridazin-2-yl]-8-methoxy-quinazoline (17.0 mg; 22%) as a yellow solid. $^1$H NMR (DMSO-d6, 400 MHz): δ 9.26 (br s, 1H); 8.70 (s, 1H); 8.55 (dd, J=1.0 Hz, J=8.7 Hz, 1H); 7.85 (m, 2H); 7.79 (m, 1H); 7.47 (m, 1H); 7.32 (dd, J=1.1 Hz, J=8.1 Hz, 1H); 5.25 (m, 1H); 5.05 (s, 2H); 3.94 (s, 3H); 2.94 (m, 1H); 2.80 (m, 1H); 2.14 (m, 2H); 1.30 (d, J=6.6 Hz, 3H).

Example 57: [4-[2-(1,1-dioxo-1,2-benzothiazol-3-yl)-4,4-dimethyl-3,5-dihydro-pyridazin-6-yl]-2-methoxy-phenyl]boronic acid

Step A: 4-(4-chloro-3-methoxy-phenyl)-2,2-dimethyl-4-oxo-butanoic acid

Magnesium turnings (0.55 g; 22.58 mmol; 5.00 eq.) were suspended in dry THF (10 mL) under inert atmosphere. A solution of 4-bromo-1-chloro-2-methoxybenzene (1.00 g; 4.52 mmol; 1.00 eq.) and 1,2-dibromoethane (0.21 mL; 2.48 mmol; 0.55 eq.) in dry THE (10 mL) was added and the reaction mixture was stirred 30 min under light reflux. Then, it was cooled down to 0° C. and 2,2-dimethylsuccinic anhydride (0.55 g; 4.29 mmol; 0.95 eq.) was added. The reaction mixture was stirred 10 min at 0° C. then 10 min at rt. Aqueous saturated NH$_4$Cl solution was added and the mixture was extracted with EtOAc and DCM. Combined organic phases were dried over MgSO$_4$, filtered and concentrated to dryness to give 4-(4-chloro-3-methoxy-phenyl)-2,2-dimethyl-4-oxo-butanoic acid (720.0 mg; 59%) as a pale yellow oil. LC-MS (Method A): Rt=1.88 min; MS: m/z=271 [M+H]$^+$

Step B: 3-(4-chloro-3-methoxy-phenyl)-5,5-dimethyl-1,4-dihydropyridazin-6-one The compound was prepared using the same procedure detailed in example 52 step C starting from 4-(4-chloro-3-methoxy-phenyl)-2,2-dimethyl-4-oxo-butanoic acid (720.0 mg; 2.66 mmol; 1.00 eq.) giving 3-(4-chloro-3-methoxy-phenyl)-5,5-dimethyl-1,4-dihydropyridazin-6-one (175.0 mg; 25%) as a white solid. $^1$H NMR (DMSO-d6, 300 MHz): δ 10.94 (s, 1H); 7.47 (m, 2H); 7.33 (dd, J=2.0 Hz, J=8.3 Hz, 1H); 3.91 (s, 3H); 2.86 (s, 2H); 1.08 (s, 6H).

Step C: 3-(4-chloro-3-methoxy-phenyl)-5,5-dimethyl-4,6-dihydro-1H-pyridazine Lithium aluminium hydride (74.7 mg; 1.97 mmol; 3.00 eq.) was added to a solution of 3-(4-chloro-3-methoxy-phenyl)-5,5-dimethyl-1,4-dihydropyridazin-6-one (175.0 mg; 0.66 mmol; 1.00 eq.) in THE (1.75 mL) in a QTube. The reaction mixture was then stirred 1 h under reflux, cooled down to rt and diluted with DCM. The organic phase obtained was washed with aqueous saturated solution of Glauber's salt (3×), dried over MgSO$_4$, filtered and concentrated to give 3-(4-chloro-3-methoxy-phenyl)-5,5-dimethyl-4,6-dihydro-1H-pyridazine (147.0 mg; 89%) as a colorless oil. $^1$H NMR (CDCl$_3$, 300 MHz): δ 7.39 (d, J=2.0 Hz, 1H); 7.30 (d, J=8.3 Hz, 1H); 7.04 (dd, J=2.0 Hz, J=8.3 Hz, 1H); 3.94 (s, 3H); 2.83 (t, J=1.3 Hz, 2H); 2.27 (t, J=1.2 Hz, 2H); 1.05 (s, 6H).

Step D: 3-[6-(4-chloro-3-methoxy-phenyl)-4,4-dimethyl-3,5-dihydropyridazin-2-yl]-1,2-benzothiazole 1,1-dioxide The compound was prepared using the same procedure detailed in example 1 step C starting from 3-chloro-1,2-benzothiazole 1,1-dioxide (example 1, step A), (115.7 mg; 0.57 mmol; 1.00 eq.) and 3-(4-chloro-3-methoxy-phenyl)-5,5-dimethyl-4,6-dihydro-1H-pyridazine (145.0 mg; 0.57 mmol; 1.00 eq.) giving 3-[6-(4-chloro-3-methoxy-phenyl)-4,4-dimethyl-3,5-dihydropyridazin-2-yl]-1,2-benzothiazole 1,1-dioxide (173.0 mg; 72%) as a white solid. $^1$H NMR (CDCl$_3$, 400 MHz): δ 8.76 (m, 1H); 7.96 (td, J=0.9 Hz, J=7.4 Hz, 1H); 7.72 (dt, J=0.9 Hz, J=7.5 Hz, 1H); 7.62 (dt, J=1.1 Hz, J=7.7 Hz, 1H); 7.48 (d, J=8.1 Hz, 1H); 7.39 (d, J=2.0 Hz, 1H); 7.23 (dd, J=2.1 Hz, J=8.3 Hz, 1H); 3.99 (s, 3H); 3.91 (s, 2H); 2.56 (s, 2H); 1.17 (s, 6H).

Step E: [4-[2-(1,1-dioxo-1,2-benzothiazol-3-yl)-4,4-dimethyl-3,5-dihydropyridazin-6-yl]-2-methoxy-phenyl]boronic acid The compound was prepared using the same procedure detailed in example 9 step J starting from 3-[6-(4-chloro-3-methoxy-phenyl)-4,4-dimethyl-3,5-dihydropyridazin-2-yl]-1,2-benzothiazole 1,1-dioxide (150.0 mg; 0.36 mmol; 1.00 eq.) giving [4-[2-(1,1-dioxo-1,2-benzothiazol-3-yl)-4,4-dimethyl-3,5-dihydropyridazin-6-yl]-2-methoxy-phenyl]boronic acid (17.0 mg; 11%) as a white solid. $^1$H NMR (CDCl$_3$, 400 MHz): δ 8.81 (d, J=7.9 Hz, 1H): 7.97 (s, 1H); 7.95 (s, 1H); 7.72 (dt, J=0.9 Hz, J=7.5 Hz, 1H); 7.63 (dd, J=1.1 Hz, J=7.5 Hz, 1H); 7.37 (s, 2H); 5.68 (s, 2H); 4.01 (s, 3H); 3.92 (s, 2H); 2.60 (s, 2H); 1.17 (s, 6H). mp: 205° C.

Example 58: [4-[4-(1,1-dioxo-1,2-benzothiazol-3-yl)-6-methyl-5,6-dihydro-1,3,4-oxadiazin-2-yl]-2-methoxy-phenyl]boronic acid

Step A: methyl 4-chloro-3-methoxy-benzoate 4-chloro-3-methoxybenzaldehyde (3.00 g; 0.02 mol: 1.00 eq.) was dissolved into MeOH (42 mL) and cooled to 0° C. A solution of KOH (2.57 g; 0.05 mol; 2.60 eq.) in MeOH (6 mL) was added. Then, iodine (5.80 g; 0.02 mol; 1.30 eq.) was added rapidly and the reaction was stirred at 0° C. until completion. The reaction mixture was quenched by adding an aqueous solution of sodium thiosulfate followed by water. The resulting precipitate was filtered, washed once with water and dried under vacuum overnight to give methyl 4-chloro-3-methoxy-benzoate (3.23 g; 92%) as a white solid. $^1$H NMR (DMSO-d6, 300 MHz): δ 7.60 (m, 2H); 7.56 (dd, J=1.7 Hz, J=7.9 Hz, 1H); 3.93 (s, 3H); 3.87 (s, 3H).

Step B: 4-chloro-3-methoxy-benzohydrazide

Hydrazine hydrate (18.57 mL; 35% w/w; 209.30 mmol; 13.00 eq.) was added to a solution of methyl 4-chloro-3-methoxy-benzoate (3.23 g; 16.10 mmol; 1.00 eq.) in EtOH (60 mL) and the reaction was stirred under reflux until completion. After being cooled to rt and diluted with water, the mixture was extracted with EtOAc (3×). Combined organic phases were dried over MgSO$_4$, filtered and concentrated to dryness to give 4-chloro-3-methoxy-benzohydrazide (3.26 g; quantitative) as a white solid. $^1$H NMR (DMSO-d6, 300 MHz): δ 9.86 (s, 1H); 7.55 (d, J=1.8 Hz, 1H); 7.50 (d, J=8.3 Hz, 1H); 7.42 (dd, J=2.0 Hz, J=8.1 Hz, 1H); 4.52 (br s, 2H); 3.90 (s, 3H).

Step C: 4-chloro-N'-(2-chloropropanoyl)-3-methoxy-benzohydrazide

2-Chloropropionyl chloride (1.56 mL; 16.10 mmol; 1.00 eq.) was added to a suspension of 4-chloro-3-methoxy-benzohydrazide (3.23 g; 16.10 mmol; 1.00 eq.) in 1,4-dioxane (50 mL) and the reaction mixture was stirred under reflux until completion. The reaction mixture was then concentrated to dryness to give crude 4-chloro-N'-(2-chloropropanoyl)-3-methoxy-benzohydrazide (5.20 g; quantitative) as a beige powder. $^1$H NMR (DMSO-d6, 300 MHz): δ 10.66 (d, J=1.3 Hz, 1H); 10.45 (d, J=1.5 Hz, 1H); 7.61 (d, J=1.8 Hz, 1H); 7.57 (d, J=8.3 Hz, 1H); 7.48 (dd, J=2.0 Hz, J=8.3 Hz, 1H); 4.64 (q, J=6.7 Hz, 1H); 3.93 (s, 3H); 1.60 (d, J=6.8 Hz, 3H).

Step D: 2-(4-chloro-3-methoxy-phenyl)-6-methyl-4H-1,3,4-oxadiazin-5-one

Triethylamine (573 μL; 4.12 mmol; 1.20 eq.) was added to a solution of 4-chloro-N'-(2-chloropropanoyl)-3-methoxy-benzohydrazide (1.00 g; 3.43 mmol; 1.00 eq.) in DMF (25 mL). The reaction was stirred 6 h at 150° C. under microwave irradiation and then diluted with water. The mixture was extracted with EtOAc (3×) and combined organic phases were dried over MgSO$_4$, filtered and concentrated. The residue was purified by column chromatography (gradient 0 to 50% of EtOAc in cyclohexane) to give 2-(4-chloro-3-methoxy-phenyl)-6-methyl-4H-1,3,4-oxadiazin-5-one (308.7 mg; 35%) as a white solid. $^1$H NMR (DMSO-d6, 300 MHz): δ 11.09 (s, 1H); 7.53 (d, J=8.4 Hz, 1H); 7.43 (d, J=1.8 Hz, 1H); 7.37 (m, 1H); 4.94 (q, J=6.6 Hz, 1H); 3.90 (s, 3H); 1.49 (d, J=6.9 Hz, 3H).

Step E: 2-(4-chloro-3-methoxy-phenyl)-6-methyl-5,6-dihydro-4H-1,3,4-oxadiazine The compound was prepared using the same procedure detailed in example 23 step A starting from 2-(4-chloro-3-methoxy-phenyl)-6-methyl-4H-1,3,4-oxadiazin-5-one (438.0 mg; 1.72 mmol; 1.00 eq.) giving 2-(4-chloro-3-methoxy-phenyl)-6-methyl-5,6-dihydro-4H-1,3,4-oxadiazine (416.8 mg) as a colorless oil, used in the next step without purification. $^1$H NMR (DMSO-d6, 300 MHz): δ 7.39 (d, J=8.3 Hz, 1H); 7.35 (d, J=1.8 Hz, 1H); 7.24 (m, 1H); 6.54 (s, 1H); 4.49 (dt, J=2.9 Hz, J=6.6 Hz, 1H); 3.86 (s, 3H); 3.25 (m, 1H); 2.75 (ddd, J=1.3 Hz, J=7.1 Hz, J=11.7 Hz, 1H); 1.32 (d, J=6.3 Hz, 3H).

Step F: 3-[2-(4-chloro-3-methoxy-phenyl)-6-methyl-5,6-dihydro-1,3,4-oxadiazin-4-yl]-1,2-benzothiazole 1,1-dioxide The compound was prepared using the same procedure detailed in example 1 step C starting from 3-chloro-1,2-benzothiazole 1,1-dioxide (example 1, step A), (350.2 mg; 1.72 mmol; 1.00 eq.) and 2-(4-chloro-3-methoxy-phenyl)-6-methyl-5,6-dihydro-4H-1,3,4-oxadiazine (416.8 mg; 1.72 mmol; 1.00 eq.) giving 3-[2-(4-chloro-3-methoxy-phenyl)-6-methyl-5,6-dihydro-1,3,4-oxadiazin-4-yl]-1,2-benzothiazole 1,1-dioxide (383.9 mg; 54%) as a yellow solid. $^1$H NMR (DMSO-d6, 300 MHz): δ 8.87 (m, 1H); 8.09 (m, 1H); 7.90 (m, 2H); 7.62 (m, 1H); 7.57 (d, J=2.0 Hz, 1H); 7.52 (m, 1H); 4.82 (ddd, J=3.0 Hz, J=6.2 Hz, J=8.7 Hz, 1H); 4.65 (dd, J=3.0 Hz, J=13.4 Hz, 1H); 3.98 (s, 3H); 3.75 (dd, J=8.6 Hz, J=13.5 Hz, 1H); 1.52 (d, J=6.4 Hz, 3H).

Step G: [4-[4-(1,1-dioxo-1,2-benzothiazol-3-yl)-6-methyl-5,6-dihydro-1,3,4-oxadiazin-2-yl]-2-methoxy-phenyl]boronic acid The compound was prepared using the same procedure detailed in example 9 step J starting from 3-[2-(4-chloro-3-methoxy-phenyl)-6-methyl-5,6-dihydro-1,3,4-oxadiazin-4-yl]-1,2-benzothiazole 1,1-dioxide (383.0 mg; 0.94 mmol; 1.00 eq.) giving [4-[4-(1,1-dioxo-1,2-benzothiazol-3-yl)-6-methyl-5,6-dihydro-1,3,4-oxadiazin-2-yl]-2-methoxy-phenyl]boronic acid (52.1 mg; 13%) as a white solid. $^1$H NMR (DMSO-d6, 400 MHz): δ 8.91 (dd, J=1.1 Hz, J=6.8 Hz, 1H); 8.09 (m, 1H); 7.93 (m, 4H); 7.68 (d, J=7.7 Hz, 1H); 7.51 (dd, J=1.4 Hz, J=7.6 Hz, 1H); 7.44 (d, J=1.3 Hz, 1H); 4.82 (dqd, J=3.0 Hz, J=6.2 Hz, J=9.0 Hz, 1H); 4.65 (dd, J=3.0 Hz, J=13.5 Hz, 1H); 3.90 (s, 3H); 3.76 (dd, J=8.6 Hz, J=13.4 Hz, 1H); 1.52 (d, J=6.4 Hz, 3H).

Example 59: [2-methoxy-4-[(E)-[methyl-(5-methylpyridazin-3-yl)hydrazono]methyl]-phenyl] boronic acid

Step A: 1-methyl-1-(5-methylpyridazin-3-yl)hydrazine

3-Chloro-5-methyl-pyridazine (200.0 mg; 1.56 mmol; 1.00 eq.) was diluted in methyl hydrazine (1.24 mL; 23.34 mmol; 15.00 eq.) and the mixture was stirred at 100° C. for 3 h. The reaction mixture was then concentrated to dryness. The residue was taken up into DCM and washed twice with water. The organic phase was dried over MgSO$_4$, filtered and concentrated under vacuum to give 1-methyl-1-(5-methylpyridazin-3-yl)hydrazine (170.0 mg; 79%) as an orange solid. $^1$H NMR (DMSO-d6, 300 MHz): δ 8.31 (d, J=1.8 Hz, 1H); 7.28 (qd, J=1.0 Hz, J=1.9 Hz, 1H); 4.65 (s, 2H); 3.28 (s, 3H); 2.19 (dd, J=0.3 Hz, J=1.0 Hz, 3H).

Step B: [2-methoxy-4-[(E)-[methyl-(5-methylpyridazin-3-yl)hydrazono]methyl]phenyl]boronic acid The compound was prepared using the same procedure detailed in example 50 step B starting from 1-methyl-1-(5-methylpyridazin-3-yl)hydrazine (170.0 mg; 1.23 mmol; 1.00 eq.) and 4-formyl-2-methoxyphenylboronic acid (243.6 mg; 1.35 mmol; 1.10 eq.) giving [2-methoxy-4-[(E)-[methyl-(5-methylpyridazin-3-yl)hydrazono]methyl]phenyl]boronic acid (204.0 mg; 55%) as a beige solid. $^1$H NMR (DMSO-d6, 400 MHz): δ 8.63 (d, J=1.8 Hz, 1H); 7.96 (s, 1H); 7.81 (dd, J=0.9 Hz, J=1.8 Hz, 1H); 7.73 (s, 2H); 7.61 (d, J=7.5 Hz, 1H); 7.42 (dd, J=1.2 Hz, J=7.6 Hz, 1H); 7.36 (d, J=1.1 Hz, 1H); 3.90 (s, 3H); 3.74 (s, 3H); 2.34 (s, 3H). mp: 205-217° C.

Example 60: N-[(E)-(1-hydroxy-3H-2,1-benzoxaborol-5-yl)methyleneamino]-5-methoxy-N-methylpyridazin-3-amine The compound was prepared using the same procedure detailed in example 55 step A starting from N-[(E)-(1-hydroxy-3H-2,1-benzoxaborol-5-yl)methyleneamino]methanamine (example 51, step C), (117.8 mg; 0.62 mmol; 1.00 eq.) and 3-chloro-5-methoxypyridazine (89.6 mg; 0.62 mmol; 1.00 eq.) giving N-[(E)-(1-hydroxy-3H-2,1-benzoxaborol-5-yl)methyleneamino]-5-methoxy-N-methylpyridazin-3-amine (12.0 mg; 6%) as a grey solid. $^1$H NMR (DMSO-d6, 400 MHz): δ 9.24 (br s, 1H); 8.54 (d, J=2.6 Hz, 1H); 8.04 (s, 1H); 7.80 (m, 3H); 7.36 (d, J=2.6 Hz, 1H); 5.04 (s, 2H); 3.98 (s, 3H); 3.76 (s, 3H).

Example 61: 2-[4-[(E)-[(1,1-dioxo-1,2-benzothiazol-3-yl)-isobutyl-hydrazono]methyl]-2-methoxy-phenyl]-6-methyl-1,3,6,2-dioxazaborocane-4,8-dione

[4-[(E)-[(1,1-dioxo-1,2-benzothiazol-3-yl)-isobutyl-hydrazono]methyl]-2-methoxy-phenyl]boronic acid (example 1, step C), (60.0 mg; 0.14 mmol; 1.00 eq.) was suspended into toluene (1.2 mL) and DMSO (120 µL). N-methyliminodiacetic acid (31.9 mg; 0.21 mmol; 1.50 eq.) was added and the mixture was stirred 2 h under reflux. Toluene was concentrated and the residue was taken up into water. The precipitate obtained was filtered, washed twice with an aqueous 10% sodium carbonate solution, then water (5×) and dried to give 2-[4-[(E)-[(1,1-dioxo-1,2-benzothiazol-3-yl)-isobutyl-hydrazono]methyl]-2-methoxy-phenyl]-6-methyl-1,3,6,2-dioxazaborocane-4,8-dione (56.0 mg; 73%) as a white solid. $^1$H NMR (DMSO-d6, 400 MHz): δ 8.89 (dd, J=0.9 Hz, J=7.0 Hz, 1H); 8.56 (s, 1H); 8.10 (m, 1H); 7.92 (dt, J=1.3 Hz, J=7.7 Hz, 1H); 7.89 (dt, J=1.1 Hz, J=7.0 Hz, 1H); 7.65 (d, J=7.5 Hz, 1H); 7.49 (dd, J=1.2 Hz, J=7.6 Hz, 1H); 7.46 (s, 1H); 4.41 (d, J=17.2 Hz, 2H); 4.29 (d, J=7.7 Hz, 2H); 4.08 (d, J=17.2 Hz, 2H); 3.86 (s, 3H); 2.64 (s, 3H); 2.28 (m, 1H); 0.99 (d, J=6.6 Hz, 6H). mp: 330° C.

Example 62: [4-[(E)-[ethyl-(7-methylthieno[3,2-d]pyrimidin-4-yl)hydrazono]methyl]-2-methoxy-phenyl]boronic acid The compound was prepared using the same procedure detailed in example 3 step B starting from (4-formyl-2-methoxy-phenyl)boronic acid (150.00 mg; 0.83 mmol; 1.00 eq.), ethyl hydrazine dihydrochloride (110.00 mg; 0.83 mmol; 1.00 eq.) and 4-chloro-7-methyl-thieno[3,2-d]pyrimidine (96.43 mg; 0.52 mmol; 1.00 eq.) giving [4-[(E)-[ethyl-(7-methylthieno[3,2-d]pyrimidin-4-yl)hydrazono]methyl]-2-methoxy-phenyl]boronic acid (83 mg, 42%) as a white powder. $^1$H NMR (DMSO-d6, 400 MHz) δ 8.72 (s, 1H); 8.26 (s, 1H); 7.98 (d, J=1.2 Hz, 1H); 7.81 (s, 2H); 7.67 (d, J=7.5 Hz, 1H); 7.66 (s, 1H); 7.50 (dd, J=7.5, 1.2 Hz, 1H); 4.53 (q, J=7.0 Hz, 2H); 3.95 (s, 3H); 2.39 (s, 3H); 1.24 (t, J=7.0 Hz, 3H). mp 188-210° C.

Example 63: [4-[(E)-[ethyl(thieno[3,2-d]pyrimidin-4-yl)hydrazono]methyl]-2-methoxy-phenyl]boronic acid The compound was prepared using the same procedure detailed in example 1 step C starting from [4-[(E)-(ethylhydrazono)methyl]-2-methoxy-phenyl]boronic acid (example 4 step A), (58 mg; 0.26 mmol; 1.00 eq.) and 4-chlorothieno[3,2-d]pyrimidine (44.57 mg; 0.26 mmol; 1.00 eq.) in propan-2-ol (1.45 ml) giving [4-[(E)-[ethyl(thieno[3,2-d]pyrimidin-4-yl)hydrazono]methyl]-2-methoxy-phenyl]boronic acid (70 mg; 75%) as an off white powder. $^1$H NMR (DMSO-d6, 400 MHz) δ 8.70 (s, 1H); 8.35 (d, J=5.6 Hz, 1H); 8.28 (s, 1H); 7.82 (s, 1H); 7.67 (d, J=7.5 Hz, 1H); 7.66 (d, J=1.0 Hz, 1H); 7.50 (dd, J=7.5 Hz, 1.3 Hz, 1H); 7.49 (s, 1H); 4.54 (q, J=7.0 Hz, 2H); 3.96 (s, 3H); 1.25 (t, J=7.0 Hz, 3H). mp=196-204° C.

Example 64: [4-[(E)-[ethyl(thiazolo[4,5-d]pyrimidin-7-yl)hydrazono]methyl]-2-methoxy-phenyl]boronic acid The compound was prepared using the same procedure detailed in example 1 Step C starting from 7-chlorothiazolo[4,5-d]pyrimidine (148.77 mg; 0.87 mmol; 1.10 eq.) and [4-[(E)-[ethyl(thieno[3,2-d]pyrimidin-4-yl)hydrazono]methyl]-2-methoxy-phenyl]boronic acid (example 4, Step A) (175 mg; 0.79 mmol; 1.00 eq.) to give [4-[(E)-[ethyl(thiazolo[4,5-d]pyrimidin-7-yl)hydrazono]methyl]-2-methoxy-phenyl]boronic acid (195.00 mg; 66%) as a yellow powder. $^1$H NMR (DMSO-d6, 400 MHz) δ 9.82 (s, 1H); 8.79 (s, 1H); 8.34 (s, 1H); 7.83 (s, 2H); 7.68 (d, J=7.48 Hz, 1H); 7.58 (d, J=1.10 Hz, 1H); 7.50 (dd, J=7.48 Hz, J=1.1 Hz, 1H); 4.54 (q, J=7.04 Hz, 2H); 3.97 (s, 3H); 1.25 (t, J=7.04 Hz, 3H). mp=192-201° C.

Example 65: [4-[(E)-[ethyl(furo[2,3-d]pyrimidin-4-yl)hydrazono]methyl]-2-methoxy-phenyl]boronic acid The compound was prepared using the same procedure detailed in example 1 Step C starting from [4-[(E)-(ethyl-hydrazono)methyl]-2-methoxy-phenyl]boronic acid (Example 4, step A) (190.00 mg; 0.73 mmol; 1.00 eq.) and 4-chlorofuro[2,3-d]pyrimidine (113.59 mg; 0.73 mmol; 1.00 eq.) giving [4-[(E)-[ethyl(furo[2,3-d]pyrimidin-4-yl)hydrazono]methyl]-2-methoxy-phenyl]boronic acid (80.00 mg, 31%) as a white powder. $^1$H NMR (DMSO-d6) δ 8.53 (s, 1H), 8.28 (s, 1H); 8.02 (d, J=2.4 Hz, 1H); 7.81 (s, 2H); 7.67 (d, J=7.5 Hz, 1H); 7.41 (s, 1H); 7.40 (d, J=7.5 Hz, 1H); 7.38 (d, J=2.4 Hz, 1H); 4.50 (q, J=6.8 Hz, 2H); 3.91 (s, 3H); 1.23 (t, J=6.8 Hz, 3H) mp=172-185° C.

Example 66: [4-[(E)-[ethyl-(7-methylpyrrolo[2,3-d]pyrimidin-4-yl)hydrazono]methyl]-2-methoxy-phenyl]boronic acid The compound was prepared using the same procedure detailed in example 1 Step C starting from [4-[(E)-(ethyl-hydrazono)methyl]-2-methoxy-phenyl]boronic acid (Example 4, step A) (180.00 mg; 0.81 mmol; 1.00 eq.) and 4-chloro-7-methyl-pyrrolo[2,3-d]pyrimidine (176.62 mg; 1.05 mmol 1.30 eq.) giving [4-[(E)-[ethyl-(7-methylpyrrolo[2,3-d]pyrimidin-4-yl)hydrazono]methyl]-2-methoxy-phenyl]boronic acid (37.00 mg, 13%) as a white powder. $^1$H NMR (DMSO-d6, 400 MHz) δ 8.40 (s, 1H); 8.17 (s, 1H); 7.77 (s, 2H); 7.66 (d, J=7.5 Hz, 1H); 7.44 (d, J=1.0 Hz, 1H); 7.36-7.41 (m, 2H); 7.07 (d, J=3.4 Hz, 1H); 4.50 (q, J=6.7 Hz, 2H); 3.91 (s, 3H); 3.78 (s, 3H); 1.22 (t, J=6.7 Hz, 3H)

Example 67: [4-[(E)-[isobutyl-(7-methylthieno[3,2-d]pyrimidin-4-yl)hydrazono]methyl]-2-methoxy-phenyl]boronic acid The compound was prepared using the same procedure detailed in example 1 Step C starting from [4-[(E)-(isobutyl-hydrazono)methyl]-2-methoxy-phenyl]boronic acid (example 1 step B) (85.00 mg; 0.30 mmol; 1.00 eq.) and 4-chloro-7-methyl-thieno[3,2-d]pyrimidine (54.77 mg; 0.30 mmol; 1.00 eq.) giving [4-[(E)-[isobutyl-(7-methylthieno[3,2-d]pyrimidin-4-yl)hydrazono]methyl]-2-methoxy-phenyl]boronic acid (15 mg, 12%) as a white powder. $^1$H NMR (DMSO-d6, 400 MHz) δ 8.70 (s, 1H); 8.24 (s, 1H); 7.99 (d, J=1.2 Hz, 1H); 7.80 (s, 2H); 7.67 (d, J=7.5 Hz, 1H) 7.66 (s, 1H); 7.51 (dd, J=7.5 Hz, J=1.2 Hz, 1H); 4.40 (br d, J=7.5 Hz, 2H); 3.95 (s, 3H); 2.38 (s, 3H); 2.23-2.33 (m, 1H); 0.94 (d, J=6.6 Hz, 6H) mp=147-167° C.

Example 68: [4-[(E)-[isobutyl-(2-methylthieno[3,2-d]pyrimidin-4-yl)hydrazono]methyl]-2-methoxy-phenyl]boronic acid The compound was prepared using the same procedure detailed in example 3 Step B starting from [(4-formyl-2-methoxy-phenyl)boronic acid (88.60 mg; 0.49 mmol; 1.00 eq.); 2-methylpropylhydrazine hydrochloride (64.42 mg; 0.52 mmol; 1.05 eq.) and 4-chloro-2-methyl-thieno[3,2-d]pyrimidine (100.00 mg; 0.54 mmol; 1.10 eq.) giving [4-

[(E)-[isobutyl-(2-methylthieno[3,2-d]pyrimidin-4-yl)hydrazono]methyl]-2-methoxy-phenyl]boronic acid (30.00 mg, 15%) as an off white powder. $^1$H NMR (DMSO-d6, 400 MHz) δ 8.29 (d, J=5.61 Hz, 1H); 8.21 (s, 1H); 7.80 (s, 2H); 7.67 (br d, J=7.3 Hz, 1H); 7.66 (br s, 1H); 7.50 (dd, J=7.3 Hz, J=0.88 Hz, 1H); 7.40 (d, J=5.61 Hz, 1H); 4.39 (br d, J=6.6 Hz, 2H); 3.95 (s, 3H); 2.57 (s, 3H); 2.27 (sept., J=6.6 Hz, 1H); 0.95 (d, J=6.60 Hz, 6H). mp=175-178° C.

Example 69: [4-[(E)-[isobutyl-(6-methylthieno[3,2-d]pyrimidin-4-yl)hydrazono]methyl]-2-methoxy-phenyl]boronic acid The compound was prepared using the same procedure detailed in example 3 Step B starting from [(4-formyl-2-methoxy-phenyl)boronic acid (88.60 mg; 0.49 mmol; 1.00 eq.); 2-methylpropylhydrazine hydrochloride (64.42 mg; 0.52 mmol; 1.05 eq.) and 4-chloro-6-methyl-thieno[3,2-d]pyrimidine (100.00 mg; 0.49 mmol; 1.00 eq.). The residue was purified by column chromatography (5% of MeOH in DCM) then triturated in NaHCO$_3$ and water to give [4-[(E)-[isobutyl-(6-methylthieno[3,2-d]pyrimidin-4-yl)hydrazono]methyl]-2-methoxy-phenyl]boronic acid (62.00 mg, 30%) as an off white powder. $^1$H NMR (DMSO-d6, 400 MHz) δ 8.61 (s, 1H); 8.21 (s, 1H); 7.81 (s, 2H); 7.72 (d, J=1.10 Hz, 1H); 7.68 (d, J=7.48 Hz, 1H); 7.45 (dd, J=7.48 Hz, J=1.10 Hz, 1H); 7.22 (s, 1H); 4.37 (br d, J=6.6 Hz, 2H); 3.98 (s, 3H); 2.62 (s, 3H); 2.26 (sept., J=6.6 Hz, 1H); 0.94 (d, J=6.6 Hz, 6H). mp=164-167° C.

Example 70: [2-methoxy-4-[(E)-[2-methoxyethyl(thieno[3,2-d]pyrimidin-4-yl) hydrazono]methyl]phenyl]boronic acid The compound was prepared using the same procedure detailed in example 1 Step C starting from [2-methoxy-4-[(E)-(2-methoxyethylhydrazono)methyl]phenyl]boronic acid (example 5 step A) (155.00 mg; 0.49 mmol; 1.00 eq.) and 4-chlorothieno[3,2-d]pyrimidine (82.88 mg; 0.49 mmol; 1.00 eq.) giving [2-methoxy-4-[(E)-[2-methoxyethyl(thieno[3,2-d]pyrimidin-4-yl)hydrazono]methyl]phenyl]boronic acid (120.00 mg, 64%) as an off white powder. $^1$H NMR (DMSO-d6, 400 MHz) δ 8.69 (s, 1H); 8.36 (d, J=5.6 Hz, 1H); 8.34 (s, 1H); 7.82 (s, 2H); 7.67 (d, J=7.5 Hz, 1H); 7.64 (d, J=0.9 Hz, 1H); 7.50 (d, J=5.6 Hz, 1H); 7.47 (dd, J=7.5 Hz, J=0.9 Hz, 1H); 4.70 (t, J=5.8 Hz, 2H); 3.95 (s, 3H); 3.69 (t, J=5.9 Hz, 2H); 3.28 (s, 3H). mp=110-118° C.

Example 71: [2-methoxy-4-[(E)-[methyl-(7-methylthieno[3,2-d]pyrimidin-4-yl) hydrazono]methyl]phenyl]boronic acid Step A: 1-methyl-1-(7-methylthieno[3,2-d]pyrimidin-4-yl)hydrazine The compound was prepared using the same procedure detailed in example 59 Step A starting from 4-chloro-7-methyl-thieno[3,2-d]pyrimidine (100.00 mg; 0.54 mmol; 1.00 eq.) and methylhydrazine (228.13 μL; 5.42 mmol; 10.00 eq.) giving 1-methyl-1-(7-methylthieno[3,2-d]pyrimidin-4-yl)hydrazine (70.00 mg, 67%) as a white powder. $^1$H NMR (DMSO-d6, 300 MHz) δ 8.36 (s, 1H); 7.63 (d, J=1.16 Hz, 1H); 5.18 (s, 2H); 3.36 (d, J=1.16 Hz, 3H); 2.29 (s, 3H).

Step B: [2-methoxy-4-[(E)-[methyl-(7-methylthieno[3,2-d]pyrimidin-4-yl)hydrazono]methyl]phenyl]boronic acid The compound was prepared using the same procedure detailed in example 50 Step B starting from 1-methyl-1-(7-methylthieno[3,2-d]pyrimidin-4-yl)hydrazine (example 71 step A) (70.00 mg; 0.36 mmol; 1.00 eq.) and (4-formyl-2-methoxy-phenyl)boronic acid (64.85 mg; 0.36 mmol; 1.00 eq.) giving [2-methoxy-4-[(E)-[methyl-(7-methylthieno[3,2-d]pyrimidin-4-yl)hydrazono]methyl]phenyl]boronic acid (35.00 mg, 27%) as a white powder. $^1$H NMR (DMSO-d6, 400 MHz) δ 8.71 (s, 1H); 8.18 (s, 1H); 7.99 (d, =1.21 Hz, 1H); 7.82 J (s, 2H); 7.67 (d, J=7.48 Hz, 1H); 7.63 (s, 1H); 7.47 (dd, J=7.48 HZ, J=1.21 Hz, 1H); 3.94 (s, 3H); 3.80 (s, 3H); 2.39 (s, 3H). mp=237-267° C.

Example 72: [2-methoxy-4-(3-methyl-2-thieno[3,2-d]pyrimidin-4-yl-4,5-dihydro-3H-pyridazin-6-yl)phenyl]boronic acid Step A: 4-[6-(4-chloro-3-methoxy-phenyl)-3-methyl-4,5-dihydro-3H-pyridazin-2-yl]thieno [3,2-d]pyrimidine The compound was prepared using the same procedure detailed in example 55 step A starting from 3-(4-chloro-3-methoxy-phenyl)-6-methyl-1,4,5,6-tetrahydropyridazine (example 52, Step C) (229.00 mg; 0.92 mmol; 1.00 eq.) and 4-chlorothieno[3,2-d]pyrimidine (157.13 mg; 0.92 mmol; 1.00 eq.) giving 4-[6-(4-chloro-3-methoxy-phenyl)-3-methyl-4,5-dihydro-3H-pyridazin-2-yl]thieno[3,2-d]pyrimidine (324 mg, 88%) as a beige powder. $^1$H NMR (DMSO-d6, 300 MHz) δ 8.95 (s, 1H); 8.56 (d, J=4.62 Hz, 1H); 7.77 (s, 1H); 7.50-7.67 (m, 3H); 5.34 (m, 1H); 4.01 (s, 3H); 3.07 (br d, J=18.80 Hz, 1H); 2.81-2.96 (m, 1H); 2.02-2.18 (m, 2H); 1.32 (d, J=6.61 Hz, 3H).

Step B: [2-methoxy-4-(3-methyl-2-thieno[3,2-d]pyrimidin-4-yl-4,5-dihydro-3H-pyridazin-6-yl)phenyl]boronic acid The compound was prepared using the same procedure detailed in example 9 step J starting from 4-[6-(4-chloro-3-methoxy-phenyl)-3-methyl-4,5-dihydro-3H-pyridazin-2-yl]thieno[3,2-d]pyrimidine (example 72, step A) giving [2-methoxy-4-(3-methyl-2-thieno[3,2-d]pyrimidin-4-yl-4,5-dihydro-3H-pyridazin-6-yl)phenyl]boronic acid (16.00 mg, 20%) as a beige powder. $^1$H NMR (DMSO-d6, 400 MHz) δ 8.65 (s, 1H); 8.30 (d, J=5.61 Hz, 1H); 7.78 (s, 2H); 7.68 (d, J=1.32 Hz, 1H); 7.67 (d, J=7.70 Hz, 1H); 7.47 (dd, J=1.32 Hz, J=7.70 Hz 1H); 7.45 (d, J=5.61 Hz, 1H); 5.30 (m, 1H); 3.96 (s, 3H); 2.95 (dd, J=18.82 Hz, J=4.95 Hz, 1H); 2.74-2.88 (m, 1H); 1.96-2.14 (m, 2H); 1.27 (d, J=6.71 Hz, 3H).

Example 73: [2-methoxy-4-[3-methyl-2-(7-methylpyrrolo[2,3-d]pyrimidin-4-yl)-4,5-dihydro-3H-pyridazin-6-yl]phenyl]boronic acid Step A: 4-chloro-7-methyl-pyrrolo[2,3-d]pyrimidine 4-chloro-7H-pyrrolo[2,3-d]pyrimidine (500 mg; 3.26 mmol; 1.00 eq.) was dissolved in DMF (5 mL). Cesium carbonate (1.59 g, 4.88 mmol; 1.50 eq.) was added and stirred at rt for 10 min. Iodomethane (405.37 μL; 6.51 mmol; 2.00 eq.) was added. The reaction mixture was stirred at rt for 1 h. The reaction mixture was filtered and the solid was washed with ethyl acetate. The filtrate was washed with water and brine, dried over magnesium sulfate, filtered and concentrated giving 4-chloro-7-methyl-pyrrolo[2,3-d]pyrimidine (540 mg, 99%) as a yellow powder. $^1$H NMR (DMSO-d6, 300 MHz) δ 8.65 (s, 1H); 7.74 (d; J=3.5 Hz, 1H); 6.64 (d, J=3.5 Hz, 1H); 3.86 (s, 3H)

Step B: 4-[6-(4-chloro-3-methoxy-phenyl)-3-methyl-4,5-dihydro-3H-pyridazin-2-yl]-7-methyl-pyrrolo[2,3-d]pyrimidine The compound was prepared using the same procedure detailed in example 55 step A starting from 4-chloro-3-methoxy-phenyl)-6-methyl-1,4,5,6-tetrahydropyridazine (example 52, Step C) (391.69 mg; 1.58 mmol; 1.10 eq.) and 4-chloro-7-methyl-pyrrolo[2,3-d]pyrimidine (example 73, Step A) (240 mg; 1.43 mmol; 1.00 eq.) to give 4-[6-(4-chloro-3-methoxy-phenyl)-3-methyl-4,5-dihydro-3H-pyridazin-2-yl]-7-methyl-pyrrolo[2,3-d]pyrimidine (163.00 mg, 31%) as a yellow oil. $^1$H NMR (DMSO-d6, 300 MHz) δ 8.37 (s, 1H); 7.60 (d, J=1.98 Hz, 1H); 7.53 (d, J=8.26 Hz, 1H); 7.39 (dd, J=8.26 Hz, J=1.98 Hz, 1H); 7.32 (d, J=3.47 Hz, 1H); 7.00 (d, J=3.47 Hz, 1H); 5.27 (m, 1H); 3.95 (s, 3H); 3.76 (s, 3H); 2.84-2.95 (m, 1H); 2.64-2.81 (m, 1H); 1.94-2.12 (m, 2H); 1.23 (d, J=6.61 Hz, 3H).

Step C: [2-methoxy-4-[3-methyl-2-(7-methylpyrrolo[2,3-d]pyrimidin-4-yl)-4,5-dihydro-3H-pyridazin-6-yl]phenyl]boronic acid The compound was prepared using the same procedure detailed in example 9 step J starting from 4-[6-(4-chloro-3-methoxy-phenyl)-3-methyl-4,5-dihydro-3H-pyridazin-2-yl]-7-methyl-pyrrolo[2,3-d]pyrimidine (example 73, Step b) (110.00 mg; 0.30 mmol; 1.00 eq.) giving [2-methoxy-4-[3-methyl-2-(7-methylpyrrolo[2,3-d]pyrimidin-4-yl)-4,5-dihydro-3H-pyridazin-6-yl]phenyl]boronic acid (12 mg, 10%) as a white powder. $^1$H NMR (DMSO-d6, 400 MHz) δ 8.36 (s, 1H); 7.76 (s, 2H); 7.65 (d, J=7.70 Hz, 1H); 7.48 (d, J=1.27 Hz, 1H); 7.38 (dd, J=7.70 Hz, J=1.27 Hz, 1H); 7.33 (d, J=3.41 Hz, 1H); 7.04 (d, J=3.41 Hz, 1H); 5.27 (m, 1H); 3.90 (s, 3H); 3.76 (s, 3H); 2.84-2.96 (m, 1H); 2.66-2.80 (m, 1H); 1.95-2.13 (m, 2H); 1.23 (d, J=6.60 Hz, 3H).

Example 74: [4-[4-(7-fluoroquinazolin-4-yl)-6-methyl-5,6-dihydro-1,3,4-oxadiazin-2-yl]-2-methoxy-phenyl]boronic acid Step A: 2-(4-chloro-3-methoxy-phenyl)-4-(7-fluoro-quinazolin-4-yl)-6-methyl-5,6-dihydro-1,3,4-oxadiazine The compound was prepared using the same procedure detailed in example 58 step F starting from 2-(4-chloro-3-methoxy-phenyl)-6-methyl-5,6-dihydro-4H-1,3,4-oxadiazine (example 58, step E) (80.00 mg; 0.30 mmol; 1.00 eq.) and 4-chloro-7-fluoro-quinazoline (54.62 mg; 0.30 mmol; 1.00 eq.) giving 2-(4-chloro-3-methoxy-phenyl)-4-(7-fluoroquinazolin-4-yl)-6-methyl-5,6-dihydro-1,3,4-oxadiazine (60.00 mg, 48%) as a beige powder. $^1$H NMR (DMSO-d6, 400 MHz) δ 9.41 (m, 1H); 8.74 (s, 1H); 7.49-7.63 (m, 5H); 4.80 (m, 2H); 3.94 (s, 3H); 3.54-3.68 (m, 1H); 1.52 (d, J=5.95 Hz, 3H).

Step B: [4-[4-(7-fluoroquinazolin-4-yl)-6-methyl-5,6-dihydro-1,3,4-oxadiazin-2-yl]-2-methoxy-phenyl]boronic acid The compound was prepared using the same procedure detailed in example 9 step J starting from 2-(4-chloro-3-methoxy-phenyl)-4-(7-fluoroquinazolin-4-yl)-6-methyl-5,6-dihydro-1,3,4-oxadiazine (example 74 step A) (60.00 mg; 0.16 mmol; 1.00 eq.) giving [4-[4-(7-fluoroquinazolin-4-yl)-6-methyl-5,6-dihydro-1,3,4-oxadiazin-2-yl]-2-methoxy-phenyl]boronic acid (15.00, 24%) as an off white powder. $^1$H NMR (DMSO-d6, 400 MHz) δ 9.46 (m, 1H); 8.66 (s, 1H); 7.85 (s, 2H); 7.65 (d, J=7.59 Hz, 1H); 7.50-7.59 (m, 2H); 7.40-7.48 (m, 2H); 4.74-4.86 (m, 2H); 3.88 (s, 3H); 3.62 (m, 1H); 1.52 (d, J=6.16 Hz, 3H).

Example 75: N-[(E)-(1-hydroxy-3H-2,1-benzoxaborol-5-yl)methyleneamino]-N-methyl-2-methylsulfanyl-thiazolo[4,5-d]pyrimidin-7-amine The compound was prepared using the same procedure detailed in example 1 step C starting from N-[(E)-(1-hydroxy-3H-2,1-benzoxaborol-5-yl)methyleneamino]methanamine (example 51 step C) (100.00 mg; 0.53 mmol; 1.00 eq.) and 7-chloro-2-methylsulfanyl-thiazolo[4,5-d]pyrimidine (114.57: 0.53 mmol; 1.00 eq.) giving N-[(E)-(1-hydroxy-3H-2,1-benzoxaborol-5-yl)methyleneamino]-N-methyl-2-methylsulfanyl-thiazolo[4,5-d]pyrimidin-7-amine 50.00 mg, 25%) as a white powder. $^1$H NMR (DMSO-d6, 400 MHz) δ 9.29 (s, 1H); 8.67 (s, 1H); 8.26 (s, 1H); 7.81-7.94 (m, 3H); 5.10 (s, 2H); 3.77 (s, 3H); 2.87 (s, 3H). mp=262-286° C.

Example 76: N-[(E)-(1-hydroxy-3H-2,1-benzoxaborol-5-yl)methyleneamino]-N,1-dimethyl-pyrazolo[3,4-d]pyrimidin-4-amine The compound was prepared using the same procedure detailed in example 1 step C starting from N-[(E)-(1-hydroxy-3H-2,1-benzoxaborol-5-yl)methyleneamino]methanamine (example 51 step C) (100.00 mg; 0.53 mmol; 1.00 eq.) and 4-chloro-1-methyl-pyrazolo[3,4-d]pyrimidine (97.60 mg; 0.58 mmol; 1.10 eq.) giving N-[(E)-(1-hydroxy-3H-2,1-benzoxaborol-5-yl)methyleneamino]-N,1-dimethyl-pyrazolo[3,4-d]pyrimidin-4-amine (95.00 mg, 56%) as a yellow solid. $^1$H NMR (DMSO-d6, 400 MHz) δ 9.28 (s, 1H); 8.52 (s, 1H); 8.47 (s, 1H); 8.33 (s, 1H); 7.78-7.93 (m, 3H); 5.10 (s, 2H); 3.99 (s, 3H); 3.81 (s, 3H). mp=250-260° C.

Example 77: N-[(E)-(1-hydroxy-3H-2,1-benzoxaborol-5-yl)methyleneamino]-N,7-dimethyl-thieno[3,2-d]pyrimidin-4-amine The compound was prepared using the same procedure detailed in example 3 step B starting from 1-hydroxy-3H-2,1-benzoxaborole-5-carbaldehyde (example 23, step C) (87.71 mg; 0.54 mmol; 1.00 eq.); methyl hydrazine (0.03 mL; 0.54 mmol; 1.00 eq.) and 4-chloro-7-methyl-thieno[3,2-d]pyrimidine (100.00 mg; 0.54 mmol; 1.00 eq.) giving N-[(E)-(1-hydroxy-3H-2,1-benzoxaborol-5-yl)methyleneamino]-N,7-dimethyl-thieno[3,2-d]pyrimidin-4-amine (85 mg, 45%) as a yellow powder. $^1$H NMR (DMSO-d6, 400 MHz) δ 9.26 (s, 1H); 8.81 (s, 1H); 8.34 (s, 1H); 8.08 (d, J=1.1 Hz, 1H); 7.98 (d, J=7.48 Hz, 1H); 7.94 (s, 1H); 7.88 (d, J=7.5 Hz, 1H); 5.10 (s, 2H); 3.85 (s, 3H); 2.42 (s, 3H). mp=231° C.

Example 78: N-ethyl-N-[(E)-(1-hydroxy-3H-2,1-benzoxaborol-5-yl)methyleneamino]-1H-pyrazolo[4,3-d]pyrimidin-7-amine Step A: N-[(E)-(1-hydroxy-3H-2,1-benzoxaborol-5-yl)methyleneamino]ethanamine The compound was prepared using the same procedure detailed in example 1 step B starting from 1-hydroxy-3H-

2,1-benzoxaborole-5-carbaldehyde (3.00 g; 18.52 mmol; 1.00 eq.) and ethylhydrazine dihydrochloride (2.46 g; 18.52 mmol; 1.00 eq.) giving N-[(E)-(1-hydroxy-3H-2,1-benzoxaborol-5-yl)methyleneamino]ethanamine as a white powder (4.04 g; 90.69%). $^1$H NMR (DMSO-d6, 400 MHz) δ 8.46 (s, 1H); 7.81 (d, J=4.8 Hz, 1H); 7.73 (s, 1H); 7.67 (d, J=4.8 Hz, 1H); 5.03 (s, 2H); 3.26 (d, J=7.2 Hz, 2H); 1.25 (t, j=7.2 Hz, 3H).

Step B: N-ethyl-N-[(E)-(1-hydroxy-3H-2,1-benzoxaborol-5-yl)methyleneamino]-1H-pyrazolo[4,3-d]pyrimidin-7-amine The compound was prepared using the same procedure detailed in example 1 step C starting from N-[(E)-(1-hydroxy-3H-2,1-benzoxaborol-5-yl)methyleneamino]ethanamine (example 78 step A) (56.02 mg; 0.23 mmol; 1.20 eq.) and 7-chloro-1H-pyrazolo[4,3-d]pyrimidine (30.00 mg; 0.19 mmol; 1.00 eq.) to give N-ethyl-N-[(E)-(1-hydroxy-3H-2,1-benzoxaborol-5-yl)methyleneamino]-1H-pyrazolo[4,3-d]pyrimidin-7-amine (30.00 mg, 48%) as a yellow powder. $^1$H NMR (DMSO-d6, 400 MHz) δ 10.48 (s, 1H); 9.27 (s, 1H); 8.41 (s, 1H); 8.27 (s, 1H); 7.85 (m, 3H); 7.70 (s, 1H); 5.09 (s, 2H); 4.55 (q, J=6.86 Hz, 2H); 1.26 (t, J=6.99 Hz, 3H).

Example 79: N7-ethyl-N7-[(E)-(1-hydroxy-3H-2,1-benzoxaborol-5-yl)methyleneamino]-N2,N2-dimethyl-thiazolo[4,5-d]pyrimidine-2,7-diamine The compound was prepared using the same procedure detailed in example 1 step C starting from N-[(E)-(1-hydroxy-3H-2,1-benzoxaborol-5-yl)methyleneamino]ethanamine (example 78 step A) (45.00 mg; 0.19 mmol; 1.00 eq.) and 7-chloro-N,N-dimethyl-thiazolo[4,5-d]pyrimidin-2-amine (40.17 mg; 0.19 mmol; 1.00 eq.) giving N7-ethyl-N7-[(E)-(1-hydroxy-3H-2,1-benzoxaborol-5-yl)methyleneamino]-N2,N2-dimethyl-thiazolo[4,5-d]pyrimidine-2,7-diamine (44.00 mg, 59%) as a pale yellow powder. $^1$H NMR (DMSO-d6, 400 MHz) δ 9.26 (s, 1H); 8.47 (s, 1H); 8.22 (s, 1H); 7.92 (s, 1H); 7.82-7.89 (m, 2H); 5.08 (s, 2H); 4.44 (q, J=6.92 Hz, 2H); 3.24 (s, 6H); 1.20 (t, J=6.92 Hz, 3H). mp=247-253° C.

Example 80: N-ethyl-N-[(E)-(1-hydroxy-3H-2,1-benzoxaborol-5-yl)methyleneamino]-3-methyl-1H-pyrazolo[4,3-d]pyrimidin-7-amine The compound was prepared using the same procedure detailed in example 1 step C starting from N-[(E)-(1-hydroxy-3H-2,1-benzoxaborol-5-yl)methyleneamino]ethanamine (example 78 step A) (55.00 mg; 0.23 mmol; 1.00 eq.) and 7-chloro-3-methyl-1H-pyrazolo[4,3-d]pyrimidine (38.55 mg; 0.23 mmol; 1.00 eq.) giving N-ethyl-N-[(E)-(1-hydroxy-3H-2,1-benzoxaborol-5-yl)methyleneamino]-3-methyl-1H-pyrazolo[4,3-d]pyrimidin-7-amine (52.00 mg, 67%) as a white powder. $^1$H NMR (DMSO-d6, 400 MHz) δ 10.17 (s, 1H); 9.27 (s, 1H); 8.49 (s, 1H); 8.37 (s, 1H); 7.99 (s, 1H); 7.87 (d, J=7.6 Hz, 1H); 7.82 (d, J=7.6 Hz, 1H); 5.09 (s, 2H); 4.53 (q, J=6.86 Hz, 2H); 1.25 (t, J=6.86 Hz, 3H). mp=265-276° C.

Example 81: N-ethyl-N-[(E)-(1-hydroxy-3H-2,1-benzoxaborol-5-yl)methyleneamino]-5H-pyrrolo[3,2-d]pyrimidin-4-amine The compound was prepared using the same procedure detailed in example 1 step C starting from N-[(E)-(1-hydroxy-3H-2,1-benzoxaborol-5-yl)methyleneamino]ethanamine (example 78 step A) (55.00 mg; 0.23 mmol; 1.00 eq.) and 4-chloro-5H-pyrrolo[3,2-d]pyrimidine (32.15 mg; 0.23 mmol; 1.00 eq.) giving N-ethyl-N-[(E)-(1-hydroxy-3H-2,1-benzoxaborol-5-yl)methyleneamino]-5H-pyrrolo[3,2-d]pyrimidin-4-amine (37.00 mg, 50%) as an off white powder. $^1$H NMR (DMSO-d6, 400 MHz) δ 10.45 (s, 1H); 9.27 (s, 1H); 8.42 (s, 1H); 8.27 (s, 1H); 7.81-7.91 (m, 3H); 7.71 (t, J=3.03 Hz, 1H); 6.54 (dd, J=2.97 Hz, J=2.09 Hz, 1H); 5.09 (s, 2H); 4.53 (q, J=6.97 Hz, 2H); 1.24 (t, J=6.99 Hz, 3H). mp=244-252° C.

Example 82: N-ethyl-N-[(E)-(1-hydroxy-3H-2,1-benzoxaborol-5-yl)methyleneamino]-2-morpholino-thiazolo[4,5-d]pyrimidin-7-amine The compound was prepared using the same procedure detailed in example 1 step C starting from N-[(E)-(1-hydroxy-3H-2,1-benzoxaborol-5-yl)methyleneamino]ethanamine (example 78 step A) (55.00 mg; 0.23 mmol; 1.00 eq.) and 4-(7-chlorothiazolo[4,5-d]pyrimidin-2-yl)morpholine (58.71 mg; 0.23 mg; 1.00 eq.) giving N-ethyl-N-[(E)-(1-hydroxy-3H-2,1-benzoxaborol-5-yl)methyleneamino]-2-morpholino-thiazolo[4,5-d]pyrimidin-7-amine (65.00 mg, 63%) as a yellow powder. $^1$H NMR (DMSO-d6, 400 MHz) δ 9.25 (s, 1H); 8.50 (s, 1H); 8.23 (s, 1H); 7.84-7.91 (m, 3H); 5.09 (s, 2H); 4.46 (q, J=6.75 Hz, 2H); 3.73-3.84 (m, 4H); 3.66-3.688 (m, 4H); 1.20 (t, J=6.75 Hz, 3H). mp=183-189° C.

Example 83: N-ethyl-N-[(E)-(1-hydroxy-3H-2,1-benzoxaborol-5-yl)methyleneamino]-2-methylsulfanyl-thiazolo[4,5-d]pyrimidin-7-amine hydrochloride The compound was prepared using the same procedure detailed in example 1 step C starting from N-[(E)-(1-hydroxy-3H-2,1-benzoxaborol-5-yl)methyleneamino]ethanamine (example 78 step A) (65.00 mg; 0.27 mmol; 1.00 eq.) and 7-chloro-2-methylsulfanyl-thiazolo[4,5-d]pyrimidine (58.84 mg; 0.27 mmol; 1.00 eq.) giving N-ethyl-N-[(E)-(1-hydroxy-3H-2,1-benzoxaborol-5-yl)methyleneamino]-2-methylsulfanyl-thiazolo[4,5-d]pyrimidin-7-amine hydrochloride (83.00 mg, 72%) as a yellow powder. $^1$H NMR (DMSO-d6, 400 MHz) δ 8.73 (s, 1H); 8.39 (s, 1H); 7.87-7.95 (m, 3H); 5.10 (s, 2H); 4.51 (q, J=6.90 Hz, 2H); 2.88 (s, 3H); 1.23 (t, J=6.90 Hz, 3H). mp=248-264° C.

Example 84: N-ethyl-N-[(E)-(1-hydroxy-3H-2,1-benzoxaborol-5-yl)methyleneamino]-7-propyl-pyrrolo[2,3-d]pyrimidin-4-amine Step A: 4-chloro-7-propyl-pyrrolo[2,3-d]pyrimidine The compound was prepared using the same procedure detailed in example 73 step A starting from 4-chloro-7H-pyrrolo[2,3-d]pyrimidine (85.00 mg; 0.55 mmol; 1.00 eq.) and. 1-iodopropane (108.15 μL; 1.11 mmol; 2.00 eq) to give 4-chloro-7-propyl-pyrrolo[2,3-d]pyrimidine (105.00 mg, 97%) as a brown powder used in the next step without purification. $^1$H NMR (CDCl$_3$, 300 MHz) δ 8.63 (s, 1H); 7.25 (d, J=3.5 Hz, 1H); 6.61 (d, J=3.6 Hz, 1H); 4.20-4.29 (m, 2H); 1.90 (sext, J=7.3 Hz, 2H); 0.94 (t, J=7.4 Hz, 3H).

Step B: N-ethyl-N-[(E)-(1-hydroxy-3H-2,1-benzoxaborol-5-yl)methyleneamino]-7-propyl-pyrrolo[2,3-d]pyrimidin-4-amine The compound was prepared using the same procedure detailed in example 1 step C starting from N-[(E)-(1- hydroxy-3H-2,1-benzoxaborol-5-yl)methyleneamino] ethanamine (example 78 step A) (110.00 mg; 0.54 mol; 1.00 eq.; then 105.00 mg; 0.54 mmol; 1.00 eq.) giving N-ethyl-N-[(E)-(1-hydroxy-3H-2,1-benzoxaborol-5-yl)methyleneamino]-7-propyl-pyrrolo[2,3-d]pyrimidin-4-amine (40.00 mg, 20%) as a white powder. ¹H NMR (DMSO-d6, 400 MHz) δ 9.28 (s, 1H); 8.39 (s, 1H); 8.23 (s, 1H); 7.74-7.86 (m, 3H); 7.44 (d, J=3.4 Hz, 1H); 7.08 (d, J=3.4 Hz, 1H); 5.08 (s, 2H); 4.53 (q, J=7.4 Hz, 2H); 4.18 (t, J=7.0 Hz, 2H); 1.80 (sext, J=7.0 Hz, 2H); 1.22 (t, J=7.0 Hz, 3H); 0.83 (t, J=7.4 Hz, 3H). mp=186-193° C.

Example 85: N,7-diethyl-N-[(E)-(1-hydroxy-3H-2,1-benzoxaborol-5-yl)methylene amino]pyrrolo [2,3-d]pyrimidin-4-amine Step A: 4-chloro-7-ethyl-pyrrolo[2,3-d]pyrimidine The compound was prepared using the same procedure detailed in example 84, step A starting from 4-chloro-7H-pyrrolo[2,3-d]pyrimidine (85.00 mg; 0.55 mmol; 1.00 eq.) and iodoethane (88.54 µL; 1.11 mmol; 2.00 eq.) giving 4-chloro-7-ethyl-pyrrolo[2,3-d]pyrimidine (100.00 mg, 100%) as a yellow powder. ¹H NMR (CDCl3, 300 MHz) δ 8.64 (s, 1H); 7.27 (d, J=3.6 Hz, 1H); 6.61 (d, J=3.6 Hz, 1H); 4.34 (q, J=7.3 Hz, 2H); 1.50 (t, J=7.3 Hz, 3H).

Step B: N,7-diethyl-N-[(E)-(1-hydroxy-3H-2,1-benzoxaborol-5-yl)methyleneamino]pyrrolo [2,3-d] pyrimidin-4-amine The compound was prepared using the same procedure detailed in example 1 step C starting from N-[(E)-(1-hydroxy-3H-2,1-benzoxaborol-5-yl)methyleneamino] ethanamine (example 78 step A) (100.00 mg; 0.49 mmol; 1.00 eq.) and 4-chloro-7-ethyl-pyrrolo[2,3-d]pyrimidine (example 85, step A) (89.02 mg; 0.49 mmol; 1.00 eq.) giving N,7-diethyl-N-[(E)-(1-hydroxy-3H-2,1-benzoxaborol-5-yl) methyleneamino]pyrrolo[2,3-d]pyrimidin-4-amine (48.00 mg, 27%) as an off white powder. ¹H NMR (DMSO-d6, 400 MHz) δ 9.28 (s, 1H); 8.39 (s, 1H); 8.23 (s, 1H); 7.77-7.87 (m, 3H); 7.46 (d, J=3.4 Hz, 1H); 7.08 (d, J=3.4 Hz, 1H); 5.08 (s, 2H); 4.53 (q, J=6.8 Hz, 2H); 4.25 (q, J=7.2 Hz, 2H); 1.37 (t, J=7.2 Hz, 3H); 1.22 (t, J=6.8 Hz, 3H). mp=210-216° C.

Example 86: N-ethyl-N-[(E)-(1-hydroxy-3H-2,1-benzoxaborol-5-yl)methyleneamino]-1H-pyrazolo[3,4-d]pyrimidin-4-amine The compound was prepared using the same procedure detailed in example 1 step C starting from N-[(E)-(1-hydroxy-3H-2,1-benzoxaborol-5-yl)methyleneamino] ethanamine (example 78 step A) (33.00 mg; 0.16 mmol; 1.00 eq.) and 4-chloro-1H-pyrazolo[3,4-d]pyrimidine (25.00 mg; 0.16 mmol; 1.00 eq.) giving N-ethyl-N-[(E)-(1-hydroxy-3H-2,1-benzoxaborol-5-yl)methyleneamino]-1H-pyrazolo[3,4-d]pyrimidin-4-amine (20.00 mg, 37%) as an orange powder. ¹H NMR (DMSO-d6, 400 MHz) δ 13.75 (s, 1H); 9.32 (s, 1H); 8.50 (s, 1H); 8.47 (d, J=1.4 Hz, 1H); 8.40 (s, 1H); 7.84-7.90 (m, 3H); 5.11 (s, 2H); 4.49-4.60 (m, 2H); 1.23 (t, J=7.0 Hz, 3H).

Example 87: N-ethyl-N-[(E)-(1-hydroxy-3H-2,1-benzoxaborol-5-yl)methyleneamino]-thiazolo[4,5-d] pyrimidin-7-amine The compound was prepared using the same procedure detailed in example 1 step C starting from N-[(E)-(1-hydroxy-3H-2,1-benzoxaborol-5-yl)methyleneamino] ethanamine (example 78 step A) (200.00 mg; 0.83 mmol; 1.00 eq.) and 7-chlorothiazolo[4,5-d]pyrimidine (185.53 mg; 1.08 mmol; 1.30 eq.) giving N-ethyl-N-[(E)-(1-hydroxy-3H-2,1-benzoxaborol-5-yl)methyleneamino]thiazolo [4,5-d]pyrimidin-7-amine (90 mg, 32%) as an off white powder. ¹H NMR (DMSO-d6, 400 MHz) δ 9.80 (s, 1H); 9.34 (s, 1H); 8.79 (s, 1H); 8.39 (s, 1H); 7.96 (m, 1H); 7.94 (d, J=7.5 Hz, 1H); 7.88 (d, J=7.5 Hz, 1H); 5.11 (s, 2H); 4.56 (q, J=6.9 Hz, 2H); 1.25 (t, J=6.9 Hz, 3H). mp=280-296° C.

Example 88: N-ethyl-N-[(E)-(1-hydroxy-3H-2,1-benzoxaborol-5-yl)methyleneamino]-2,7-dimethyl-thieno[3,2-d]pyrimidin-4-amine The compound was prepared using the same procedure detailed in example 1 step C starting from N-[(E)-(1-hydroxy-3H-2,1-benzoxaborol-5-yl)methyleneamino] ethanamine (example 78 step A) (200.00 mg; 1.01 mmol; 1.00 eq.) and 4-chloro-2,7-dimethyl-thieno[3,2-d]pyrimidine (205.40 mg; 1.01 mmol; 1.00 eq.). The residue was purified by chromatography (0 to 10% of EtOH in DCM) to give N-ethyl-N-[(E)-(1-hydroxy-3H-2,1-benzoxaborol-5-yl) methyleneamino]-2,7-dimethyl-thieno[3,2-d]pyrimidin-4-amine (33.00 mg, 9%) as a pale yellow powder. ¹H NMR (DMSO-d6, 400 MHz) δ 9.29 (s, 1H); 8.28 (s, 1H); 7.99 (d, J=7.8 Hz, 1H); 7.94 (s, 1H); 7.90 (d, J=1.2 Hz, 1H); 7.85 (d, J=7.5 Hz, 1H); 5.09 (s, 2H); 4.54 (q, J=7.0 Hz, 2H); 2.62 (s, 3H); 2.36 (s, 3H); 1.23 (t, J=7.0 Hz, 3H).

Example 89: N-ethyl-7-fluoro-N-[(E)-(1-hydroxy-3H-2,1-benzoxaborol-5-yl)-methyleneamino]quinazolin-4-amine The compound was prepared using the same procedure detailed in example 1 step C starting from N-[(E)-(1-hydroxy-3H-2,1-benzoxaborol-5-yl)methyleneamino] ethanamine (example 78 step A) (100.00 mg; 0.42 mmol; 1.00 eq.) and 4-chloro-7-fluoro-quinazoline (91.10 mg; 0.50 mmol; 1.20 eq.) giving N-ethyl-7-fluoro-N-[(E)-(1-hydroxy-3H-2,1-benzoxaborol-5-yl)methyleneamino]quinazolin-4-amine (58.00 mg; 40%) as an off white powder. ¹H NMR (DMSO-d6, 400 MHz) δ 9.31 (s, 1H); 9.17 (dd, J=10.2 Hz, J=6.5 Hz, 1H); 8.77 (s, 1H); 8.41 (s, 1H); 7.81-7.86 (m, 1H); 7.74-7.80 (m, 2H); 7.54-7.63 (m, 2H); 5.07 (s, 2H); 4.51-4.64 (m, 2H); 1.28 (t, J=6.9 Hz, 3H). mp=216-232° C.

Example 90: N-ethyl-N-[(E)-(1-hydroxy-3H-2,1-benzoxaborol-5-yl)methyleneamino]-6-methyl-thieno[3,2-d]pyrimidin-4-amine The compound was prepared using the same procedure detailed in example 3 step B starting from 1-hydroxy-3H-2,1-benzoxaborole-5-carbaldehyde (example 23, step C) (50.00 mg; 0.31 mmol; 1.00 eq.), ethylhydrazine dihydrochloride (41.07 mg; 0.31 mmol; 1.00 eq.) and 4-chloro-6-methyl-thieno[3,2-d]pyrimidine (57.01 mg; 0.31 mmol; 1.00 eq.). The residue was purified by preparative chromatography (Column: Kinetex C18, 30×150 mm 5 µm (phenomenex), Flowrate: 42 ml/min, Mobile phase: H₂O with 0.1% FA/ACN+0.1% FA; gradient: gradient B 10-30-45-90-100 run 20 min) to give N-ethyl-N-[(E)-(1-hydroxy-3H-2,1-benzoxaborol-5-yl)methyleneamino]-6-methyl-thieno[3,2-d]pyrimidin-4-amine (20.00 mg, 18%) as a beige powder. ¹H NMR (DMSO-d6, 400 MHz) δ 9.29 (s, 1H); 8.63 (s, 1H); 8.30 (s, 1H); 7.96-8.01 (m, 1H); 7.94 (s, 1H); 7.87 (d, J=7.5

Hz, 1H); 7.21 (d, J=1.1 Hz, 1H); 5.11 (s, 2H); 4.52 (q, J=7.0 Hz, 2H); 2.66 (s, 3H); 1.23 (t, J=7.0 Hz, 3H).

Example 91: N-ethyl-N-[(E)-(1-hydroxy-3H-2,1-benzoxaborol-5-yl)methyleneamino]-6,7,8,9-tetrahydrobenzothiopheno[3,2-d]pyrimidin-4-amine Step A: 6,7,8,9-tetrahydro-4aH-benzothiopheno[3,2-d]pyrimidin-4-one Methyl 3-amino-4,5,6,7-tetrahydrobenzothiophene-2-carboxylate (0.50 g; 2.37 mmol; 1.00 eq.) was dissolved in EtOH (2.50 mL) followed by addition of formamidine acetate (0.37 g; 3.55 mmol; 1.50 eq.). The reaction mixture was stirred at 100° C. until completion. The reaction mixture was cooled to rt and poured onto ice water, then stirred for 30 min at 0° C. It was filtered and washed with water, then dried to give 6,7,8,9-tetrahydro-4aH-benzothiopheno[3,2-d]pyrimidin-4-one (390.00 mg, 40%) as an off white powder used in the next step without further purification. $^1$H NMR (DMSO-d6, 300 MHz) δ 12.39 (br s, 1H); 8.12 (s, 1H); 2.84 (t, J=6.0 Hz, 2H); 2.63-2.71 (m, 2H); 1.76-1.93 (m, 4H).

Step B: 4-chloro-6,7,8,9-tetrahydrobenzothiopheno[3,2-d]pyrimidine 6,7,8,9-tetrahydro-4aH-benzothiopheno[3,2-d]pyrimidin-4-one (example 91, step A) (380.00 mg; 1.84 mmol; 1.00 eq.) was dissolved in toluene (3.80 mL). POCl$_3$ (521.51 μL; 5.53 mmol; 3 eq.) and DMF (10.00 μL) were added. The reaction mixture was stirred at 110° C. for 90 min. The reaction mixture was cooled and poured onto ice water and stirred for 30 min at 0° C. The precipitate was filtered and washed with water to give 4-chloro-6,7,8,9-tetrahydrobenzothiopheno[3,2-d]pyrimidine (225.00 mg, 54%) as a pale yellow powder. $^1$H NMR (DMSO-d6, 300 MHz) δ 8.97 (s, 1H); 2.98 (t, J=6.0 Hz, 2H); 2.79 (t, J=5.9 Hz, 2H); 1.80-1.99 (m, 4H).

Step C: N-ethyl-N-[(E)-(1-hydroxy-3H-2,1-benzoxaborol-5-yl)methyleneamino]-6,7,8,9-tetrahydrobenzothiopheno[3,2-d]pyrimidin-4-amine The compound was prepared using the same procedure detailed in example 1 step C starting from N-[(E)-(1-hydroxy-3H-2,1-benzoxaborol-5-yl)methyleneamino]ethanamine (example 78 step A) (189.00 mg; 0.79 mmol; 1.00 eq.) and 4-chloro-6,7,8,9-tetrahydrobenzothiopheno[3,2-d]pyrimidine (185.43 mg; 0.83 mmol; 1.05 eq.) giving N-ethyl-N-[(E)-(1-hydroxy-3H-2,1-benzoxaborol-5-yl)methyleneamino]-6,7,8,9-tetrahydro benzothiopheno[3,2-d]pyrimidin-4-amine (100.00 mg, 32%) as a white powder. $^1$H NMR (DMSO-d6, 400 MHz) δ 9.31 (br s, 1H); 8.72 (s, 1H); 8.35 (s, 1H); 7.99 (d, J=7.7 Hz, 1H); 7.94 (s, 1H); 7.87 (d, J=7.6 Hz, 1H); 5.10 (s, 2H); 4.48-4.61 (m, 2H); 2.94 (t, J=5.7 Hz, 2H); 2.74 (t, J=5.7 Hz, 2H); 1.78-1.95 (m, 4H); 1.24 (t, J=7.0 Hz, 3H). mp=232-276° C.

Example 92: N-[(E)-(1-hydroxy-3H-2,1-benzoxaborol-5-yl)methyleneamino]-N-isobutyl-2-methylsulfanyl-thiazolo[4,5-d]pyrimidin-7-amine The compound was prepared using the same procedure detailed in example 1 Step C starting from N-[(E)-(1-hydroxy-3H-2,1-benzoxaborol-5-yl)methyleneamino]-2-methyl-propan-1-amine (example 23 step D) (150.00 mg; 0.56 mmol; 1.00 eq.) and 7-chloro-2-methylsulfanyl-thiazolo[4,5-d]pyrimidine (121.60 mg; 0.56 mmol; 1.00 eq.) giving N-[(E)-(1-hydroxy-3H-2,1-benzoxaborol-5-yl)methyleneamino]-N-isobutyl-2-methylsulfanyl-thiazolo [4,5-d]pyrimidin-7-amine (66.00 mg, 29%) as an off white powder. $^1$H NMR (DMSO-d6, 400 MHz) δ 9.29 (s, 1H); 8.66 (s, 1H); 8.34 (s, 1H); 7.94 (s, 1H); 7.85-7.92 (m, 2H); 5.10 (s, 2H); 4.36 (d, J=7.48 Hz, 2H); 2.87 (s, 3H); 2.19-2.32 (m, 1H); 0.93 (d, J=6.71 Hz, 6H). mp=214-246° C.

Example 93: N-[(E)-(1-hydroxy-3H-2,1-benzoxaborol-5-yl)methyleneamino]-N-isobutyl-7-methyl-thieno[3,2-d]pyrimidin-4-amine The compound was prepared using the same procedure detailed in example 1 Step C starting from N-[(E)-(1-hydroxy-3H-2,1-benzoxaborol-5-yl)methyleneamino]-2-methyl-propan-1-amine (example 23 step D) (200.00 mg; 0.74 mmol; 1.00 eq.) and 4-chloro-7-methyl-thieno[3,2-d]pyrimidine (137.51 mg; 0.74 mmol; 1.00 eq.) giving N-[(E)-(1-hydroxy-3H-2,1-benzoxaborol-5-yl)methyleneamino]-N-isobutyl-7-methyl-thieno[3,2-d]pyrimidin-4-amine (33.00 mg, 11%) as a white powder. $^1$H NMR (DMSO-d6, 400 MHz) δ 9.30 (s, 1H); 8.70 (s, 1H); 8.30 (s, 1H); 8.01 (d, J=7.8 Hz, 1H); 7.93-7.98 (m, 2H); 7.86 (d, J=7.6 Hz, 1H); 5.10 (s, 2H); 4.42 (d, J=7.0 Hz, 2H); 2.39 (s, 3H); 2.21-2.33 (m, 1H); 0.94 (d, J=6.6 Hz, 6H). mp=162-182° C.

Example 94: N-[(E)-(1-hydroxy-3H-2,1-benzoxaborol-5-yl)methyleneamino]-N-(2-methoxyethyl)-7-methyl-thieno[3,2-d]pyrimidin-4-amine The compound was prepared using the same procedure detailed in example 3 step B starting from 1-hydroxy-3H-2,1-benzoxaborole-5-carbaldehyde (example 23, step C) (50.00 mg; 0.31 mmol; 1.00 eq.), (2-methoxyethyl)hydrazine dichloride (50.34 mg; 0.31 mmol; 1.00 eq.) and 4-chloro-7-methyl-thieno[3,2-d]pyrimidine (57.01 mg; 0.31 mmol; 1.00 eq.) giving N-[(E)-(1-hydroxy-3H-2,1-benzoxaborol-5-yl)methyleneamino]-N-(2-methoxyethyl)-7-methyl-thieno[3,2-d]pyrimidin-4-amine (75.00 mg, 62%) as a white powder. $^1$H NMR (DMSO-d6, 400 MHz) δ 9.31 (s, 1H); 8.72 (s, 1H); 8.39 (s, 1H); 7.95-8.01 (m, 2H); 7.92 (s, 1H); 7.86 (d, J=7.6 Hz, 1H); 5.10 (s, 2H); 4.71 (t, J=5.9 Hz, 2H); 3.69 (t, J=5.8 Hz, 2H); 3.28 (s, 3H); 2.39 (s, 3H). mp=240-253° C.

Example 95: N-[(E)-(1-hydroxy-3H-2,1-benzoxaborol-5-yl)methyleneamino]-N-(2-methoxyethyl)-2-methylsulfanyl-thiazolo[4,5-d]pyrimidin-7-amine, hydrochloride The compound was prepared using the same procedure detailed in example 3 step B starting from 1-hydroxy-3H-2,1-benzoxaborole-5-carbaldehyde (example 23, step C) (100.00 mg; 0.62 mmol; 1.00 eq.); (2-methoxyethyl)hydrazine dichloride (100.68 mg; 0.31 mmol; 1.00 eq.) and 7-chloro-2-methylsulfanyl-thiazolo[4,5-d]pyrimidine (134.42 mg; 0.62 mmol; 1.00 eq.) giving N-[(E)-(1-hydroxy-3H-2,1-benzoxaborol-5-yl)methyleneamino]-N-(2-methoxyethyl)-2-methylsulfanyl-thiazolo[4,5-d]pyrimidin-7-amine, hydrochloride (164.00 mg, 63%) as a white powder. $^1$H NMR (DMSO-d6, 400 MHz) δ 9.29 (s, 1H); 8.67 (s, 1H); 8.42 (s, 1H); 7.86-7.92 (m, 3H); 5.09 (s, 2H); 4.66 (t, J=5.78 Hz, 2H); 3.67 (t, J=5.78 Hz, 2H); 3.27 (s, 3H); 2.87 (s, 3H). mp=252-264° C.

Example 96: N-[(E)-(1-hydroxy-3H-2,1-benzoxaborol-5-yl)methyleneamino]-N-(3-methoxypropyl)-2-methylsulfanyl-thiazolo[4,5-d]pyrimidin-7-amine The compound was prepared using the same procedure detailed in example 3 step B starting from 1-hydroxy-3H-2,1-benzoxaborole-5-carbaldehyde (example 23, step C) (250.00 mg; 1.54 mmol; 1.00 eq.), (2-methoxypropyl)hydrazine dichloride (217.06 mg; 1.54 mmol; 1.00 eq.) and 7-chloro-2-methylsulfanyl-thiazolo[4,5-d]pyrimidine (168.03 mg; 0.77 mmol; 0.50 eq.) giving N-[(E)-(1-hydroxy-3H-2,1-benzoxaborol-5-yl)methyleneamino]-N-(3-methoxypropyl)-2-methylsulfanyl-thiazolo[4,5-d]pyrimidin-7-amine (25 mg, 4%) as an off white powder. $^1$H NMR (DMSO-d6, 400 MHz) δ 9.29 (s, 1H); 8.68 (s, 1H); 8.31 (s, 1H); 7.91 (s, 1H); 7.87 (d, J=0.77 Hz, 2H); 5.10 (s, 2H); 4.50 (t, J=7.10 Hz, 2H); 3.43 (t, J=6.00 Hz, 2H); 3.24 (s, 3H); 2.87 (s, 3H); 1.85-1.95 (m, 2H).

Example 97: 2-[[(E)-(1-hydroxy-3H-2,1-benzoxaborol-5-yl)methyleneamino]-(7-methylthieno[3,2-d]pyrimidin-4-yl)amino]ethanol The compound was prepared using the same procedure detailed in example 3 step B starting from 1-hydroxy-3H-2,1-benzoxaborole-5-carbaldehyde (example 23, step C) (250.00 mg; 1.54 mmol; 1.00 eq.); 2-hydroxyethylhydrazine (104.70 μL; 1.54 mmol; 1.00 eq.) and 4-chloro-7-methyl-thieno[3,2-d]pyrimidine (285.03 mg; 1.54 mmol; 1.00 eq.) giving 2-[[(E)-(1-hydroxy-3H-2,1-benzoxaborol-5-yl)methyleneamino]-(7-methylthieno[3,2-d]pyrimidin-4-yl)amino]ethanol (48.00 mg, 8%) as a yellow powder. $^1$H NMR (DMSO-d6, 400 MHz) δ 9.29 (s, 1H); 8.70 (s, 1H); 8.43 (s, 1H); 7.97 (td, J=3.88 Hz, J=0.83 Hz, 2H); 7.91 (s, 1H); 7.86 (d, J=7.48 Hz, 1H); 5.10 (s, 2H); 4.98-5.04 (m, 1H); 4.58 (t, J=6.27 Hz, 2H); 3.74 (q, J=6.27 Hz, 2H); 2.39 (s, 3H).

Example 98: 6-[[(E)-(1-hydroxy-3H-2,1-benzoxaborol-5-yl)methyleneamino]-methyl-amino]-9-methyl-7H-purin-8-one Step A: 6-[amino(methyl)amino]-9-methyl-7H-purin-8-one In a MW tube, 6-chloro-9-methyl-7H-purin-8-one (114.44 mg; 0.62 mmol; 1.00 eq.) was suspended in methylhydrazine (0.33 mL; 6.20 mmol; 10.00 eq.). The sealed vial was irradiated for 15 min at 100° C. The reaction mixture was diluted with water and the precipitate was filtered, washed 3 times with water and dried to give 6-[amino(methyl)amino]-9-methyl-7H-purin-8-one (90.00 mg, 75%) as a white solid. $^1$H NMR (DMSO-d6, 300 MHz) δ 10.09 (br s, 1H); 8.02 (s, 1H); 4.89 (br s, 2H); 3.22 (s, 6H).

Step B: 6-[[(E)-(1-hydroxy-3H-2,1-benzoxaborol-5-yl)methyleneamino]-methyl-amino]-9-methyl-7H-purin-8-one The compound was prepared using the same procedure detailed in example 50 step B starting from 6-[amino(methyl)amino]-9-methyl-7H-purin-8-one (example 98, step A) (90.00 mg; 0.46 mmol; 1.00 eq.) and 1-hydroxy-3H-2,1-benzoxaborole-5-carbaldehyde (example 23, step C) (75.06 mg; 0.46 mmol; 1.00 eq.) giving 6-[[(E)-(1-hydroxy-3H-2,1-benzoxaborol-5-yl)methyleneamino]-methyl-amino]-9-methyl-7H-purin-8-one (44.00 mg, 27%) as a white powder. $^1$H NMR (DMSO-d6, 400 MHz) δ 10.01 (s, 1H); 9.26 (br s, 1H); 8.30 (s, 1H); 8.07 (s, 1H); 7.73-7.83 (m, 3H); 5.06 (s, 2H); 3.66 (s, 3H); 3.30 (s, 3H). mp=180-200° C.

Example 99: 4-[[(E)-(1-hydroxy-3H-2,1-benzoxaborol-5-yl)methyleneamino]-methyl-amino]-7-methyl-5H-pyrrolo[2,3-d]pyrimidin-6-one Step A: 4-[amino(methyl)amino]-7-methyl-5H-pyrrolo[2,3-d]pyrimidin-6-one The compound was prepared using the same procedure detailed in example 98 step A starting from 4-chloro-7-methyl-5H-pyrrolo[2,3-d]pyrimidin-6-one (200.00 mg; 1.09 mmol; 1.00 eq.) and methylhydrazine (0.58 mmol; 10.089 mmol; 10.00 eq.) giving 4-[amino(methyl)amino]-7-methyl-5H-pyrrolo[2,3-d]pyrimidin-6-one (220.0 mg; quantitative) as a pale yellow solid. $^1$H NMR (DMSO-d6, 300 MHz) δ 8.18 (s, 1H); 4.77 (s, 2H); 3.74 (s, 2H); 3.24 (s, 3H); 3.04 (s, 3H).

Step B: 4-[[(E)-(1-hydroxy-3H-2,1-benzoxaborol-5-yl)methyleneamino]-methyl-amino]-7-methyl-5H-pyrrolo[2,3-d]pyrimidin-6-one The compound was prepared using the same procedure detailed in example 50 step B starting from 4-[amino(methyl)amino]-7-methyl-5H-pyrrolo[2,3-d]pyrimidin-6-one (210.47 mg; 10.9 mmol; 1.00 eq.) and 1-hydroxy-3H-2,1-benzoxaborole-5-carbaldehyde (example 23, step C) (211.71 mg; 1.31 mmol; 1.20 eq.) giving 4-[[(E)-(1-hydroxy-3H-2,1-benzoxaborol-5-yl)methyleneamino]-methyl-amino]-7-methyl-5H-pyrrolo[2,3-d]pyrimidin-6-one (185.00 mg, 49%) as a beige powder. $^1$H NMR (DMSO-d6, 400 MHz) δ 9.28 (s, 1H); 8.47 (s, 1H); 8.07 (s, 1H); 7.79-7.84 (m, 1H); 7.68-7.75 (m, 2H); 5.06 (s, 2H); 3.94 (s, 2H); 3.67 (s, 3H); 3.12 (s, 3H). mp=288-307° C.

Example 100: 4-[[(E)-(1-hydroxy-3H-2,1-benzoxaborol-5-yl)methyleneamino]-methyl-amino]-6,8-dihydro-5H-pyrido[2,3-d]pyrimidin-7-one Step A: 4-[amino(methyl)amino]-6,8-dihydro-5H-pyrido[2,3-d]pyrimidin-7-one The compound was prepared using the same procedure detailed in example 50 step A starting from 4-chloro-6,8-dihydro-5H-pyrido[2,3-d]pyrimidin-7-one (160.00 mg; 0.87 mmol; 1.00 eq.) and methylhydrazine (0.46 mL; 8.71 mmol; 10.00 eq.) in EtOH (1.60 mL) giving 4-[amino(methyl)amino]-6,8-dihydro-5H-pyrido[2,3-d]pyrimidin-7-one (80.00 mg, 48%) as a white powder. $^1$H NMR (DMSO-d6, 300 MHz) δ 10.24 (s, 1H); 8.10 (s, 1H); 4.71 (s, 2H); 3.32 (s, 2H); 3.21 (t, J=7.27 Hz, 2H); 2.40 (dd, J=8.26 Hz, J=7.27 Hz, 2H).

Step B: 4-[[(E)-(1-hydroxy-3H-2,1-benzoxaborol-5-yl)methyleneamino]-methyl-amino]-6,8-dihydro-5H-pyrido[2,3-d]pyrimidin-7-one The compound was prepared using the same procedure detailed in example 50 step B starting from 4-[amino(methyl)amino]-6,8-dihydro-5H-pyrido[2,3-d]pyrimidin-7-one (example 100, step A) (80.00 mg; 0.41 mmol; 1.00 eq.) and 1-hydroxy-3H-2,1-benzoxaborole-5-carbaldehyde (example 23, step C) (67.06 mg; 0.41 mmol; 1.00 eq.) giving 4-[[(E)-(1-hydroxy-3H-2,1-benzoxaborol-5-yl)methyleneamino]-methyl-amino]-6,8-dihydro-5H-pyrido[2,3-d]pyrimidin-7-one (85.00 mg, 60%) as a white powder. $^1$H NMR (DMSO-d6, 400 MHz) δ ppm 10.66 (s, 1H); 9.23 (s, 1H); 8.37 (s, 1H); 8.35-8.40 (m, 1H); 7.94 (s, 1H); 7.74-7.78 (m, 1H); 7.69 (s, 1H); 7.64-7.68 (m, 1H); 5.02 (s, 2H); 3.61 (s, 3H); 3.29 (t, J=7.65 Hz, 2H); 2.52 (t, J=7.65 Hz, 2H). mp=290-307° C.

Example 101: N-[(E)-(1-hydroxy-3H-2,1-benzoxaborol-5-yl)methyleneamino]-N-methyl-5,6-dihydrofuro[2,3-d]pyrimidin-4-amine Step A: 1-(5,6-dihydrofuro[2,3-d]pyrimidin-4-yl)-1-methyl-hydrazine The compound was prepared using the same procedure detailed in example 50 step A starting from 4-chloro-5,6-dihydrofuro[2,3-d]pyrimidine (100.00 mg; 0.64 mmol; 1.00 eq.) and methylhydrazine (0.34 mL; 6.40 mmol; 10.00 eq.) giving 1-(5,6-dihydrofuro[2,3-d]pyrimidin-4-yl)-1-methyl-hydrazine (107.00 mg, quantitative) as a pale yellow solid. $^1$H NMR (DMSO-d6, 300 MHz) δ 7.97 (s, 1H); 4.67-4.86 (m, 2H); 4.41 (t, J=8.92 Hz, 2H); 3.41 (t, J=8.67 Hz, 2H); 2.59 (s, 3H).

Step B: N-[(E)-(1-hydroxy-3H-2,1-benzoxaborol-5-yl)methyleneamino]-N-methyl-5,6-dihydrofuro[2,3-d]pyrimidin-4-amine The compound was prepared using the same procedure detailed in example 50 step B starting from 1-(5,6-dihydrofuro[2,3-d]pyrimidin-4-yl)-1-methyl-hydrazine (example 101, step A) (106.14 mg; 0.64 mmol; 1.00 eq.) and 1-hydroxy-3H-2,1-benzoxaborole-5-carbaldehyde (example 23, step C) (113.70 mg; 0.70 mmol; 1.10 eq.) giving N-[(E)-(1-hydroxy-3H-2,1-benzoxaborol-5-yl)methyleneamino]-N-methyl-5,6-dihydrofuro[2,3-d]pyrimidin-4-amine (100.00 mg, 49%) as an off white powder. $^1$H NMR (DMSO-d6, 400 MHz) δ 9.26 (s, 1H); 8.26 (s, 1H); 8.04 (s, 1H); 7.76-7.81 (m, 1H); 7.66-7.72 (m, 2H); 5.04 (s, 2H); 4.61 (t, J=8.80 Hz, 2H); 3.66 (s, 3H); 3.6 (t, J=8.80 Hz, 2H).

Example 102: N-[(E)-(1-hydroxy-3H-2,1-benzoxaborol-5-yl)methyleneamino]-N-methyl-7-phenyl-thieno[3,2-d]pyrimidin-4-amine Step A: 4-methylsulfanyl-7-phenyl-thieno[3,2-d]pyrimidine 7-bromo-4-chloro-thieno[3,2-d]pyrimidine (500.00 mg; 2.00 mmol; 1.00 eq.) was dissolved in THF (6.80 mL). Sodium methanethiolate (154.54 mg; 2.20 mmol; 1.10 eq.) was added. The reaction mixture was stirred at rt for 24 h. The reaction mixture was cooled with ice (−10° C.) and ice water was added. The precipitate was filtered and washed with cooled water and dried to give 7-bromo-4-methylsulfanyl-thieno[3,2-d]pyrimidine (530.00 mg, quantitative) as a white powder. $^1$H NMR (DMSO-d6, 300 MHz) δ 9.09 (s, 1H); 8.57 (s, 1H); 2.77 (s, 3H).

Step B: 4-methylsulfanyl-7-phenyl-thieno[3,2-d]pyrimidine 7-bromo-4-methylsulfanyl-thieno[3,2-d]pyrimidine (example 102, step A) (335.00 mg; 1.28 mmol; 1.00 eq.) was dissolved 1,4-dioxane (10.05 mL). Phenylboronic acid (250.24 mg; 2.05 mmol; 1.60 eq.) and Pd(PPh$_3$)$_4$ (93.38 mg; 0.08 mmol; 0.06 eq.) were added. The reaction mixture was degassed. A solution of Na$_2$CO$_3$ (2.05 mL; 2 mol/L; 4.10 mmol; 3.20 eq.) was added. The reaction mixture was stirred at 100° C. until completion. The reaction mixture was diluted with EtOAc and water and extracted. The organic layer was washed with brine, dried over MgSO$_4$, filtered and concentrated. The residue was purified by chromatography (0 to 30% of EtOAc in cyclohexane) to give 4-methylsulfanyl-7-phenyl-thieno[3,2-d]pyrimidine (275.00 mg, 80%) as a white powder. $^1$H NMR (DMSO-d6, 300 MHz) δ 9.10 (s, 1H); 8.62 (s, 1H); 8.04-8.12 (m, 2H); 7.47-7.57 (m, 2H); 7.37-7.46 (m, 1H); 2.78 (s, 3H).

Step C: 4-chloro-7-phenyl-thieno[3,2-d]pyrimidine 4-methylsulfanyl-7-phenyl-thieno[3,2-d]pyrimidine (example 102, step B) (95.00 mg; 0.37 mmol; 1.00 eq.) was dissolved in ACN (7.40 mL). The reaction mixture was cooled at 0° C. with an ice bath and a solution of sulfuryl chloride (148.86 μL; 1.84 mmol; 5.00 eq.) in DCM (10.00 mL) was added dropwise. The reaction mixture was stirred at 0° C. for 30 min. The product was diluted with DCM and washed with a saturated solution of NaHCO$_3$, then brine. The organic layer was dried over MgSO$_4$, filtered and concentrated. The residue was purified by chromatography (20 to 60% of EtOAc in cyclohexane) to give 4-chloro-7-phenyl-thieno[3,2-d]pyrimidine (100.00 mg, quantitative) as a white powder. $^1$H NMR (DMSO-d6, 300 MHz) δ 9.16 (s, 1H); 8.84 (s, 1H); 8.02-8.10 (m, 2H); 7.50-7.60 (m, 2H); 7.40-7.49 (m, 1H).

Step D: 1-methyl-1-(7-phenylthieno[3,2-d]pyrimidin-4-yl)hydrazine

The compound was prepared using the same procedure detailed in example 50 step A starting from 4-chloro-7-phenyl-thieno[3,2-d]pyrimidine (example 102, step C) (90.00 mg; 0.35 mmol; 1.00 eq.) and methylhydrazine (186.31 μL; 3.51 mmol; 10.00 eq.) giving 1-methyl-1-(7-phenylthieno[3,2-d]pyrimidin-4-yl)hydrazine (90.00 mg; 91%) as a pale yellow solid. $^1$H NMR (DMSO-d6, 300 MHz) δ 8.43 (s, 1H); 8.26 (s, 1H); 8.06 (d, J=1.32 Hz, 1H); 8.03-8.05 (m, 1H); 7.40-7.49 (m, 2H); 7.30-7.38 (m, 1H); 5.29 (s, 2H); 3.39 (s, 3H); 2.55 (s, 3H).

Step E: N-[(E)-(1-hydroxy-3H-2,1-benzoxaborol-5-yl)methyleneamino]-N-methyl-7-phenyl-thieno[3,2-d]pyrimidin-4-amine The compound was prepared using the same procedure detailed in example 50 step B starting from 1-methyl-1-(7-phenylthieno[3,2-d]pyrimidin-4-yl)hydrazine (example 102, step D) (90.00 mg; 0.35 mmol; 1.00 eq.) and 1-hydroxy-3H-2,1-benzoxaborole-5-carbaldehyde (example 23, step C) (68.06 mg; 0.42 mmol; 1.20 eq.) giving N-[(E)-(1-hydroxy-3H-2,1-benzoxaborol-5-yl)methyleneamino]-N-methyl-7-phenyl-thieno[3,2-d]pyrimidin-4-amine (52.00 mg; 36%) as a white powder. $^1$H NMR (DMSO-d6, 400 MHz) δ 9.33 (s, 1H); 8.79 (s, 1H); 8.58 (s, 1H); 8.30 (s, 1H); 8.08 (dd, J=8.3 Hz, J=1.3 Hz, 2H); 8.01 (d, J=7.6 Hz, 1H); 7.97 (s, 1H); 7.89 (d, J=7.6 Hz, 1H); 7.45-7.54 (m, 2H); 7.34-7.44 (m, 1H); 5.12 (s, 2H); 3.85 (s, 3H). mp=151-168° C.

Example 103: 7-cyclopropyl-N-[(E)-(1-hydroxy-3H-2,1-benzoxaborol-5-yl)methylene amino]-N-methyl-thieno[3,2-d]pyrimidin-4-amine Step A: 7-cyclopropyl-4-methylsulfanyl-thieno[3,2-d]pyrimidine The compound was prepared using the same procedure detailed in example 102 step B starting from 4-methylsulfanyl-7-phenyl-thieno[3,2-d]pyrimidine (example 102 step A) (350.00 mg; 1.34 mmol; 1.00 eq.) and cyclopropyl boronic acid (230.23 mg; 2.68 mmol; 2.00 eq.) giving 7-cyclopropyl-4-methylsulfanyl-thieno[3,2-d]pyrimidine (205.00 mg, 62%) as a pink solid. $^1$H NMR (DMSO-d6, 300 MHz) δ 9.01 (s, 1H); 7.80 (s, 1H); 2.74 (s, 3H); 2.25-2.40 (m, 1H); 0.98-1.05 (m, 2H); 0.90-0.97 (m, 2H).

Step B: 4-chloro-7-cyclopropyl-thieno[3,2-d]pyrimidine

The compound was prepared using the same procedure detailed in example 102 step C starting from 7-cyclopropyl-4-methylsulfanyl-thieno[3,2-d]pyrimidine (example 103, step A) (200.00 mg; 0.81 mmol; 1.00 eq.) and sulfuryl chloride (0.33 mL; 4.05 mmol; 5.00 eq.) giving 4-chloro-7-cyclopropyl-thieno[3,2-d]pyrimidine (200.00 mg, quantitative) as a white solid. $^1$H NMR (DMSO-d6, 300 MHz) δ 9.06 (s, 1H); 8.05 (s, 1H); 2.28-2.41 (m, 1H); 1.00-1.09 (m, 2H); 0.90-1.00 (m, 2H).

Step C: 1-(7-cyclopropylthieno[3,2-d]pyrimidin-4-yl)-1-methyl-hydrazine

The compound was prepared using the same procedure detailed in example 50 step A starting from 4-chloro-7-cyclopropyl-thieno[3,2-d]pyrimidine (example 103, step B) (200.00 mg; 0.90 mmol; 1.00 eq.) and methylhydrazine (0.48 mL; 9.02 mmol; 10.00 eq.) giving 1-(7-cyclopropylthieno[3,2-d]pyrimidin-4-yl)-1-methyl-hydrazine (150 mg 72%) as a beige solid. $^1$H NMR (DMSO-d6, 300 MHz) δ 8.35 (s, 1H); 7.40 (s, 1H); 5.17 (s, 2H); 3.35 (s, 3H); 2.17-2.29 (m, 1H); 0.88-0.96 (m, 2H); 0.76-0.83 (m, 2H).

Step D: 7-cyclopropyl-N-[(E)-(1-hydroxy-3H-2,1-benzoxaborol-5-yl)methyleneamino]-N-methyl-thieno[3,2-d]pyrimidin-4-amine The compound was prepared using the same procedure detailed in example 50 step B starting from 1-(7-cyclopropylthieno[3,2-d]pyrimidin-4-yl)-1-methyl-hydrazine (example 103, step C) (150.00 mg; 0.68 mmol; 1.00 eq.) and 1-hydroxy-3H-2,1-benzoxaborole-5-carbaldehyde (example 23, step C) (146.05 mg; 0.90 mmol; 1.32 eq.) giving 7-cyclopropyl-N-[(E)-(1-hydroxy-3H-2,1-benzoxaborol-5-yl)methyleneamino]-N-methyl-thieno[3,2-d]pyrimidin-4-amine (145.00 mg, 59%) as an off white powder. $^1$H NMR (DMSO-d6, 400 MHz) δ 9.30 (s, 1H); 8.71 (s, 1H); 8.24 (s, 1H); 7.94 (m, 1H); 7.93 (s, 1H); 7.86 (d, J=7.6 Hz, 1H); 7.75 (s, 1H); 5.09 (s, 2H); 3.81 (s, 3H); 2.30-2.40 (m, 1H); 0.95-1.04 (m, 2H); 0.85-0.91 (m, 2H). mp=221-277° C.

Example 104: N-[(E)-(1-hydroxy-3H-2,1-benzoxaborol-5-yl)methyleneamino]-N-methyl-7-morpholino-thieno[3,2-d]pyrimidin-4-amine Step A: 4-(4-methylsulfanylthieno[3,2-d]pyrimidin-7-yl)morpholine In sealed vial, Pd$_2$(dba)$_3$ (59.52 mg; 0.06 mmol; 0.06 eq.); 4,5-bis(diphenylphosphino)-9,9-dimethylxanthene (37.61 mg; 0.06 mmol; 0.05 eq.) and Cs$_2$CO$_3$ (1 270.69 mg; 3.90 mmol; 3.00 eq.) were dissolved in 1,4-dioxane (3.40 mL). The mixture was heated in an oil bath at 80° C. for 5 min and degassed. Then to the hot mixture was added 4-methylsulfanyl-7-phenyl-thieno[3,2-d]pyrimidine (example 102 step A) (350.00 mg; 1.30 mmol; 1.00 eq.) and a solution of morpholine (0.17 mL; 1.95 mmol; 1.50 eq.) in 1,4-dioxane (3.40 mL). The reaction mixture was stirred at 100° C. overnight. Water was added. The mixture was extracted with EtOAc. The organic layer was washed with brine, then water (2×). The organic layers were dried over MgSO$_4$, filtered and concentrated. The residue was purified by chromatography (0 to 50% of EtOAc in cyclohexane) to give 4-(4-methylsulfanylthieno[3,2-d]pyrimidin-7-yl)morpholine (110.00 mg, 32%) as an off-white powder. $^1$H NMR (CDCl$_3$, 300 MHz) δ 8.94 (s, 1H); 6.73 (s, 1H); 3.93-4.01 (m, 4H); 3.37-3.44 (m, 4H).

Step B: 1-methyl-1-(7-morpholinothieno[3,2-d]pyrimidin-4-yl)hydrazine

The compound was prepared using the same procedure detailed in example 58 step A starting from 4-(4-methylsulfanylthieno[3,2-d]pyrimidin-7-yl)morpholine (example 104, step A) (82.00 mg; 0.07 mmol; 1.00 eq.) to give 1-methyl-1-(7-morpholinothieno[3,2-d]pyrimidin-4-yl)hydrazine (86.00 mg, 85%) as a beige resin. $^1$H NMR (DMSO-d6, 300 MHz) δ 8.31 (s, 1H); 6.90 (s, 1H); 5.18 (s, 2H); 3.73-3.81 (m, 4H); 3.34 (s, 3H); 3.23-3.29 (m, 4H).

Step C: N-[(E)-(1-hydroxy-3H-2,1-benzoxaborol-5-yl)methyleneamino]-N-methyl-7-morpholino-thieno[3,2-d]pyrimidin-4-amine The compound was prepared using the same procedure detailed in example 50 step B starting from 1-methyl-1-(7-morpholinothieno[3,2-d]pyrimidin-4-yl)hydrazine (example 103, step B) (86.00 mg; 0.32 mmol; 1.00 eq.) and 1-hydroxy-3H-2,1-benzoxaborole-5-carbaldehyde (example 23, step C) (78.74 mg; 0.49 mmol; 1.50 eq.) giving N-[(E)-(1-hydroxy-3H-2,1-benzoxaborol-5-yl)methyleneamino]-N-methyl-7-morpholino-thieno[3,2-d]pyrimidin-4-amine (40.00 mg, 30%) as an off white powder. $^1$H NMR (DMSO-d6+D$_2$O, 400 MHz) δ 8.67 (s, 1H); 8.23 (s, 1H); 7.97 (d, J=7.81 Hz, 1H); 7.94 (s, 1H); 7.87 (d, J=7.59 Hz, 1H); 7.22 (s, 1H); 5.10 (s, 2H); 3.77-3.83 (m, 4H); 3.80 (s, 3H); 3.33 (m, 4H).

Example 105: 7-ethyl-N-[(E)-(1-hydroxy-3H-2,1-benzoxaborol-5-yl)methyleneamino]-N-methyl-thieno[3,2-d]pyrimidin-4-amine Step A: 7-ethyl-4-methylsulfanyl-thieno[3,2-d]pyrimidine Under nitrogen, 4-methylsulfanyl-7-phenyl-thieno[3,2-d]pyrimidine (500.00 mg; 1.72 mmol; 1.00 eq.) was dissolved in THF (4 500.00 µL). 1,1'-bis(diphenylphosphino)ferrocene-palladium(II)dichloride dichloromethane complex (211.07 mg; 0.26 mmol; 0.15 eq.) and potassium phosphate, tribasic (1 097.24 mg; 5.17 mmol; 3.00 eq.) and water (450.00 µL) were added. The reaction mixture was degassed and triethylborane (3.45 mL; 1.00 mol/L in hexane; 3.45 mmol; 2.00 eq.) was added. The reaction mixture was stirred until completion. The reaction mixture was concentrated then diluted with DCM and washed with water then brine. The organic layer was dried on MgSO$_4$ and concentrated. The residue was purified by chromatography (0 to 20% of EtOAc in cyclohexane) to give 7-ethyl-4-methylsulfanyl-thieno[3,2-d]pyrimidine (126.00 mg, 35%) as a pale yellow powder. $^1$H NMR (DMSO-d6, 300 MHz) δ 9.01 (s, 1H); 8.01 (s, 1H); 2.87 (q, J=7.51 Hz, 2H); 2.74 (s, 3H); 1.29 (t, J=7.51 Hz, 3H).

Step B: 1-(7-ethylthieno[3,2-d]pyrimidin-4-yl)-1-methyl-hydrazine

The compound was prepared using the same procedure detailed in example 50 step A starting from 7-ethyl-4-methylsulfanyl-thieno[3,2-d]pyrimidine (example 105, step A) (180.00 mg; 0.76 mmol; 1.00 eq.) and methylhydrazine (405.23 μL; 7.62 mmol; 10.00 eq.) giving 1-(7-ethylthieno[3,2-d]pyrimidin-4-yl)-1-methyl-hydrazine (156.00 mg, 69%) as a white powder. $^1$H NMR (DMSO-d6, 300 MHz) δ 8.35 (s, 1H); 7.63 (s, 1H); 5.18 (s, 2H); 3.35 (s, 3H); 2.70-2.80 (m, 2H); 1.24 (t, J=7.51 Hz, 3H).

Step C: 7-ethyl-N-[(E)-(1-hydroxy-3H-2,1-benzoxaborol-5-yl)methyleneamino]-N-methyl-thieno[3,2-d]pyrimidin-4-amine The compound was prepared using the same procedure detailed in example 50 step B starting from 1-(7-ethylthieno[3,2-d]pyrimidin-4-yl)-1-methyl-hydrazine (example 105, step B) (150.00 mg; 0.72 mmol; 1.00 eq.) and 1-hydroxy-3H-2,1-benzoxaborole-5-carbaldehyde (example 23, step C) (128.30 mg; 0.79 mmol; 1.10 eq.) giving 7-ethyl-N-[(E)-(1-hydroxy-3H-2,1-benzoxaborol-5-yl)methyleneamino]-N-methyl-thieno[3,2-d]-pyrimidin-4-amine (120.00 mg, 47%) as a white powder. $^1$H NMR (400 MHz, DMSO-d6) δ 9.29 (s, 1H); 8.70 (s, 1H); 8.23 (s, 1H); 7.97 (m, 2H); 7.93 (s, 1H); 7.86 (d, J=7.59 Hz, 1H); 5.10 (s, 2H); 3.81 (s, 3H); 2.80-2.90 (m, 2H); 1.29 (t, J=7.48 Hz, 3H). mp=225-245° C.

Example 106: N-[(E)-(1-hydroxy-3H-2,1-benzoxaborol-5-yl)methyleneamino]-N,7-dimethyl-5,6-dihydropyrrolo[2,3-d]pyrimidin-4-amine

Step A: 4-chloro-7-methyl-5,6-dihydropyrrolo[2,3-d]pyrimidine

The compound was prepared using the same procedure detailed in example 84 step A starting from 4-chloro-6,7-dihydro-5H-pyrrolo[2,3-d]pyrimidine (200.00 mg; 1.29 mmol; 1.00 eq.) and dimethyl sulfate (182.86 μL; 1.93 mmol; 1.50 eq.) to give 4-chloro-7-methyl-5,6-dihydropyrrolo[2,3-d]pyrimidine (208.00 mg, 84%) as a beige powder. $^1$H NMR (DMSO-d6, 300 MHz) δ 8.09 (s, 1H); 3.58-3.66 (m, 2H); 2.96-3.04 (m, 2H); 2.90 (s, 3H).

Step B: 1-methyl-1-(7-methyl-5,6-dihydropyrrolo[2,3-d]pyrimidin-4-yl)hydrazine The compound was prepared using the same procedure detailed in example 50 step A starting from 4-chloro-7-methyl-5,6-dihydropyrrolo[2,3-d]pyrimidine (example 106, step A) (100.00 mg; 0.52 mmol; 1.00 eq.) and methylhydrazine (276.03 μL; 5.19 mmol; 10.00 eq.) giving 1-methyl-1-(7-methyl-5,6-dihydropyrrolo[2,3-d]pyrimidin-4-yl)hydrazine (100.00 mg, quantitative) as a pale yellow solid. $^1$H NMR (DMSO-d6, 300 MHz) δ 7.87 (s, 1H); 4.58 (br s, 2H); 3.25-3.30 (m, 2H); 3.18-3.24 (m, 2H); 2.77 (s, 3H); 2.59 (s, 4H).

Step C: N-[(E)-(1-hydroxy-3H-2,1-benzoxaborol-5-yl)methyleneamino]-N,7-dimethyl-5,6-dihydropyrrolo[2,3-d]pyrimidin-4-amine The compound was prepared using the same procedure detailed in example 50 step B starting from 1-methyl-1-(7-methyl-5,6-dihydropyrrolo[2,3-d]pyrimidin-4-yl)hydrazine (example 106, step B) (92.99 mg; 0.52 mmol; 1.00 eq.) and 1-hydroxy-3H-2,1-benzoxaborole-5-carbaldehyde (example 23, step C) (84.03 mg; 0.52 mmol; 1.00 eq.). The residue was purified by chromatography (2 to 10% of EtOH in DCM) to give N-[(E)-(1-hydroxy-3H-2,1-benzoxaborol-5-yl)methyleneamino]-N,7-dimethyl-5,6-dihydropyrrolo[2,3-d]pyrimidin-4-amine (60.00 mg, 36%) as a yellow powder. $^1$H NMR (DMSO-d6, 400 MHz) δ 9.20 (s, 1H); 8.08 (s, 1H); 7.89 (s, 1H); 7.76 (d, J=7.48 Hz, 1H); 7.63-7.69 (m, 2H); 5.03 (s, 2H); 3.59 (s, 3H); 3.48-3.55 (m, 2H); 3.36-3.44 (m, 2H); 2.88 (s, 3H).

Example 107: 9-cyclobutyl-6-[[(E)-(1-hydroxy-3H-2,1-benzoxaborol-5-yl)methylene amino]-methyl-amino]-7H-purin-8-one

Step A: 6-chloro-N4-cyclobutyl-pyrimidine-4,5-diamine

Under nitrogen, 4,6-dichloro-5-aminopyrimidine (100.00 mg; 0.61 mmol; 1.00 eq.) was dissolved in EtOH (2.00 mL). TEA (127.14 μL; 0.91 mmol; 1.50 eq.) and cyclobutylamine (78.38 μL; 0.91 mmol; 1.50 eq.) were added and the reaction mixture was stirred at 85° C. until completion. The reaction mixture was concentrated under reduced pressure. The residue was purified by chromatography (0 to 40% of EtOAc in cyclohexane) to give 6-chloro-N4-cyclobutyl-pyrimidine-4,5-diamine (115.00 mg, 95%) as an off white powder. $^1$H NMR (DMSO-d6, 300 MHz) δ 7.70 (s, 1H); 6.97 (br s, 1H); 5.04 (s, 2H); 4.45 (sext, J=7.79 Hz, 1H); 2.24-2.36 (m, 2H); 1.86-2.02 (m, 2H); 1.65-1.77 (m, 2H).

Step B: 6-chloro-9-cyclobutyl-7H-purin-8-one

Under nitrogen, 6-chloro-N4-cyclobutyl-pyrimidine-4,5-diamine (example 107, step A) (115.00 mg; 0.58 mmol; 1.00 eq.) was dissolved in THF (2.30 mL). CDI (187.74 mg; 1.16 mmol; 2.00 eq.) was added and the reaction mixture was stirred under reflux until completion. The reaction mixture was concentrated. The residue was purified by chromatography (0 to 30% of EtOAc in cyclohexane) to give 6-chloro-9-cyclobutyl-7H-purin-8-one (100.00 mg, 77%) as a white powder. $^1$H NMR (DMSO-d6, 300 MHz) δ 12.06 (br m, 1H); 8.46 (s, 1H); 4.74-4.93 (m, 1H); 2.87-3.06 (m, 2H); 2.16-2.31 (m, 2H); 1.71-1.92 (m, 2H).

Step C: 6-[amino(methyl)amino]-9-cyclobutyl-7H-purin-8-one

The compound was prepared using the same procedure detailed in example 50 step A starting from 6-chloro-9-cyclobutyl-7H-purin-8-one (example 107, step B) (100.00 mg; 0.45 mmol; 1.00 eq.) and methylhydrazine (236.82 μM; 4.45 mmol; 10.00 eq.) giving 6-[amino(methyl)amino]-9-cyclobutyl-7H-purin-8-one (130.00 mg, quantitative) as a pale grey solid. $^1$H NMR (DMSO-d6, 300 MHz) δ 8.05 (s, 1H); 4.88 (br s, 2H); 4.75-4.86 (m, 1H); 2.92-3.08 (m, 3H); 2.57 (s, 3H); 2.17 (m, 2H); 1.67-1.88 (m, 2H).

Step D: 9-cyclobutyl-6-[[(E)-(1-hydroxy-3H-2,1-benzoxaborol-5-yl)methyleneamino]-methyl-amino]-7H-purin-8-one The compound was prepared using the same procedure detailed in example 50 step B starting from 6-[amino(methyl)amino]-9-cyclobutyl-7H-purin-8-one (example 107, step C) (104.28 mg; 0.45 mmol; 1.00 eq.) and 1-hydroxy-3H-2,1-benzoxaborole-5-carbaldehyde (example 23, step C) (72.09 mg; 0.45 mmol; 1.00 eq.) giving 9-cyclobutyl-6-[[(E)-(1-hydroxy-3H-2,1-benzoxaborol-5-yl) methyleneamino]-methyl-amino]-7H-purin-8-one (125.00 mg, 74%) as a white powder. $^1$H NMR (DMSO-d6, 400 MHz) δ 10.02 (s, 1H); 9.25 (s, 1H); 8.33 (s, 1H); 8.07 (s, 1H); 7.73-7.82 (m, 3H); 5.06 (s, 2H); 4.84-4.95 (m, 1H); 3.66 (s, 3H); 2.97-3.11 (m, 2H); 2.23 (qt, J=8.27 Hz, J=2.50 Hz, 2H); 1.72-1.91 (m, 2H). mp=261-270° C.

Example 108: 6-[[(E)-(1-hydroxy-3H-2,1-benzoxaborol-5-yl)methyleneamino]-methyl-amino]-9-[3-(methoxymethyl)cyclobutyl]-7H-purin-8-one Step A: 6-chloro-N4-[3-(methoxymethyl)cyclobutyl] pyrimidine-4,5-diamine The compound was prepared using the same procedure detailed in example 107 step A starting from 4,6-dichloro-5-aminopyrimidine (200.00 mg; 1.22 mmol; 1.00 eq.) and 3-(methoxymethyl)cyclobutan-1-amine (280.92 mg; 2.44 mmol; 2.00 eq.). The residue was purified by chromatography (2 to 10% of MeOH in DCM) to give 6-chloro-N4-[3-(methoxymethyl)cyclobutyl]pyrimidine-4,5-diamine (278.00 mg, 93%) as a white powder. $^1$H NMR (DMSO-d6, 300 MHz) δ 7.70 (s, 1H); 6.92 (d, J=6.77 Hz, 1H); 5.04 (s, 2H); 4.27-4.42 (m, 1H); 3.3 (t, J=5.78 Hz, 2H); 3.25 (s, 3H); 2.31-2.44 (m, 2H); 2.16-2.29 (m, 1H); 1.63-1.77 (m, 2H).

Step B: 6-chloro-9-[3-(methoxymethyl)cyclobutyl]-7H-purin-8-one

The compound was prepared using the same procedure detailed in example 107 step B starting from 6-chloro-N4-[3-(methoxymethyl)cyclobutyl]pyrimidine-4,5-diamine (example 108, step A) (270.00 mg; 1.11 mmol; 1.00 eq.) and CDI (360.77 mg; 2.22 mmol; 2.00 eq.). The residue was purified by chromatography (20 to 70% of EtOAc in cyclohexane) to give 6-chloro-9-[3-(methoxymethyl)cyclobutyl]-7H-purin-8-one (252.00 mg, 76%) as a white powder. $^1$H NMR (DMSO-d6, 300 MHz) δ 12.06 (s, 1H); 8.45 (s, 1H); 4.66-4.81 (m, 1H); 3.44 (d, J=5.94 Hz, 2H); 3.25 (s, 3H); 2.59-2.77 (m, 2H); 2.28-2.43 (m, 3H).

Step C: 6-[amino(methyl)amino]-9-[3-(methoxymethyl)cyclobutyl]-7H-purin-8-one

The compound was prepared using the same procedure detailed in example 50 step A starting from 6-chloro-9-[3-(methoxymethyl)cyclobutyl]-7H-purin-8-one (example 108, step B) (250.00 mg; 0.84 mmol; 1.00 eq.) and methylhydrazine (221.72 μL; 4.19 mmol; 5.00 eq.) giving 6-[amino(methyl)amino]-9-[3-(methoxymethyl)cyclobutyl]-7H-purin-8-one (250.00 mg, quantitative) as a white powder. $^1$H NMR (300 MHz, DMSO-d6) δ 10.05 (s, 1H); 8.04 (s, 1H); 4.88 (br s, 2H); 4.71 (s, 1H); 3.45 (m, 2H); 3.25 (s, 3H); 3.22 (s, 3H); 2.75 (m, 2H); 2.30 (m, 3H).

Step D: 6-[[(E)-(1-hydroxy-3H-2,1-benzoxaborol-5-yl)methyleneamino]-methyl-amino]-9-[3-(methoxymethyl)cyclobutyl]-7H-purin-8-one The compound was prepared using the same procedure detailed in example 50 step B starting from 6-[amino(methyl)amino]-9-[3-(methoxymethyl)cyclobutyl]-7H-purin-8-one (example 108, step C) (100.00 mg; 0.36 mmol; 1.00 eq.) and 1-hydroxy-3H-2,1-benzoxaborole-5-carbaldehyde (example 23, step C) (61.10 mg; 0.38 mmol; 1.05 eq.). The residue was purified by preparative LC-MS (column: X BRIDGE C18, 30×100 mm 5 μm (WATERS); Flow rate: 42 mL/min; elution: H$_2$O+0.1% NH$_3$/ACN+0.1% NH$_3$; gradient: 10 to 90% of ACN+0.1% NH$_3$ over 40 min) to give 6-[[(E)-(1-hydroxy-3H-2,1-benzoxaborol-5-yl)methyleneamino]-methyl-amino]-9-[3-(methoxymethyl)cyclobutyl]-7H-purin-8-one (28.00 mg, 18%) as a white powder. $^1$H NMR (DMSO-d6, 400 MHz) δ 10.01 (s, 1H); 9.26 (br s, 1H); 8.32 (s, 1H); 8.07 (s, 1H); 7.73-7.84 (m, 3H); 5.05 (s, 2H); 4.74-4.85 (m, 1H); 3.66 (s, 3H); 3.46 (d, J=5.94 Hz, 2H); 3.26 (s, 3H); 2.66-2.80 (m, 2H); 2.28-2.43 (m, 3H). mp=200-210° C.

Example 109: 6-[[(E)-(1-hydroxy-3H-2,1-benzoxaborol-5-yl)methyleneamino]-methyl-amino]-9-(3-hydroxycyclobutyl)-7H-purin-8-one hydrochloride Step A: 3-[(5-amino-6-chloro-pyrimidin-4-yl)amino] cyclobutanol The compound was prepared using the same procedure detailed in example 107 step A starting from 4,6-dichloro-5-aminopyrimidine (400.00 mg; 2.44 mmol; 1.00 eq.) and 3-aminocyclobutan-1-ol hydrochloride (602.86 mg; 4.88 mmol; 2.00 eq.). The residue was purified by chromatography (10 to 70% of EtOAc in cyclohexane) to give 3-[(5-amino-6-chloro-pyrimidin-4-yl)amino]cyclobutanol (686.00 mg, quantitative) as a pale yellow oil. $^1$H NMR (DMSO-d6, 500 MHz) δ 7.69 (s, 1H); 7.01 (d, J=6.60 Hz, 1H); 5.12 (d, J=5.91 Hz, 1H); 5.10 (s, 2H); 3.83-3.97 (m, 2H); 2.59-2.67 (m, 2H); 1.76-1.84 (m, 2H).

Step B: N4-[3-[tert-butyl(dimethyl)silyl]oxycyclobutyl]-6-chloro-pyrimidine-4,5-diamine To a solution of 3-[(5-amino-6-chloro-pyrimidin-4-yl)amino]cyclobutanol (example 109, step A) (680.00 mg; 3.17 mmol; 1.00 eq.) in THF (13.60 mL) were added imidazole (237.23 mg; 3.48 mmol; 1.10 eq.), 4-dimethylaminopyridine 99% (116.11 mg; 0.95 mmol; 0.30 eq.) and TBDMSCl (525.23 mg; 3.48 mmol; 1.10 eq.). The reaction mixture was stirred at rt until completion. The reaction mixture was quenched with water and extracted with DCM (2×). The organic layers were washed with brine, dried over MgSO4, filtered and concentrated to give N4-[3-[tert-butyl(dimethyl)silyl]oxycyclobutyl]-6-chloro-pyrimidine-4,5-diamine (430.00 mg, 41%) as a white resin. $^1$H NMR (DMSO-d6, 300 MHz) δ 7.7 (s, 1H); 6.95 (br d, J=6.61 Hz, 1H); 4.96-5.08 (m, 2H); 3.94-4.11 (m, 2H); 2.63-2.77 (m, 2H); 1.78-1.91 (m, 2H); 0.82-0.90 (m, 9H); 0.01-0.08 (m, 6H).

Step C: 9-[3-[tert-butyl(dimethyl)silyl]oxycyclobutyl]-6-chloro-7H-purin-8-one

The compound was prepared using the same procedure detailed in example 107 step B starting from N4-[3-[tert-butyl(dimethyl)silyl]oxycyclobutyl]-6-chloro-pyrimidine-4,5-diamine (example 109, step B) (425.00 mg; 1.29 mmol; 1.00 eq.) and CDI (523.80 mg; 3.23 mmol; 2.50 eq.). The residue was purified by chromatography (20 to 100% of EtOAc in cyclohexane) to give 9-[3-[tert-butyl(dimethyl) silyl]oxycyclobutyl]-6-chloro-7H-purin-8-one (420.00 mg, 92%) as an off white powder. $^1$H NMR (DMSO-d6, 300 MHz) δ 12.06 (br s, 1H); 8.44 (s, 1H); 4.33 (tt, J=9.76 Hz, J=7.41 Hz, 1H); 4.06-4.23 (m, 1H); 2.81-2.97 (m, 2H); 2.53-2.69 (m, 2H); 0.85-0.91 (m, 9H); 0.04-0.11 (m, 6H).

Step D: 6-[amino(methyl)amino]-9-[3-[tert-butyl(dimethyl)silyl]oxycyclobutyl]-7H-purin-8-one The compound was prepared using the same procedure detailed in example 50 step A starting from 9-[3-[tert-butyl(dimethyl)silyl]oxycyclobutyl]-6-chloro-7H-purin-8-one (410.00 mg; 1.16 mmol; 1.00 eq.) and methylhydrazine (611.77 µL; 11.55 mmol; 10.00 eq.) giving 6-[amino(methyl)amino]-9-[3-[tert-butyl(dimethyl)silyl]oxycyclobutyl]-7H-purin-8-one (300.00 mg, 70%) as a white powder. $^1$H NMR (DMSO-d6+D$_2$O, 300 MHz) δ 10.10 (br s, 1H); 7.97 (s, 1H); 4.82 (br s, 2H); 4.25 (tt, J=9.85 Hz, J=7.41 Hz, 1H); 4.04 (m, 1H); 3.15 (s, 3H); 2.9 (m, 2H); 2.51 (m, 2H); 0.88 (s, 9H); 0.06 (s, 6H).

Step E: 6-[[(E)-(1-hydroxy-3H-2,1-benzoxaborol-5-yl)methyleneamino]-methyl-amino]-9-(3-hydroxycyclobutyl)-7H-purin-8-one hydrochloride The compound was prepared using the same procedure detailed in example 50 step B starting from 6-[amino(methyl)amino]-9-[3-[tert-butyl(dimethyl)silyl]oxycyclobutyl]-7H-purin-8-one (example 109, step D) (220.00 mg; 0.60 mmol; 1.00 eq.) and 1-hydroxy-3H-2,1-benzoxaborole-5-carbaldehyde (example 23, step C) (0.10 g; 0.60 mmol; 1.00 eq.). HCl 4M in 1,4-dioxane (1.51 mL; 4.00 mol/L; 6.04 mmol; 10.00 eq.) was added. The reaction mixture was stirred at rt until completion. The reaction mixture was filtered and the filtrate washed with isopropanol. After drying, the solid was washed with THF and then acetonitrile. The product was freeze-dried to give 6-[[(E)-(1-hydroxy-3H-2,1-benzoxaborol-5-yl)methyleneamino]-methyl-amino]-9-(3-hydroxycyclobutyl)-7H-purin-8-one hydrochloride (165.00 mg, 62%) as a yellow powder. $^1$H NMR (DMSO-d6, 400 MHz) δ 10.02 (s, 1H); 8.32 (s, 1H); 8.07 (s, 1H); 7.73-7.83 (m, 3H); 5.05 (s, 2H); 4.35 (tt, J=9.74 Hz, J=7.48 Hz, 1H); 3.89 (m, 1H); 3.58 (s, 3H); 2.83 (m, 2H); 2.46 (m, 2H). mp=260-335° C.

Example 110: 9-(3-bicyclo[1.1.1]pentanyl)-6-[[(E)-(1-hydroxy-3H-2,1-benzoxaborol-5-yl)methyleneamino]-methyl-amino]-7H-purin-8-one Step A: N4-(3-bicyclo[1.1.1]pentanyl)-6-chloropyrimidine-4,5-diamine The compound was prepared using the same procedure detailed in example 107 step A starting from 4,6-dichloro-5-aminopyrimidine (250.00 mg; 1.52 mmol; 1.00 eq.) and 1-bicyclo[1.1.1]pentylamine hydrochloride (364.63 mg; 3.05 mmol; 2.00 eq.) giving N4-(3-bicyclo[1.1.1]pentanyl)-6-chloro-pyrimidine-4,5-diamine (330.00 mg, quantitative) as a beige powder. $^1$H NMR (DMSO-d6, 300 MHz) δ 7.75 (m, 1H); 7.36 (s, 1H); 5.01 (br s, 2H); 2.14 (m, 6H); 2.11 (m, 1H).

Step B: 9-(3-bicyclo[1.1.1]pentanyl)-6-chloro-7H-purin-8-one

The compound was prepared using the same procedure detailed in example 107 step B starting from N4-(3-bicyclo[1.1.1]pentanyl)-6-chloro-pyrimidine-4,5-diamine (example 110, step A) (320.00 mg; 0.15 mmol; 1.00 eq.) and CDI (492.62 mg; 0.30 mmol; 2.00 eq.). The residue was purified by chromatography (20 to 100% of EtOAc in cyclohexane) to give 9-(3-bicyclo[1.1.1]pentanyl)-6-chloro-7H-purin-8-one (260.00 mg, 70%) as an off white powder. $^1$H NMR (DMSO-d6, 300 MHz) δ 12.02 (br s, 1H); 8.42 (s, 1H); 2.63 (s, 1H); 2.41 (s, 6H);

Step C: 6-[amino(methyl)amino]-9-(3-bicyclo[1.1.1]pentanyl)-7H-purin-8-one

The compound was prepared using the same procedure detailed in example 104 step B starting from 9-(3-bicyclo[1.1.1]pentanyl)-6-chloro-7H-purin-8-one (example 110, step B) (250.00 mg; 1.02 mmol; 1.00 eq.) and methylhydrazine (542.64 µL; 10.25 mmol; 10.00 eq.) giving 6-[amino(methyl)amino]-9-(3-bicyclo[1.1.1]pentanyl)-7H-purin-8-one (200.00 mg, 79%) as a white powder. $^1$H NMR (DMSO-d6, 300 MHz) δ 10.00 (br s, 1H); 8.00 (s, 1H); 4.87 (br s, 2H); 3.21 (s, 3H); 2.57 (s, 1H); 2.37 (s, 6H).

Step D: 9-(3-bicyclo[1.1.1]pentanyl)-6-[[(E)-(1-hydroxy-3H-2,1-benzoxaborol-5-yl)methyleneamino]-methyl-amino]-7H-purin-8-one The compound was prepared using the same procedure detailed in example 50 step B starting from 6-[amino(methyl)amino]-9-(3-bicyclo[1.1.1]pentanyl)-7H-purin-8-one (example 110, step C) (80.00 mg; 0.32 mmol; 1.00 eq.) and 1-hydroxy-3H-2,1-benzoxaborole-5-carbaldehyde (example 23, step C) (52.61 mg; 0.32 mmol; 1.00 eq.) giving 9-(3-bicyclo[1.1.1]pentanyl)-6-[[(E)-(1-hydroxy-3H-2,1-benzoxaborol-5-yl)methylene amino]-methyl-amino]-7H-purin-8-one (90.00 mg, 71%) as a white powder. $^1$H NMR (DMSO-d6, 400 MHz) δ 9.99 (s, 1H); 9.25 (s, 1H); 8.29 (s, 1H); 8.06 (s, 1H); 7.72-7.82 (m, 3H); 5.05 (s, 2H); 3.64 (s, 3H); 2.62 (s, 1H); 2.42 (s, 6H). mp=259-270° C.

Example 111: 7-cyclobutyl-4-[[(E)-(1-hydroxy-3H-2,1-benzoxaborol-5-yl)methylene amino]-methyl-amino]-5H-pyrrolo[2,3-d]pyrimidin-6-one Step A: 4-chloro-7-cyclobutyl-5H-pyrrolo[2,3-d]pyrimidin-6-one To a solution of methyl 2-(4,6-dichloropyrimidin-5-yl)acetate (200.00 mg; 0.90 mmol; 1.00 eq.) in ACN (2.00 mL), cyclobutylamine (93.04 µL; 1.09 mmol; 1.20 eq.) and DIPEA (224.31 µL; 1.36 mmol; 1.50 eq.) were added. The reaction mixture was stirred at 85° C. until completion. HCl 4M in 1,4-dioxane (2.26 mL; 4.00 mol/L; 9.05 mmol; 10.00 eq.) and water (81.50 µL; 4.52 mmol; 5.00 eq.) were added. The reaction mixture was stirred at 100° C. for 2 h. After cooling to RT, the reaction mixture was concentrated and the residue was diluted with DCM and water and then extracted. The aqueous layer was extracted with DCM (2×). The organic layers were washed with brine, dried on MgSO$_4$, filtered and concentrated. The residue was purified by chromatography (20 to 70% of EtOAc in cyclohexane) to give 4-chloro-7-cyclobutyl-5H-pyrrolo[2,3-d]pyrimidin-6-one (101.00 mg, 50%) as a white powder. $^1$H NMR (DMSO-d6, 300 MHz) δ 8.67 (s, 1H); 4.80 (quint, J=9.46 Hz, 1H); 3.68 (s, 2H); 2.93 (m, 2H); 2.14 (m, 2H); 1.82 (m, 2H).

Step B: 4-[amino(methyl)amino]-7-cyclobutyl-5H-pyrrolo[2,3-d]pyrimidin-6-one

The compound was prepared using the same procedure detailed in example 50 step A starting from 4-chloro-7- cyclobutyl-5H-pyrrolo[2,3-d]pyrimidin-6-one (example 111, step A) (100.00 mg; 0.45 mmol; 1.00 eq.) and methylhydrazine (237.87 µL; 4.47 mmol; 10.00 eq.) giving 4-[amino(methyl)amino]-7-cyclobutyl-5H-pyrrolo[2,3-d]pyrimidin-6-one (60.00 mg, 47%) as a pale yellow solid. $^1$H NMR (DMSO-d6, 300 MHz) δ 8.20 (s, 1H); 4.77 (m, 1H); 4.75 (s, 2H): 3.72 (s, 2H); 3.24 (s, 3H); 2.9 (m, 2H); 2.08 (m, 2H); 1.76 (m, 2H).

Step C: 7-cyclobutyl-4-[[(E)-(1-hydroxy-3H-2,1-benzoxaborol-5-yl)methyleneamino]-methyl-amino]-5H-pyrrolo[2,3-d]pyrimidin-6-one The compound was prepared using the same procedure detailed in example 50 step B starting from 4-[amino(methyl)amino]-7-cyclobutyl-5H-pyrrolo[2,3-d]pyrimidin-6-one (example 111, step B) (60.00 mg; 0.26 mmol; 1.00 eq.) and 1-hydroxy-3H-2,1-benzoxaborole-5-carbaldehyde (example 23, step C) (86.89 mg; 0.54 mmol; 2.08 eq.) giving 7-cyclobutyl-4-[[(E)-(1-hydroxy-3H-2,1-benzoxaborol-5-yl)methyleneamino]-methyl-amino]-5H-pyrrolo[2,3-d]pyrimidin-6-one (68.00 mg, 69%) as a white powder. $^1$H NMR (DMSO-d6, 400 MHz) δ 9.26 (s, 1H); 8.49 (s, 1H); 8.06 (s, 1H); 7.81 (d, J=8.14 Hz, 1H); 7.68-7.75 (m, 2H); 5.05 (s, 2H); 4.85 (quint, J=8.80 Hz, 1H); 3.93 (s, 2H); 3.66 (s, 3H); 3.01 (m, 2H); 2.14 (m, 2H); 1.78 (m, 2H).

Example 112: 4-[ethyl-[(E)-(1-hydroxy-3H-2,1-benzoxaborol-5-yl)methyleneamino]-amino]-N-propyl-thieno[3,2-d]pyrimidine-7-carboxamide Step A: 4-chlorothieno[3,2-d]pyrimidine-7-carboxylic acid Methyl 4-chlorothieno[3,2-d]pyrimidine-7-carboxylate (300.00 mg; 1.31 mmol; 1 eq.) was dissolved in THF (6 mL). A solution of lithium hydroxide (47.13 mg; 1.50 eq.) in H$_2$O (2 mL) was added. The reaction mixture was stirred at rt for 15 min. The reaction mixture was acidified with 1M HCl until pH=1 and concentrated. The resulting aqueous layer was filtered and washed with H$_2$O (3x) and dried to give 4-chlorothieno[3,2-d]pyrimidine-7-carboxylic acid (235.00 mg, 83%) as a yellow solid. $^1$H NMR (DMSO-d6, 300 MHz) δ 9.23 (s, 1H); 9.15 (s, 1H).

Step B: 4-[ethyl-[(E)-(1-hydroxy-3H-2,1-benzoxaborol-5-yl)methyleneamino]-amino]thieno[3,2-d]pyrimidine-7-carboxylic acid The compound was prepared using the same procedure detailed in example 3 Step B starting from ethylhydrazine dichloride (92.04 mg; 0.69 mmol; 1.10 eq.), 1-hydroxy-3H-2,1-benzoxaborole-5-carbaldehyde (example 78, step A) (101.87 mg; 0.63 mmol; 1.00 eq.) and 4-chlorothieno[3,2-d]pyrimidine-7-carboxylic acid (example 112, step A) (135 mg; 0.63 mmol; 1.00 eq.) to give 4-[ethyl-[(E)-(1-hydroxy-3H-2,1-benzoxaborol-5-yl)methylene amino]amino]thieno[3,2-d]pyrimidine-7-carboxylic acid (200.00 mg, 83%) as a yellow brown powder. $^1$H NMR (DMSO-d6, 300 MHz) δ 9.23 (s, 1H); 8.93 (s, 1H); 8.68 (s, 1H); 8.04 (dd, J=7.93 Hz, J=1.16 Hz, 1H); 7.99 (s, 1H); 7.97-8.10 (m, 1H); 7.89-7.96 (m, 1H); 5.12 (s, 2H); 4.65 (m, 2H); 1.31 (t, J=7.02 Hz, 3H).

Step C: 4-[ethyl-[(E)-(1-hydroxy-3H-2,1-benzoxaborol-5-yl)methyleneamino]amino]-N-propyl-thieno[3,2-d]pyrimidine-7-carboxamide 4-[ethyl-[(E)-(1-hydroxy-3H-2,1-benzoxaborol-5-yl)methyleneamino]amino]thieno[3,2-d]pyrimidine-7-carboxylic acid (Example 112, Step B) (100.00 mg; 0.26 mmol; 1.00 eq.) was dissolved in DMF (3 mL). TEA (72.74 µL; 0.52 mmol; 2.00 eq.), EDCl (60.19 mg; 0.31 mmol; 1.20 eq.) and HOBt (7.07 mg; 0.05 mmol; 0.20 eq.) were added. The reaction mixture was stirred at rt overnight. The reaction mixture was concentrated to dryness. The residue was purified by column chromatography (gradient 0 to 10% of MeOH in DCM) to give 4-[ethyl-[(E)-(1-hydroxy-3H-2,1-benzoxaborol-5-yl)methyleneamino]amino]-N-propyl-thieno[3,2-d]pyrimidine-7-carboxamide (30.00 mg, 27%) as a yellow powder. $^1$H NMR (DMSO-d6, 400 MHz) δ 9.61 (t, J=5.8 Hz, 1H); 9.31 (s, 1H); 8.91 (s, 1H); 8.82 (s, 1H); 8.41 (s, 1H); 8.00 (d, J=7.7 Hz, 1H); 7.94 (s, 1H); 7.87 (d, J=7.6 Hz, 1H); 5.11 (s, 2H); 4.57 (m, 2H); 3.37 (q, J=6.8 Hz, 2H); 1.60 (sext, J=7.2 Hz, 2H); 1.26 (t, J=7.0 Hz, 3H); 0.96 (t, J=7.4 Hz, 3H). mp=234° C.

Example 113: 4-[ethyl-[(E)-(1-hydroxy-3H-2,1-benzoxaborol-5-yl)methyleneamino]-amino]-N,N-dimethyl-thieno[3,2-d]pyrimidine-7-carboxamide The compound was prepared using the same procedure detailed in example 112, Step C starting from 4-[ethyl-[(E)-(1-hydroxy-3H-2,1-benzoxaborol-5-yl)methyleneamino]-amino]thieno[3,2-d]pyrimidine-7-carboxylic acid (example 112, Step B) (100.00 mg; 0.26 mmol; 1.00 eq.), DEA 2M in THF (392.46 µL; 0.78 mmol; 3.00 eq.), HATU (119.38 mg; 0.31 mmol; 1.20 eq.) and NMP (34.52 mg; 0.31 mmol; 1.20 eq.) in DMF (3.00 mL) to give 4-[ethyl-[(E)-(1-hydroxy-3H-2,1-benzoxaborol-5-yl)methyleneamino]amino]-N,N-dimethyl-thieno [3,2-d]pyrimidine-7-carboxamide (43.00 mg, 40%) as a white powder. $^1$H NMR (DMSO-d6, 400 MHz) δ 9.31 (s, 1H); 8.72 (s, 1H); 8.40 (s, 1H); 8.37 (s, 1H); 8.01 (d, J=7.7 Hz, 1H); 7.96 (s, 1H); 7.87 (d, J=7.6 Hz, 1H); 5.10 (s, 2H); 4.57 (m, 2H); 3.05 (s, 3H); 2.82 (s, 3H); 1.25 (t, J=7.0 Hz, 3H). mp=289° C.

Example 114: N,N-dibutyl-4-[ethyl-[(E)-(1-hydroxy-3H-2,1-benzoxaborol-5-yl)methyleneamino] amino]thieno[3,2-d]pyrimidine-7-carboxamide The compound was prepared using the same procedure detailed in example 112, Step C starting from 4-[ethyl-[(E)-(1-hydroxy-3H-2,1-benzoxaborol-5-yl)methyleneamino] amino]-thieno[3,2-d]pyrimidine-7-carboxylic acid (example 112, Step B) (200.00 mg; 0.52 mmol; 1.00 eq.) and dibutylamine (133.48 µL; 0.78 mmol, 1.50 eq.) giving N,N-dibutyl-4-[ethyl-[(E)-(1-hydroxy-3H-2,1-benzoxaborol-5-yl)methyleneamino]amino]thieno[3,2-d]pyrimidine-7-carboxamide (44 mg, 16%) as a yellow powder. $^1$H NMR (DMSO-d6, 400 MHz) δ 9.32 (s, 1H); 8.72 (s, 1H); 8.37 (s, 1H); 8.36 (s, 1H); 8.02 (m, 1H); 7.95 (s, 1H); 7.87 (d, J=7.59 Hz, 1H); 5.11 (s, 2H); 4.56 (q, J=6.93 Hz, 2H); 3.46 (t, J=7.37 Hz, 2H); 3.06 (t, J=7.8 Hz, 2H); 1.61 (m, 1H); 1.40 (m, 4H); 1.25 (t, J=6.99 Hz, 3H); 0.93-1.05 (m, 5H); 0.61 (t, J=7.37 Hz, 3H).

Example: 115: 4-[ethyl-[(E)-(1-hydroxy-3H-2,1-benzoxaborol-5-yl)methyleneamino]amino]-N-(oxetan-3-yl)thieno[3,2-d]pyrimidine-7-carboxamide The compound was prepared using the same procedure detailed in example 112, Step C starting from 4-[ethyl-[(E)-(1-hydroxy-3H-2,1-benzoxaborol-5-yl)methyleneamino] amino]-thieno[3,2-d]pyrimidine-7-carboxylic acid (example 112, Step B) (200.00 mg; 0.52 mmol; 1.00 eq.) and 3-oxetanamine hydrochloride (85.99 mg; 0.78 mmol; 1.50 eq.)

giving 4-[ethyl-[(E)-(1-hydroxy-3H-2,1-benzoxaborol-5-yl)methyleneamino]amino]-N-(oxetan-3-yl) thieno[3,2-d]pyrimidine-7-carboxamide (47.00 mg, 19%) as a yellow powder. $^1$H NMR (DMSO-d6, 400 MHz) δ 10.16 (d, J=6.71 Hz, 1H); 9.34 (s, 1H); 8.95 (s, 1H); 8.87 (s, 1H); 8.41 (s, 1H); 8.01 (m, 1H); 7.94 (s, 1H); 7.87 (d, J=7.59 Hz, 1H); 5.03-5.13 (m, 3H); 4.88 (t, J=7.04 Hz, 2H); 4.51-4.63 (m, 4H); 1.26 (t, J=7.04 Hz, 3H).

Example 116: 4-[ethyl-[(E)-(1-hydroxy-3H-2,1-benzoxaborol-5-yl)methyleneamino]-amino]-N-(4-methoxybutyl)thieno[3,2-d]pyrimidine-7-carboxamide The compound was prepared using the same procedure detailed in example 112, Step C starting from 4-[ethyl-[(E)-(1-hydroxy-3H-2,1-benzoxaborol-5-yl)methyleneamino]amino]-thieno[3,2-d]pyrimidine-7-carboxylic acid (example 112, Step B) (110.00 mg; 0.29 mmol; 1.00 eq.) and 4-methoxybutan-1-amine (59.38 mg; 0.58 mmol; 2.00 eq.) giving 4-[ethyl-[(E)-(1-hydroxy-3H-2,1-benzoxaborol-5-yl)methyleneamino]amino]-N-(4-methoxybutyl)-thieno[3,2-d]pyrimidine-7-carboxamide (12 mg, 9%) as an off white powder. $^1$H NMR (DMSO-d6, 400 MHz) δ 9.59 (t, J=5.78 Hz, 1H); 9.31 (s, 1H); 8.91 (s, 1H); 8.83 (s, 1H); 8.41 (s, 1H); 8.01 (dd, J=7.70 Hz, J=0.88 Hz, 1H); 7.95 (s, 1H); 7.88 (d, J=7.59 Hz, 1H); 5.11 (s, 2H); 4.57 (q, J=6.79 Hz, 2H); 3.42 (m, 2H); 3.36 (m, 2H); 3.23 (s, 3H); 1.54-1.67 (m, 4H); 1.26 (t, J=7.04 Hz, 3H).

Example 117: 4-[6-(1-hydroxy-3H-2,1-benzoxaborol-5-yl)-3-methyl-4,5-dihydro-3H-pyridazin-2-yl]furo[2,3-d]pyrimidine

Step A: 3-(1-hydroxy-3H-2,1-benzoxaborol-5-yl)-6-methyl-1,4,5,6-tetrahydropyridazine Tert-butyl-[[2-chloro-5-(6-methyl-1,4,5,6-tetrahydropyridazin-3-yl)phenyl]methoxy]-dimethyl-silane (Example 53, step C) (16.00 g; 0.04 mol; 1.00 eq.) was dissolved in 1,4-dioxane (160 mL). A solution of HCl 4N in 1,4-dioxane (25 mL; 0.10 mol; 2.26 eq.) was added at 0° C. The reaction mixture was stirred at 0° C. for 30 min. The precipitate obtained was filtered, washed with 1,4-dioxane (3×) to give 3-(1-hydroxy-3H-2,1-benzoxaborol-5-yl)-6-methyl-1,4,5,6-tetrahydropyridazine (8.20 g; 70%) as an off white solid. $^1$H NMR (DMSO-d6, 300 MHz) δ 7.72-7.83 (m, 3H); 5.02 (s, 2H); 3.20-3.35 (m, 1H); 2.76-2.98 (m, 2H); 2.07 (m, 1H); 7.80 (m, 1H); 1.29 (d, J=6.44 Hz, 3H).

Step B: 4-[6-(1-hydroxy-3H-2,1-benzoxaborol-5-yl)-3-methyl-4,5-dihydro-3H-pyridazin-2-yl]furo[2,3-d]pyrimidine 3-(1-hydroxy-3H-2,1-benzoxaborol-5-yl)-6-methyl-1,4,5,6-tetrahydropyridazine (Example 117, Step A); (200.00 mg; 0.75 mmol; 1 eq.) and 4-chlorofuro[2,3-d]pyrimidine (115.97 mg; 0.75 mmol; 1.00 eq.) were put in suspension in ACN (3 mL). CuI (57.16 mg, 0.30 mmol; 0.40 eq.) was added. The reaction mixture was stirred and irradiated under MW at 160° C. for 1 h. The reaction mixture was concentrated to dryness. The residue was purified by column chromatography (gradient 0 to 10% of MeOH in DCM) to give 4-[6-(1-hydroxy-3H-2,1-benzoxaborol-5-yi)-3-methyl-4,5-dihydro-3H-pyridazin-2-yl]furo[2,3-d]pyrimidine (11 mg, 4%) as a white powder. $^1$H NMR (DMSO-d6, 400 MHz) δ 9.27 (s, 1H); 8.49 (s, 1H); 7.95 (d, J=2.42 Hz, 1H); 7.84 (s, 3H); 7.31 (d, J=2.42 Hz, 1H); 5.25 (m, 1H); 5.08 (s, 2H); 2.90 (m, 1H); 2.77 (m, 1H); 2.10 (m, 2H); 1.25 (d, J=6.60 Hz, 3H).

Example 118: 4-[6-(1-hydroxy-3H-2,1-benzoxaborol-5-yi)-3-methyl-4,5-dihydro-3H-pyridazin-2-yl]-7-methyl-thieno[3,2-d]pyrimidine The compound was prepared using the same procedure detailed in example 117, Step B starting from 3-(1-hydroxy-3H-2,1-benzoxaborol-5-yl)-6-methyl-1,4,5,6-tetrahydro pyridazine (example 117, step A) (150 mg; 0.56 mmol; 1.00 eq.), 4-chloro-7-methyl-thieno[3,2-d]pyrimidine (100 mg; 0.56 mmol; 1.00 eq.) and CuI (5.36 mg; 0.028 mmol; 0.05 eq.) in ACN (10 mL). The residue was purified by column chromatography (0 to 10% of MeOH in DCM) then triturated in DMF and ACN to give 4-[6-(1-hydroxy-3H-2,1-benzoxaborol-5-yl)-3-methyl-4,5-dihydro-3H-pyridazin-2-yl]-7-methyl-thieno[3,2-d]pyrimidine (46.00 mg, 18%) as an off white powder. $^1$H NMR (DMSO-d6, 400 MHz) δ 9.28 (s, 1H); 8.68 (s, 1H); 8.04 (d, J=7.70 Hz, 1H); 7.96 (s, 1H); 7.91 (s, 1H); 7.84 (d, J=7.70 Hz, 1H); 5.25-5.35 (m, 1H); 5.09 (s, 2H); 2.95 (m, 1H); 2.85 (m, 1H); 2.37 (s, 3H); 2.05 (m, 2H); 1.27 (d, J=6.49 Hz, 3H). mp=179-222° C.

Example 119 and 120: (+) 4-[6-(1-hydroxy-3H-2,1-benzoxaborol-5-yl)-3-methyl-4,5-dihydro-3H-pyridazin-2-yl]-7-methyl-thieno[3,2-d]pyrimidine and (−) 4-[6-(1-hydroxy-3H-2,1-benzoxaborol-5-yl)-3-methyl-4,5-dihydro-3H-pyridazin-2-yl]-7-methyl-thieno[3,2-d]pyrimidine Enantiomers of 4-[6-(1-hydroxy-3H-2,1-benzoxaborol-5-yl)-3-methyl-4,5-dihydro-3H-pyridazin-2-yl]-7-methyl-thieno[3,2-d]pyrimidine (example 118) (150 mg) were separated by chiral LC-MS (Column: Chiralpak IC, 250*20 mm*5 μm; Mobile phase: 95% heptane/5% ethanol; Flow rate: 18 mL/min; T ° column: 25° C.) to give:

(−) 4-[6-(1-hydroxy-3H-2,1-benzoxaborol-5-yl)-3-methyl-4,5-dihydro-3H-pyridazin-2-yl]-7-methyl-thieno[3,2-d] pyrimidine (45.00 mg) as an off white powder. $^1$H NMR (DMSO-d6, 400 MHz) δ 9.28 (s, 1H); 8.68 (s, 1H); 8.04 (dd, J=7.81 Hz, J=1.32 Hz, 1H); 7.97 (s, 1H); 7.91 (d, J=1.21 Hz, 1H); 7.84 (d, J=7.70 Hz, 1H); 5.29 (m, 1H); 5.09 (s, 2H); 2.92 (m, 1H); 2.81 (m, 1H); 2.37 (s, 3H); 2.07 (m, 2H); 1.27 (d, J=6.60 Hz, 3H); αD=−152° (0.47%, DMSO, 27° C.). ee=100.0%; and (+) 4-[6-(1-hydroxy-3H-2,1-benzoxaborol-5-yl)-3-methyl-4,5-dihydro-3H-pyridazin-2-yl]-7-methyl-thieno[3,2-d]pyrimidine (50.00 mg) as a white powder. $^1$H NMR (DMSO-d6, 400 MHz) δ 9.28 (s, 1H); 8.68 (s, 1H); 8.04 (dd, J=7.81 Hz, J=1.32 Hz, 1H); 7.97 (s, 1H); 7.91 (d, J=1.21 Hz, 1H); 7.84 (d, J=7.81 Hz, 1H); 5.29 (m, 1H); 5.09 (s, 2H); 2.92 (d, J=4.62 Hz, 1H); 2.81 (m, 1H); 2.37 (s, 3H); 2.06 (m, 2H); 1.26 (d, J=6.60 Hz, 3H). αD=+147° (0.37%, DMSO, 28° C.). ee=99.5%.

Example 121: 4-[6-(1-hydroxy-3H-2,1-benzoxaborol-5-yl)-3-methyl-4,5-dihydro-3H-pyridazin-2-yl]thieno[3,2-d]pyrimidine The compound was prepared using the same procedure detailed in example 117, Step B starting from 3-(1-hydroxy-3H-2,1-benzoxaborol-5-yl)-6-methyl-1,4,5,6-tetrahydro-pyridazine (example 117, step A) (100.00 mg; 0.43 mmol; 1.00 eq.), 4-chloro-thieno[3,2-d]pyrimidine (88.99 mg; 0.52 mmol; 1.20 eq.) and CuI (33.11 mg; 0.17 mmol; 0.40 eq.).

The residue was purified by preparative LC-MS (column: KinetexXB-C18 30×150 mm 5 µm (phenomenex); Flow rate: 42 mL/min; Elution: H₂O with 0.1% HCOOH/ACN+0.1% HCOOH; gradient: 30-45% of ACN+0.1% HCOOH over 20 min) to give 4-[6-(1-hydroxy-3H-2,1-benzoxaborol-5-yl)-3-methyl-4,5-dihydro-3H-pyridazin-2-yl]thieno[3,2-d]pyrimidine (10.00 mg, 6%) as an off white powder. $^1$H NMR (DMSO-d6, 400 MHz) δ 9.28 (s, 1H); 8.65 (s, 1H); 8.27 (d, J=5.50 Hz, 1H); 8.03 (dd, J=7.76 Hz, J=1.38 Hz, 1H); 7.97 (s, 1H); 7.84 (d, J=7.70 Hz, 1H); 7.45 (d, J=5.61 Hz, 1H); 5.31 (m, 1H); 5.09 (s, 2H); 2.96 (m, 1H); 2.85 (m, 1H); 2.08 (m, 2H); 1.27 (d, J=6.71 Hz, 3H).

Example 122: 4-[6-(1-hydroxy-3H-2,1-benzoxaborol-5-yl)-3-methyl-4,5-dihydro-3H-pyridazin-2-yl]-6,7,8,9-tetrahydrobenzothiopheno[3,2-d]pyrimidine The compound was prepared using the same procedure detailed in example 117, Step B starting from 3-(1-hydroxy-3H-2,1-benzoxaborol-5-yl)-6-methyl-1,4,5,6-tetrahydropyridazine (example 117, step A) (100.00 mg; 0.43 mmol; 1.00 eq.), 4-chloro-6,7,8,9-tetrahydrobenzothiopheno[3,2-d]pyrimidine (126.97 mg; 0.57 mmol; 1.30 eq.) (example 91, step B) and CuI (33.11 mg; 0.17 mmol; 0.40 eq.). The residue was purified by preparative LC-MS (column: KinetexXB-C18 30×150 mm 5 µm (phenomenex); Flow rate: 42 mL/min; Elution: H₂O with 0.1% HCOOH/ACN+0.1% HCOOH; gradient: 40-55% of ACN+0.1% HCOOH over 12 min) to give 4-[6-(1-hydroxy-3H-2,1-benzoxaborol-5-yl)-3-methyl-4,5-dihydro-3H-pyridazin-2-yi]-6,7,8,9-tetrahydrobenzo-thiopheno[3,2-d]pyrimidine (38.00 mg, 20%) as an orange powder. H NMR (DMSO-d6, 400 MHz) δ 9.26 (s, 1H); 8.61 (s, 1H); 8.01 (dd, J=7.87 Hz, J=1.27 Hz, 1H); 7.96 (s, 1H); 7.83 (d, J=7.81 Hz, 1H); 5.29 (m, 1H); 5.08 (s, 2H); 2.77-3.32 (m, 4H); 2.71 (m, 2H); 2.05 (m, 2H); 1.76-1.94 (m, 4H); 1.25 (d, J=6.60 Hz, 3H). mp=100-146° C.

Example 123: 7-[6-(1-hydroxy-3H-2,1-benzoxaborol-5-yl)-3-methyl-4,5-dihydro-3H-pyridazin-2-yl]-2-methylsulfanyl-thiazolo[4,5-d]pyrimidine The compound was prepared using the same procedure detailed in example 117, Step B starting from 3-(1-hydroxy-3H-2,1-benzoxaborol-5-yl)-6-methyl-1,4,5,6-tetrahydropyridazine (example 117, step A) (100.00 mg; 0.43 mmol; 1.00 eq.), 7-chloro-2-methylsulfanyl-thiazolo[4,5-d]pyrimidine (141.93 mg; 0.43 mmol; 1.50 eq.) and CuI (33.11 mg; 0.17 mmol; 0.40 eq.). The residue was purified by preparative LC-MS (column: KinetexXB-C18 30×150 mm 5 µm (phenomenex); Flow rate: 42 mL/min; Elution: H₂O with 0.1% HCOOH/ACN+0.1% HCOOH; gradient: 30-45% of ACN+0.1% HCOOH over 20 min) to give 7-[6-(1-hydroxy-3H-2,1-benzoxaborol-5-yl)-3-methyl-4,5-dihydro-3H-pyridazin-2-yl]-2-methylsulfanyl-thiazolo[4,5-d]pyrimidine 17.00 mg, 10%) as an off white powder. $^1$H NMR (DMSO-d6, 400 MHz) δ 9.28 (s, 1H); 8.64 (s, 1H); 7.95 (s, 1H); 7.91 (m, 1H); 7.86 (m, 1H); 5.23 (m, 1H); 5.08 (s, 2H); 2.96 (m, 1H); 2.83 (s, 3H); 2.80 (m, 1H); 2.05 (m, 2H); 1.26 (d, J=6.71 Hz, 3H).

Example 124 and 125: [2-methoxy-4-[2-(8-methoxyquinazolin-4-yl)-3-methyl-4,5-dihydro-3H-pyridazin-6-yl]phenyl]boronic acid (isomer 1) and [2-methoxy-4-[2-(8-methoxyquinazolin-4-yl)-3-methyl-4,5-dihydro-3H-pyridazin-6-yl]phenyl]boronic acid (isomer 2)

Enantiomers of [2-methoxy-4-[2-(8-methoxyquinazolin-4-yl)-3-methyl-4,5-dihydro-3H-pyridazin-6-yl]phenyl]boronic acid (example 55) (133 mg) were separated by chiral LC-MS (Column: Chiralpak IC, 250*20 mm*5 µm; Mobile phase: 75% heptane/25% ethanol, Flow rate: 18 mL/min, T° column: 25° C.) to give:

[2-methoxy-4-[2-(8-methoxyquinazolin-4-yl)-3-methyl-4,5-dihydro-3H-pyridazin-6-yl]phenyl]boronic acid (isomer 1) (34.00 mg) as an off white powder. $^1$H NMR (DMSO-d6, 400 MHz) δ 8.70 (s, 1H); 8.63 (dd, J=8.8 Hz, J=0.8 Hz, 1H); 7.75 (s, 2H); 7.64 (d, J=7.6 Hz, 1H); 7.50 (s, 1H); 7.45 (d, J=8.8 Hz, 1H); 7.38 (dd, J=7.6 Hz, J=1.2 Hz, 1H); 7.31 (d, J=7.2 Hz, 1H); 5.26 (m, 1H); 3.93 (s, 3H); 3.85 (s, 3H); 2.90 (m, 1H); 2.78 (m, 1H); 2.10 (m, 2H); 1.30 (d, J=6.4 Hz). Rt: 25.4 min (Column: Chiralpak IC, 250*4.6 mm*5 µm, Mobile phase: 75% heptane/25% ethanol, Flow rate: 0.5 mL/min, T° column: 25° C.), ee=100%; and

[2-methoxy-4-[2-(8-methoxyquinazolin-4-yl)-3-methyl-4,5-dihydro-3H-pyridazin-6-yl]phenyl]boronic acid (isomer 2) (34.00 mg) as a white powder. $^1$H NMR (DMSO-d6, 400 MHz) δ 8.70 (s, 1H); 8.63 (dd, J=8.8 Hz, J=0.8 Hz, 1H); 7.75 (s, 2H); 7.64 (d, J=7.6 Hz, 1H); 7.50 (s, 1H); 7.45 (d, J=8.8 Hz, 1H); 7.38 (dd, J=7.6 Hz, J=1.2 Hz, 1H); 7.31 (d, J=7.2 Hz, 1H); 5.26 (m, 1H); 3.93 (s, 3H); 3.85 (s, 3H); 2.90 (m, 1H); 2.78 (m, 1H); 2.10 (m, 2H); 1.30 (d, J=6.4 Hz). Rt: 42.5 min (Column: Chiralpak IC, 250*4.6 mm*5 µm, Mobile phase: 75% heptane/25% ethanol, Flow rate: 0.5 mL/min, T° column: 25° C.), ee=100%.

Example 126: N-[(E)-(1-hydroxy-3H-2,1-benzoxaborol-5-yl)methyleneamino]-7-(methoxymethyl)-N-methyl-thieno[3,2-d]pyrimidin-4-amine Step A: 7-(methoxymethyl)-4-methylsulfanyl-thieno[3,2-d]pyrimidine 4,4-di-tert-butyl-2,2-dipyridyl (6.01 mg; 0.02 mmol; 0.03 eq.) and dichloro(dimethoxyethane)nickel (4.92 mg; 0.02 mmol; 0.03 eq.) were weighed into a dried 2-5 mL MW reactor. Tetrahydrofuran (1.50 mL) was added and the mixture was heated briefly until obtaining a pale green solution. The solvent was then removed under vacuum to yield a ligated nickel complex that was pale evergreen. 7-bromo-4-methylsulfanyl-thieno[3,2-d]pyrimidine (195.00 mg; 0.75 mmol; 1.00 eq.), potassium methoxy-methyltrifluoroborate (136.16 mg; 0.90 mmol; 1.20 eq.), (4,4'-di-t-butyl-2,2'-bipyridine)bis[3,5-difluoro-2-[5-trifluoromethyl-2-pyridinyl-kappan)phenyl-kappac]iridium(III) hexafluorophosphate (33.51 mg; 0.03 mmol; 0.04 eq.) and dipotassium hydrogeno-phosphate (390.15 mg; 2.24 mmol; 3.00 eq.) were added sequentially. The tube sealed and subsequently purged four times with argon. 1,4-dioxane (15.00 ml) and N,N-dimethylacetamide (3.00 ml) were added under inert atmosphere. The resulting mixture was stirred in a Photoredox box 34 W blue led Lamp for 24 h. The reaction mixture was filtered through a plug of Celite and washed with DCM and EtOAc. The resulting solution was concentrated. The crude residue was purified by chromatography (cyclohexane/AcOEt 90/10) to give 7-(methoxymethyl)-4-methylsulfanyl-thieno[3,2-d]pyrimidine (35 mg, 20%) as an off white solid. $^1$H NMR (DMSO-d6, 300 MHz) δ 9.02 (d, J=1.2 Hz, 1H); 8.26 (d, J=0.8 Hz, 1H); 4.69 (s, 2H); 3.36 (d, J=1.2 Hz, 3H); 2.75 (d, J=1.2 Hz, 3H)

Step B: N-[(E)-(1-hydroxy-3H-2,1-benzoxaborol-5-yl)methyleneamino]-7-(methoxymethyl)-N-methyl-thieno[3,2-d]pyrimidin-4-amine The compound was prepared using the same procedure detailed in example 3, Step B starting from 7-(methoxymethyl)-4-methylsulfanyl-thieno[3,2-d]pyrimidine (example 126, step A) (35.00 mg; 0.15 mmol; 1.00 eq.), methylhydrazine (0.20 mL; 3.76 mmol; 24.31 eq.) and 1-hydroxy-3H-2,1-benzoxaborole-5-carbaldehyde (30.05 mg; 0.19 mmol; 1.20 eq.) in ethanol (1.75 mL) to give N-[(E)-(1-hydroxy-3H-2,1-benzoxaborol-5-yl)methyleneamino]-7-(methoxymethyl)-N-methyl-thieno[3,2-d]pyrimidin-4-amine (41 mg; 68.5%) as an off white powder. $^1$H NMR (DMSO-d6, 300 MHz) δ 9.34 (s, 1H); 8.70 (s, 1H); 8.25 (s, 1H); 8.21 (6, 1H); 7.98 (d, J=8.0 Hz, 1H); 7.92 (s, 1H); 7.86 (d, J=8.0 Hz, 1H); 5.08 (s, 2H); 4.67 (s, 2H); 3.81 (s, 3H); 3.88 (s, 3H).

Assays

Effect of Compounds on the Cell-Based TEAD-GAL4 Transactivation Assay

To identify inhibitors of YAP-TEAD interaction, a transient transactivation assay was carried out on HEK293 cell line (HEK293 GripTite™ 293 MSR (Invitrogen R795-07)) using plasmids containing the full length TEAD1 sequences, the full length YAP mutant (S127A, S397A) and a luciferase gene reporter. All expression constructs were performed into a pSG5 backbone plasmid in which the SV40 promoter was replaced by the CMV promoter. The TEAD1 construct was prepared by cloning the full-length human TEAD1 cDNA in fusion with the Gal4 DNA Binding Domain (AA 1-148) into pSG5_CMV to create the TEAD1 (FL)_hum_pSG5Gal4_CMV. The full-length YAP mutant (S127A, S397A) was also cloned into pSG5_CMV to create the YAP (FL)_hum_pSG5_mutS127A_S397A_CMV. The reporter plasmid GAL4(5×RE)_TK(−105/+56)_pGL3-Basic contains 5 copies of the GAL4 responsive element (5'-TCGGAGGACAGTACTCC-3') upstream of the thymidine kinase (TK) promoter (−105/+56) inserted in a pGL3-Basic vector. To evaluate the selectivity of our compounds in blocking the YAP-TEAD interaction, a counter-screening protein-protein interaction transactivation assay was also established. Briefly, two other expression plasmids, the pBD-P53 which expresses the P53 (AA 72-390) in fusion with Gal4 and the pAD-SV40T which expresses the SV40 large T antigen (AA 84-708,AgT), were created. HEK293 cells were seeded at 5×10$^4$ cells/well in 96 well plates (assay plates) in DMEM medium containing 4.5 g/L D-glucose, 10% high inactivated (HI) fetal bovine serum 1% Glutamax, 1% non-essential amino acid and 1% sodium pyruvate and 0.5% penicillin/streptomycin at 37° C. in a humidified atmosphere of 8% CO2. After 24 h, transfections were performed using Jet-PEI as transfectant (101B-010 Polyplus Transfection), according to the instructions of the manufacturer (N/P=10) and a ratio YAP/TEAD=10 (per well: 50 ng of YAP(FL), 5 ng of TEAD(FL) and 50 ng of reporter plasmid). Six hours after cell transfection, the plates ('assay plate') were washed with 100 µl PBS per well and cells were treated with compounds in semi-log from 0.1 µM to 30 µM or DMSO 0.5% as control in DMEM, 4.5 g/L D-Glucose without phenol red, 0.3% BSA, 1% glutamax, 1% NEAA, 1% sodium pyruvate. 24 h later, the luciferase activity was determined after addition of 100 µl of Steady Glo™ luciferase assay system (Promega E2550) according to the manufacturer's directions. Luciferase activity in cell extracts was measured by reading luminescence using the Envision device.

The cellular response was determined by fitting the concentration response curves using a 3-parameter curve fit equation and determining the concentration that inhibited the luciferase activity by 50%.

TABLE 1

TEAD-GAL4 Transactivation activity

| EX | IC50 (µM) | Max Act (%) |
|---|---|---|
| Ex 1 | 7.31 | 86 |
| Ex 2 | 2.28 | 95 |
| Ex 3 | 2.61 | 89 |
| Ex 4 | 6.16 | 76 |
| Ex 5 | 7.10 | 67 |
| Ex 6 |  | 62 |
| Ex 7 | 3.43 | 95 |
| Ex 8 |  | 74 |
| Ex 9 | 2.33 | 98 |
| Ex 10 | 4.36 | 78 |
| Ex 11 |  | 85 |
| Ex 12 | 2.97 | 98 |
| Ex 13 | 5.78 | 95 |
| Ex 14 |  | 90 |
| Ex 15 |  | 95 |
| Ex 16 | 4.16 | 76 |
| Ex 17 | 7.74 | 98 |
| Ex 18 | 2.18 | 80 |
| Ex 19 | 3.36 | 97 |
| Ex 20 | 1.34 | 87 |
| Ex 21 | 1.77 | 90 |
| Ex 22 | 2.57 | 97 |
| Ex 23 | 3.11 | 88 |
| Ex 24 | 5.19 | 76 |
| Ex 25 | 2.78 | 78 |
| Ex 26 | 3.41 | 78 |
| Ex 27 | 6.46 | 83 |
| Ex 28 | 2.75 | 90 |
| Ex 29 |  | 91 |
| Ex 30 | 3.84 | 86 |
| Ex 31 | 4.13 | 90 |
| Ex 32 | 1.59 | 86 |
| Ex 33 | 4.00 | 86 |
| Ex 34 | 1.12 | 81 |
| Ex 35 | 1.36 | 87 |
| Ex 36 |  | 60 |
| Ex 37 | 4.55 | 92 |
| Ex 38 | 0.51 | 81 |
| Ex 39 | 1.20 | 81 |
| Ex 40 | 0.69 | 85 |
| Ex 41 | 0.57 | 83 |
| Ex 42 | 0.26 | 81 |
| Ex 43 | 0.42 | 78 |
| Ex 44 | 0.92 | 78 |
| Ex 45 | 1.02 | 63 |
| Ex 46 |  | 72 |
| Ex 47 |  | 73 |
| Ex 48 |  | 77 |
| Ex 49 | 4.68 | 88 |
| Ex 50 | 5.13 | 81 |
| Ex 51 | 8.48 | 75 |
| Ex 52 | 1.66 | 70 |
| Ex 53 | 3.04 | 87 |
| Ex 54 | 2.35 | 76 |
| Ex 55 | 1.53 | 92 |
| Ex 56 | 1.00 | 84 |
| Ex 57 | 3.06 | 84 |
| Ex 58 | 3.24 | 81 |
| Ex 59 |  | 71 |
| Ex 60 | 5.00 | 79 |
| Ex 61 | 6.63 | 87 |
| Ex62 | 0.99 | 58 |
| Ex63 | 0.69 | 63 |
| Ex64 | 2.76 | 96 |
| Ex65 | 1.98 | 92 |
| Ex66 | 2.15 | 87 |
| Ex67 | 3.82 | 89 |
| Ex68 | 2.63 | 84 |
| Ex69 | 2.34 | 92 |
| Ex70 | 1.88 | 87 |
| Ex71 | 1.14 | 68 |
| Ex72 | 1.86 | 85 |
| Ex73 | 2.24 | 88 |
| Ex74 | 2.36 | 83 |
| Ex75 | 0.90 | 94 |
| Ex76 | 0.96 | 86 |

TABLE 1-continued

TEAD-GAL4 Transactivation activity

| EX | IC50 (μM) | Max Act (%) |
|---|---|---|
| Ex77 | 0.32 | 82 |
| Ex78 | 2.22 | 75 |
| Ex79 | 1.01 | 90 |
| Ex80 | 1.96 | 69 |
| Ex81 | 1.75 | 79 |
| Ex82 | 2.37 | 89 |
| Ex83 | 0.23 | 94 |
| Ex84 | 1.03 | 85 |
| Ex85 | 0.61 | 81 |
| Ex86 | 0.65 | 81 |
| Ex87 | 0.59 | 82 |
| Ex88 | 0.63 | 80 |
| Ex89 | 0.82 | 85 |
| Ex90 | 1.26 | 83 |
| Ex91 | 0.64 | 85 |
| Ex92 | 0.17 | 91 |
| Ex93 | 0.71 | 80 |
| Ex94 | 0.46 | 80 |
| Ex95 | 0.13 | 85 |
| Ex96 | 0.10 | 87 |
| Ex97 | 0.66 | 79 |
| Ex98 | 1.31 | 86 |
| Ex99 | 2.12 | 91 |
| Ex100 | 1.41 | 85 |
| Ex101 | 0.90 | 94 |
| Ex102 | 1.99 | 87 |
| Ex103 | 0.71 | 79 |
| Ex104 | 1.76 | 79 |
| Ex105 | 0.51 | 83 |
| Ex106 | 1.06 | 83 |
| Ex107 | 1.65 | 87 |
| Ex108 | 2.59 | 82 |
| Ex109 | 1.65 | 86 |
| Ex110 | 2.41 | 81 |
| Ex111 | 1.58 | 83 |
| Ex112 | 1.87 | 79 |
| Ex113 | 5.21 | 70 |
| Ex114 | 1.74 | 83 |
| Ex115 | 1.74 | 79 |
| Ex116 | 1.94 | 86 |
| Ex117 | 0.69 | 82 |
| Ex118 | 0.27 | 86 |
| Ex119 | 0.43 | 77 |
| Ex120 | 0.50 | 84 |
| Ex121 | 0.72 | 80 |
| Ex122 | 0.82 | 94 |
| Ex123 | 0.20 | 96 |
| Ex124 | 7.27 | 93 |
| Ex125 | 3.52 | 86 |
| Ex126 | 0.70 | 83 |

Inhibition of Malignant Mesothelioma Tumor Cell Growth

The tumor cell growth inhibitory activity of the YAP-TEAD interaction inhibitors was evaluated in NCI-H-2052 mesothelioma cell line harboring a NF2 mutation. This cell line was selected based on its mutational status and the ability of a siRNA directed against YAP, TAZ or TEAD1-4 to inhibit cell proliferation. The nuclear localization of YAP at confluence was also taken into account. Based on these observations we were able to classify several "YAP dependent cells" where YAP is clearly nuclear and in which a cell growth inhibition is observed by using siRNA (NCI-H-2052, SKOV-3, ACHN, A549) and the "YAP independent cells" where YAP is preferentially located in the cytoplasm and in which no inhibition of cell growth is observed by using a siRNA (SW620, Met-5a). 10,000 cells/well were plated in a 96-well black plate with clear flat bottom TC-Treated Imaging plate (Falcon #353219) in regular medium (as suggested from ATCC for each cell line) with serum, which was replaced the day after with starvation medium containing 1% serum. After one day growth in the starvation medium, cells were incubated with compounds. The starting concentration was 30 μM and serial dilutions in DMSO and medium were performed until 0.1 μM to achieve a final DMSO concentration of 0.5%. The cells were then allowed to grow for 3 days, and then, EdU (Invitrogen, Molecular Probe) was added in each well at a final concentration of 10 μM and the cells were returned to the incubator for an additional 24 h. The starvation medium was removed and 100 μl of PFA 4% containing Hoechst dye was adding in each well to fix the cells. Plates were then incubated at rt for 15 min, washed twice with PBS and the cells were permeabilized by adding 100 μl per well of triton-100 containing 0.3% BSA. After 20 min, cells were washed with PBS and EdU detection was performed according to the instructions of the manufacturer. Image acquisition was performed using the ImageXpress Micro and analyzed using the MetaXpress software (Molecular Device). Results were expressed as a percent of inhibition (%) of the cell proliferation values obtained with 0.5% DMSO treatment alone. The cellular response was determined by fitting the concentration response curves using a 3 parameter curve fit equation and determining the concentration that inhibited cell growth between 50% and 100%.

Compounds (Ex 1, 5, 20, 42, 75, 118) inhibited NCI-H2052 mesothelioma cell proliferation (NF2 mutated cell line; FIG. 1 (x)) without showing any effect in the Met5A cell line, a "YAP-independent cell line", FIG. 1 (■). In addition, compounds of the invention inhibited other mesothelioma and non-small cell lung cancer cell growth (data not shown).

REFERENCES

WO 2016/055394
WO 2013/068554
Aranyos et al., JACS, 1999, 121(18), 4369-4378
Avruch et al., Cell Cycle 2012, 1090-1096
Badouel et al., Curr Opin Cell Biol 2009, 21, 837-43
WO 2008156817
Bandarage et al., Bioorg. Med. Chem. Lett., 2009, 19(17), 5191-5194
Berg at al., Chem Med Chem, 2009, 4(2), 249-260
Bianchi et al., Nat Genet 1994, 6, 185-192
Bianchi et al., Natl Acad. Sci. USA, 1995, 92, 10854-10858
Blanchet et al., Journal of Organic Chemistry, 72(9), 3199-3206; 2007
WO 20151025025
Bott et al., Nat Genet 2011, 43, 668-672
WO 2009/062258
WO 2009/029998
Carbone et al., Clin Cancer Res 2012, 18, 598-604
Chad et al., Cancer Res 2010, 70, 8517-25
Chen et al., JACS, 2014, 136(49), 17337-17342
Dastbaravardeh et al., Org. Lett., 2012, 14(7), 1930-1933
De Christofaro at al., Eur J Cancer 2011, 926-933
Deguen et al., Int J Cancer 1998, 77, 554-560
Deniau et al., Tetrahedron, 2001, 57(13), 2581-2588
Differding at al., Helvetica Chimica Acta, 72(6), 1248-52; 1989
Dong et al., Cell, 2007, 130:1120-1133
WO 2013/078126
Dutta at al. US 2014/0309427 Dzhevakov et al., Adv. Synth. Catal., 2016, 358(6), 977-983
WO 2011/157397
WO 2013/192352
Forbe et al., Nucleic Acids Res 2011, 39, D945-950

Fuchida et al., Bul. Chem. Soc. Jp., 2015, 88(6) 784-791
Garcia et al., Chem. Commun. (Cambridge, United Kingdom), 2016, 52(58), 9059-9062
Gouault et al., Journal of Pharmacy and Pharmacology, 2001, 53(7), 981-985
WO 00/04013
Green et al., Protective Group in Organic Synthesis, Wiley, third edition
Haffner et al., Bioorganic & Medicinal Chemistry Letters, 20(23), 6989-6992; 2010
Haffner et al., Bioorganic & Medicinal Chemistry Letters, 20(23), 6983-6988; 2010
Harvey et al., Nat Rev Cancer, 2013, 13, 246-257
Hishikawa K et al., Journal of the American Chemical Society, 2009, 131(22), 7488-7489
Holden J, Cancers, 2018, 10, ASAP
Hong W et al., Cell Dev Biol 2012, 23, 785-793
Huang et al., Cell 2005, 122, 421-34
Hudlicky Reductions in Organic Chemistry ACS monograph 188 second edition
Karakaya et al., Org. Lett. 2015, 17, 3294,
Keglevich et al., Heteroatom Chem., 2012, 23(6), 574-582
Kim et al., Bioorg. Med. Chem. Lett., 2008, 18(14), 4181-4185
Krasavin, M. et al Syn. Commun., 2005, 35(19), 2587-2595
Kurian et al., Bioorganic & Medicinal Chemistry Letters, 24(17), 4176-4180; 2014
Lafitte G et al. Tetrahedron Letters 2017, 58, 3757-3759
Lei et al., Mol Cell Biol 2008, 28, 2426-36)
Li et al., Org. Proc. Res. Dev., 2016, 20(8), 1489-1499
Lin K et al., Trends Biochem Science, 2017, 42, 862-872
Liu et al., Molecules, 2012, 17, 4545-4559
Loghmani-Khouzani et al., Journal of Chemical Research, Synopses, (2), 80-81; 2001
Luehr et al., Bioorg. Med. Chem., 2010, 18(4), 1388-1395
WO 2004/013141
WO 2016/109559
WO 2012/084804
Molander G et al., J Am Chem Soc, 2012, 134, 11667-11673
Meyers et al., Bioorg. Med. Chem. Left., 2010, 20(5), 1543-1547
Moon S et at Cell Mol Life Science, 2018, 13, 2303-2319
Mukhina et al., Angew. Chem., Inter. Ed., 2015, 54(39), 11516-11520
Murakami et al., Cancer Res 2011, 71, 873-883
Murphy et al., Org. Lett., 2007, 9(5), 757-760
WO 2014/028384
Noncovich, A et al Tetrahedron Letters, 2015, 56(33), 4836-4839
Omura et al., Tetrahedron, 1978, 34 (11), 1651-1660
U.S. Pat. No. 6,197,766
Park et al., Environ Health Perspect 2011, 119, 514-518
WO 2010/100139
Pobbati A, Cancer Biol therapy, 2013, 390-398
Raw et al., Tetrahedron Letters, 52(50), 6775-6778; 2011
Ruttledge et al., Nat Genet 1994, 6, 180-184
Sakai et al. Chemistry Letters, 2015, 44(11), 1503-1505
Sam et al., JACS, 1972, 94, 4024-4025
Sandgren V et al Bioorganic & Medicinal Chemistry, 20(14), 4377-4389; 2012
Schneider et al., Organic Letters, 13(14), 3588-3591; 2011
WO 2007/038367
Sekido et al., Cancer Res 1995, 55, 1227
Sekido et al., Pathol Int 2011, 61, 331-344
Sekido et al., Cancers, 2018, ASAP
Steinhardt et al., Hum. Pathol 2008, 39, 1582-9
WO 2014/077401
U.S. Pat. No. 5,306,818
Sun et al., 2008, JOC, 73(18), 7361-7364
Timmer et al., Chem. Commun. (Cambridge, United Kingdom), 2016, 52(83), 12326-12329
Tohma et al., Adv. Syn. Catal., 2004, 346, 111-124
WO 2014/025942
Tumaneng K et al., Curr Biol, 2013, 22, R368-379
Tzchucke et al., Org. Lett., 2007, 9(5), 761-764
Vaid et al., Synthesis, 2012, 44(15), 2396-2400
Wang L et al., Tumour Biol 2014, 14, 463-468
Wang et al., Cancer Sci 2010, 101, 1279-85
WO 2017/133517
Winton. et al., Journal of Heterocyclic Chemistry, 1984, 21(3), 889-91
Woodward et al., Transl. Lung Res., 2017, 6, 335-342
Wulff, J, Diss. Abstr. Int., B 2005, 2004, 65(12), 6399
Xie et al., Eur. J. Med. Chem., 2016, 115, 132-140
Yamada S et al., Tetrahedron Letters, 1992, 33, 4329-4332
Yokoyama et al., Carcinogenesis 2008, 29, 2139-2146
Yu Fx et al., Genes Dev 2013, 27, 355-371
Zeng et al., Cancer Cell 2008, 13, 188-192
Zhang et al., Bioorg. Med; Chem. Lett., 2008, 18(23), 6067-6070
Zhang et al., J. Med. Chem., 2009, 52(18) 5703-5711
Zhao et al., Cancer Res 2009, 69, 1089-98
Zhao et al., Gens Dev 2008, 22, 1962-71
Zhao et al. Genes Dev 2007, 21: 2747-2761
Zhou et al., Oncogene 2011, 30, 2181-86
Zil'berman et al., Russ. Chem. Rev., 1984, 53, 900-912

The invention claimed is:

1. A compound of formula (I):

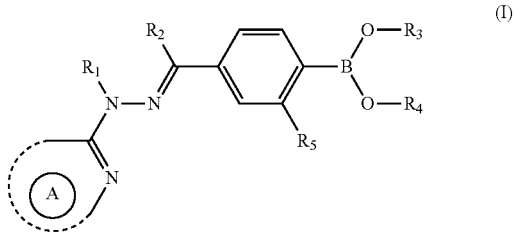

wherein:

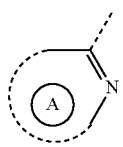

is a substituted or unsubstituted N-containing monocyclic, bicyclic or tricyclic heteroaryl;

$R_1$ is H, an alkyl optionally substituted with one or two groups $R_6$ or an aryl optionally substituted with one or more groups $R_6$;

$R_2$ is H or alkyl; or $R_1$ and $R_2$ are bound together to form a 5- or 6-membered heterocycle;

$R_3$ and $R_4$ are each independently H or an alkyl optionally substituted with one or two groups $R_6$; or $R_3$ and $R_4$ are bound together to form a 5- to 8-membered heterocycle;

R₅ is H, a halogen, an alkyl optionally substituted with 1 or 2 groups R₆, or an alkoxy optionally substituted with 1 or 2 groups R₆; or R₄ and R₅ are bound together to form a 5- to 7-membered heterocyle;

R₆ is hydroxy, alkoxy, —NR₁₅R₁₆, —CO—Y—R₁₇, —CN, —CF₃, or aryl;

R₁₅ and R₁₆ are each independently H, alkyl, —CO-alkyl or form together with the nitrogen atom a 3- to 6-membered cyclic group;

Y is —O— or —NR₁₈—;

R₁₇ is H or alkyl; and

R₁₈ is H, alkyl or hydroxyalkyl;

provided that when R₃ is H and R₄ and R₅ are bound together to form a 5-membered heterocycle, then R₁ is not H;

or a pharmaceutically acceptable salt thereof.

2. The compound of claim 1, or a pharmaceutically acceptable salt thereof, wherein:

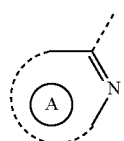

is selected from the groups of formulae (II), (III), (IV), (V), (VI), (VII), (VIII), (IX), (X), (XI), (XII), (XIII), (XIV), (XV), (XVI), (XVII) and (XVIII):

(II)
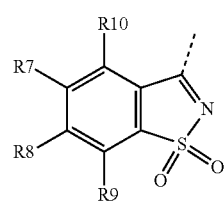

(III)
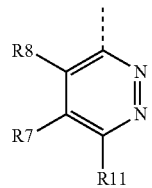

(IV)
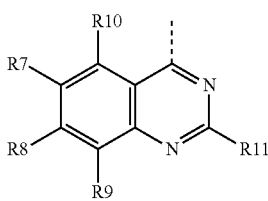

(V)
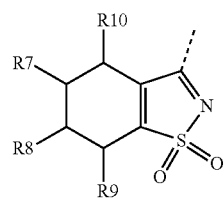

(VI)
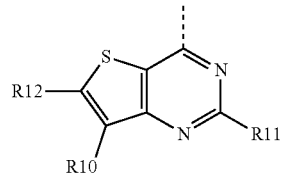

(VII)
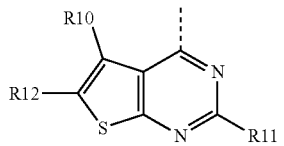

(VIII)
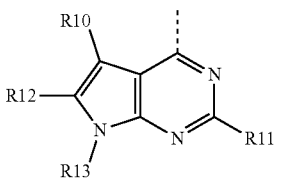

(IX)
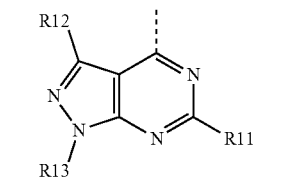

(X)
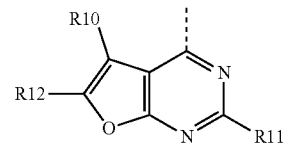

(XI)
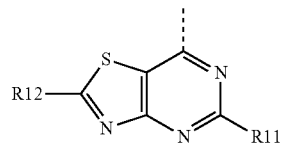

(XII)
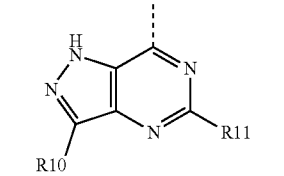

(XIII)
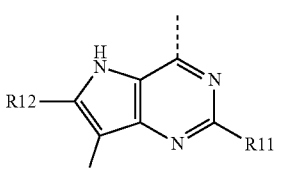

(XIV)
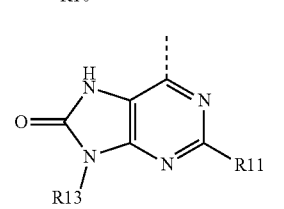

-continued

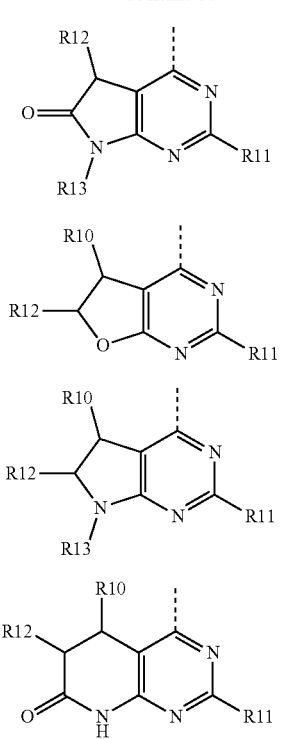

(XV)

(XVI)

(XVII)

(XVIII)

wherein:
R$_7$, R$_8$, R$_9$ and R$_{10}$ are each independently H, a halogen, an alkyl optionally substituted with 1 or 2 groups R$_6$, a perfluoroalkyl, an alkoxy optionally substituted with 1 or 2 groups R$_6$, or a cyano group;
R$_{10}$ can also represent a cycloalkyl, an aryl, —NR$_{15}$R$_{16}$, or —CO—Y—R$_{22}$ where R$_{22}$ is H, alkyl optionally substituted with hydroxy or alkoxy, or —NR$_{15}$R$_{16}$;
R$_{10}$ can also be bound together with R$_{12}$ to form a 6-membered carbocycle;
R$_{11}$, R$_{12}$, and R$_{13}$ are each independently H, an alkyl optionally substituted with 1 or 2 groups R$_6$, or a perfluoroalkyl;
R$_{12}$ can also represent an alkylthio or a group —NR$_{15}$R$_{16}$;
R$_{13}$ can also represent a cycloalkyl optionally substituted with hydroxyl or alkoxyalkyl.

3. The compound of claim 1, or a pharmaceutically acceptable salt thereof, wherein R$_1$ is an alkyl optionally substituted with one or two groups R$_6$ or an aryl optionally substituted with one or more groups R$_6$ and R$_6$ is hydroxy, alkoxy, —NR$_{15}$R$_{16}$, —CO—Y—R$_{17}$, —CN, —CF$_3$, or aryl.

4. The compound of claim 1, or a pharmaceutically acceptable salt thereof, wherein:
R$_3$ and R$_4$ are each independently H or an alkyl; or R$_3$ and R$_4$ are bound together to form a 5- to 8-membered heterocycle;
R$_5$ is H, a halogen, an alkyl optionally substituted with 1 or 2 groups R$_6$, or an alkoxy optionally substituted with 1 or 2 groups R$_6$ and R$_6$ is hydroxy, alkoxy, —NR$_{15}$R$_{16}$, —CO—Y—R$_{17}$, —CN, —CF$_3$, or aryl.

5. The compound of claim 4, which is selected from:
[4-[(E)-[(1,1-dioxo-1,2-benzothiazol-3-yl)-isobutyl-hydrazono]methyl]-2-methoxy-phenyl]boronic acid;
[4-[(E)-[isobutyl-(5-methoxy-1,1-dioxo-1,2-benzothiazol-3-yl)hydrazono]methyl]-2-methoxy-phenyl]boronic acid;
[4-[(E)-[(5,7-dimethoxy-1,1-dioxo-1,2-benzothiazol-3-yl)-isobutyl-hydrazono]methyl]-2-methoxy-phenyl]boronic acid;
[4-[(E)-[(1,1-dioxo-1,2-benzothiazol-3-yl)-ethyl-hydrazono]methyl]-2-methoxy-phenyl]boronic acid;
[4-[(E)-[(1,1-dioxo-1,2-benzothiazol-3-yl)-(2-methoxyethyl)hydrazono]methyl]-2-methoxy-phenyl]boronic acid;
[2-chloro-4-[(E)-[(1,1-dioxo-1,2-benzothiazol-3-yl)-isobutyl-hydrazono]methyl]phenyl]boronic acid;
[4-[(E)-[isobutyl-(5-methyl-1,1-dioxo-1,2-benzothiazol-3-yl)hydrazono]methyl]-2-methoxy-phenyl]boronic acid;
[4-[(E)-[(1,1-dioxo-1,2-benzothiazol-3-yl)-isobutyl-hydrazono]methyl]phenyl]boronic acid;
[4-[(E)-[isobutyl-[5-(2-methoxyethoxy)-1,1-dioxo-1,2-benzothiazol-3-yl]hydrazono]methyl]-2-methoxy-phenyl]boronic acid;
[4-[(E)-[(6-cyano-1,1-dioxo-1,2-benzothiazol-3-yl)-isobutyl-hydrazono]methyl]-2-methoxy-phenyl]boronic acid;
[4-[(E)-[(1,1-dioxo-1,2-benzothiazol-3-yl)-isobutyl-hydrazono]methyl]-2-(2-methoxyethoxy)phenyl]boronic acid;
[4-[(E)-[[5-(3-hydroxypropoxy)-1,1-dioxo-1,2-benzothiazol-3-yl]-isobutyl-hydrazono]methyl]-2-methoxy-phenyl]boronic acid;
[4-[(E)-[isobutyl-(8-methoxyquinazolin-4-yl)hydrazono]methyl]-2-methoxy-phenyl]boronic acid;
[4-[(E)-[(1,1-dioxo-1,2-benzothiazol-3-yl)-isobutyl-hydrazono]methyl]-2-ethoxy-phenyl]boronic acid;
[2-chloro-4-[(E)-[(5,7-dimethoxy-1,1-dioxo-1,2-benzothiazol-3-yl)-isobutyl-hydrazono]methyl]phenyl]boronic acid;
[4-[(E)-[(1,1-dioxo-1,2-benzothiazol-3-yl)-sec-butyl-hydrazono]methyl]-2-methoxy-phenyl]boronic acid;
[4-[(E)-[(6,8-dimethoxyquinazolin-4-yl)-isobutyl-hydrazono]methyl]-2-methoxy-phenyl]boronic acid;
[4-[(E)-[(7-fluoroquinazolin-4-yl)-isobutyl-hydrazono]methyl]-2-methoxy-phenyl]boronic acid;
[4-[(E)-[isobutyl-(6-methoxyquinazolin-4-yl)hydrazono]methyl]-2-methoxy-phenyl]boronic acid;
[4-[(E)-[isobutyl(thieno[3,2-d]pyrimidin-4-yl)hydrazono]methyl]-2-methoxy-phenyl]boronic acid;
[4-[(E)-[ethyl-(8-methoxyquinazolin-4-yl)hydrazono]methyl]-2-methoxy-phenyl]boronic acid;
[2-methoxy-4-[(E)-[(8-methoxyquinazolin-4-yl)-methyl-hydrazono]methyl]phenyl]-boronic acid;
[4-[2-(1,1-dioxo-1,2-benzothiazol-3-yl)-3-methyl-4,5-dihydro-3H-pyridazin-6-yl]-2-methoxy-phenyl]boronic acid;
[4-[2-(5,7-dimethoxy-1,1-dioxo-1,2-benzothiazol-3-yl)-3-methyl-4,5-dihydro-3H-pyridazin-6-yl]-2-methoxy-phenyl]boronic acid;
[2-methoxy-4-[2-(8-methoxyquinazolin-4-yl)-3-methyl-4,5-dihydro-3H-pyridazin-6-yl]phenyl]boronic acid;
[4-[2-(1,1-dioxo-1,2-benzothiazol-3-yl)-4,4-dimethyl-3,5-dihydropyridazin-6-yl]-2-methoxy-phenyl]boronic acid;
[4-[4-(1,1-dioxo-1,2-benzothiazol-3-yl)-6-methyl-5,6-dihydro-1,3,4-oxadiazin-2-yl]-2-methoxy-phenyl]boronic acid;
[2-methoxy-4-[(E)-[methyl-(5-methylpyridazin-3-yl)hydrazono]methyl]phenyl]boronic acid;
2-[4-[(E)-[(1,1-dioxo-1,2-benzothiazol-3-yl)-isobutyl-hydrazono]methyl]-2-methoxy-phenyl]-6-methyl-1,3,6,2-dioxazaborocane-4,8-dione;

[4-[(E)-[ethyl-(7-methylthieno[3,2-d]pyrimidin-4-yl)hydrazono]methyl]-2-methoxy-phenyl]boronic acid;
[4-[(E)-[ethyl(thieno[3,2-d]pyrimidin-4-yl)hydrazono]methyl]-2-methoxy-phenyl]boronic acid;
[4-[(E)-[ethyl(thiazolo[4,5-d]pyrimidin-7-yl)hydrazono]methyl]-2-methoxy-phenyl]boronic acid;
[4-[(E)-[ethyl(furo[2,3-d]pyrimidin-4-yl)hydrazono]methyl]-2-methoxy-phenyl]boronic acid;
[4-[(E)-[ethyl-(7-methylpyrrolo[2,3-d]pyrimidin-4-yl)hydrazono]methyl]-2-methoxy-phenyl]boronic acid;
[4-[(E)-[isobutyl-(7-methylthieno[3,2-d]pyrimidin-4-yl)hydrazono]methyl]-2-methoxy-phenyl]boronic acid;
[4-[(E)-[isobutyl-(2-methylthieno[3,2-d]pyrimidin-4-yl)hydrazono]methyl]-2-methoxy-phenyl]boronic acid;
[4-[(E)-[isobutyl-(6-methylthieno[3,2-d]pyrimidin-4-yl)hydrazono]methyl]-2-methoxy-phenyl]boronic acid;
[2-methoxy-4-[(E)-[2-methoxyethyl(thieno[3,2-d]pyrimidin-4-yl)hydrazono]methyl]-phenyl]boronic acid;
[2-methoxy-4-[(E)-[methyl-(7-methylthieno[3,2-d]pyrimidin-4-yl)hydrazono]methyl]-phenyl]boronic acid;
[2-methoxy-4-(3-methyl-2-thieno[3,2-d]pyrimidin-4-yl-4,5-dihydro-3H-pyridazin-6-yl)phenyl]boronic acid;
[2-methoxy-4-[3-methyl-2-(7-methylpyrrolo[2,3-d]pyrimidin-4-yl)-4,5-dihydro-3H-pyridazin-6-yl]phenyl]boronic acid;
[4-[4-(7-fluoroquinazolin-4-yl)-6-methyl-5,6-dihydro-1,3,4-oxadiazin-2-yl]-2-methoxy-phenyl]boronic acid,
and
pharmaceutically acceptable salts thereof.

6. The compound of claim 1, or a pharmaceutically acceptable salt thereof, wherein:
R$_3$ is H or an alkyl optionally substituted with one or two groups R$_6$;
R$_4$ and R$_5$ are bound together to form a 5- to 7-membered heterocycle;
R$_6$ is hydroxy, alkoxy, —NR$_{15}$R$_{16}$, —CO—Y—R$_{17}$, —CN, —CF$_3$, or aryl.

7. The compound of claim 1, or a pharmaceutically acceptable salt thereof, represented by formula (Ib):

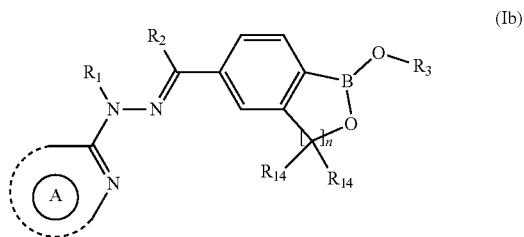

(Ib)

wherein:
R$_1$ is H, an alkyl optionally substituted with one or two groups R$_6$ or an aryl optionally substituted with one or more groups R$_6$;
R$_2$ is H or alkyl;
R$_3$ is H or an alkyl optionally substituted with one or two groups R$_6$;
each R$_{14}$ is independently H, an alkyl optionally substituted with one or two groups R$_6$, an aryl, —NR$_{15}$R$_{16}$, or —CO—Y—R$_{17}$;
R$_6$ is hydroxy, alkoxy, —NR$_{15}$R$_{16}$, —CO—Y—R$_{17}$, —CN, —CF$_3$, or aryl;
R$_{15}$ and R$_{16}$ are each independently H, alkyl, —CO-alkyl or form together with the nitrogen atom a 3- to 6-membered cyclic group;

Y is —O— or —NR$_{18}$—;
R$_{17}$ is H or alky;
R$_{18}$ is H, alkyl or hydroxyalkyl;
n is 1, 2 or 3; and
is a substituted or unsubstituted N-containing monocyclic, bicyclic or tricyclic heteroraryl.

8. The compound of claim 6, which is selected from:
N-[(E)-(1-hydroxy-3H-2,1-benzoxaborol-5-yl)methyleneamino]-N-isobutyl-1,1-dioxo-1,2-benzothiazol-3-amine;
N-[(E)-(1-hydroxy-3H-2,1-benzoxaborol-5-yl)methyleneamino]-N-(2-methoxyethyl)-1,1-dioxo-1,2-benzothiazol-3-amine;
N-[(E)-(1-hydroxy-3H-2,1-benzoxaborol-5-yl)methyleneamino]-N-(3-methoxypropyl)-1,1-dioxo-1,2-benzothiazol-3-amine;
N-[(E)-(1-hydroxy-3H-2,1-benzoxaborol-5-yl)methyleneamino]-N-methyl-1,1-dioxo-1,2-benzothiazol-3-amine;
N-ethyl-N-[(E)-(1-hydroxy-3H-2,1-benzoxaborol-5-yl)methyleneamino]-1,1-dioxo-1,2-benzothiazol-3-amine;
5-fluoro-N-[(E)-(1-hydroxy-3H-2,1-benzoxaborol-5-yl)methyleneamino]-N-isobutyl-1,1-dioxo-1,2-benzothiazol-3-amine;
N-[(E)-(1-hydroxy-3H-2,1-benzoxaborol-5-yl)methyleneamino]-N-isobutyl-5-methyl-1,1-dioxo-1,2-benzothiazol-3-amine;
N-[(E)-(1-hydroxy-3H-2,1-benzoxaborol-5-yl)methyleneamino]-N-isobutyl-6-methoxy-1,1-dioxo-1,2-benzothiazol-3-amine;
N-[(E)-(1-hydroxy-3H-2,1-benzoxaborol-5-yl)methyleneamino]-N-isobutyl-6-methyl-1,1-dioxo-1,2-benzothiazol-3-amine;
N-[(E)-(1-hydroxy-3H-2,1-benzoxaborol-5-yl)methyleneamino]-N-isobutyl-8-methoxy-quinazolin-4-amine;
N-[(E)-(1-hydroxy-3H-2,1-benzoxaborol-5-yl)methyleneamino]-8-methoxy-N-methyl-quinazolin-4-amine;
N-ethyl-N-[(E)-(1-hydroxy-3H-2,1-benzoxaborol-5-yl)methyleneamino]-8-methoxy-quinazolin-4-amine;
N-[(E)-(1-hydroxy-3H-2,1-benzoxaborol-5-yl)methyleneamino]-N-isobutyl-thieno[3,2-d]pyrimidin-4-amine;
N-[(E)-(1-hydroxy-3H-2,1-benzoxaborol-5-yl)methyleneamino]-N,5-dimethyl-1,1-dioxo-1,2-benzothiazol-3-amine;
N-[(E)-(1-hydroxy-3H-2,1-benzoxaborol-5-yl)methyleneamino]-5-methoxy-N-methyl-1,1-dioxo-1,2-benzothiazol-3-amine;
N-ethyl-N-[(E)-(1-hydroxy-3H-2,1-benzoxaborol-5-yl)methyleneamino]thieno[3,2-d]pyrimidin-4-amine;
N-ethyl-N-[(E)-(1-hydroxy-3H-2,1-benzoxaborol-5-yl)methyleneamino]-7H-pyrrolo[2,3-d]pyrimidin-4-amine;
N-ethyl-N-[(E)-(1-hydroxy-3H-2,1-benzoxaborol-5-yl)methyleneamino]thieno[2,3-d]pyrimidin-4-amine;
N-ethyl-N-[(E)-(1-hydroxy-3H-2,1-benzoxaborol-5-yl)methyleneamino]-1-methyl-pyrazolo[3,4-d]pyrimidin-4-amine;
N-ethyl-N-[(E)-(1-hydroxy-3H-2,1-benzoxaborol-5-yl)methyleneamino]-7-methyl-thieno[3,2-d]pyrimidin-4-amine;
N-ethyl-N-[(E)-(1-hydroxy-3H-2,1-benzoxaborol-5-yl)methyleneamino]furo[2,3-d]pyrimidin-4-amine;
N-ethyl-N-[(E)-(1-hydroxy-3H-2,1-benzoxaborol-5-yl)methyleneamino]-7-methyl-pyrrolo[2,3-d]pyrimidin-4-amine;

N-ethyl-N-[(E)-(1-hydroxy-3H-2,1-benzoxaborol-5-yl)
methyleneamino]-2-methyl-thieno[3,2-d]pyrimidin-4-
amine;

N-[(E)-(1-hydroxy-3,4-dihydro-2,1-benzoxaborinin-6-yl)
methyleneamino]-N-isobutyl-1,1-dioxo-1,2-benzothi-
azol-3-amine;

N-[(E)-(1-hydroxy-4,5-dihydro-3H-2,1-benzoxaborepin-
7-yl)methyleneamino]-N-isobutyl-1,1-dioxo-1,2-ben-
zothiazol-3-amine;

N-[(E)-(1-hydroxy-7-methoxy-3H-2,1-benzoxaborol-5-
yl)methyleneamino]-N-isobutyl-1,1-dioxo-1,2-benzo-
thiazol-3-amine;

N-[(E)-(1-hydroxy-3-methyl-3H-2,1-benzoxaborol-5-yl)
methyleneamino]-N-isobutyl-1,1-dioxo-1,2-benzothi-
azol-3-amine;

N-[(E)-(1-hydroxy-3-methyl-3H-2,1-benzoxaborol-5-yl)
methyleneamino]-N-methyl-1,1-dioxo-1,2-benzothi-
azol-3-amine;

N-[(E)-(1-hydroxy-3H-2,1-benzoxaborol-5-yl)methyl-
eneamino]-N-methyl-1,1-dioxo-4,5,6,7-tetrahydro-1,
2-benzothiazol-3-amine;

3-[6-(1-hydroxy-3H-2,1-benzoxaborol-5-yl)-3-methyl-4,
5-dihydro-3H-pyridazin-2-yl]-1,2-benzothiazole 1,1-
dioxide;

4-[6-(1-hydroxy-3H-2,1-benzoxaborol-5-yl)-3-methyl-4,
5-dihydro-3H-pyridazin-2-yl]-8-methoxy-quinazoline;

N-[(E)-(1-hydroxy-3H-2,1-benzoxaborol-5-yl)methyl-
eneamino]-5-methoxy-N-methyl-pyridazin-3-amine;

N-[(E)-(1-hydroxy-3H-2,1-benzoxaborol-5-yl)methyl-
eneamino]-N-methyl-2-methylsulfanyl-thiazolo[4,5-d]
pyrimidin-7-amine;

N-[(E)-(1-hydroxy-3H-2,1-benzoxaborol-5-yl)methyl-
eneamino]-N,1-dimethyl-pyrazolo[3,4-d]pyrimidin-4-
amine;

N-[(E)-(1-hydroxy-3H-2,1-benzoxaborol-5-yl)methyl-
eneamino]-N,7-dimethyl-thieno[3,2-d]pyrimidin-4-
amine;

N-ethyl-N-[(E)-(1-hydroxy-3H-2,1-benzoxaborol-5-yl)
methyleneamino]-1H-pyrazolo[4,3-d]pyrimidin-7-
amine;

N7-ethyl-N7-[(E)-(1-hydroxy-3H-2,1-benzoxaborol-5-
yl)methyleneamino]-N2,N2-dimethyl-thiazolo[4,5-d]
pyrimidine-2,7-diamine;

N-[(E)-(1-hydroxy-3H-2,1-benzoxaborol-5-yl)
methyleneamino]-3-methyl-1H-pyrazolo[4,3-d]py-
rimidin-7-amine;

N-ethyl-N-[(E)-(1-hydroxy-3H-2,1-benzoxaborol-5-yl)
methyleneamino]-5H-pyrrolo[3,2-d]pyrimidin-4-
amine;

N-ethyl-N-[(E)-(1-hydroxy-3H-2,1-benzoxaborol-5-yl)
methyleneamino]-2-morpholino-thiazolo[4,5-d]py-
rimidin-7-amine;

N-ethyl-N-[(E)-(1-hydroxy-3H-2,1-benzoxaborol-5-yl)
methyleneamino]-2-methylsulfanyl-thiazolo[4,5-d]py-
rimidin-7-amine;

N-ethyl-N-[(E)-(1-hydroxy-3H-2,1-benzoxaborol-5-yl)
methyleneamino]-7-propyl-pyrrolo[2,3-d]pyrimidin-4-
amine;

N,7-diethyl-N-[(E)-(1-hydroxy-3H-2,1-benzoxaborol-5-
yl) methylene amino]pyrrolo[2,3-d]pyrimidin-4-
amine;

N-ethyl-N-[(E)-(1-hydroxy-3H-2,1-benzoxaborol-5-yl)
methyleneamino]-1H-pyrazolo[3,4-d]pyrimidin-4-
amine;

N-ethyl-N-[(E)-(1-hydroxy-3H-2,1-benzoxaborol-5-yl)
methyleneamino]thiazolo[4,5-d]pyrimidin-7-amine;

N-ethyl-N-[(E)-(1-hydroxy-3H-2,1-benzoxaborol-5-yl)
methyleneamino]-2,7-dimethyl-thieno[3,2-d]pyrimi-
din-4-amine;

N-ethyl-7-fluoro-N-[(E)-(1-hydroxy-3H-2,1-benzoxa-
borol-5-yl)methyleneamino]quinazolin-4-amine;

N-ethyl-N-[(E)-(1-hydroxy-3H-2,1-benzoxaborol-5-yl)
methyleneamino]-6-methyl-thieno[3,2-d]pyrimidin-4-
amine;

N-ethyl-N-[(E)-(1-hydroxy-3H-2,1-benzoxaborol-5-yl)
methyleneamino]-6,7,8,9-tetrahydrobenzothiopheno[3,
2-d]pyrimidin-4-amine;

N-[(E)-(1-hydroxy-3H-2,1-benzoxaborol-5-yl)methyl-
eneamino]-N-isobutyl-2-methylsulfanyl-thiazolo[4,5-
d]pyrimidin-7-amine;

N-[(E)-(1-hydroxy-3H-2,1-benzoxaborol-5-yl)methyl-
eneamino]-N-isobutyl-7-methyl-thieno[3,2-d]pyrimi-
din-4-amine;

N-[(E)-(1-hydroxy-3H-2,1-benzoxaborol-5-yl)methyl-
eneamino]-N-(2-methoxyethyl)-7-methyl-thieno[3,2-
d]pyrimidin-4-amine;

N-[(E)-(1-hydroxy-3H-2,1-benzoxaborol-5-yl)methyl-
eneamino]-N-(2-methoxyethyl)-2-methylsulfanyl-thi-
azolo[4,5-d]pyrimidin-7-amine;

N-[(E)-(1-hydroxy-3H-2,1-benzoxaborol-5-yl)methyl-
eneamino]-N-(3-methoxypropyl)-2-methylsulfanyl-
thiazolo[4,5-d]pyrimidin-7-amine;

2-[[(E)-(1-hydroxy-3H-2,1-benzoxaborol-5-yl)methyl-
eneamino]-(7-methylthieno[3,2-d]pyrimidin-4-yl)
amino]ethanol;

6-[[(E)-(1-hydroxy-3H-2,1-benzoxaborol-5-yl)methyl-
eneamino]-methyl-amino]-9-methyl-7H-purin-8-one;

4-[[(E)-(1-hydroxy-3H-2,1-benzoxaborol-5-yl)methyl-
eneamino]-methyl-amino]-7-methyl-5H-pyrrolo[2,3-
d]pyrimidin-6-one;

4-[[(E)-(1-hydroxy-3H-2,1-benzoxaborol-5-yl)methyl-
eneamino]-methyl-amino]-6,8-dihydro-5H-pyrido[2,3-
d]pyrimidin-7-one;

N-[(E)-(1-hydroxy-3H-2,1-benzoxaborol-5-yl)methyl-
eneamino]-N-methyl-5,6-dihydrofuro[2,3-d]pyrimi-
din-4-amine;

N-[(E)-(1-hydroxy-3H-2,1-benzoxaborol-5-yl)methyl-
eneamino]-N-methyl-7-phenyl-thieno[3,2-d]pyrimi-
din-4-amine;

7-cyclopropyl-N-[(E)-(1-hydroxy-3H-2,1-benzoxaborol-
5-yl)methyleneamino]-N-methyl-thieno[3,2-d]pyrimi-
din-4-amine;

N-[(E)-(1-hydroxy-3H-2,1-benzoxaborol-5-yl)methyl-
eneamino]-N-methyl-7-morpholino-thieno[3,2-d]py-
rimidin-4-amine;

7-ethyl-N-[(E)-(1-hydroxy-3H-2,1-benzoxaborol-5-yl)
methyleneamino]-N-methyl-thieno[3,2-d]pyrimidin-4-
amine;

N-[(E)-(1-hydroxy-3H-2,1-benzoxaborol-5-yl)methyl-
eneamino]-N,7-dimethyl-5,6-dihydropyrrolo[2,3-d]py-
rimidin-4-amine;

9-cyclobutyl-6-[[(E)-(1-hydroxy-3H-2,1-benzoxaborol-
5-yl)methyleneamino]-methyl-amino]-7H-purin-8-
one;

6-[[(E)-(1-hydroxy-3H-2,1-benzoxaborol-5-yl)methyl-
eneamino]-methyl-amino]-9-[3-(methoxymethyl)cy-
clobutyl]-7H-purin-8-one;

6-[[(E)-(1-hydroxy-3H-2,1-benzoxaborol-5-yl)methyl-
eneamino]-methyl-amino]-9-(3-hydroxycyclobutyl)-
7H-purin-8-one;

9-(3-bicyclo[1.1.1]pentanyl)-6-[[(E)-(1-hydroxy-3H-2,1-
benzoxaborol-5-yl)methyleneamino]-methyl-amino]-
7H-purin-8-one;

7-cyclobutyl-4-[[(E)-(1-hydroxy-3H-2,1-benzoxaborol-5-yl)methyleneamino]-methyl-amino]-5H-pyrrolo[2,3-d]pyrimidin-6-one;
4-[ethyl-[(E)-(1-hydroxy-3H-2,1-benzoxaborol-5-yl)methyleneamino]amino]-N-propyl-thieno[3,2-d]pyrimidine-7-carboxamide;
4-[ethyl-[(E)-(1-hydroxy-3H-2,1-benzoxaborol-5-yl)methyleneamino]amino]-N,N-dimethyl-thieno[3,2-d]pyrimidine-7-carboxamide;
N,N-dibutyl-4-[ethyl-[(E)-(1-hydroxy-3H-2,1-benzoxaborol-5-yl)methyleneamino]-amino]thieno[3,2-d]pyrimidine-7-carboxamide;
4-[ethyl-[(E)-(1-hydroxy-3H-2,1-benzoxaborol-5-yl)methyleneamino]amino]-N-(oxetan-3-yl)thieno[3,2-d]pyrimidine-7-carboxamide;
4-[ethyl-[(E)-(1-hydroxy-3H-2,1-benzoxaborol-5-yl)methyleneamino]amino]-N-(4-methoxybutyl)thieno[3,2-d]pyrimidine-7-carboxamide;
4-[6-(1-hydroxy-3H-2,1-benzoxaborol-5-yl)-3-methyl-4,5-dihydro-3H-pyridazin-2-yl]furo[2,3-d]pyrimidine;
4-[6-(1-hydroxy-3H-2,1-benzoxaborol-5-yl)-3-methyl-4,5-dihydro-3H-pyridazin-2-yl]-7-methyl-thieno[3,2-d]pyrimidine;
(+) 4-[6-(1-hydroxy-3H-2,1-benzoxaborol-5-yl)-3-methyl-4,5-dihydro-3H-pyridazin-2-yl]-7-methyl-thieno[3,2-d]pyrimidine;
(−) 4-[6-(1-hydroxy-3H-2,1-benzoxaborol-5-yl)-3-methyl-4,5-dihydro-3H-pyridazin-2-yl]-7-methyl-thieno[3,2-d]pyrimidine;
4-[6-(1-hydroxy-3H-2,1-benzoxaborol-5-yl)-3-methyl-4,5-dihydro-3H-pyridazin-2-yl]thieno[3,2-d]pyrimidine;
4-[6-(1-hydroxy-3H-2,1-benzoxaborol-5-yl)-3-methyl-4,5-dihydro-3H-pyridazin-2-yl]-6,7,8,9-tetrahydrobenzothiopheno[3,2-d]pyrimidine;
7-[6-(1-hydroxy-3H-2,1-benzoxaborol-5-yl)-3-methyl-4,5-dihydro-3H-pyridazin-2-yl]-2-methylsulfanyl-thiazolo[4,5-d]pyrimidine;
N-[(E)-(1-hydroxy-3H-2,1-benzoxaborol-5-yl)methyleneamino]-7-(methoxymethyl)-N-methyl-thieno[3,2-d]pyrimidin-4-amine; and
pharmaceutically acceptable salts thereof.

9. A pharmaceutical composition comprising a compound of claim 1, or a pharmaceutically acceptable salt thereof, and a pharmaceutically acceptable excipient.

10. A method of treating a cancer where YAP is localized in the nucleus of the tumor cells, which comprises administering to a subject in need thereof a compound of claim 1, or a pharmaceutically acceptable salt thereof.

11. The method of claim 10, wherein the cancer is lung cancer, thyroid cancer, ovarian cancer, colorectal cancer, prostate cancer, pancreas cancer, esophagus cancer, liver cancer, breast cancer or skin cancer.

12. The method of claim 10, wherein the cancer is malignant mesothelioma.

13. A pharmaceutical composition comprising a compound of claim 5, or a pharmaceutically acceptable salt thereof, and a pharmaceutically acceptable excipient.

14. A pharmaceutical composition comprising a compound of claim 8, or a pharmaceutically acceptable salt thereof, and a pharmaceutically acceptable excipient.

15. A method of treating a cancer where YAP is localized in the nucleus of the tumor cells, which comprises administering to a subject in need thereof a compound of claim 5, or a pharmaceutically acceptable salt thereof.

16. The method of claim 15, wherein the cancer is malignant mesothelioma.

17. A method of treating a cancer where YAP is localized in the nucleus of the tumor cells, which comprises administering to a subject in need thereof a compound of claim 8, or a pharmaceutically acceptable salt thereof.

18. The method of claim 17, wherein the cancer is malignant mesothelioma.

19. The compound of claim 2, or a pharmaceutically acceptable salt thereof, wherein

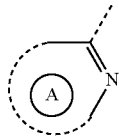

is a group of formula (VI):

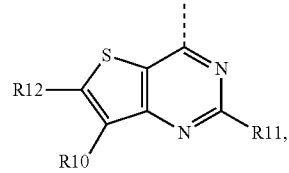

(VI)

* * * * *